(12) United States Patent
Murthy et al.

(10) Patent No.: US 6,602,879 B2
(45) Date of Patent: Aug. 5, 2003

(54) PYRROLE-TYPE COMPOUNDS, COMPOSITIONS, AND METHODS FOR TREATING CANCER OR VIRAL DISEASES

(75) Inventors: Madiraju S. R. Murthy, Brossard (CA); Nancy A. E. Steenaart, Dorval (CA); Roy A. Johnson, Sausalito (CA); Gordon C. Shore, Montreal (CA)

(73) Assignee: Gemin X Biotechnologies Inc., Montreal (CA)

( * ) Notice: Subject to any disclaimer, the term of this patent is extended or adjusted under 35 U.S.C. 154(b) by 0 days.

This patent is subject to a terminal disclaimer.

(21) Appl. No.: 10/116,094

(22) Filed: Apr. 4, 2002

(65) Prior Publication Data

US 2003/0009032 A1 Jan. 9, 2003

Related U.S. Application Data

(63) Continuation of application No. 09/491,712, filed on Jan. 26, 2000, now Pat. No. 6,407,244.

(51) Int. Cl.$^7$ ........................ A61K 31/403; A61P 43/00
(52) U.S. Cl. ........................ 514/277; 514/339; 514/414; 514/451; 514/459; 514/460
(58) Field of Search ................................ 514/277, 339, 514/414, 451, 459, 460

(56) References Cited

U.S. PATENT DOCUMENTS

| | | |
|---|---|---|
| 5,691,334 A | 11/1997 | Doria et al. |
| 5,847,127 A | 12/1998 | D'Alessio et al. |
| 6,407,244 B1 | 6/2002 | Murthy et al. |

FOREIGN PATENT DOCUMENTS

| | | |
|---|---|---|
| CA | 2155096 | 6/1995 |
| JP | 61-34403 | 8/1986 |
| JP | 61280429 | 12/1986 |
| JP | 2-250828 | 10/1990 |
| JP | 5-86374 | 12/1993 |
| JP | 09030967 | 2/1997 |
| JP | 10-120562 | 5/1998 |
| JP | 10-120563 | 5/1998 |
| JP | 11-209283 | 8/1999 |
| WO | WO98/11894 | 3/1998 |
| WO | WO 98/40380 | 9/1998 |
| WO | WO 99/15690 | 4/1999 |
| WO | WO 99/29309 | 6/1999 |
| WO | WO 99/40069 | 8/1999 |

OTHER PUBLICATIONS

Appelbaum, 1992, "The role of the immune system in the pathogenesis of cancer", Semin. Oncol. Nurs. 8(1):51–62.

Azuma et al., 2000, "Induction of apoptosis of activated murine splenic T cells by cycloprodigiosin hydrochloride, a novel immunosuppressant", Immunopharmacology 46(1):29–37.

Balitskii and Struk, 1968, "Activation of Protection Reactions of the Organism in Malignant Growths", Zh. Eksp. Klin. Med. (USSR) 8:3–8.

Barbagallo et al., 1979, "Cytological Activity of Prodigiosin by *Allium cepa* L. Test", Riv. Biol. Norm. Patol. 5:25–31 (in italian w/ Eng. summary).

Botti et al., 1998, "Immunosupressive factors: role in cancer development and progession", Int'l. J. Biol. Mark. 13(2):51–69.

Birkeland et al., 2000, "Cancer risk in patients on dialysis and after renal transplantation", Lancet 355)9218):1886–7.

Cortesina et al., 1993, "Immunomodulation therapy for squamous cell carcinoma of the head and neck", Head Neck. 15(3):266–70.

Boger and Patel, 1988, "Total Synthesis of Prodigiosin, Prodigiosene, and Desmethosyprodigiosin: Diels–Alder Reactions of Heterocyclic Azadienes and Development of an Effective Palladium(III)–Promoted 2,2'–Bipyrrole Coupling Procedure", J. Org. Chem. 53:1405–1415.

Boger and Patel, 1987, "Total Synthesis of Prodigiosin", Tetrahedron Lett. 28:2499–2502.

D'Alessio and Rossi, 1996, "Short Synthesis of Undecyprodigiosine. A New Route to 2,2'–Bipyrrolyl–Pyrromethene Systems", Synlett 6:513–514.

Fürstner et al., 1998, "Platinum– and Acid–Catalyzed Enyne Metathesis Reactions: Mechanistic Studies and Applications to the Syntheses of Streptorubin B and Metacycloprodigiosin", J. Am. Chem. Soc. 120:8305–8314.

Gerber and Gauthier, 1979, "New Prodigiosin–Like Pigment from *Alteromonas rubra*", Appl. Environ. Microbiol. 37:1176–1179.

(List continued on next page.)

Primary Examiner—Joseph K. McKane
Assistant Examiner—Andrea D. Small
(74) Attorney, Agent, or Firm—Pennie & Edmonds LLP

(57) ABSTRACT

The present invention relates to novel Pyrrole-Type compounds, compositions comprising Pyrrole-Type compounds, and methods useful for treating or preventing cancer or a neoplastic disorder comprising administering a composition comprising a Pyrrole-Type compound. The compounds, compositions, and methods of the invention are also useful for inhibiting the growth of a cancer cell or neoplastic cell. The present invention also relates to novel Pyrrole-Type compounds, compositions, and methods useful for treating or preventing a viral infection. The compounds, compositions, and methods of the invention are also useful for inhibiting the replication and/or infectivity of a virus.

88 Claims, No Drawings

OTHER PUBLICATIONS

Gerber et al., "Biosynthesis of Prodiginines. $^{13}$C Resonance Assignments and Enrichment Patterns in Nonyl-Cyclononyl-, Methylcycodecyl-, and Butylcycloheptyl-prodiginine Produced by Actinomycete Cultures Supplemented with $^{13}$C–Labeled Acetate and $^{15}$N–Labeled Nitrate", Can. J. Chem. 56:1155–1163.

Gerber and Lechevalier, 1976, "Prodiginine (Prodigiosin–Like) Pigments from Streptomyces and Other Aerobic Actinomycetes", Can. J. Microbiol. 22:658–667.

Gerber and Stahly, 1975, "Prodiginine (Prodigiosin–Like) Pigments from *Streptoverticillium rubrireticuli,* an Organism That Causes Pink Staining of Polyvinyl Chloride", Appl. Microbiol. 30:807–810.

Gerber, 1975, "Prodigiosin–Like Pigments", CRC Crit. Rev. Microbiol. 3:469–485.

Gerber, 1975, "A New Prodiginine (Prodigiosin–Like) Pigment from Streptomyces. Antimalarial Activity of Several Prodiginines", J. Antibiotics 28:194–199.

Gerber, 1973, "Minor Prodiginine Pigments from *Actionomadura madurae* and *Actinomadura pelletieri*", J. Heterocycl. Chem. 10:925–929.

Goping et al., 1998, "Regulated Targeting of BAX to Mitochondria ", J. Cell Biol. 143:207–215.

Guseva and Balshin, 1992, "Comparative Efficacy of Prodigiosan and Proper–Myl Action on Neutrophil Phagocytosis in Acute Myeloblastic Leukemia", Antibiot. Khimioter. 37:44–46 (in Russian w/Eng. abstr.).

Guseva and Tishenko, 1989, "The Effect of Prodigiosan on Antibody–Dependent Cytotoxicity of Neutrophils in Chronic Myeloid Leukemia", Vopr. Onkol. 35:30–34 (in Russian w/Eng. abstr.).

Hojo et al., 1999, "Cyclosporine Induces Cancer Progression by a Cell–Autonomous Mechanism", Nature 397:530–534.

Hong et al., 1999, "Cloning and Functional Analysis of Infectious Pancreatic Necrosis Virus VP5: A Novel Bcl–2 Family with Regulation of Viral Expression and Anti–Cell Death Activity", Cold Spring Harbor Symposium on Programmed Cell Death, Sep. 29–Oct. 3, 1999, p. 93.

Korsmeyer, 1992, "Bcl–2: A Repressor of Lymphocyte Death", Immunol. Today 13:285–288.

Laatsch et al., 1991, "Butyl–meta–Cycloheptylprodiginine—a Revision of the Structure of the Former Ortho–Isomer", J. Antibiot. 44:187–191.

Laatsch and Thomson, 1983, "A Revised Structure for Cycloprodigiosin", Tetrahedron Lett. 24:2701–2704.

Magae et al., 1996, "Effect of Metacycloprodigiosin, an Inhibitor of Killer T Cells, on Murine Skin and Heart Transplants", J. Antibiot. 49:86–90.

Marshall et al., 1999, "Epstein–Barr Virus Encodes a Novel Homolog of the bcl–2 Oncogene That Inhibits Appoptosis and Associates with Bax and Bak", J. Virol. 73:5181–5185.

Matsunaga et al., 1986, "Bioactive Marine Metabolites. VIII. Isolation of an Antimicrobial Blue Pigment from the Bryozoan *Bugula dentata*", Experientia 42:84.

Mitsuya et al., 1991, "Targeted Therapy of Human Immunodeficiency Virus–Related Disease", FASEB J. 5:2369–2381.

Molecular Biology of the Cell (2ed. 1989) edited et al., Garland Publishing, Inc.:New York, pp. 727–761 and 1203–1215.

Montaner et al., 2000, "Prodigiosin from the supernatant of Serratia marcescens induces apoptosis in haematopoietic cancer cell lines", Br. J. Pharmacol. 131(3):585–93.

Mortellaro et al., 1999, "New Immunosuppressive Drug PNU156804 Blocks IL–2 Dependent Proliferation and NF–κB and AP–1 Activation", J. Immunol. 162:7102–7109.

Myasoedov et al., 1987, "Topical Application of Chemopreparations and Embolization of the Blood Vessels in the Complex Treatment of Tumors", Klin. Khir. 4:7–9 (English abstract only)).

Nakamura et al., 1986, "Selective Suppression by Prodigiosin of the Mitogenic Response of Murine Splenocytes", J. Antibiotics 39:1155–1159.

Ng and Shore, 1998, "Bcl–$X_L$ Cooperatively Associates with Bap31 Complex in the Endoplasmic Reticulum, Dependent on Procaspase–8 and Ced–4 Adaptor", J. Biol. Chem. 273:3140–3143.

Ng et al., 1997, "p 28 Bap31, a Bcl–2/Bcl–$X^L$– and Procaspase–8–Associated Protein in the Endoplasmic Reticulum", J. Cell. Biol. 139:327–338.

Nguyen et al., 1998, "E1A–Induced Processing of Procaspase–8 Can Occur Independently of FADD and is Inhibited by Bcl–2", J. Biol. Chem. 273–33099–33102.

Nicot et al., 1997, "Activation of Bcl–2 Expression in Human Encothelial Cells Chronically Expressing the Human T–Cell Lymphotropic Virus Type I", Virol. 236:47–53.

Penn, 2000, "Cancers in renal transplant recipients", Adv. Ren. Replace. Ther. 7(2):147–56.

Piontek and Porschen, 1994, "Growth Inhibition of Human Gastrointestinal Cancer Cells by Cyclosporin A", J. Cancer Res. Clin. Oncol. 120:695–699.

Rapoport and Holden, 1962, "The Synthesis of Prodigiosin", J. Am. Chen. Soc. 84:635–642.

Rubinstein et al., 1990, "Comparison of In Vitro Anticancer–Drug–Screening Data Generated with a Tetrazolium Assay versus a Protein Assay Against a Diverse Panel of Human Tumor Cell Lines", J. Natl. Cancer Inst. 82:1113–1118.

Shapovalova, 1972, "Effect of Antitumor Antibiotics on Resistance to Bacterial Infections of Animals with Transplanted Lymphadenosis NK/LI", Antibiotiki 17:339–343 (In Russian w/Eng. abstract).

Skehan et al., 1990, "New Colorimetric Cytotoxicity Assay for Anticancer–Drug Screening", J. Natl. Cancer Inst. 82:1107–1112.

Strauss and Berger, 1983, "Methylosin A und B, Pigmente aus *Methylosinus trichosporium*", Zeitschr. für Allgemeine Mikrobiologie 23:661–668 (in German w/Eng. abstr.).

Swinne et al., 2000, "Transplantation–related lymphoproliferative disorder: a model for human immunodeficiency virus–related lymphomas", Semin. Oncol. 27(4):402–8.

Thomas and Banks, 1999, "Human Papillomavirus (HPV) E6 Interactions with Bak are Conserved amongst E6 Proteins from High and Low Rish HPV Types", J. Gen. Virol. 80:1513–1517.

Thomas and Banks, 1998, "Inhibition of Bak–Induced Apoptosis by HPV–18 E6", Oncogene 17:2943–2954.

Tsao et al., 1985, "Identification of a Red Pigment from *Streptomyces coelicolor* A3(2) as a Mixture of Prodigiosin Derivatives", J. Antibiotics 38:128–131.

Tsujimoto et al., 1984, "Cloning of the Chromosome Breakpoint of Neoplastic B Cells with the t(14;18) Chromosome Translocation", Science 226:1097–1099.

Tsukahara et al., 1999, "Induction of Bcl-$x_L$ Expression by Human T–Cell Leukemia Virus Type 1 Tax through NF–κB in Apoptosis–Resistant T–Cell Transfectants with Tax", J. Virol. 73:7981–7987.

Wasserman et al., 1961, "Der Prodigiosin–Ähnliche Pilzfarbstoff aus *Streptomyces longisporus ruber*", Angew. Chem. 73:467 (In German).

Wasserman et al., 1969, "The Synthesis of Metacycloprodigiosin", J. Am. Chem. Soc. 91:1264–1265.

Wasserman et al., 1976, "Undecylprodigiosin", Tetrahedron 32:1851–1854.

Wasserman et al., 1976, "The Structure of Matacycloprodigiosin", Tetrahedron 32:1855–1861.

Wasserman et al., 1976, "The Synthesis of Metacycloprodigiosin", Tetrahedron 32:1867–1871.

Waters, 1998, "Chloroquine–Resistance—Discovering the Missing Link?", Nature Med. 4:23–24.

Yamamoto et al., 1999, "Cycloprodigiosin Hydrochloride, a New $H^+/Cl^-$ Symporter, Incuces Apoptosis in Human and Rat Hepatocellular Cancer Cell Lines in vitro and Inhibits the Growth of Hepatocellular Carcinoma Xenografts in Nude Mice", Hepatol. 30:894–902.

Yayon et al., 1984, "Identification of the Acidic Compartment of *Plasmodium falciparum*–Infected Human Erythrocytes as the Target of the Anticalarial Drug Chloroquine", EMBO J. 3:2695–2700.

*htpp://www.dtp.nci.nih.gov/main.html* Developmental Therapeutics Program, National Cancer Institute, National Institutes of Health (1999).

*http://dbs.p.kanazawa–u.ac.ip/~seika/home–e.html* Faculty of Pharmaceutical Science at the University of Kanazawa (2000).

The Merck Index (12$^{th}$ ed., 1996) entry 7948, p. 1334.

PYRROLE-TYPE COMPOUNDS, COMPOSITIONS, AND METHODS FOR TREATING CANCER OR VIRAL DISEASES

This application is a con of 09/491,712 Jan. 26, 2000 now U.S. Pat. No. 6,407,244 Jun. 18, 2002. This is a continuation of application Ser. No. 09/491,712, filed Jan. 26, 2000, now U.S. Pat. No. 6,407,244 allowed, the entire contents of which is incorporated herein by reference in its entirety.

1. FIELD OF THE INVENTION

The present invention relates to Pyrrole-Type compounds, compositions comprising Pyrrole-Type compounds, and methods useful for treating or preventing cancer or a neoplastic disorder comprising administering a composition comprising a Pyrrole-Type compound. The compounds, compositions, and methods of the invention are also useful for inhibiting the growth of a cancer cell or neoplastic cell. The present invention also relates to Pyrrole-Type compounds, compositions, and methods useful for treating or preventing a viral infection. The compounds, compositions, and methods of the invention are also useful for inhibiting the replication or infectivity of a virus.

2. BACKGROUND OF THE INVENTION

2.1. Cancer and Neoplastic Disease

Cancer affects approximately million adults and children worldwide, and this year, more than 9 million new cases will be diagnosed (International Agency for Research on Cancer; www.irac.fr). According to the American Cancer Society, about 563,100 Americans are expected to die of cancer this year, more than 1500 people a day. Since 1990, in the United States alone, nearly five million lives have been lost to cancer, and approximately 12 million new cases have been diagnosed.

Currently, cancer therapy involves surgery, chemotherapy and/or radiation treatment to eradicate neoplastic cells in a patient (see, for example, Stockdale, 1998, "Principles of Cancer Patient Management", in *Scientific American: Medicine*, vol. 3, Rubenstein and Federman, eds., Chapter 12, Section IV). All of these approaches pose significant drawbacks for the patient. Surgery, for example, may be contraindicated due to the health of the patient or may be unacceptable to the patient. Additionally, surgery may not completely remove the neoplastic tissue. Radiation therapy is effective only when the irradiated neoplastic tissue exhibits a higher sensitivity to radiation than normal tissue, and radiation therapy can also often elicit serious side effects. (Id.) With respect to chemotherapy, there are a variety of chemotherapeutic agents available for treatment of neoplastic disease. However, despite the availability of a variety of chemotherapeutic agents, chemotherapy has many drawbacks (see, for example, Stockdale, 1998, "Principles Of Cancer Patient Management" in *Scientific American Medicine*, vol. 3, Rubenstein and Federman, eds., ch. 12, sect. 10). Almost all chemotherapeutic agents are toxic, and chemotherapy causes significant, and often dangerous, side effects, including severe nausea, bone marrow depression, immunosuppression, etc. Additionally, many tumor cells are resistant or develop resistance to chemotherapeutic agents through multi-drug resistance.

Tamura et al., JP93086374, discloses metacycloprodigiosin and/or prodigiosin-25C as being useful for treating leukemia, but provides data for only prodigiosin-25C activity against L-5178Y cells in vitro. Hirata et al., JP-10120562, discloses the use of cycloprodigiosin as an inhibitor of the vacuolar ATPase proton pump and states that cycloprodigiosin may have anti-tumor enhancing activity. Hirata et al., JP-10120563 discloses the use of cycloprodigiosin as a therapeutic drug for leukemia, as an immunosuppressant, and as an apoptosis inducer. JP61034403, to Kirin Brewery Co. Ltd, describes prodigiosin for increasing the survival time of mice with leukemia. Boger, 1988, J. Org. Chem. 53:1405–1415 discloses in vitro cytotoxic activity of prodigiosin, prodigiosene, and 2-methyl-3-pentylprodigiosene against mouse P388 leukemia cells. The National Cancer Institute, http://dtp.nci.nih.gov, discloses data obtained from the results of a human-tumor-cell-line screen, including screening of butylcycloheptyl-prodiginine HCl; however, the screen provides no indication that the compounds of the screen are selective for cancer cells (e.g., as compared to normal cells).

Therefore, there is a significant need in the art for novel compounds and compositions, and methods that are useful for treating cancer or neoplastic disease with reduced or without the aforementioned side effects. Further, there is a need for cancer treatments that provide cancer-cell-specific therapies with increased specificity and decreased toxicity.

2.2. Viruses and Disease

In addition to cancer, an enormous number of human and animal diseases result from virulent and opportunistic viral infections (see Belshe (Ed.) 1984 *Textbook of Human Virology*, PSG Publishing, Littleton, Mass.). Viral diseases of a wide array of tissues, including the respiratory tract, CNS, skin, genitourinary tract, eyes, ears, immune system, gastrointestinal tract, and musculoskeletal system, affect a vast number of humans of all ages (see Table 328-2 In: Wyngaarden and Smith, 1988, *Cecil Textbook of Medicine*, 18th Ed., W. B. Saunders Co., Philadelphia, pp. 1750–1753).

Although considerable effort has been invested in the design of effective anti-viral therapies, viral infections continue to threaten the lives of millions of people worldwide. In general, attempts to develop anti-viral drugs have focused on several stages of viral life cycle (See e.g., Mitsuya, H., et al., 1991, FASEB J. 5:2369–2381, discussing HIV). However, a common drawback associated with using of many current anti-viral drugs is their deleterious side effects, such as toxicity to the host or resistance by certain viral strains.

Accordingly, there is a need in the art for anti-viral compounds, compositions, and methods that allow for safe and effective treatment of viral disease without the above-mentioned disadvantages.

Citation or identification of any reference in Section 2 of this application is not an admission that such reference is available as prior art to the present invention.

3. SUMMARY OF THE INVENTION

FORMULA I

The present invention encompasses novel compounds having the general Formula (I):

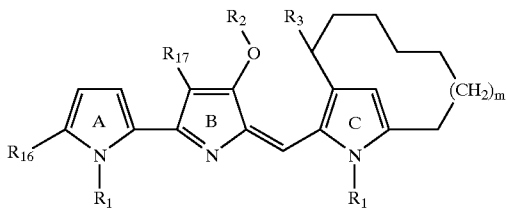

and pharmaceutically acceptable salts thereof, wherein:

each $R_1$ is independently selected from the group consisting of —H, —$CH_3$, —$CH_2CH_3$, —$CH_2C_6H_5$, —C(O)OC($CH_3$)$_3$, —C(O)O$CH_2C_6H_5$, and —C(O)$CH_3$;

$R_2$ is selected from the group consisting of —H, $C_1$–$C_{12}$ straight chain alkyl, —$CH_2C_6H_5$, —$SiR_{10}R_{11}R_{12}$, —C(O)$CH_3$, —C(O)$C_6H_5$, -2-tetrahydropyranyl, —$OCH_2OCH_3$, and —C(O)$OCH_2CCl_3$;

$R_3$ is selected from the group consisting of —H, $C_1$–$C_{12}$ straight chain alkyl, —CH($R_{14}$)($R_{15}$) wherein $R_{14}$ and $R_{15}$ are independently $C_1$–$C_{12}$ straight chain alkyl, —C(O)$C_1$–$C_9$ straight chain alkyl, —CH(OH)$C_1$–$C_9$ straight chain alkyl, —CH(Cl)$C_1$–$C_9$ straight chain alkyl, -(2-pyridyl)methyl, -(3-pyridyl)methyl, -(4-pyridyl)methyl, and —$CH_2C_6H_5$, the —$CH_2C_6H_5$ being unsubstituted or substituted on phenyl with one cyano or one or more halo, methoxyl, or trifluoromethyl groups;

$R_{10}$ is selected from the group consisting of $C_1$–$C_4$ straight or branched chain alkyl and —$C_6H_5$;

$R_{11}$ and $R_{12}$ are independently $C_1$–$C_3$ straight or branched chain alkyl;

$R_{16}$ and $R_{17}$ is —H; and m is an integer ranging from 1 to 5;

with the proviso that the compound of Formula (I) is not:
butyl-meta-cycloheptylprodiginine,
metacycloprodigiosin,
4-ethoxy-5-((3,5-nonamethylene-2H-pyrrol-2-ylidene)methyl)-2,2'-bi-1H-pyrrole, or
4-propoxy-5-((3,5-nonamethylene-2H-pyrrol-2-ylidene)methyl)-2,2'-bi-1H-pyrrole.

The compounds of Formula (I) and pharmaceutically acceptable salts thereof are useful for treating or preventing cancer or neoplastic disease in a patient in need of such treatment or prevention. The compounds of Formula (I) and pharmaceutically acceptable salts thereof are also useful for inhibiting the growth of a cancer cell or neoplastic cell. The compounds of Formula (I) and pharmaceutically acceptable salts thereof are useful for treating or preventing a viral infection in a patient in need of such treatment or prevention. The compounds of Formula (I) and pharmaceutically acceptable salts thereof are also useful for inhibiting the replication or infectivity of a virus.

The present invention provides compositions comprising a pharmaceutically acceptable carrier and a therapeutically effective amount of a compound of Formula (I) or a pharmaceutically acceptable salt thereof, wherein, in the compound of Formula (I):

each $R_1$ is independently selected from the group consisting of —H, —$CH_3$, —$CH_2CH_3$, —$CH_2C_6H_5$, —C(O)OC($CH_3$)$_3$, —C(O)O$CH_2C_6H_5$, and —C(O)$CH_3$;

$R_2$ is selected from the group consisting of —H, $C_1$–$C_{12}$ straight chain alkyl, —$CH_2C_6H_5$, —$SiR_{10}R_{11}R_{12}$, —C(O)$CH_3$, —C(O)$C_6H_5$, -2-tetrahydropyranyl, —$OCH_2OCH_3$, and —C(O)$OCH_2CCl_3$;

$R_3$ is selected from the group consisting of —H, $C_1$–$C_{12}$ straight chain alkyl, —CH($R_{14}$)($R_{15}$) wherein $R_{14}$ and $R_{15}$ are independently $C_1$–$C_{12}$ straight chain alkyl, —C(O)$C_1$–$C_9$ straight chain alkyl, —CH(OH)$C_1$–$C_9$ straight chain alkyl, —CH(Cl)$C_1$–$C_9$ straight chain alkyl, -(2-pyridyl)methyl, -(3-pyridyl)methyl, -(4-pyridyl)methyl, and —$CH_2C_6H_5$, the —$CH_2C_6H_5$ being unsubstituted or substituted on phenyl with one cyano or one or more halo, methoxyl, or trifluoromethyl groups;

$R_{10}$ is selected from the group consisting of $C_1$–$C_4$ straight or branched chain alkyl and —$C_6H_5$;

$R_{11}$ and $R_{12}$ are independently $C_1$–$C_3$ straight or branched chain alkyl;

$R_{16}$ and $R_{17}$ are —H; and m is an integer ranging from 1 to 5;

with the proviso that the compound of Formula (I) is not:
butyl-meta-cycloheptylprodiginine,
metacycloprodigiosin,
4-ethoxy-5-((3,5-nonamethylene-2H-pyrrol-2-ylidene)methyl)-2,2'-bi-1H-pyrrole, or
4-propoxy-5-((3,5-nonamethylene-2H-pyrrol-2-ylidene)methyl)-2,2'-bi-1H-pyrrole.

The compositions comprising a pharmaceutically acceptable carrier and a compound of Formula (I) or a pharmaceutically acceptable salt thereof are useful for treating or preventing cancer or neoplastic disease in a patient in need of such treatment or prevention. These compositions are also useful for inhibiting the growth of a cancer cell or neoplastic cell. The compositions comprising a pharmaceutically acceptable carrier and a compound of Formula (I) or a pharmaceutically acceptable salt thereof are also useful for treating or preventing a viral infection in a patient in need of such treatment or prevention. These compositions are also useful for inhibiting the replication or infectivity of a virus.

The invention further provides methods for treating or preventing cancer or neoplastic disease in a patient comprising administering to a patient in need of such treatment or prevention a composition comprising a therapeutically effective amount of a compound of Formula (I) or a pharmaceutically acceptable salt thereof, wherein, in the compound of Formula (I):

each $R_1$ is independently selected from the group consisting of —H, —$CH_3$, —$CH_2CH_3$, —$CH_2C_6H_5$, —C(O)OC($CH_3$)$_3$, —C(O)O$CH_2C_6H_5$, and —C(O)$CH_3$;

$R_2$ is selected from the group consisting of —H, $C_1$–$C_{12}$ straight chain alkyl, —$CH_2C_6H_5$, —$SiR_{10}R_{11}R_{12}$, —C(O)$CH_3$, —C(O)$C_6H_5$, -2-tetrahydropyranyl, —$OCH_2OCH_3$, and —C(O)$OCH_2CCl_3$;

$R_3$ is selected from the group consisting of —H, $C_1$–$C_{12}$ straight chain alkyl, —CH($R_{14}$)($R_{15}$) wherein $R_{14}$ and $R_{15}$ are independently $C_1$–$C_{12}$ straight chain alkyl, —C(O)$C_1$–$C_9$ straight chain alkyl, —CH(OH)$C_1$–$C_9$ straight chain alkyl, —CH(Cl)$C_1$–$C_9$ straight chain alkyl, -(2-pyridyl)methyl, -(3-pyridyl)methyl, -(4-pyridyl)methyl, and —$CH_2C_6H_5$, the —$CH_2C_6H_5$ being unsubstituted or substituted on phenyl with one cyano or one or more halo, methoxyl, or trifluoromethyl groups;

$R_{10}$ is selected from the group consisting of $C_1$–$C_4$ straight or branched chain alkyl and —$C_6H_5$;

$R_{11}$ and $R_{12}$ are independently $C_1$–$C_3$ straight or branched chain alkyl;

m is an integer ranging from 1 to 5; and when m is 3 and $R_2$ is —$CH_2CH_3$, then $R_{16}$ is —H or —$CH_3$ and $R_{17}$ is —H;

when m is 3 and $R_2$ is —$CH_3$, then $R_{16}$ is —H or —$CH_3$ and $R_{17}$ is —H or —COOEt; and when m is other than 3 and $R_2$ is other than —$CH_3$ or —$CH_2CH_3$, then $R_{16}$ and $R_{17}$ are —H only;

with the proviso that the compound of Formula (I) is not: metacycloprodigiosin.

The invention further provides methods for inhibiting the growth of a cancer cell or neoplastic cell comprising a contacting a cancer cell or neoplastic cell with an effective amount of a composition comprising a pharmaceutically acceptable carrier and a compound having the general Formula (I) or a pharmaceutically acceptable salt thereof, wherein, in the compound of Formula (I):

each $R_1$ is independently selected from the group consisting of —H, —$CH_3$, —$CH_2CH_3$, —$CH_2C_6H_5$, —C(O)OC($CH_3$)$_3$, —C(O)O$CH_2C_6H_5$, and —C(O)$CH_3$;

$R_2$ is selected from the group consisting of —H, $C_1$–$C_{12}$ straight chain alkyl, —$CH_2C_6H_5$, —$SiR_{10}R_{11}R_{12}$, —C(O)$CH_3$, —C(O)$C_6H_5$, -2-tetrahydropyranyl, —O$CH_2$O$CH_3$, and —C(O)O$CH_2CCl_3$;

$R_3$ is selected from the group consisting of —H, $C_1$–$C_{12}$ straight chain alkyl, —CH($R_{14}$)($R_{15}$) wherein $R_{14}$ and $R_{15}$ are independently $C_1$–$C_{12}$ straight chain alkyl, —C(O)$C_1$–$C_9$ straight chain alkyl, —CH(OH)$C_1$–$C_9$ straight chain alkyl, —CH(Cl)$C_1$–$C_9$ straight chain alkyl, -(2-pyridyl)methyl, -(3-pyridyl)methyl, -(4-pyridyl)methyl, and —$CH_2C_6H_5$, the —$CH_2C_6H_5$ being unsubstituted or substituted on phenyl with one cyano or one or more halo, methoxyl, or trifluoromethyl groups;

$R_{10}$ is selected from the group consisting of $C_1$–$C_4$ straight or branched chain alkyl and —$C_6H_5$;

$R_{11}$ and $R_{12}$ are independently $C_1$–$C_3$ straight or branched chain alkyl;

m is an integer ranging from 1 to 5;

when m is 3 and $R_2$ is —$CH_2CH_3$, then $R_{16}$ is —H or —$CH_3$ and $R_{17}$ is —H;

when m is 3 and $R_2$ is —$CH_3$, then $R_{16}$ is —H or —$CH_3$ and $R_{17}$ is —H or —COOEt; and when m is other than 3 and $R_2$ is other than —$CH_3$ or —$CH_2CH_3$, then $R_{16}$ and $R_{17}$ are —H only;

with the proviso that the compound of Formula (I) is not: metacycloprodigiosin.

The invention further provides methods for treating or preventing a viral infection in a patient comprising administering to a patient in need of such treatment or prevention a therapeutically effective amount of a composition comprising a pharmaceutically acceptable carrier and a compound of Formula (I) or a pharmaceutically acceptable salt thereof, wherein, in the compound of Formula (I):

each $R_1$ is independently selected from the group consisting of —H, —$CH_3$, —$CH_2CH_3$, —$CH_2C_6H_5$, —C(O)OC($CH_3$)$_3$, —C(O)O$CH_2C_6H_5$, and —C(O)$CH_3$;

$R_2$ is selected from the group consisting of —H, $C_1$–$C_{12}$ straight chain alkyl, —$CH_2C_6H_5$, —$SiR_{10}R_{11}R_{12}$, —C(O)$CH_3$, —C(O)$C_6H_5$, -2-tetrahydropyranyl, —O$CH_2$O$CH_3$, and —C(O)O$CH_2CCl_3$;

$R_3$ is selected from the group consisting of —H, $C_1$–$C_{12}$ straight chain alkyl, —CH($R_{14}$)($R_{15}$) wherein $R_{14}$ and $R_{15}$ are independently $C_1$–$C_{12}$ straight chain alkyl, —C(O)$C_1$–$C_9$ straight chain alkyl, —CH(OH)$C_1$–$C_9$ straight chain alkyl, —CH(Cl)$C_1$–$C_9$ straight chain alkyl, -(2-pyridyl)methyl, -(3-pyridyl)methyl, -(4-pyridyl)methyl, and —$CH_2C_6H_5$, the —$CH_2C_6H_5$ being unsubstituted or substituted on phenyl with one cyano or one or more halo, methoxyl, or trifluoromethyl groups;

$R_{10}$ is selected from the group consisting of $C_1$–$C_4$ straight or branched chain alkyl and —$C_6H_5$;

$R_{11}$ and $R_{12}$ are independently $C_1$–$C_3$ straight or branched chain alkyl;

m is an integer ranging from 1 to 5; and when m is 3 and $R_2$ is —$CH_2CH_3$, then $R_{16}$ is —H or —$CH_3$ and $R_{17}$ is —H;

when m is 3 and $R_2$ is —$CH_3$, then $R_{16}$ is —H or —$CH_3$ and $R_{17}$ is —H or —COOEt; and when m is other than 3 and $R_2$ is other than —$CH_3$ or —$CH_2CH_3$, then $R_{16}$ and $R_{17}$ are —H only.

The invention further provides methods for inhibiting the replication or infectivity of a virus comprising a contacting a virus or a virus-infected cell with an effective amount of a composition comprising a pharmaceutically acceptable carrier and a compound having the general Formula (I) or a pharmaceutically acceptable salt thereof, wherein, in the compound of Formula (I):

each $R_1$ is independently selected from the group consisting of —H, —$CH_3$, —$CH_2CH_3$, —$CH_2C_6H_5$, —C(O)OC($CH_3$)$_3$, —C(O)O$CH_2C_6H_5$, and —C(O)$CH_3$;

$R_2$ is selected from the group consisting of —H, $C_1$–$C_{12}$ straight chain alkyl, —$CH_2C_6H_5$, —$SiR_{10}R_{11}R_{12}$, —C(O)$CH_3$, —C(O)$C_6H_5$, -2-tetrahydropyranyl, —O$CH_2$O$CH_3$, and —C(O)O$CH_2CCl_3$;

$R_3$ is selected from the group consisting of —H, $C_1$–$C_{12}$ straight chain alkyl, —CH($R_{14}$)($R_{15}$) wherein $R_{14}$ and $R_{15}$ are independently $C_1$–$C_{12}$ straight chain alkyl, —C(O)$C_1$–$C_9$ straight chain alkyl, —CH(OH)$C_1$–$C_9$ straight chain alkyl, —CH(Cl)$C_1$–$C_9$ straight chain alkyl, -(2-pyridyl)methyl, -(3-pyridyl)methyl, -(4-pyridyl)methyl, and —$CH_2C_6H_5$, the —$CH_2C_6H_5$ being unsubstituted or substituted on phenyl with one cyano or one or more halo, methoxyl, or trifluoromethyl groups;

$R_{10}$ is selected from the group consisting of $C_1$–$C_4$ straight or branched chain alkyl and —$C_6H_5$;

$R_{11}$ and $R_{12}$ are independently $C_1$–$C_3$ straight or branched chain alkyl;

m is an integer ranging from 1 to 5; and when m is 3 and $R_2$ is —$CH_2CH_3$, then $R_{16}$ is —H or —$CH_3$ and $R_{17}$ is —H;

when m is 3 and $R_2$ is —$CH_3$, then $R_{16}$ is —H or —$CH_3$ and $R_{17}$ is —H or —COOEt; and when m is other than 3 and $R_2$ is other than —$CH_3$ or —$CH_2CH_3$, then $R_{16}$ and $R_{17}$ are —H only.

FORMULA II

The present invention still further provides novel compounds having the general Formula (E):

II and pharmaceutically acceptable salts thereof, wherein:

each $R_1$ is independently selected from the group consisting of —H, —$CH_3$, —$CH_2CH_3$, —$CH_2C_6H_5$, —C(O)OC($CH_3$)$_3$, —C(O)O$CH_2C_6H_5$, and —C(O)$CH_3$;

$R_2$ is selected from the group consisting of —H, $C_1$–$C_{12}$ straight chain alkyl, —$CH_2C_6H_5$, —$SiR_{10}R_{11}R_{12}$, —C(O)$CH_3$, —C(O)$C_6H_5$, -2-tetrahydropyranyl, —O$CH_2$O$CH_3$, and —C(O)O$CH_2CCl_3$;

$R_4$ is selected from the group consisting of —H and $C_1$–$C_{12}$ straight chain alkyl;

$R_5$ is selected from the group consisting of —H, $C_1$–$C_4$ straight chain alkyl and —$C_6H_5$;

$R_{10}$ is selected from the group consisting of —$C_1$–$C_4$, straight or branched chain alkyl and —$C_6H_5$;

$R_{11}$ and $R_{12}$ are independently $C_1$–$C_3$ straight or branched chained alkyl; and n is an integer ranging from 1 to 6;

with the proviso that the compound of Formula (II) is not:
cycloprodigiosin, or
4-ethyl-2,4,5,6-tetrahydro-3-((3-methoxy-5-(1H-pyrrol-2-yl-)-2H-pyrrol-2-ylidene)methyl)-1-methyl-cyclopenta(c)pyrrole.

The compounds of Formula (II) and pharmaceutically acceptable salts thereof are useful for treating or preventing cancer or neoplastic disease in a patient in need of such treatment or prevention. The compounds of Formula (II) and pharmaceutically acceptable salts thereof are also useful for inhibiting the growth of a cancer cell or neoplastic cell. The compounds of Formula (II) and pharmaceutically acceptable salts thereof are useful for treating or preventing a viral infection in a patient in need of such treatment or prevention. The compounds of Formula (II) and pharmaceutically acceptable salts thereof are also useful for inhibiting the replication or infectivity of a virus.

The present invention further provides compositions comprising a pharmaceutically acceptable carrier and a therapeutically effective amount of a compound of Formula (II) or a pharmaceutically acceptable salt thereof, wherein, in the compound of Formula (II):

each $R_1$ is independently selected from the group consisting of —H, —$CH_3$, —$CH_2CH_3$, —$CH_2C_6H_5$, —$C(O)OC(CH_3)_3$, —$C(O)OCH_2C_6H_5$, and —$C(O)CH_3$;

$R_2$ is selected from the group consisting of —H, $C_1$–$C_{12}$ straight chain alkyl, —$CH_2C_6H_5$, —$SiR_{10}R_{11}R_{12}$, —$C(O)CH_3$, —$C(O)C_6H_5$, -2-tetrahydropyranyl, —$OCH_2OCH_3$, and —$C(O)OCH_2CCl_3$;

$R_4$ is selected from the group consisting of —H and $C_1$–$C_{12}$ straight chain alkyl;

$R_5$ is selected from the group consisting of —H, $C_1$–$C_4$ straight chain alkyl and —$C_6H_5$;

$R_{10}$ is selected from the group consisting of $C_1$–$C_4$ straight or branched chain alkyl, and —$C_6H_5$;

$R_{11}$ and $R_{12}$ are independently selected from the group consisting of —$CH_3$, —$CH_2CH_3$, and —$C_3H_7$; and n is an integer ranging from 1 to 6; with the proviso that the compound of Formula (II) is not:
cycloprodigiosin, or
4-ethyl-2,4,5,6-tetrahydro-3-((3-methoxy-5-(1H-pyrrol-2-yl-)-2H-pyrrol-2-ylidene)methyl)-1-methyl-cyclopenta(c)pyrrole.

The compositions comprising a pharmaceutically acceptable carrier and a compound of Formula (II) or a pharmaceutically acceptable salt thereof are useful for treating or preventing cancer or neoplastic disease in a patient in need of such treatment or prevention. These compositions are also useful for inhibiting the growth of a cancer cell or neoplastic cell. The compositions comprising a pharmaceutically acceptable carrier and a compound of Formula (II) or a pharmaceutically acceptable salt thereof are useful for treating or preventing a viral infection in a patient in need of such treatment or prevention. These compositions are also useful for inhibiting the replication and/or infectivity of a virus.

The invention provides methods for treating or preventing cancer or a neoplastic disease comprising administering to a patient in need of such treatment or prevention a composition comprising a therapeutically effective amount of a compound of Formula (II) or a pharmaceutically acceptable salt thereof, wherein:

each $R_1$ is independently selected from the group consisting of —H, —$CH_3$, —$CH_2CH_3$, —$CH_2C_6H_5$, —$C(O)OC(CH_3)_3$, —$C(O)OCH_2C_6H_5$ and —$C(O)CH_3$;

$R_2$ is selected from the group consisting of —H, $C_1$–$C_{12}$ straight chain alkyl, —$CH_2C_6H_5$, —$SiR_{10}R_{11}R_{12}$, —$C(O)CH_3$, —$C(O)C_6H_5$, -2-tetrahydropyranyl, —$OCH_2OCH_3$, and —$C(O)OCH_2CCl_3$;

$R_4$ is selected from the group consisting of —H and $C_1$–$C_{12}$ straight chain alkyl;

$R_5$ is selected from the group consisting of —H, $C_1$–$C_4$ straight chain alkyl and —$C_6H_5$;

$R_{10}$ is selected from the group consisting of $C_1$–$C_4$ straight or branched chain alkyl and —$C_6H_5$;

$R_{11}$ and $R_{12}$ are independently selected from the group consisting of $C_1$–$C_3$ straight or branched chain alkyl; and n is an integer ranging from 1 to 6;

with the proviso that the compound of Formula (II) is not:
cycloprodigiosin.

The invention provides methods for inhibiting the growth of a cancer cell or neoplastic cell comprising a contacting a cancer cell or neoplastic cell with an effective amount of a composition comprising a pharmaceutically acceptable carrier and a compound having the general Formula (II) or a pharmaceutically acceptable salt thereof, wherein:

each $R_1$ is independently selected from the group consisting of —H, —$CH_3$, —$CH_2CH_3$, —$CH_2C_6H_5$, —$C(O)OC(CH_3)_3$, —$C(O)OCH_2C_6H_5$, and —$C(O)CH_3$;

$R_2$ is selected from the group consisting of —H, $C_1$–$C_{12}$ straight chain alkyl, —$CH_2C_6H_5$, —$SiR_{10}R_{11}R_{12}$, —$C(O)CH_3$, —$C(O)C_6H_5$, -2-tetrahydropyranyl, —$OCH_2OCH_3$, and —$C(O)OCH_2CCl_3$;

$R_4$ is selected from the group consisting of —H and $C_1$–$C_{12}$ straight chain alkyl;

$R_5$ is selected from the group consisting of —H, $C_1$–$C_4$ straight chain alkyl and —$C_6H_5$;

$R_{10}$ is selected from the group consisting of $C_1$–$C_4$ straight or branched chain alkyl and —$C_6H_5$;

$R_{11}$ and $R_{12}$ are independently $C_1$–$C_3$ straight or branched chain alkyl; and n is a integer from 1 to 6;

with the proviso that the compound of Formula (II) is not:
cycloprodigiosin.

The invention provides methods for treating or preventing a viral infection comprising administering to a patient in need of such treatment or prevention a therapeutically effective amount of a composition comprising a pharmaceutically acceptable carrier and a compound of Formula (II) or a pharmaceutically acceptable salt thereof, wherein:

each $R_1$ is independently selected from the group consisting of —H, —$CH_3$, —$CH_2CH_3$, —$CH_2C_6H_5$, —$C(O)OC(CH_3)_3$, —$C(O)OCH_2C_6H_5$, and —$C(O)CH_3$;

$R_2$ is selected from the group consisting of —H, $C_1$–$C_{12}$ straight chain alkyl, —$CH_2C_6H_5$, —$SiR_{10}R_{11}R_{12}$, —$C(O)CH_3$, —$C(O)C_6H_5$, -2-tetrahydropyranyl, —$OCH_2OCH_3$, and —$C(O)OCH_2CCl_3$;

$R_4$ is selected from the group consisting of —H and $C_1$–$C_{12}$ straight chain alkyl;

$R_5$ is selected from the group consisting of —H, $C_1$–$C_4$ straight chain alkyl and —$C_6H_5$;

$R_{10}$ is selected from the group consisting of $C_1$–$C_4$ straight or branched chain alkyl, and —$C_6H_5$;

$R_{11}$ and $R_{12}$ are independently $C_1$–$C_3$ straight or branched chain alkyl; and n is a integer from 1 to 6.

The invention provides methods for inhibiting the replication or infectivity of a virus comprising contacting a virus or a virus-infected cell with an effective amount of a composition comprising a pharmaceutically acceptable carrier and a compound having the general Formula (II) or a pharmaceutically acceptable salt thereof, wherein:

each $R_1$ is independently selected from the group consisting of —H, —$CH_3$, —$CH_2CH_3$, —$CH_2C_6H_5$, —C(O)OC($CH_3$)$_3$, —C(O)O$CH_2C_6H_5$, and —C(O)$CH_3$;

$R_2$ is selected from the group consisting of —H, $C_1$–$C_{12}$ straight chain alkyl, —$CH_2C_6H_5$, —Si$R_{10}R_{11}R_{12}$, —C(O)$CH_3$, —C(O)$C_6H_5$, -2-tetrahydropyranyl, —O$CH_2OCH_3$, and —C(O)O$CH_2CCl_3$;

$R_4$ is selected from the group consisting of —H and $C_1$–$C_{12}$ straight chain alkyl;

$R_5$ is selected from the group consisting of —H, $C_1$–$C_4$ straight chain alkyl and —$C_6H_5$;

$R_{10}$ is selected from the group consisting of $C_1$–$C_4$ straight or branched chain alkyl and $C_6H_5$;

$R_{11}$ and $R_{12}$ are independently $C_1$–$C_3$ straight or branched chain alkyl; and n is a integer from 1 to 6.

FORMULA III

The present invention still further provides novel compounds having the general Formula (III):

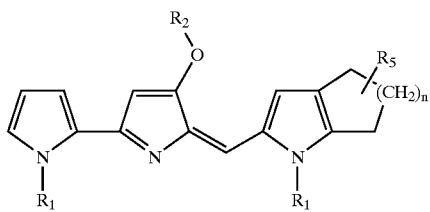

III and pharmaceutically acceptable salts thereof, wherein:

each $R_1$ is independently selected from the group consisting of —H, —$CH_3$, —$CH_2CH_3$, —$CH_2C_6H_5$, —C(O)OC($CH_3$)$_3$, —C(O)O$CH_2C_6H_5$, and —C(O)$CH_3$;

$R_2$ is selected from the group consisting of —H, $C_1$–$C_{12}$ straight chain alkyl, —$CH_2C_6H_5$, —Si$R_{10}R_{11}R_{12}$, —C(O)$CH_3$, —C(O)$C_6H_5$, -2-tetrahydropyranyl, —O$CH_2OCH_3$, and —C(O)O$CH_2CCl_3$;

$R_5$ is selected from the group consisting of —H, $C_1$–$C_6$ straight chain alkyl and —$C_6H_5$;

$R_{10}$ is selected from the group consisting of $C_1$–$C_4$ straight or branched chain alkyl and —$C_6H_5$;

$R_{11}$ and $R_{12}$ are independently $C_1$–$C_3$ straight or branched chain alkyl; and n is an integer ranging from 1 to 6;
with the proviso that the compound of Formula (III) is not:
orthobutylcycloheptylprodiginine,
4-methoxy-5-((4,5,6,7-tetrahydro-2H-indol-2-ylidene)methyl)-2,2'-bi-1H-pyrrole),
4-methoxy-5-(4-hexyl-(4,5,6,7-tetrahydro-2H-indol-2-ylidene)methyl)-2,2'-bi-1H-pyrrole),
4-ethoxy-5-(4-hexyl-(4,5,6,7-tetrahydro-2H-indol-2-ylidene)methyl)-2,2'-bi-1H-pyrrole), or
4-propoxy-5-(4-hexyl-(4,5,6,7-tetrahydro-2H-indol-2-ylidene)methyl)-2, 2'-bi-1H-pyrrole).

The compounds of Formula (III) and pharmaceutically acceptable salts thereof are useful for treating or preventing cancer or neoplastic disease in a patient in need of such treatment or prevention. The compounds of Formula (III) and pharmaceutically acceptable salts thereof are also useful for inhibiting the growth of a cancer cell or neoplastic cell. The compounds of Formula (III) and pharmaceutically acceptable salts thereof are useful for treating or preventing a viral infection in a patient in need of such treatment or prevention. The compounds of Formula (III) and pharmaceutically acceptable salts thereof are also useful for inhibiting the replication or infectivity of a virus.

The present invention further provides compositions comprising a pharmaceutically acceptable carrier and a therapeutically effective amount of a compound of Formula (III) or a pharmaceutically acceptable salt thereof, wherein:

each $R_1$ is independently selected from the group consisting of —H, —$CH_3$, —$CH_2CH_3$, —$CH_2C_6H_5$, —C(O)OC($CH_3$)$_3$, —C(O)O$CH_2C_6H_5$, and —C(O)$CH_3$;

$R_2$ is selected from the group consisting of —H, $C_1$–$C_{12}$ straight chain alkyl, —$CH_2C_6H_5$, —Si$R_{10}R_{11}R_{12}$, —C(O)$CH_3$, —C(O)$C_6H_5$, -2-tetrahydropyranyl, —O$CH_2OCH_3$, and —C(O)O$CH_2CCl_3$;

$R_5$ is selected from the group consisting of —H, $C_1$–$C_6$ straight chain alkyl and —$C_6H_5$;

$R_{10}$ is selected from the group consisting of $C_1$–$C_6$ straight or branched chain alkyl and —$C_6H_5$;

$R_{11}$ and $R_{12}$ are independently $C_1$–$C_3$ straight or branched chain alkyl; and n is an integer ranging from 1 to 6;
with the proviso that the compound of Formula (III) is not:
orthobutylcycloheptylprodiginine;
4-methoxy-5-((4,5,6,7-tetrahydro-2H-indol-2-ylidene)methyl)-2,2'-bi 1H-pyrrole),
4-methoxy-5-(4-hexyl-(4,5,6,7-tetrahydro-2H-indol-2-ylidene)methyl)-2,2'-bi 1H-pyrrole),
4-ethoxy-5-(4-hexyl-(4,5,6,7-tetrahydro-2H-indol-2-ylidene)methyl)-2,2'-bi 1H-pyrrole), or
4-propoxy-5-(4-hexyl-(4,5,6,7-tetrahydro-2H-indol-2-ylidene)methyl)-2,2'-bi 1H-pyrrole).

The compositions comprising a pharmaceutically acceptable carrier and a compound of Formula (III) or a pharmaceutically acceptable salt thereof are useful for treating or preventing cancer or neoplastic disease in a patient in need of such treatment or prevention.

These compositions are also useful for inhibiting the growth of a cancer cell or neoplastic cell. The compositions comprising a pharmaceutically acceptable carrier and a compound of Formula (III) or a pharmaceutically acceptable salt thereof are useful for treating or preventing a viral infection in a patient in need of such treatment or prevention. These compositions are also useful for inhibiting the replication or infectivity of a virus.

The invention further provides methods for treating or preventing cancer or a neoplastic disease comprising administering to a patient in need of such treatment or prevention a composition comprising a therapeutically effective amount of a compound of Formula (III) or a pharmaceutically acceptable salt thereof, wherein:

each $R_1$ is independently selected from the group consisting of —H, —$CH_3$, —$CH_2CH_3$, —$CH_2C_6H_5$, —C(O)OC($CH_3$)$_3$, —C(O)O$CH_2C_6H_5$, and —C(O)$CH_3$;

$R_2$ is selected from the group consisting of —H, $C_1$–$C_{12}$ straight chain alkyl, —$CH_2C_6H_5$, —Si$R_{10}R_{11}R_{12}$ —C(O)$CH_3$, —C(O)$C_6H_5$, -2-tetrahydropyranyl, —O$CH_2OCH_3$, and —C(O)O$CH_2CCl_3$;

$R_5$ is selected from the group consisting of —H, $C_1$–$C_6$ straight chain alkyl and —$C_6H_5$;

$R_{10}$ is selected from the group consisting of $C_1$–$C_4$ straight or branched chain alkyl and —$C_6H_5$;

$R_1$ and $R_{12}$ are independently $C_1$–$C_3$ straight or branched chain alkyl; and n is an integer ranging from 1 to 6.

The invention further provides methods for inhibiting the growth of a cancer cell or neoplastic cell comprising a contacting a cancer cell or neoplastic cell with an effective amount of a composition comprising a pharmaceutically acceptable carrier and a compound having the general Formula (III) or a pharmaceutically acceptable salt thereof, wherein:

each $R_1$ is independently selected from the group consisting of —H, —$CH_3$, —$CH_2CH_3$, —$CH_2C_6H_5$, —$C(O)OC(CH_3)_3$, —$C(O)OCH_2C_6H_5$, and —$C(O)CH_3$;

$R_2$ is selected from the group consisting of —H, $C_1$–$C_{12}$ straight chain alkyl, —$CH_2C_6H_5$, —$SiR_{10}R_{11}R_{12}$, —$C(O)CH_3$, —$C(O)C_6H_5$, -2-tetrahydropyranyl, —$OCH_2OCH_3$, and —$C(O)OCH_2CCl_3$;

$R_5$ is selected from the group consisting of —H, $C_1$–$C_6$ straight chain alkyl and —$C_6H_5$;

$R_{10}$ is selected from the group consisting of $C_1$–$C_4$ straight or branched chain alkyl and —$C_6H_5$;

$R_{11}$ and $R_{12}$ are independently $C_1$–$C_3$ straight or branched chain alkyl; and n is an integer ranging from 1 to 6.

The invention further provides methods for treating or preventing a viral infection in a patient comprising administering to a patient in need of such treatment or prevention a therapeutically effective amount of a composition comprising a pharmaceutically acceptable carrier and a compound of Formula (III) and pharmaceutically acceptable salts thereof, wherein:

each $R_1$ is independently selected from the group consisting of —H, —$CH_3$, —$CH_2CH_3$, —$CH_2C_6H_5$, —$C(O)OC(CH_3)_3$, —$C(O)OCH_2C_6H_5$, and —$C(O)CH_3$;

$R_2$ is selected from the group consisting of —H, $C_1$–$C_{12}$ straight chain alkyl, —$CH_2C_6H_5$, —$SiR_{10}R_{11}R_{12}$, —$C(O)CH_3$, —$C(O)C_6H_5$, -2-tetrahydropyranyl, —$OCH_2OCH_3$, and —$C(O)OCH_2CCl_3$;

$R_5$ is selected from the group consisting of —H, $C_1$–$C_6$ straight chain alkyl and —$C_6H_5$; $R_{10}$ is selected from the group consisting of $C_1$–$C_4$ straight or branched chain alkyl and —$C_6H_5$;

$R_{11}$ and $R_{12}$ are independently $C_1$–$C_3$ straight or branched chain alkyl; and n is an integer ranging from 1 to 6.

The invention further provides methods for inhibiting the replication or infectivity of a virus comprising contacting a virus or a virus-infected cell with an effective amount of a composition comprising a pharmaceutically acceptable carrier and a compound having the general Formula (III) or a pharmaceutically acceptable salt thereof, wherein:

each $R_1$ is independently selected from the group consisting of —H, —$CH_3$, —$CH_2CH_3$, —$CH_2C_6H_5$, —$C(O)OC(CH_3)_3$, —$C(O)OCH_2C_6H_5$, and —$C(O)CH_3$;

$R_2$ is selected from the group consisting of —H, $C_1$–$C_{12}$ straight chain alkyl, —$CH_2C_6H_5$, —$SiR_{10}R_{11}R_{12}$, —$C(O)CH_3$, —$C(O)C_6H_5$, -2-tetrahydropyranyl, —$OCH_2OCH_3$, and —$C(O)OCH_2CCl_3$;

$R_5$ is selected from the group consisting of —H, $C_1$–$C_6$ straight chain alkyl and —$C_6H_5$;

$R_1$ is selected from the group consisting of $C_1$–$C_4$ straight or branched chain alkyl and —$C_6H_5$;

$R_{11}$ and $R_{12}$ are independently $C_1$–$C_3$ straight or branched chain alkyl; and n is an integer ranging from 1 to 6.

FORMULA IV

The present invention encompasses novel compounds having the general Formula (IV):

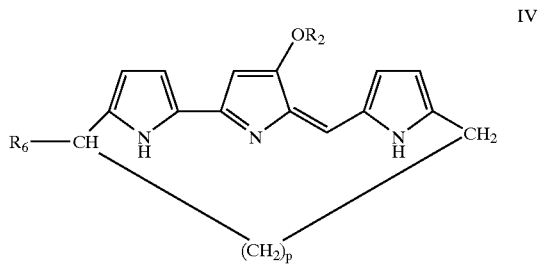

IV and pharmaceutically acceptable salts thereof, wherein:

$R_2$ is selected from the group consisting of —H, $C_1$–$C_{12}$ straight chain alkyl, —$CH_2C_6H_5$, —$SiR_{10}R_{11}R_{12}$, —$C(O)CH_3$, —$C(O)C_6H_5$, -2-tetrahydropyranyl, —$OCH_2OCH_3$, and —$C(O)OCH_2CCl_3$;

$R_6$ is selected from the group consisting of —H, —$CH_3$, and —$CH_2CH_3$;

$R_{10}$ is selected from the group consisting of $C_1$–$C_4$ straight or branched chain alkyl and —$C_6H_5$;

$R_{11}$ and $R_{12}$ are independently $C_1$–$C_3$ straight or branched chain alkyl; and p is as integer from 6 to 8;

with the proviso that the compound of Formula (IV) is not:
cyclononylprodiginine,
methylcyclooctylprodiginine,
methylcyclodecylprodiginine,
ethylcyclononylprodiginine,
R39FF,
R39MF,
R39SF,
610FF, or
610MF.

The compounds of Formula (IV) and pharmaceutically acceptable salts thereof are useful for treating or preventing cancer or neoplastic disease in a patient in need of such treatment or prevention. The compounds of Formula (IV) and pharmaceutically acceptable salts thereof are also useful for inhibiting the growth of a cancer cell or neoplastic cell. The compounds of Formula (IV) and pharmaceutically acceptable salts thereof are useful for treating or preventing a viral infection in a patient in need of such treatment or prevention. The compounds of Formula (IV) and pharmaceutically acceptable salts thereof are also useful for inhibiting the replication or infectivity of a virus.

The present invention further provides compositions comprising a pharmaceutically acceptable carrier and a therapeutically effective amount of a compound of Formula (IV) or a pharmaceutically acceptable salt thereof, wherein:

$R_2$ is selected from the group consisting of —H, $C_1$–$C_{12}$ straight chain alkyl, —$CH_2C_6H_5$, —$SiR_{10}R_{11}R_{12}$, —$C(O)CH_3$, —$C(O)C_6H_5$, -2-tetrahydropyranyl, —$OCH_2OCH_3$, and —$C(O)OCH_2CCl_3$;

$R_6$ is selected from the group consisting of —H, —$CH_3$, and —$CH_2CH_3$;

$R_{10}$ is selected from the group consisting of $C_1$–$C_4$ straight or branched chain alkyl and —$C_6H_5$;

$R_{11}$ and $R_{12}$ are independently $C_1$–$C_3$ straight or branched chain alkyl; and p is an integer ranging from 6 to 8;

with the proviso that the compound of Formula (IV) is not:
cyclononylprodiginine, methylcyclooctylprodiginine,
methylcyclodecylprodiginine,
ethylcyclononylprodiginine,
R39FF,
R39MF,
R39SF,
610FF, or
610MF.

The compositions comprising a pharmaceutically acceptable carrier and a compound of Formula (IV) or a pharmaceutically acceptable salt thereof are useful for treating or preventing cancer or neoplastic disease in a patient in need of such treatment or prevention. These compositions are also useful for inhibiting the growth of a cancer cell or neoplastic cell. The compositions comprising a pharmaceutically acceptable carrier and a compound of Formula (IV) or a pharmaceutically acceptable salt thereof are useful for treating or preventing a viral infection in a patient in need of such treatment or prevention. These compositions are also useful for inhibiting the replication or infectivity of a virus.

The invention further provides methods for treating or preventing cancer or a neoplastic disease comprising administering to a patient in need of such treatment or prevention a composition comprising a therapeutically effective amount of a compound of Formula (IV) or a pharmaceutically acceptable salt thereof, wherein:

$R_2$ is selected from the group consisting of —H, $C_1$–$C_{12}$ straight chain alkyl, —$CH_2C_6H_5$, —$SiR_{10}R_{11}R_{12}$, —C(O)$CH_3$, —C(O)$C_6H_5$, -2-tetrahydropyranyl, —$OCH_2OCH_3$, and —C(O)$OCH_2CCl_3$;

$R_6$ is selected from the group consisting of —H, —$CH_3$, and —$CH_2CH_3$;

$R_{10}$ is selected from the group consisting of $C_1$–$C_4$ straight or branched chain alkyl and —$C_6H_5$;

$R_{11}$ and $R_{12}$ are independently $C_1$–$C_3$ straight or branched chain alkyl; and p is an integer ranging from 6 to 8.

The invention further provides methods for inhibiting the growth of a cancer cell or neoplastic cell comprising a contacting a cancer cell or neoplastic cell with an effective amount of a composition comprising a pharmaceutically acceptable carrier and a compound having the general Formula (IV) or a pharmaceutically acceptable salt thereof, wherein:

$R_2$ is selected from the group consisting of —H, $C_1$–$C_{12}$ straight chain alkyl, —$CH_2C_6H_5$, —$SiR_{10}R_{11}R_{12}$, —C(O)$CH_3$, —C(O)$C_6H_5$, -2-tetrahydropyranyl, —$OCH_2OCH_3$, and —C(O)$OCH_2CCl_3$;

$R_6$ is selected from the group consisting of —H, —$CH_3$, and —$CH_2CH_3$;

$R_{10}$ is selected from the group consisting of $C_1$–$C_4$ straight or branched chain alkyl and —$C_6H_5$;

$R_{11}$ and $R_{12}$ are independently $C_1$–$C_3$ straight or branched chain alkyl; and p is an integer ranging from 6 to 8.

The invention further provides methods for treating or preventing a viral infection in a patient comprising administering to a patient in need of such treatment or prevention a therapeutically effective amount of a composition comprising a pharmaceutically acceptable carrier and a compound of Formula (IV) or a pharmaceutically acceptable salt thereof, wherein:

$R_2$ is selected from the group consisting of —H, $C_1$–$C_{12}$ straight chain alkyl, —$CH_2C_6H_5$, —$SiR_{10}R_{11}R_{12}$, —C(O)$CH_3$, —C(O)$C_6H_5$, -2-tetrahydropyranyl, —$OCH_2OCH_3$, and —C(O)$OCH_2CCl_3$;

$R_6$ is selected from the group consisting of —H, —$CH_3$, and —$CH_2CH_3$;

$R_{10}$ is selected from the group consisting of $C_1$–$C_4$ straight or branched-chain alkyl, and —$C_6H_5$;

$R_{11}$ and $R_{12}$ are independently $C_1$–$C_3$ straight or branched chain alkyl; and p is an integer ranging from 6 to 8.

The invention further provides methods for inhibiting the replication or infectivity of a virus comprising a contacting a virus or a virus-infected cell with an effective amount of a composition comprising a pharmaceutically acceptable carrier and a compound having the general Formula (IV) or a pharmaceutically acceptable salt thereof, wherein:

$R_2$ is selected from the group consisting of —H, $C_1$–$C_{12}$ straight chain alkyl, —$CH_2C_6H_5$, —$SiR_{10}R_{11}R_{12}$, —C(O)$CH_3$, —C(O)$C_6H_5$, -2-tetrahydropyranyl, —$OCH_2OCH_3$, and —C(O)$OCH_2CCl_3$;

$R_6$ is selected from the group consisting of —H, —$CH_3$, and —$CH_2CH_3$;

$R_{10}$ is selected from the group consisting of $C_1$–$C_4$ straight or branched chain alkyl and —$C_6H_5$;

$R_{11}$ and $R_{12}$ are independently $C_1$–$C_3$ straight or branched chain alkyl; and p is an integer ranging from 6 to 8.

FORMULA V

The present invention provides methods for treating or preventing cancer or a neoplastic disease comprising administering to a patient in need of such treatment or prevention a composition comprising a therapeutically effective amount of a compound of Formula (V):

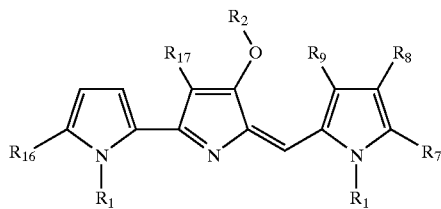

V or a pharmaceutically acceptable salt thereof, wherein:

$R_1$ is selected from the group consisting of —H, —$CH_3$, —$CH_2CH_3$, —$CH_2C_6H_5$, —C(O)OC$(CH_3)_3$, —C(O)$OCH_2C_6H_5$, and —C(O)$CH_3$;

$R_2$ is selected from the group consisting of —H, $C_1$–$C_{12}$ straight chain alkyl, —$CH_2C_6H_5$, —$SiR_{10}R_{11}R_{12}$, —C(O)$CH_3$, —C(O)$C_6H_5$, -2-tetrahydropyranyl, —$OCH_2OCH_3$, and —C(O)$OCH_2CCl_3$;

$R_7$ is selected from the group consisting of —H, $C_1$–$C_5$ straight chain alkyl, —$(CH_2)_9CH$=$CH_2$, —$(CH_2)_6F$, —$(CH_2)_5OC_6H_5$, —$(CH_2)_6OH$, —$(CH_2)_7CN$, —$CH_2CH_2C_6H_5$, —$(CH_2)_4COOH$, —$(CH_2)_5COOH$, —$(CH_2)_5COOMe$, —$(CH_2)_{11}COOH$, —$(CH_2)_{12}COOH$, —$(CH_2)_{12}OH$, —$(CH_2)_{13}OH$, —$(CH_2)_{11}CN$, —$(CH_2)_{11}OC(O)NH_2$, —$(CH_2)_{11}COOEt$, —C(O)$(CH_2)_9CH_3$, —$(CH_2)_5C(O)N(CH_2CH_2)_2$ 0, $C_3$–$C_7$ cycloalkyl, —$C_6H_5$, 2-pyrrolyl, -3-pyrrolyl, 2-pyridyl, 3-pyridyl, 4-pyridyl, 2-furanyl, and 3-furanyl, the phenyl being substituted with one or more halo, methyl, methoxyl, hydroxyl, methoxycarbonyl or trifluoromethyl groups;

$R_8$ is selected from the group consisting of —H, $C_1$–$C_{11}$ straight chain alkyl, —$(CH_2)_4COOEt$, and —$C_6H_5$;

when $R_7$ is other than 2-pyrrolyl, then $R_9$ is selected from the group consisting of —H, —$CH_3$, —$CH_2CH_3$, and —$CH_2CH_2CH_3$;

when $R_7$ is 2-pyrrolyl, then $R_9$ is selected from the group consisting of —H, —$CH_3$, —$CH_2CH_3$, —$CH_2CH_2CH_3$, and —$OCH_3$;

$R_{10}$ is selected from the group consisting of $C_1$–$C_4$ straight or branched chain alkyl and —$C_6H_5$;

$R_{11}$ and $R_{12}$ are independently selected from the group consisting of —$CH_3$, —$CH_2CH_3$, and —$C_3H_7$;

$R_{16}$ is selected from the group consisting of —H, —$CH_3$, —$CH_2CH_2CH_3$, and —$(CH_2)_6CH_3$; and $R_{17}$ is selected from the group consisting of —H, —CN, —COOMe, —COOEt, and —COOH;

with the proviso that the compound of Formula (V) is not:
prodigiosin,
undecylprodigiosin,
norprodigiosin, or
nonylprodigiosin.

The present invention provides methods for inhibiting the growth of a cancer cell or neoplastic cell comprising a contacting a cancer cell or neoplastic cell with an effective amount of a composition comprising a pharmaceutically acceptable carrier and a compound having the general Formula (V) or a pharmaceutically acceptable salt thereof, wherein:

$R_1$ is selected from the group consisting of —H, —$CH_3$, —$CH_2CH_3$, —$CH_2C_6H_5$, —C(O)OC($CH_3$)$_3$, —C(O)OCH$_2$C$_6$H$_5$, and —C(O)CH$_3$;

$R_2$ is selected from the group consisting of —H, $C_1$–$C_{12}$ straight chain alkyl, —$CH_2C_6H_5$, —Si$R_{10}R_{11}R_{12}$, —C(O)CH$_3$, —C(O)C$_6$H$_5$, -2-tetrahydropyranyl, —OCH$_2$OCH$_3$, and —C(O)OCH$_2$CCl$_3$;

$R_7$ is selected from the group consisting of —H, $C_1$–$C_5$ straight chain alkyl, —(CH$_2$)$_9$CH=CH$_2$, —(CH$_2$)$_6$F, —(CH$_2$)$_5$OC$_6$H$_5$, —(CH$_2$)$_6$OH, —(CH$_2$)$_7$CN, —CH$_2$CH$_2$C$_6$H$_5$, —(CH$_2$)$_4$COOH, —(CH$_2$)$_5$COOH, —(CH$_2$)$_5$COOMe, —(CH$_2$)$_1$COOH, —(CH$_2$)$_{12}$COOH, —(CH$_2$)$_{12}$OH, —(CH$_2$)$_{13}$OH, —(CH$_2$)$_{11}$CN, —(CH$_2$)$_{11}$OC(O)NH$_2$, —(CH$_2$)$_{11}$COOEt, —C(O)(CH$_2$)$_9$CH$_3$, —(CH$_2$)$_5$C(O)N(CH$_2$CH$_2$)$_2$O, $C_3$–$C_7$ cycloalkyl, —$C_6H_5$, 2-pyrrolyl, -3-pyrrolyl, 2-pyridyl, 3-pyridyl, 4-pyridyl, 2-furanyl, and 3-furanyl, the phenyl being substituted with one or more halo, methyl, methoxyl, hydroxyl, methoxycarbonyl or trifluoromethyl groups;

$R_8$ is selected from the group consisting of —H, $C_1$–$C_{11}$, straight chain alkyl, —(CH$_2$)$_4$COOEt, and —$C_6H_5$;

when $R_7$ is other than 2-pyrrolyl, $R_9$ is selected from the group consisting of —H, —$CH_3$, —$CH_2CH_3$, and —$CH_2CH_2CH_3$;

when $R_7$ is 2-pyrrolyl, then $R_9$ is selected from the group consisting of —H, —$CH_3$, —$CH_2CH_3$, —$CH_2CH_2CH_3$, and —$OCH_3$; $R_{10}$ is selected from the group consisting of $C_1$–$C_4$ straight or branched chain alkyl and —$C_6H_5$;

$R_{11}$ and $R_{12}$ are independently selected from the group consisting of —$CH_3$, —$CH_2CH_3$, and —$C_3H_7$;

$R_{16}$ is selected from the group consisting of —H, —$CH_3$, —$CH_2CH_2CH_3$, and —(CH$_2$)$_6$CH$_3$; and $R_{17}$ is selected from the group consisting of —H, —CN, —COOMe, —COOEt, and —COOH;

with the proviso that the compound of Formula (V) is not:
prodigiosin,
undecylprodigiosin,
norprodigiosin, or
nonylprodigiosin.

The present invention provides methods for treating or preventing a viral infection in a patient comprising administering to a patient in need of such treatment or prevention a therapeutically effective amount of a composition comprising a pharmaceutically acceptable carrier and a compound of Formula (V) or a pharmaceutically acceptable salt thereof, wherein:

$R_1$ is selected from the group consisting of —H, —$CH_3$, —$CH_2CH_3$, —$CH_2C_6H_5$, —C(O)OC($CH_3$)$_3$, —C(O)OCH$_2$C$_6$H$_5$, and —C(O)CH$_3$;

$R_2$ is selected from the group consisting of —H, $C_1$–$C_{12}$ straight chain alkyl, —$CH_2C_6H_5$, —Si$R_{10}R_{11}R_{12}$, —C(O)CH$_3$, —C(O)C$_6$H$_5$, -2-tetrahydropyranyl, —OCH$_2$OCH$_3$, and —C(O)OCH$_2$CCl$_3$;

$R_7$ is selected from the group consisting of —H, $C_1$–$C_{15}$ straight chain alkyl, —(CH$_2$)$_9$CH=CH$_2$, —(CH$_2$)$_6$F, —(CH$_2$)$_5$OC$_6$H$_5$, —(CH$_2$)$_6$OH, —(CH$_2$)$_7$CN, —CH$_2$CH$_2$C$_6$H$_5$, —(CH$_2$)$_4$COOH, —(CH$_2$)$_5$COOH, —(CH$_2$)$_5$COOMe, —(CH$_2$)$_{11}$COOH, —(CH$_2$)$_{12}$COOH, —(CH$_2$)$_{12}$OH, —(CH$_2$)$_{13}$OH, —(CH$_2$)$_{11}$CN, —(CH$_2$)$_{11}$OC(O)NH$_2$, —(CH$_2$)$_{11}$COOEt, —C(O)(CH$_2$)$_9$CH$_3$, —(CH$_2$)$_5$C(O)N(CH$_2$CH$_2$)$_2$O, $C_3$–$C_7$ cycloalkyl, —$C_6H_5$, 2-pyrrolyl, -3-pyrrolyl, 2-pyridyl, 3-pyridyl, 4-pyridyl, 2-furanyl, and 3-furanyl, the phenyl being substituted with one or more halo, methyl, methoxyl, hydroxyl, methoxycarbonyl or trifluoromethyl groups;

$R_8$ is selected from the group consisting of —H, $C_1$–$C_{11}$ straight chain alkyl, —(CH$_2$)$_4$COOEt, and —$C_6H_5$;

when $R_7$ is other than 2-pyrrolyl, $R_9$ is selected from the group consisting of —H, —$CH_3$, —$CH_2CH_3$, and —$CH_2CH_2CH_3$;

when $R_7$ is 2-pyrrolyl, then $R_9$ is selected from the group consisting of —H, —$CH_3$, —$CH_2CH_3$, —$CH_2CH_2CH_3$, and —$OCH_3$;

$R_{10}$ is selected from the group consisting of $C_1$–$C_4$ straight or branched chain alkyl and —$C_6H_5$;

$R_{11}$ and $R_{12}$ are independently selected from the group consisting of —$CH_3$, —$CH_2CH_3$, and —$C_3H_7$;

$R_{16}$ is selected from the group consisting of —H, —$CH_3$, —$CH_2CH_2CH_3$, and —(CH$_2$)$_6$CH$_3$; and $R_{17}$ is selected from the group consisting of —H, —CN, —COOMe, —COOEt, and —COOH.

The present invention provides methods for inhibiting the replication or infectivity of a virus comprising a contacting a virus or a virus-infected cell with an effective amount of a composition comprising a pharmaceutically acceptable carrier and a compound having the general Formula (V) or a pharmaceutically acceptable salt thereof, wherein:

$R_1$ is selected from the group consisting of —H, —$CH_3$, —$CH_2CH_3$, —$CH_2C_6H_5$, —C(O)OC($CH_3$)$_3$, —C(O)OCH$_2$C$_6$H$_5$, and —C(O)CH$_3$;

$R_2$ is selected from the group consisting of —H, $C_1$–$C_{12}$ straight chain alkyl, —$CH_2C_6H_5$, —Si$R_{10}R_{11}R_{12}$, —C(O)CH$_3$, —C(O)C$_6$H$_5$, -2-tetrahydropyranyl, —OCH$_2$OCH$_3$, and —C(O)OCH$_2$CCl$_3$;

$R_7$ is selected from the group consisting of —H, $C_1$–$C_{15}$ straight chain alkyl, —(CH$_2$)$_9$CH=CH$_2$, —(CH$_2$)$_6$F, —(CH$_2$)$_5$OC$_6$H$_5$, —(CH$_2$)$_6$OH, —(CH$_2$)$_7$CN, —CH$_2$CH$_2$C$_6$H$_5$, —(CH$_2$)$_4$COOH, —(CH$_2$)$_5$COOH, —(CH$_2$)$_5$COOMe, —(CH$_2$), COOH, —(CH$_2$)$_{12}$COOH, —(CH$_2$)$_{12}$OH, —(CH$_2$)$_{13}$OH, —(CH$_2$)$_{11}$CN, —(CH$_2$)$_{11}$OC(O)NH$_2$, —(CH$_2$)$_{11}$COOEt, —C(O)(CH$_2$)$_9$CH$_3$, —(CH$_2$)$_5$C(O)N(CH$_2$CH$_2$)$_2$O, $C_3$–$C_7$ cycloalkyl, —$C_6H_5$, 2-pyrrolyl, -3-pyrrolyl, 2-pyridyl, 3-pyridyl, 4-pyridyl, 2-furanyl, and 3-furanyl, the phenyl being substituted with one or more halo, methyl, methoxyl, hydroxyl, methoxycarbonyl or trifluoromethyl groups;

$R_8$ is selected from the group consisting of —H, $C_1$–$C_{11}$ straight chain alkyl, —(CH$_2$)$_4$COOEt, and —$C_6H_5$;

when $R_7$ is other than 2-pyrrolyl, $R_9$ is selected from the group consisting of —H, —$CH_3$, —$CH_2CH_3$, and —$CH_2CH_2CH_3$;

when $R_7$ is 2-pyrrolyl, then $R_9$ is selected from the group consisting of —H, —$CH_3$, —$CH_2CH_3$, —$CH_2CH_2CH_3$, and —$OCH_3$;

$R_{10}$ is selected from the group consisting of $C_1$–$C_4$ straight or branched chain alkyl and —$C_6H_5$;

$R_{11}$ and $R_{12}$ are independently selected from the group consisting of —$CH_3$, —$CH_2CH_3$, and —$C_3H_7$;

$R_{16}$ is selected from the group consisting of —H, —$CH_3$, —$CH_2CH_2CH_3$, and —$(CH_2)_6CH_3$; and $R_{17}$ is selected from the group consisting of —H, —CN, —COOMe, —COOEt, and —COOH.

The present invention may be understood more fully by reference to the following figures, schemes, detailed description and illustrative examples which are intended to exemplify non-limiting embodiments of the invention.

3.1. DEFINITIONS AND ABBREVIATIONS

Examples of $C_1$–$C_3$ straight or branched chain alkyl groups include but are not limited to methyl, ethyl, 1-propyl, and 2-propyl.

Examples of $C_1$–$C_4$ straight or branched chain alkyl groups include but are not limited to methyl, ethyl, 1-propyl, 2-propyl, 1-butyl, 2-butyl, 2-methyl-1-propyl, and 2-methyl-2-propyl.

Examples of $C_1$–$C_6$ straight or branched chain alkyl groups include but are not limited to methyl, ethyl, 1-propyl, 2-propyl, 1-butyl, 2-butyl, 2-methyl-1-propyl, 2-methyl-2-propyl, 1-pentyl, 2-pentyl, 3-pentyl, 2-methyl-1-butyl, 3-methyl-1-butyl, 2-methyl-3-butyl, 2,2-dimethyl-1-propyl, 1-hexyl, 2-hexyl, 3-hexyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, and 2-ethyl-1-butyl.

Examples of $C_1$–$C_6$ straight chain alkyl groups include but are not limited to methyl, ethyl, 1-propyl, 1-butyl, 1-pentyl, and 1-hexyl.

Examples of $C_1$–$C_{10}$ straight chain alkyl groups include but are not limited to methyl, ethyl, 1-propyl, 1-butyl, 1-pentyl, 1-hexyl, 1-heptyl, 1-octyl, 1-nonyl, and 1-decyl.

Examples of $C_5$–$C_{10}$ straight chain alkyl groups include but are not limited to 1-pentyl, 1-hexyl, 1-heptyl, 1-octyl, 1-nonyl, and 1-decyl.

Examples of $C_1$–$C_6$ straight chain alkyl groups include but are not limited to methyl, ethyl, 1-propyl, 1-butyl, 1-pentyl, 1-hexyl, 1-heptyl, 1-octyl, 1-nonyl, 1-decyl, and 1-undecyl.

Examples of $C_6$–$C_{11}$ straight chain alkyl groups include but are not limited to 1-hexyl, 1-heptyl, 1-octyl, 1-nonyl, 1-decyl, and 1-undecyl.

Examples of $C_1$–$C_{12}$ straight chain alkyl groups include but are not limited to methyl, ethyl, 1-propyl, 1-butyl, 1-pentyl, 1-hexyl, 1-heptyl, 1-octyl, 1-nonyl, 1-decyl, 1-undecyl, and 1-dodecyl.

Examples of $C_3$–$C_{12}$ straight chain alkyl groups include but are not limited to 1-propyl, 1-butyl, 1-pentyl, 1-hexyl, 1-heptyl, 1-octyl, 1-nonyl, 1-decyl, 1-undecyl, 1-dodecyl.

Examples of $C_1$–$C_{15}$ straight chain alkyl groups include, but are not limited to methyl, ethyl, 1-propyl, 1-butyl, 1-pentyl, 1-hexyl, 1-heptyl, 1-octyl, 1-nonyl, 1-decyl, 1-undecyl, 1-dodecyl, 1-tridecyl, 1-tetradecyl, and 1-pentadecyl.

Examples of $C_3$–$C_{15}$ straight chain alkyl groups include but are not limited to 1-propyl, 1-butyl, 1-pentyl, 1-hexyl, 1-heptyl, 1-octyl, 1-nonyl, 1-decyl, 1-undecyl, 1-dodecyl, 1-tridecyl, 1-tetradecyl, and 1-pentadecyl.

Examples of $C_8$–$C_{15}$ straight chain alkyl groups include but are not limited to 1-octyl, 1-nonyl, 1-decyl, 1-undecyl, 1-dodecyl, 1-tridecyl, 1-tetradecyl, and 1-pentadecyl.

Examples of $C(O)C_1$–$C_9$ straight chain alkyl groups include but are not limited to (methyl)-C(O)—, (ethyl)-C(O)—, (1-propyl)-C(O)—, (1-butyl)-C(O)—, (1-pentyl)-C(O)—, (1-hexyl)-C(O)—, (1-heptyl)-C(O)—, (1-octyl)-C(O)—, and (1-nonyl)-C(O)—.

Examples of $CH(OH)C_1$–$C_9$ straight chain alkyl groups include but are not limited to CH(OH)-(methyl), CH(OH)-(ethyl), CH(OH)-(1-propyl), CH(OH)-(1-butyl), CH(OH)-(1-pentyl), CH(OH)-(1-hexyl), CH(OH)-(1-heptyl), CH(OH)-(1-octyl), and CH(OH)-(1-nonyl).

Examples of $CH(Cl)C_1$–$C_9$ straight chain alkyl groups include but are not limited to CH(Cl)-(methyl), CH(Cl)-(ethyl), CH(Cl)-(1-propyl), CH(Cl)-(1-butyl), CH(Cl)-(1-pentyl), CH(Cl)-(1-hexyl), CH(Cl)-(1-heptyl), CH(Cl)-(1-octyl), and CH(Cl)-(1-nonyl).

Examples of $C_3$–$C_7$ cycloalkyl groups include but are not limited to cyclopropyl, cyclobutyl, cyclopentyl, cyclohexyl, and cycloheptyl.

As used herein, unless defined otherwise, the abbreviation (BOC) denotes —$C(O)OC(CH_3)_3$, (Cbz) denotes $C(O)OCH_2C_6H_5$, (THP) denotes -2-tetrahydropyranyl, (MOM) denotes —$OCH_2OCH_3$, and (TROC) denotes —$C(O)OCH_2C(Cl)_3$.

It is to be understood that the $R_5$ group of the compounds of Formula II and Formula III can be attached to any carbon atom of the five to ten membered ring to which $R_5$ is attached.

The structures of compounds R39FF, R39MF, R39SF, 610FF and 610MF are disclosed at page 925 of Gerber et al., 1973, J. Heterocycl. Chem. 10:925–9 and in Table 1.

TABLE 1

| Compound R39FF: R = | —CH(CH$_2$)$_7$—<br>\|<br>CH$_3$ |
|---|---|
| Compound 610FF: R = | —CH(CH$_2$)$_8$—<br>\|<br>CH$_2$CH$_3$ |
| Compound R39MF: R = | —(CH$_2$)$_8$C(O)— |
| Compound R39SF: R = | —CH(OH)(CH$_2$)$_8$— |
| Compounds 610MF: R = | —CHC(X)(CH$_2$)$_7$C(Y)—<br>\|<br>CH$_3$ |

(X = O and Y = HOH) and (X = HOH and Y = O)

In certain instances, the compounds of the invention are known by more than one name. The following Table 2 indicates synonyms of compounds described herein.

TABLE 2

| Name as used herein: | Other synonyms: | Reference |
|---|---|---|
| prodigiosin | prodiginine, 2-methyl-3-pentyl-prodiginine 4-methoxy-5-((5-methyl-4-pentyl-2H-pyrrol-2-ylidene)methyl)-2-2'-bi-1H-pyrrole | Boger and Patel, 1988. J. Org. Chem. 53: 1405–15 Gerber and Lechevalier, 1976. Can. J. Microbio. 22: 658 |
| cycloprodigiosin | cyclic prodigiosin 4,5,6,7-Tetrahydro-3-((3-methoxy-5-(1H-pyrrol-2-yl)-2H-pyrrol-2-ylidene)-methyl)-1,4-dimethyl-2H-isoindole | Nakamura et al., 1986. J. Antibiotics 39: 1155 |
| cyclononylprodiginine | cyclic nonylprodiginine | Gerber et al., 1978. Can. J. Chem. 56: 1155–63 |
| undecylprodigiosin | undecylprodiginine prodigiosin-25C Compound 2c | Gerber, 1975. CRC Critical Reviews in Microbiol. 469–84 Boger and Patel, 1987. Tetrahedron Lett. 28: 2499–2502 Boger and Patel, 1988. J. Org. Chem. 53: 1405 |
| norprodigiosin | Compound 2b | Boger and Patel, 1988. J. Org. Chem. 53: 1405 |
| methylosin A | | Strauss and Berger, 1983. Z. Allg. Mikrobiol. 23: 661–8 |
| nonylprodigiosin | nonylprodiginine Compound 2d | Boger and Patel, 1987. Tetrahedron Lett. 28: 2499–2502 Boger and Patel, 1988. J. Org. Chem. 53: 1405 |
| 6-methoxy-2-methyl-3-heptylprodigiosene 4-ethyl-2,4,5,6-tetrahydro-3-((3-methoxy-5-(1H-pyrrol-2-yl-)-2H-pyrrol-2-ylidene)methyl)-1-methyl-cyclopenta(c)pyrrole | Methylosin B | Strauss and Berger, 1983. Z. Allg. Mikrobiol. 23: 661–8 Gerber, 1979. Appl. Environ. Microbiol. 37: 1176–9 |
| butyl-meta-cycloheptylprodiginine | butylmetacycloheptyl-prodiginine meta-butylcycloheptylprodiginine Streptorubin B butylcycloheptylprodiginine 2-Butyl-11-((3-methoxy-5-(1H-pyrrol-2-yl)-2H-pyrrol-2-ylidene)methyl)-10-azabicyclo[7.2.1]dodeca-9(12),11-diene | Fuerstner et al., 1998. J. Am. Chem. Soc. 120: 8305 Laatsch, H. et al., 1991. J. Antibiot. 44: 187–91 |
| orthobutylcycloheptylprodiginine | butylcycloheptylprodiginine | Gerber, 1975, J. Antibiot. 28: 194–99 (reported incorrect structure for butly-meta-cycloheptylprodiginine; structure corrected in Gerber, et al., 1978. Can. J. Chem. 56: 1155–63 and Laatsch, H., et al., 1991. J. Antibiot. 44: 187–91) |
| metacycloprodigiosin | Streptorubin A metacycloprodiginine ethyl-meta-cycloprodigiosin | Gerber, 1975, J. Antibiot. 28: 194 Gerber, 1978, Can. J. Chem. 56: 1155–63 |
| methylcyclodecylprodiginine | cyclomethyldecylprodiginine | Gerber, 1978 Can. J. Chem 56: 1155-63 |
| ethylcyclononylprodiginine | cycloethylnonylprodiginine | Gerber, 1978 Can. J. Chem 56: 1155-63 |
| 4-methoxy-5-((3-methoxy-5-(1H-pyrrol-2-yl)-2H-pyrrol-2-ylidene)methyl)2,2'-bi-1H-pyrrol | blue pigment | Matsunaga 1986 Experimentia 42: 84 Tsao et al. 1985 J. Antibiot. 38: 128–31 |
| 3-heptyl-5-((3-methoxy-5-pyrrol-2-yl-2H-pyrrol-2-ylidene)methyl)-2-methyl-4-propyl-pyrrole | prodigiosin-like fungal pigment | Wasserman, H. et al., 1961. Angew. Chem. 73: 467 |
| methylcyclooctylprodiginine | | Gerber et al., 1978, Can. J. Chem. 56: 1155–1163 |

When administered to a patient, e.g., a mammal for veterinary use or a human for clinical use, the Pyrrole-Type compounds are administered in isolated form. As used herein, "isolated" means that the Pyrrole-Type compounds are separated from other components of either (a) a natural source, such as a plant or cell, preferably bacterial culture, or (b) a synthetic organic chemical reaction mixture. Preferably, via conventional techniques, the Pyrrole-Type compounds are purified. As used herein, "purified" means that when isolated, the isolate contains at least 95%, preferably at least 98%, of a single Pyrrole-Type compound by weight of the isolate.

4. DETAILED DESCRIPTION OF THE INVENTION

4.1. FORMULA I

The present invention encompasses novel compounds having the general Formula (I):

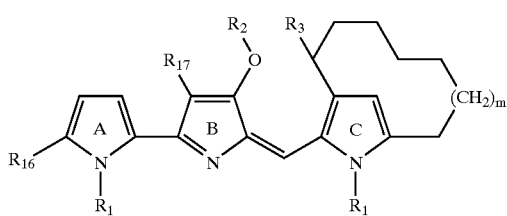

and pharmaceutically acceptable salts thereof, wherein:

each $R_1$ is independently selected from the group consisting of —H, —$CH_3$, —$CH_2CH_3$, —$CH_2C_6H_5$, —C(O)OC($CH_3$)$_3$, —C(O)OCH$_2$C$_6$H$_5$, and —C(O)CH$_3$;

$R_2$ is selected from the group consisting of —H, $C_1$–$C_{12}$ straight chain alkyl, —$CH_2C_6H_5$, —Si$R_{10}R_{11}R_{12}$, —C(O)CH$_3$, —C(O)C$_6$H$_5$, -2-tetrahydropyranyl, —OCH$_2$OCH$_3$, and —C(O)OCH$_2$CCl$_3$;

$R_3$ is selected from the group consisting of —H, $C_1$–$C_{12}$ straight chain alkyl, —CH($R_{14}$)($R_{15}$) wherein $R_{14}$ and $R_{15}$ are independently $C_1$–$C_{12}$ straight chain alkyl, —C(O)$C_1$–$C_9$ straight chain alkyl, —CH(OH)$C_1$–$C_9$ straight chain alkyl, —CH(Cl)$C_1$–$C_9$ straight chain alkyl, -(2-pyridyl)methyl, -(3-pyridyl)methyl, -(4-pyridyl)methyl, and —$CH_2C_6H_5$, the —$CH_2C_6H_5$ being unsubstituted or substituted on phenyl with one cyano or one or more halo, methoxyl, or trifluoromethyl groups;

$R_{10}$ is selected from the group consisting of $C_1$–$C_4$ straight or branched chain alkyl and —$C_6H_5$;

$R_{11}$ and $R_{12}$ are independently $C_1$–$C_3$ straight or branched chain alkyl;

$R_{16}$ and $R_{17}$ is —H; and m is an integer ranging from 1 to 5;

with the proviso that the compound of Formula (I) is not:
butyl-meta-cycloheptylprodiginine,
metacycloprodigiosin,
4-ethoxy-5-((3,5-nonamethylene-2H-pyrrol-2-ylidene)methyl)-2,2'-bi-1H-pyrrole,
or 4-propoxy-5-((3,5-nonamethylene-2H-pyrrol-2-ylidene)methyl)-2,2'-bi-1H-pyrrole.

The compounds of Formula (I) and pharmaceutically acceptable salts thereof are useful for treating or preventing cancer or neoplastic disease in a patient in need of such treatment or prevention. The compounds of Formula (I) and pharmaceutically acceptable salts thereof are also useful for inhibiting the growth of a cancer cell or neoplastic cell. The compounds of Formula (I) and pharmaceutically acceptable salts thereof are useful for treating or preventing a viral infection in a patient in need of such treatment or prevention. The compounds of Formula (I) and pharmaceutically acceptable salts thereof are also useful for inhibiting the replication or infectivity of a virus.

Where $R_3$ of the compounds of Formula (I) is a —$CH_2C_6H_5$ group substituted with one cyano or one or more halo, methoxyl or trifluoromethyl groups, $R_3$ is preferably 4-chlorobenzyl, -2-methoxybenzyl, -3-methoxybenzyl, -4-methoxybenzyl, 2,4-dichlorobenzyl, 2,4-difluorobenzyl, 4-cyanobenzyl, or 4-trifluoromethylbenzyl.

A preferred subclass of the compounds of Formula (I) is that wherein:

each $R_1$ is independently selected from the group consisting of —H and —$CH_3$;

$R_2$ is selected from the group consisting of —$CH_3$, —$CH_2CH_3$, and —$CH_2C_6H_5$;

$R_3$ is selected from the group consisting of —H, $C_1$–$C_{10}$ straight chain alkyl, (1-methyl)butyl, —$CH_2C_6H_5$, butyroyl, (1-hydroxy)butyl, and (1-chloro)butyl;

$R_{16}$ and $R_{17}$ are —H; and m is an integer ranging from 1 to 5;

with the proviso that the compound of Formula (I) is not:
butyl-meta-cycloheptylprodiginine,
metacycloprodigiosin,
4-ethoxy-5-((3,5-nonamethylene-2H-pyrrol-2-ylidene)methyl)-2,2'-bi-1H-pyrrole,
or 4-propoxy-5-((3,5-nonamethylene-2H-pyrrol-2-ylidene)methyl)-2,2'-bi-1H-pyrrole. A second preferred subclass of the compounds of Formula (I) is that wherein:

each $R_1$ is —H;

$R_2$ is selected from the group consisting of —$CH_3$ and —$CH_2C_6H_5$;

$R_3$ is selected from the group consisting of —H, n-$C_1$–$C_{10}$ alkyl and —$CH_2C_6H_5$;

$R_{16}$ and $R_{17}$ are —H; and m is an integer ranging from 1 to 5;

with the proviso that the compound of Formula (I) is not:
butyl-meta-cycloheptylprodiginine,
met acycloprodigiosin,
4-ethoxy-5-((3,5-nonamethylene-2H-pyrrol-2-ylidene)methyl)-2,2'-bi-1H-pyrrole,
or 4-propoxy-5-((3,5-nonamethylene-2H-pyrrol-2-ylidene)methyl)-2,2'-bi-1H-pyrrole.

A third preferred subclass of the compounds of Formula (I) is that wherein: each $R_1$ is independently selected from the group consisting of —H and —$CH_3$;

$R_2$ is selected from the group consisting of —$CH_3$ and —$CH_2C_6H_5$;

$R_3$ is selected from the group consisting of —H, $C_1$–$C_{10}$ straight chain alkyl, —$CH_2C_6H_5$, butyroyl, (1-hydroxy)butyl, and (1-chloro)butyl;

$R_{16}$ and $R_{17}$ are —H; and m is an integer ranging from 1 to 5;

with the proviso that when m is 3, $R_3$ is not —$CH_2CH_3$ and when m is 1, $R_3$ is not —($CH_2$)$_3$$CH_3$.

A fourth preferred subclass of the compounds of Formula (I) is that wherein: each $R_1$ is independently selected from the group consisting of —H and —$CH_3$;

$R_2$ is selected from the group consisting of —$CH_3$ and —$CH_2C_6H_5$;

$R_3$ is selected from the group consisting of —H, —$CH_3$, - n-$C_3H_7$, -i-$C_3H_7$, $C_5$–$C_{10}$ straight chain alkyl, (1-methyl)butyl, —$CH_2C_6H_5$, butyroyl, (1-hydroxy)butyl, and (1-chloro)butyl;

$R_{16}$ and $R_{17}$ are —H; and m is an integer ranging from 1 to 5.

A fifth preferred subclass of the compounds of Formula (I) are those wherein: each $R_1$ is independently selected from the group consisting of —H and —$CH_3$;

$R_2$ is selected from the group consisting of —$CH_3$ and —$CH_2C_6H_5$;

$R_3$ is selected from the group consisting of —H, $C_1$–$C_{10}$ straight chain alkyl, —$CH_2C_6H_5$, butyroyl, (1-hydroxy)butyl, and (1-chloro)butyl;

$R_{16}$ and $R_1$ are —H; and m is 2, 4, or 5.

In one embodiment, preferred compounds of Formula (I) are selected from the group consisting of:

2-Ethyl-11-((3-methoxy-5-(1H-pyrrol-2-yl)-2H-pyrrol-2-ylidene)methyl)-10-azabicyclo[7.2.1]dodeca-9(12),11-diene;

11-((3-Methoxy-5-(1H-pyrrol-2-yl)-2H-pyrrol-2-ylidene)methyl)-10-azabicyclo[7.2.1]dodeca-9(12),11-diene;

2-Methyl-11-((3-methoxy-5-(1H-pyrrol-2-yl)-2H-pyrrol-2-ylidene)methyl)-10-azabicyclo[7.2.1]dodeca-9(12),11-diene;

2-n-Propyl-11-((3-methoxy-5-(1H-pyrrol-2-yl)-2H-pyrrol-2-ylidene)methyl)-10-azabicyclo[7.2.1]dodeca-9(12),11-diene;

2-n-Pentyl-11-((3-methoxy-5-(1H-pyrrol-2-yl)-2H-pyrrol-2-ylidene)methyl)-10-azabicyclo[7.2.1]dodeca-9(12),11-diene;

2-Benzyl-11-((3-methoxy-5-(1H-pyrrol-2-yl)-2H-pyrrol-2-ylidene)methyl)-10-azabicyclo[7.2.1]dodeca-9(12)11-diene;

(S)-2-n-Pentyl-11-((3-methoxy-5-(1H-pyrrol-2-yl)-2H-pyrrol-2-ylidene)methyl)-10-azabicyclo[7.2.1] dodeca-9(12)11-diene;

(R)-2-n-Pentyl-11-((3-methoxy-5-(1H-pyrrol-2-yl)-2H-pyrrol-2-ylidene)methyl)-10-azabicyclo[7.2.1]dodeca-9(12)11-diene;

(S)-2-n-Butyl-11-((3-methoxy-5-(1H-pyrrol-2-yl)-2H-pyrrol-2-ylidene)methyl)-10-azabicyclo[7.2.1] dodeca-9(12),11-diene;

(R)-2-n-Butyl-11-((3-methoxy-5-(1H-pyrrol-2-yl)-2H-pyrrol-2-ylidene)methyl)-10-azabicyclo[7.2.1]dodeca-9(12),11-diene;

(S)-2-Ethyl-11-((3-methoxy-5-(1H-pyrrol-2-yl)-2H-pyrrol-2-ylidene)methyl)-10-azabicyclo[7.2.1]dodeca-9(12),11-diene;

(R)-2-Ethyl-11-((3-methoxy-5-(1H-pyrrol-2-yl)-2H-pyrrol-2-ylidene)methyl)-10-azabicyclo[7.2.1]dodeca-9(12)11-diene;

(S)-2-Methyl-11-((3-methoxy-5-(1H-pyrrol-2-yl)-2H-pyrrol-2-ylidene)methyl)-10-azabicyclo[7.2.1]dodeca-9(12),11-diene;

(R)-2-Methyl-11-((3-methoxy-5-(1H-pyrrol-2-yl)-2H-pyrrol-2-ylidene)methyl)-10-azabicyclo[7.2.1]dodeca-9(12),11-diene;

(S)-2-n-Propyl-11-((3-methoxy-5-(1H-pyrrol-2-yl)-2H-pyrrol-2-ylidene)methyl)-10-azabicyclo[7.2.1]dodeca-9(12),11-diene;

(R)-2-n-Propyl-11-((3-methoxy-5-(1H-pyrrol-2-yl)-2H-pyrrol-2-ylidene)methyl)-10-azabicyclo[7.2.1]dodeca-9(12),11-diene; 2-Methyl-12-((3-methoxy-5-(1H-pyrrol-2-yl)-2H-pyrrol-2-ylidene)methyl)-11-azabicyclo[8.2.1]trideca-10(13),12-diene;

2-Ethyl-12-((3-methoxy-5-(1H-pyrrol-2-yl)-2H-pyrrol-2-ylidene)methyl)-11-azabicyclo[8.2.1]trideca-10(13),12-diene;

2-n-Propyl-12-((3-methoxy-5-(1H-pyrrol-2-yl)-2H-pyrrol-2-ylidene)methyl)-11-azabicyclo[8.2.1]trideca-10(13),12-diene;

2-n-Butyl-12-((3-methoxy-5-(1H-pyrrol-2-yl)-2H-pyrrol-2-ylidene)methyl)-11-azabicyclo[8.2.1]trideca-10(13),12-diene;

2-n-Pentyl-12-((3-methoxy-5-(1H-pyrrol-2-yl)-2H-pyrrol-2-ylidene)methyl)-11-azabicyclo[8.2.1]trideca-10(13),12-diene;

12-((3-Methoxy-5-(1H-pyrrol-2-yl)-2H-pyrrol-2-ylidene)methyl)-11-azabicyclo[8.2.1]trideca-10(13),12-diene;

2-Methyl-13-((3-methoxy-5-(1H-pyrrol-2-yl)-2H-pyrrol-2-ylidene)methyl)-12-azabicyclo[9.2.1]tetradeca-11(14),13-diene;

13-((3-Methoxy-5-(1H-pyrrol-2-yl)-2H-pyrrol-2-ylidene)methyl)-12-azabicyclo[9.2.1]tetradeca-11(14),13-diene;

2-Ethyl-12-methyl-13-((3-methoxy-5-(1-methyl-iH-pyrrol-2-yl)-2H-pyrrol-2-ylidene)methyl)-12-azabicyclo[9.2.1]tetradeca-11(14),13-diene;

2-Ethyl-12-methyl-13-((3-methoxy-5-(1H-pyrrol-2-yl)-2H-pyrrol-2-ylidene)methyl)-12-azabicyclo[9.2.1]tetradeca-11(14),13-diene;

2-n-Propyl-13-((3-methoxy-5-(1H-pyrrol-2-yl)-2H-pyrrol-2-ylidene)methyl)-12-azabicyclo[9.2.1]tetradeca-11(14),13-diene;

2-n-Butyl-13-((3-methoxy-5-(1H-pyrrol-2-yl)-2H-pyrrol-2-ylidene)methyl)-12-azabicyclo[9.2.1]tetradeca-11(14),13-diene;

14-((3-Methoxy-5-(1H-pyrrol-2-yl)-2H-pyrrol-2-ylidene)methyl)-13-azabicyclo[10.2.1]pentadeca-12(15),14-diene;

2-Butyl-11-((3-methoxy-5-(1-methyl-1H-pyrrol-2-yl)-2H-pyrrol-2-ylidene)methyl)-10-azabicyclo[7.2.1]dodeca-9(12),11-diene;

2-Butyl-11-((3-methoxy-5-(1-methyl-1H-pyrrol-2-yl)-2H-pyrrol-2-ylidene)methyl)-10-methyl-10-azabicyclo[7.2.1]dodeca-9(12),11-diene;

2-Butyl-11-((3-methoxy-5-(1H-pyrrol-2-yl)-2H-pyrrol-2-ylidene)methyl)-10-methyl-10-azabicyclo[7.2.1]dodeca-9(12),11-diene;

2-Ethyl-11-((3-benzyloxy-5-(1H-pyrrol-2-yl)-2H-pyrrol-2-ylidene)methyl)-10-azabicyclo[7.2.1]dodeca-9(12),11-diene;

2-Butyl-11-((3-hydroxy-5-(1H-pyrrol-2-yl)-2H-pyrrol-2-ylidene)methyl)-10-azabicyclo[7.2.1]dodeca-9(12),11-diene;

2-Butyl-11-((3-benzyloxy-5-(1H-pyrrol-2-yl)-2H-pyrrol-2-ylidene)methyl)-10-azabicyclo[7.2.1]dodeca-9(12),11-diene;

11-((3-Benzyloxy-5-(1H-pyrrol-2-yl)-2H-pyrrol-2-ylidene)methyl)-10-azabicyclo[7.2.1]dodeca-9(12),11-diene;

2-Methyl-11-((3-benzyloxy-5-(1H-pyrrol-2-yl)-2H-pyrrol-2-ylidene)methyl)-10-azabicyclo[7.2.1]dodeca-9(12),11-diene;

2-n-Propyl-11-((3-benzyloxy-5-(1H-pyrrol-2-yl)-2H-pyrrol-2-ylidene)methyl)-10-azabicyclo[7.2.1]dodeca-9(12),11-diene;

2-n-Pentyl-11-((3-benzyloxy-5-(1H-pyrrol-2-yl)-2H-pyrrol-2-ylidene)methyl)-10-azabicyclo[7.2.1]dodeca-9(12),11-diene;

2-Benzyl-11-((3-benzyloxy-5-(1H-pyrrol-2-yl)-2H-pyrrol-2-ylidene)methyl)-10-azabicyclo[7.2.1]dodeca-9(12),11-diene;

2-Methyl-14-((3-methoxy-5-(1H-pyrrol-2-yl)-2H-pyrrol-2-ylidene)methyl)-13-azabicyclo[10.2.1]pentadeca-12(15),14-diene;

15-((3-Methoxy-5-(1H-pyrrol-2-yl)-2H-pyrrol-2-ylidene)methyl)-14-azabicyclo[11.2.1]pentadeca-13(16),15-diene;

2-Methyl-15-((3-methoxy-5-(1H-pyrrol-2-yl)-2H-pyrrol-2-ylidene)methyl)-14-azabicyclo[11.2.1]pentadeca-13(16),15-diene;

2-(2-Hydroxy-n-butyl)-11-((3-methoxy-5-(1H-pyrrol-2-yl)-2H-pyrrol-2-ylidene)methyl)-10-azabicyclo[7.2.1]dodeca-9(12),11-diene;

2-(2-Chloro-n-butyl)-11-((3-methoxy-5-(1H-pyrrol-2-yl)-2H-pyrrol-2-ylidene)methyl)-10-azabicyclo[7.2.1]dodeca-9(12),11-diene;

2-Butyl-11-((3-ethoxy-5-(1H-pyrrol-2-yl)-2H-pyrrol-2-ylidene)methyl)-10-azabicyclo[7.2.1]dodeca-9(12),11-diene;

11-((3-Ethoxy-5-(1H-pyrrol-2-yl)-2H-pyrrol-2-ylidene)methyl)-10-azabicyclo[7.2.1]dodeca-9(12),11-diene;

2-Methyl-1-((3-ethoxy-5-(1H-pyrrol-2-yl)-2H-pyrrol-2-ylidene)methyl)-10-azabicyclo[7.2.1]dodeca-9(12),11-diene;

2-n-Propyl-11-((3-ethoxy-5-(1H-pyrrol-2-yl)-2H-pyrrol-2-ylidene)methyl)-10-azabicyclo[7.2.1]dodeca-9(12),11-diene;

2-n-Pentyl-11-((3-ethoxy-5-(1H-pyrrol-2-yl)-2H-pyrrol-2-ylidene)methyl)-10-azabicyclo[7.2.1]dodeca-9(12),11-diene;

2-Benzyl-11-((3-ethoxy-5-(1H-pyrrol-2-yl)-2H-pyrrol-2-ylidene)methyl) 10-azabicyclo[7.2.1]dodeca-9(12),11-diene;

2-Ethyl-11-((3-ethoxy-5-(1H-pyrrol-2-yl)-2H-pyrrol-2-ylidene)methyl)-10-azabicyclo[7.2.1]dodeca-9(12),11-diene;

2-Methyl-13-((3-benzyloxy-5-(1H-pyrrol-2-yl)-2H-pyrrol-2-ylidene)methyl)-12-azabicyclo[9.2.1]tetradeca-11(14),13-diene;

13-((3-Benzyloxy-5-(1H-pyrrol-2-yl)-2H-pyrrol-2-ylidene)methyl)-12-azabicyclo[9.2.1]tetradeca-11(14),13-diene;

2-Ethyl-12-methyl-13-((3-benzyloxy-5-(1-methyl-1H-pyrrol-2-yl)-2H-pyrrol-2-ylidene)methyl)-12-azabicyclo[9.2.1]tetradeca-11(14),13-diene;

2-Ethyl-12-methyl-13-((3-benzyloxy-5-(1H-pyrrol-2-yl)-2H-pyrrol-2-ylidene)methyl)-12-azabicyclo[9.2.1]tetradeca-11(14),13-diene;

2-n-Propyl-13-((3-benzyloxy-5-(1H-pyrrol-2-yl)-2H-pyrrol-2-ylidene)methyl)-12-azabicyclo[9.2.1]tetradeca-11(14),13-diene; and 2-n-Butyl-13-((3-benzyloxy-5-(1H-pyrrol-2-yl)-2H-pyrrol-2-ylidene)methyl)-12-azabicyclo[9.2.1]tetradeca-11(14),13-diene or a pharmaceutically acceptable salt thereof.

The present invention provides compositions comprising a pharmaceutically acceptable carrier and a therapeutically effective amount of a compound of Formula (I) or a pharmaceutically acceptable salt thereof, wherein, in the compound of Formula (I):

each $R_1$ is independently selected from the group consisting of —H, —CH$_3$, —CH$_2$CH$_3$, —CH$_2$C$_6$H$_5$, —C(O)OC(CH$_3$)$_3$, —C(O)OCH$_2$C$_6$H$_5$, and —C(O)CH$_3$;

$R_2$ is selected from the group consisting of —H, $C_1$–$C_{12}$ straight chain alkyl, —CH$_2$C$_6$H$_5$, —SiR$_{10}$R$_{11}$R$_{12}$, —C(O)CH$_3$, —C(O)C$_6$H$_5$, -2-tetrahydropyranyl, —OCH$_2$OCH$_3$, and —C(O)OCH$_2$CCl$_3$;

$R_3$ is selected from the group consisting of —H, $C_1$–$C_{12}$ straight chain alkyl, —CH(R$_{14}$)(R$_{15}$) wherein $R_{14}$ and $R_{15}$ are independently $C_1$–$C_{12}$ straight chain alkyl, —C(O)$C_1$–$C_9$ straight chain alkyl, —CH(OH)$C_1$–$C_9$ straight chain alkyl, —CH(Cl)$C_1$–$C_9$ straight chain alkyl, -(2-pyridyl)methyl, -(3-pyridyl)methyl, -(4-pyridyl)methyl, and —CH$_2$C$_6$H$_5$, the —CH$_2$C$_6$H$_5$ being unsubstituted or substituted on phenyl with one cyano or one or more halo, methoxyl, or trifluoromethyl groups;

$R_{10}$ is selected from the group consisting of $C_1$–$C_4$ straight or branched chain alkyl and —C$_6$H$_5$;

$R_{11}$ and $R_{12}$ are independently $C_1$–$C_3$ straight or branched chain alkyl;

$R_{16}$ and $R_{17}$ are —H; and m is an integer ranging from 1 to 5;

with the proviso that the compound of Formula (I) is not:
butyl-meta-cycloheptylprodiginine,
metacycloprodigiosin,
4-ethoxy-5-((3,5-nonamethylene-2H-pyrrol-2-ylidene)methyl)-2,2'-bi-1H-pyrrole,
or 4-propoxy-5-((3,5-nonamethylene-2H-pyrrol-2-ylidene)methyl)-2,2'-bi-1H-pyrrole.

The compositions comprising a pharmaceutically acceptable carrier and a compound of Formula (I) or a pharmaceutically acceptable salt thereof are useful for treating or preventing cancer or neoplastic disease in a patient in need of such treatment or prevention. These compositions are also useful for inhibiting the growth of a cancer cell or neoplastic cell. The compositions comprising a pharmaceutically acceptable carrier and a compound of Formula (I) or a pharmaceutically acceptable salt thereof are useful for treating or preventing a viral infection in a patient in need of such treatment or prevention. These compositions are also useful for inhibiting the replication or infectivity of a virus.

A preferred subclass of the compositions comprising a pharmaceutically acceptable carrier and a compound of Formula (I) or a pharmaceutically acceptable salt thereof is that wherein, in the compound of Formula (I):

each $R_1$ is independently selected from the group consisting of —H and —CH$_3$;

$R_2$ is selected from the group consisting of —CH$_3$, —CH$_2$CH$_3$ and —CH$_2$C$_6$H$_5$;

$R_3$ is selected from the group consisting of —H, $C_1$–$C_{10}$ straight chain alkyl, (1-methyl)butyl, —CH$_2$C$_6$H$_5$butyroyl, (1-hydroxy)butyl, and (1-chloro)butyl;

$R_{16}$ and $R_{17}$ are —H; and m is an integer ranging from 1 to 5;

with the proviso that the compound of Formula (I) is not:
butyl-meta-cycloheptylprodiginine,
metacycloprodigiosin,
4-ethoxy-5-((3,5-nonamethylene-2H-pyrrol-2-ylidene)methyl)-2,2'-bi-1H-pyrrole,
or 4-propoxy-5-((3,5-nonamethylene-2H-pyrrol-2-ylidene)methyl)-2,2'-bi-1H-pyrrole.

A second preferred subclass of the compositions comprising a pharmaceutically acceptable carrier and a compound of Formula (I) or a pharmaceutically acceptable salt thereof are those wherein, in the compound of Formula (I):

each $R_1$ is —H;

$R_2$ is selected from the group consisting of —CH$_3$ and —CH$_2$C$_6$H$_5$;

$R_3$ is selected from the group consisting of —H, $C_1$–$C_{10}$ straight chain alkyl, and —CH$_2$C$_6$H$_5$;

$R_{16}$ and $R_{17}$ are —H; and m is an integer ranging from 1 to 5;

with the proviso that the compound of Formula (I) is not:
butyl-meta-cycloheptylprodiginine,
metacycloprodigiosin,
4-ethoxy-5-((3,5-nonamethylene-2H-pyrrol-2-ylidene)methyl)-2,2'-bi-1H-pyrrole,
or 4-propoxy-5-((3,5-nonamethylene-2H-pyrrol-2-ylidene)methyl)-2,2'-bi-1H-pyrrole.

A third preferred subclass of the compositions comprising a pharmaceutically acceptable carrier and a compound of Formula (D or a pharmaceutically acceptable salt thereof is that wherein, in the compound of Formula (I):

each $R_1$ is independently selected from the group consisting of —H and —CH$_3$;

$R_2$ is selected from the group consisting of —CH$_3$ and —CH$_2$C$_6$H$_5$;

$R_3$ is selected from the group consisting of —H, $C_1$–$C_{10}$ straight chain alkyl, —CH$_2$C$_6$H$_5$, butyroyl, (1-hydroxy)butyl, and (1-chloro)butyl;

$R_{16}$ and $R_{17}$ are —H; and m is an integer ranging from 1 to 5;

with the proviso that when m is 3, $R_3$ is not —$CH_2CH_3$ and when m is 1, $R_3$ is not —$(CH_2)_3CH_3$.

A fourth preferred subclass of the compositions comprising a pharmaceutically acceptable carrier and a compound of Formula (I) or a pharmaceutically acceptable salt thereof are those wherein, in the compound of Formula (I):

each $R_1$ is independently selected from the group consisting of —H and —$CH_3$;

$R_2$ is selected from the group consisting of —$CH_3$ and —$CH_2C_6H_5$;

$R_3$ is selected from the group consisting of —H, —$CH_3$, -n-$C_3H_7$, -i-$C_3H_7$, $C_5$–$C_{10}$, straight chain alkyl, (1-methyl)butyl, —$CH_2C_6H_5$, butyroyl, (1-hydroxy)butyl, and (1-chloro)butyl;

$R_{16}$ and $R_{17}$ are —H; and m is an integer ranging from 1 to 5.

A fifth preferred subclass of the compositions comprising a pharmaceutically acceptable carrier and a compound of Formula (I) or a pharmaceutically acceptable salt thereof is that, in the compound of Formula (I):

each $R_1$ is independently selected from the group consisting of —H and —$CH_3$;

$R_2$ is selected from the group consisting of —$CH_3$ and —$CH_2C_6H_5$;

$R_3$ is selected from the group consisting of —H, $C_1$–$C_{10}$ straight chain alkyl, —$CH_2C_6H_5$, butyroyl, (1-hydroxy)butyl, and (1-chloro)butyl;

$R_{16}$ and $R_{17}$ are —H; and m is 2, 4, or 5.

In one embodiment, preferred compounds of Formula (I) are selected from the group consisting of.

2-Ethyl-11-((3-methoxy-5-(1H-pyrrol-2-yl)-2H-pyrrol-2-ylidene)methyl)-10-azabicyclo[7.2.1]dodeca-9(12),11-diene;

11-((3-Methoxy-5-(1H-pyrrol-2-yl)-2H-pyrrol-2-ylidene)methyl)-10-azabicyclo[7.2.1]dodeca-9(12),11-diene;

2-Methyl-1-((3-methoxy-(1H-pyrrol-2-yl)-2H-pyrrol-2-ylidene)methyl)-10-azabicyclo[7.2.1]dodeca-9(12),11-diene;

2-n-Propyl-11-((3-methoxy-5-(1H-pyrrol-2-yl)-2H-pyrrol-2-ylidene)methyl)-10-azabicyclo[7.2.1]dodeca-9(12),11-diene;

2-n-Pentyl-11-((3-methoxy-5-(1H-pyrrol-2-yl)-2H-pyrrol-2-ylidene)methyl)-10-azabicyclo[7.2.1]dodeca-9(12),11-diene;

2-Benzyl-11-((3-methoxy-5-(1H-pyrrol-2-yl)-2H-pyrrol-2-ylidene)methyl)-10-azabicyclo[7.2.1]dodeca-9(12),11-diene;

(S)-2-n-Pentyl-11-((3-methoxy-5-(1H-pyrrol-2-yl)-2H-pyrrol-2-ylidene)methyl)-10-azabicyclo[7.2.1]dodeca-9(12),11-diene;

(R)-2-n-Pentyl-11-((3-methoxy-5-(1H-pyrrol-2-yl)-2H-pyrrol-2-ylidene)methyl)-10-azabicyclo[7.2.1]dodeca-9(12),11-diene;

(S)-2-n-Butyl-11-((3-methoxy-5-(1H-pyrrol-2-yl)-2H-pyrrol-2-ylidene)methyl)-10-azabicyclo[7.2.1]dodeca-9(12),11-diene;

(R)-2-n-Butyl-11-((3-methoxy-5-(1H-pyrrol-2-yl)-2H-pyrrol-2-ylidene)methyl)-10-azabicyclo[7.2.1]dodeca-9(12),11-diene;

(S)-2-Ethyl-11-((3-methoxy-5-(1H-pyrrol-2-yl)-2H-pyrrol-2-ylidene)methyl)-10-azabicyclo[7.2.1]dodeca-9(12),11-diene;

(R)-2-Ethyl-11-((3-methoxy-5-(1H-pyrrol-2-yl)-2H-pyrrol-2-ylidene)methyl)-10-azabicyclo[7.2.1]dodeca-9(12),11-diene;

(S)-2-Methyl-11-((3-methoxy-5-(1H-pyrrol-2-yl)-2H-pyrrol-2-ylidene)methyl)-10-azabicyclo[7.2.1]dodeca-9(12),11-diene;

(R)-2-Methyl-11-((3-methoxy-5-(1H-pyrrol-2-yl)-2H-pyrrol-2-ylidene)methyl)-10-azabicyclo[7.2.1]dodeca-9(12),11-diene;

(S)-2-n-Propyl-11-((3-methoxy-5-(1H-pyrrol-2-yl)-2H-pyrrol-2-ylidene)methyl)-10-azabicyclo[7.2.1]dodeca-9(12),11-diene;

(R)-2-n-Propyl-11-((3-methoxy-5-(1H-pyrrol-2-yl)-2H-pyrrol-2-ylidene)methyl)-10-azabicyclo[7.2.1]dodeca-9(12),11-diene;

2-Methyl-12-((3-methoxy-5-(1H-pyrrol-2-yl)-2H-pyrrol-2-ylidene)methyl)-1-azabicyclo[8.2.1]trideca-10(13),12-diene;

2-Ethyl-12-((3-methoxy-5-(1H-pyrrol-2-yl)-2H-pyrrol-2-ylidene)methyl)-11-azabicyclo[8.2.1]trideca-10(13),12-diene;

2-n-Propyl-12-((3-methoxy-5-(1H-pyrrol-2-yl)-2H-pyrrol-2-ylidene)methyl)-1-azabicyclo[8.2.1]trideca-10(13),12-diene;

2-n-Butyl-12-((3-methoxy-5-(1H-pyrrol-2-yl)-2H-pyrrol-2-ylidene)methyl)-11-azabicyclo[8.2.1]trideca-10(13),12-diene;

2-n-Pentyl-12-((3-methoxy-5-(1H-pyrrol-2-yl)-2H-pyrrol-2-ylidene)methyl)-11-azabicyclo[8.2.1]trideca-10(13),12-diene;

12-((3-Methoxy-5-(1H-pyrrol-2-yl)-2H-pyrrol-2-ylidene)methyl)-11-azabicyclo[8.2.1]trideca-10(13),12-diene;

2-Methyl-13-((3-methoxy-5-(1H-pyrrol-2-yl)-2H-pyrrol-2-ylidene)methyl)-12-azabicyclo[9.2.1]tetradeca-11(14),13-diene;

13-((3-Methoxy-5-(1H-pyrrol-2-yl)-2H-pyrrol-2-ylidene)methyl)-12-azabicyclo[9.2.1]tetradeca-11(14),13-diene;

2-Ethyl-12-methyl-13-((3-methoxy-5-(1-methyl-1H-pyrrol-2-yl)-2H-pyrrol-2-ylidene)methyl)-12-azabicyclo[9.2.1]tetradeca-11(14),13-diene;

2-Ethyl-12-methyl-13-((3-methoxy-5-(1H-pyrrol-2-yl)-2H-pyrrol-2-ylidene)methyl)-12-azabicyclo[9.2.1]tetradeca-11(14),13-diene;

2-n-Propyl-13-((3-methoxy-5-(1H-pyrrol-2-yl)-2H-pyrrol-2-ylidene)methyl)-12-azabicyclo[9.2.1]tetradeca-11(14),13-diene;

2-n-Butyl-13-((3-methoxy-5-(1H-pyrrol-2-yl)-2H-pyrrol-2-ylidene)methyl)-12-azabicyclo[9.2.1]tetradeca-11(14),13-diene;

14-((3-Methoxy-5-(1H-pyrrol-2-yl)-2H-pyrrol-2-ylidene)methyl)-13-azabicyclo[10.2.1]pentadeca-12(15),14-diene;

2-Butyl-11-((3-methoxy-5-(1-methyl-1H-pyrrol-2-yl)-2H-pyrrol-2-ylidene)methyl)-10-azabicyclo[7.2.1]dodeca-9(12),11-diene;

2-Butyl-11-((3-methoxy-5-(1-methyl-1H-pyrrol-2-yl)-2H-pyrrol-2-ylidene)methyl)-10-methyl-10-azabicyclo[7.2.1]dodeca-9(12),11-diene;

2-Butyl-11-((3-methoxy-5-(1H-pyrrol-2-yl)-2H-pyrrol-2-ylidene)methyl)-10-methyl-10-azabicyclo[7.2.1]dodeca-9(12),11-diene;

2-Ethyl-11-((3-benzyloxy-5-(1H-pyrrol-2-yl)-2H-pyrrol-2-ylidene)methyl)-10-azabicyclo[7.2.1]dodeca-9(12),11-diene;

2-Butyl-11-((3-hydroxy-5-(1H-pyrrol-2-yl)-2H-pyrrol-2-ylidene)methyl)-10-azabicyclo[7.2.1]dodeca-9(12),11-diene;

2-Butyl-11-((3-benzyloxy-5-(1H-pyrrol-2-yl)-2H-pyrrol-2-ylidene)methyl)-10-azabicyclo[7.2.1]dodeca-9(12),11-diene;

11-((3-Benzyloxy-5-(1H-pyrrol-2-yl)-2H-pyrrol-2-ylidene)methyl)-10-azabicyclo[7.2.1]dodeca-9(12),11-diene;

2-Methyl-11-((3-benzyloxy-5-(1H-pyrrol-2-yl)-2H-pyrrol-2-ylidene)methyl)-10-azabicyclo[7.2.1]dodeca-9 (12),11-diene;

2-n-Propyl-11-((3-benzyloxy-5-(1H-pyrrol-2-yl)-2H-pyrrol-2-ylidene)methyl)-10-azabicyclo[7.2.1]dodeca-9 (12),11-diene;

2-n-Pentyl-11-((3-benzyloxy-5-(1H-pyrrol-2-yl)-2H-pyrrol-2-ylidene)methyl)-10-azabicyclo[7.2.1]dodeca-9 (12),11-diene;

2-Benzyl-11-((3-benzyloxy-5-(1H-pyrrol-2-yl)-2H-pyrrol-2-ylidene)methyl)-10-azabicyclo[7.2.1]dodeca-9 (12),11-diene;

2-Methyl-14-((3-methoxy-5-(1H-pyrrol-2-yl)-2H-pyrrol-2-ylidene)methyl)-13-azabicyclo[10.2.1]pentadeca-12(15), 14-diene;

15-((3-Methoxy-5-(1H-pyrrol-2-yl)-2H-pyrrol-2-ylidene) methyl)-14-azabicyclo[11.2.1]pentadeca-13(16),15-diene;

2-Methyl-15-((3-methoxy-5-(1H-pyrrol-2-yl)-2H-pyrrol-2-ylidene)methyl)-14-azabicyclo[11.2.1]pentadeca-13(16), 15-diene;

2-(2-Hydroxy-n-butyl)-11-((3-methoxy-5-(1H-pyrrol-2-yl)-2H-pyrrol-2-ylidene)methyl)-10-azabicyclo[7.2.1] dodeca-9(12),11-diene;

2-(2-Chloro-n-butyl)-11-((3-methoxy-5-(1H-pyrrol-2-yl)-2H-pyrrol-2-ylidene)methyl)-10-azabicyclo[7.2.1] dodeca-9(12),11-diene;

2-Butyl-11-((3-ethoxy-5-(1H-pyrrol-2-yl)-2H-pyrrol-2-ylidene)methyl)-10-azabicyclo[7.2.1]dodeca-9(12),11-diene;

11-((3-Ethoxy-5-(1H-pyrrol-2-yl)-2H-pyrrol-2-ylidene) methyl)-10-azabicyclo[7.2.1]dodeca-9(12),11-diene;

2-Methyl-1-((3-ethoxy-5-(1H-pyrrol-2-yl)-2H-pyrrol-2-ylidene)methyl)-10-azabicyclo[7.2.1]dodeca-9(12),11-diene;

2-n-Propyl-11-((3-ethoxy-5-(1H-pyrrol-2-yl)-2H-pyrrol-2-ylidene)methyl)-10-azabicyclo[7.2.1]dodeca-9(12),11-diene;

2-n-Pentyl-11-((3-ethoxy-5-(1H-pyrrol-2-yl)-2H-pyrrol-2-ylidene)methyl)-10-azabicyclo[7.2.1]dodeca-9(12),11-diene;

2-Benzyl-11-((3-ethoxy-5-(1H-pyrrol-2-yl)-2H-pyrrol-2-ylidene)methyl)-10-azabicyclo[7.2.1]dodeca-9(12),11-diene;

2-Ethyl-11-((3-ethoxy-5-(1H-pyrrol-2-yl)-2H-pyrrol-2-ylidene)methyl)-10-azabicyclo[7.2.1]dodeca-9(12)11-diene; 2-Methyl-13-((3-benzyloxy-5-(1H-pyrrol-2-yl)-2H-pyrrol-2-ylidene)methyl)-12-azabicyclo[9.2.1]tetradeca-11(14),13-diene;

13-((3-Benzyloxy-5-(1H-pyrrol-2-yl)-2H-pyrrol-2-ylidene)methyl)-12-azabicyclo[9.2.1]tetradeca-11(14),13-diene;

2-Ethyl-12-methyl-13-((3-benzyloxy-5-(1-methyl-1H-pyrrol-2-yl)-2H-pyrrol-2-ylidene)methyl)-12-azabicyclo [9.2.1]tetradeca-11(14),13-diene;

2-Ethyl-12-methyl-13-((3-benzyloxy-5-(1H-pyrrol-2-yl)-2H-pyrrol-2-ylidene)methyl)-12-azabicyclo[9.2.1] tetradeca-11(14),13-diene;

2-n-Propyl-13-((3-benzyloxy-5-(1H-pyrrol-2-yl)-2H-pyrrol-2-ylidene)methyl)-12-azabicyclo[9.2.1]tetradeca-11 (14),13-diene; and 2-n-Butyl-13-((3-benzyloxy-5-(1H-pyrrol-2-yl)-2H-pyrrol-2-ylidene)methyl)-12-azabicyclo[9.2.1]tetradeca-11 (14),13-diene or a pharmaceutically acceptable salt thereof.

The invention further provides methods for treating or preventing cancer or neoplastic disease in a patient comprising administering to a patient in need of such treatment or prevention a composition comprising a therapeutically effective amount of a compound of Formula (I) or a pharmaceutically acceptable salt thereof, wherein, in the compound of Formula (I):

each $R_1$ is independently selected from the group consisting of —H, —CH$_3$, —CH$_2$CH$_3$, —CH$_2$C$_6$H$_5$, —C(O) OC(CH$_3$)$_3$, —C(O)OCH$_2$C$_6$H$_5$ and —C(O)CH$_3$;

$R_2$ is selected from the group consisting of —H, $C_1$–$C_{12}$ straight chain alkyl, —CH$_2$C$_6$H$_5$, —SiR$_{10}$R$_{11}$R$_{12}$, —C(O) CH$_3$, —C(O)C$_6$H$_5$, -2-tetrahydropyranyl, —OCH$_2$OCH$_3$, and —C(O)OCH$_2$CCl$_3$;

$R_3$ is selected from the group consisting of —H, $C_1$–$C_{12}$ straight chain alkyl, —CH(R$_{14}$)(R$_{15}$) wherein $R_{14}$ and $R_{15}$ are independently $C_1$–$C_{12}$ straight chain alkyl, —C(O) $C_1$–$C_9$ straight chain alkyl, —CH(OH)$C_1$–$C_9$ straight chain alkyl, —CH(Cl)$C_1$–$C_9$ straight chain alkyl, -(2-pyridyl) methyl, -(3-pyridyl)methyl, -(4-pyridyl)methyl, and —CH$_2$C$_6$H$_5$, the —CH$_2$C$_6$H$_5$ being unsubstituted or substituted on phenyl with one cyano or one or more halo, methoxyl, or trifluoromethyl groups;

$R_{10}$ is selected from the group consisting of $C_1$–$C_4$ straight or branched chain alkyl and —C$_6$H$_5$;

$R_{11}$ and $R_{12}$ are independently $C_1$–$C_3$ straight or branched chain alkyl;

m is an integer ranging from 1 to 5; and when m is 3 and $R_2$ is —CH$_2$CH$_3$, then $R_{16}$ is —H or —CH$_3$ and $R_{17}$ is —H;

when m is 3 and $R_2$ is —CH$_3$, then $R_{16}$ is —H or —CH$_3$ and $R_{17}$ is —H or —COOEt; and when m is other than 3 and $R_2$ is other than —CH$_3$ or —CH$_2$CH$_3$, then $R_{16}$ and $R_{17}$ are —H only;

with the proviso that the compound of Formula (I) is not: metacycloprodigiosin.

A preferred compound for use in the methods for treating or preventing cancer or neoplastic disease is butyl-metacycloheptylprodiginine or a pharmaceutically acceptable salt thereof.

Other preferred compounds for use in the methods for treating or preventing cancer or neoplastic disease are selected from the group consisting of:

2-Ethyl-11-((3-methoxy-5-(1H-pyrrol-2-yl)-2H-pyrrol-2-ylidene)methyl)-10-azabicyclo[7.2.1]dodeca-9(12),11-diene;

11-((3-Methoxy-5-(1H-pyrrol-2-yl)-2H-pyrrol-2-ylidene) methyl)-10-azabicyclo[7.2.1]dodeca-9(12),11-diene;

2-Methyl-11-((3-methoxy-5-(1H-pyrrol-2-yl)-2H-pyrrol-2-ylidene)methyl)-10-azabicyclo[7.2.1]dodeca-9(12),11-diene;

2-n-Propyl-11-((3-methoxy-5-(1H-pyrrol-2-yl)-2H-pyrrol-2-ylidene)methyl)-10-azabicyclo[7.2.1]dodeca-9 (12),11-diene;

2-n-Pentyl-11-((3-methoxy-5-(1H-pyrrol-2-yl)-2H-pyrrol-2-ylidene)methyl)-10-azabicyclo[7.2.1]dodeca-9 (12),11-diene;

2-Benzyl-11-((3-methoxy-5-(1H-pyrrol-2-yl)-2H-pyrrol-2-ylidene)methyl)-10-azabicyclo[7.2.1]dodeca-9(12),11-diene;

(S)-2-n-Pentyl-11-((3-methoxy-5-(1H-pyrrol-2-yl)-2H-pyrrol-2-ylidene)methyl)-10-azabicyclo[7.2.1]dodeca-9 (12),11-diene;

(R)-2-n-Pentyl-11-((3-methoxy-5-(1H-pyrrol-2-yl)-2H-pyrrol-2-ylidene)methyl)-10-azabicyclo[7.2.1]dodeca-9 (12),11-diene;

(S)-2-n-Butyl-11-((3-methoxy-5-(1H-pyrrol-2-yl)-2H-pyrrol-2-ylidene)methyl)-10-azabicyclo[7.2.1]dodeca-9 (12),11-diene;

(R)-2-n-Butyl-11-((3-methoxy-5-(1H-pyrrol-2-yl)-2H-pyrrol-2-ylidene)methyl)-10-azabicyclo[7.2.1]dodeca-9 (12),11-diene;

(S)-2-Ethyl-11-((3-methoxy-5-(1H-pyrrol-2-yl)-2H-pyrrol-2-ylidene)methyl)-10-azabicyclo[7.2.1]dodeca-9(12),11-diene;

(R)-2-Ethyl-11-((3-methoxy-5-(1H-pyrrol-2-yl)-2H-pyrrol-2-ylidene)methyl)-10-azabicyclo[7.2.1]dodeca-9(12),11-diene;

(S)-2-Methyl-11-((3-methoxy-5-(1H-pyrrol-2-yl)-2H-pyrrol-2-ylidene)methyl)-10-azabicyclo[7.2.1]dodeca-9(12),11-diene;

(R)-2-Methyl-11-((3-methoxy-5-(1H-pyrrol-2-yl)-2H-pyrrol-2-ylidene)methyl)-10-azabicyclo[7.2.1]dodeca-9(12),11-diene;

(S)-2-n-Propyl-11-((3-methoxy-5-(1H-pyrrol-2-yl)-2H-pyrrol-2-ylidene)methyl)-11-azabicyclo[7.2.1]dodeca-9(12),11-diene;

(R)-2-n-Propyl-11-((3-methoxy-5-(1H-pyrrol-2-yl)-2H-pyrrol-2-ylidene)methyl)-10-azabicyclo[7.2.1]dodeca-9(12),11-diene;

2-Methyl-12-((3-methoxy-5-(1H-pyrrol-2-yl)-2H-pyrrol-2-ylidene)methyl)-11-azabicyclo[8.2.1]trideca-10(13),12-diene;

2-Ethyl-12-((3-methoxy-5-(1H-pyrrol-2-yl)-2H-pyrrol-2-ylidene)methyl)-11-azabicyclo[8.2.1]trideca-10(13),12-diene;

2-n-Propyl-12-((3-methoxy-5-(1H-pyrrol-2-yl)-2H-pyrrol-2-ylidene)methyl)-11-azabicyclo[8.2.1]trideca-10(13),12-diene;

2-n-Butyl-12-((3-methoxy-5-(1H-pyrrol-2-yl)-2H-pyrrol-2-ylidene)methyl)-11-azabicyclo[8.2.1]trideca-10(13),12-diene;

2-n-Pentyl-12-((3-methoxy-5-(1H-pyrrol-2-yl)-2H-pyrrol-2-ylidene)methyl)-11-azabicyclo[8.2.1]trideca-10(13),12-diene;

12-((3-Methoxy-5-(1H-pyrrol-2-yl)-2H-pyrrol-2-ylidene)methyl)-11-azabicyclo[8.2.1]trideca-10(13),12-diene;

2-Methyl-13-((3-methoxy-5-(1H-pyrrol-2-yl)-2H-pyrrol-2-ylidene)methyl)-12-azabicyclo[9.2.1]tetradeca-11(14),13-diene;

13-((3-Methoxy-5-(1H-pyrrol-2-yl)-2H-pyrrol-2-ylidene)methyl)-12-azabicyclo[9.2.1]tetradeca-11(14),13-diene;

2-Ethyl-12-methyl-13-((3-methoxy-5-(1-methyl-1H-pyrrol-2-yl)-2H-pyrrol-2-ylidene)methyl)-12-azabicyclo[9.2.1]tetradeca-11(14),13-diene;

2-Ethyl-12-methyl-13-((3-methoxy-5-(1H-pyrrol-2-yl)-2H-pyrrol-2-ylidene)methyl)-12-azabicyclo[9.2.1]tetradeca-11(14),13-diene;

2-n-Propyl-13-((3-methoxy-5-(1H-pyrrol-2-yl)-2H-pyrrol-2-ylidene)methyl)-12-azabicyclo[9.2.1]tetradeca-11(14),13-diene;

2-n-Butyl-13-((3-methoxy-5-(1H-pyrrol-2-yl)-2H-pyrrol-2-ylidene)methyl)-12-azabicyclo[9.2.1]tetradeca-11(14),13-diene;

14-((3-Methoxy-5-(1H-pyrrol-2-yl)-2H-pyrrol-2-ylidene)methyl)-13-azabicyclo[10.2.1]pentadeca-12(15),14-diene;

2-Butyl-11-((3-methoxy-5-(1-methyl-1H-pyrrol-2-yl)-2H-pyrrol-2-ylidene)methyl)-10-azabicyclo[7.2.1]dodeca-9(12),11-diene;

2-Butyl-11-((3-methoxy-5-(1-methyl-1H-pyrrol-2-yl)-2H-pyrrol-2-ylidene)methyl)-10-methyl-10-azabicyclo[7.2.1]dodeca-9(12)11-diene;

2-Butyl-11-((3-methoxy-5-(1H-pyrrol-2-yl)-2H-pyrrol-2-ylidene)methyl)-10-methyl-10-azabicyclo[7.2.1]dodeca-9(12),11-diene;

2-Ethyl-11-((3-benzyloxy-5-(1H-pyrrol-2-yl)-2H-pyrrol-2-ylidene)methyl)-10-azabicyclo[7.2.1]dodeca-9(12),11-diene;

2-Butyl-11-((3-hydroxy-5-(1H-pyrrol-2-yl)-2H-pyrrol-2-ylidene)methyl)-10-azabicyclo[7.2.1]dodeca-9(12),11-diene;

2-Butyl-11-((3-benzyloxy-5-(1H-pyrrol-2-yl)-2H-pyrrol-2-ylidene)methyl)-10-azabicyclo[7.2.1]dodeca-9(12),11-diene;

11-((3-Benzyloxy-5-(1H-pyrrol-2-yl)-2H-pyrrol-2-ylidene)methyl)-10-azabicyclo[7.2.1]dodeca-9(12),11-diene;

2-Methyl-11-((3-benzyloxy-5-(1H-pyrrol-2-yl)-2H-pyrrol-2-ylidene)methyl)-10-azabicyclo[7.2.1]dodeca-9(12),11-diene;

2-n-Propyl-11-((3-benzyloxy-5-(1H-pyrrol-2-yl)-2H-pyrrol-2-ylidene)methyl)-10-azabicyclo[7.2.1]dodeca-9(12),11-diene;

2-n-Pentyl-11-((3-benzyloxy-5-(1H-pyrrol-2-yl)-2H-pyrrol-2-ylidene)methyl)-10-azabicyclo[7.2.1]dodeca-9(12),11-diene;

2-Benzyl-11-((3-benzyloxy-5-(1H-pyrrol-2-yl)-2H-pyrrol-2-ylidene)methyl)-10-azabicyclo[7.2.1]dodeca-9(12),11-diene;

2-Methyl-14-((3-methoxy-5-(1H-pyrrol-2-yl)-2H-pyrrol-2-ylidene)methyl)-13-azabicyclo[10.2.1]pentadeca-12(15),14-diene;

15-((3-Methoxy-5-(1H-pyrrol-2-yl)-2H-pyrrol-2-ylidene)methyl)-14-azabicyclo[11.2.1]pentadeca-13(16),15-diene;

2-Methyl-15-((3-methoxy-5-(1H-pyrrol-2-yl)-2H-pyrrol-2-ylidene)methyl)-14-azabicyclo[11.2.1]pentadeca-13(16),15-diene;

2-(2-Hydroxy-n-butyl)-11-((3-methoxy-5-(1H-pyrrol-2-yl)-2H-pyrrol-2-ylidene)methyl)-10-azabicyclo[7.2.1]dodeca-9(12),11-diene;

2-(2-Chloro-n-butyl)-11-((3-methoxy-5-(1H-pyrrol-2-yl)-2H-pyrrol-2-ylidene)methyl)-10-azabicyclo[7.2.1]dodeca-9(12),11-diene;

2-Butyl-11-((3-ethoxy-5-(1H-pyrrol-2-yl)-2H-pyrrol-2-ylidene)methyl)-10-azabicyclo[7.2.1]dodeca-9(12),11-diene;

11-((3-Ethoxy-5-(1H-pyrrol-2-yl)-2H-pyrrol-2-ylidene)methyl)-10-azabicyclo[7.2.1]dodeca-9(12),11-diene;

2-Methyl-11-((3-ethoxy-5-(1H-pyrrol-2-yl)-2H-pyrrol-2-ylidene)methyl)-10-azabicyclo[7.2.1]dodeca-9(12),11-diene;

2-n-Propyl-11-((3-ethoxy-5-(1H-pyrrol-2-yl)-2H-pyrrol-2-ylidene)methyl)-10-azabicyclo[7.2.1]dodeca-9(12),11-diene;

2-n-Pentyl-11-((3-ethoxy-5-(1H-pyrrol-2-yl)-2H-pyrrol-2-ylidene)methyl)-10-azabicyclo[7.2.1]dodeca-9(12),11-diene;

2-Benzyl-11-((3-ethoxy-5-(1H-pyrrol-2-yl)-2H-pyrrol-2-ylidene)methyl)-10-azabicyclo[7.2.1]dodeca-9(12),11-diene;

2-Ethyl-11-((3-ethoxy-5-(1H-pyrrol-2-yl)-2H-pyrrol-2-ylidene)methyl)-10-azabicyclo[7.2.1]dodeca-9(12),11-diene;

2-Methyl-13-((3-benzyloxy-5-(1H-pyrrol-2-yl)-2H-pyrrol-2-ylidene)methyl)-12-azabicyclo[9.2.1]tetradeca-11(14),13-diene;

13-((3-Benzyloxy-5-(1H-pyrrol-2-yl)-2H-pyrrol-2-ylidene)methyl)-12-azabicyclo[9.2.1]tetradeca-11(14),13-diene;

2-Ethyl-12-methyl-13-((3-benzyloxy-5-(1-methyl-1H-pyrrol-2-yl)-2H-pyrrol-2-ylidene)methyl)-12-azabicyclo[9.2.1]tetradeca-11(14),13-diene;

2-Ethyl-12-methyl-13-((3-benzyloxy-5-(1H-pyrrol-2-yl)-2H-pyrrol-2-ylidene)methyl)-12-azabicyclo[9.2.1]tetradeca-11(14),13-diene;

2-n-Propyl-13-((3-benzyloxy-5-(1H-pyrrol-2-yl)-2H-pyrrol-2-ylidene)methyl)-12-azabicyclo[9.2.1]tetradeca-11(14),13-diene; and 2-n-Butyl-13-((3-benzyloxy-5-(1H-pyrrol-2-yl)-2H-pyrrol-2-ylidene)methyl)-12-azabicyclo[9.2.1]tetradeca-11(14),13-diene or a pharmaceutically acceptable salt thereof.

For use in the methods for treating or preventing cancer or neoplastic disease, a preferred subclass of the compounds of Formula (I) is that wherein, in the compound of Formula (I):

each $R_1$ is independently selected from the group consisting of —H, —$CH_3$, —$CH_2CH_3$, —$CH_2C_6H_5$, —C(O)OC($CH_3$)$_3$, —C(O)O$CH_2C_6H_5$, and —C(O)$CH_3$;

$R_2$ is selected from the group consisting of —H, $C_1$–$C_{12}$ straight chain alkyl, —$CH_2C_6H_5$, —$SiR_{10}R_{11}R_{12}$, —C(O)$CH_3$, —C(O)$C_6H_5$, -2-tetrahydropyranyl, —$OCH_2OCH_3$, and —C(O)O$CH_2CCl_3$;

$R_3$ is selected from the group consisting of —H, $C_1$–$C_{12}$ straight chain alkyl, —CH($R_{14}$)($R_{15}$) wherein $R_{14}$ and $R_{15}$ are independently $C_1$–$C_{12}$ straight chain alkyl, —C(O)$C_1$–$C_9$ straight chain alkyl, —CH(OH)$C_1$–$C_9$ straight chain alkyl, —CH(Cl)$C_1$–$C_9$ straight chain alkyl, -(2-pyridyl)methyl, -(3-pyridyl)methyl, -(4-pyridyl)methyl, and —$CH_2C_6H_5$, the —$CH_2C_6H_5$ being unsubstituted or substituted on phenyl with one cyano or one or more halo, methoxyl, or trifluoromethyl groups;

$R_{10}$ is selected from the group consisting of $C_1$–$C_4$ straight or branched chain alkyl and —$C_6H_5$;

$R_{11}$ and $R_{12}$ are independently $C_1$–$C_3$ straight or branched chain alkyl; and $R_{16}$ and $R_{17}$ are —H; and m is an integer ranging from 1 to 5;

with the proviso that the compound of Formula (I) is not: metacycloprodigiosin.

For use in the methods for treating or preventing cancer or neoplastic disease, a second preferred subclass of the compounds of Formula (I) is that wherein, in the compound of Formula (I):

each $R_1$ is independently selected from the group consisting of —H and —$CH_3$;

$R_2$ is selected from the group consisting of —$CH_3$, —$CH_2CH_3$, and —$CH_2C_6H_5$;

$R_3$ is selected from the group consisting of —H, $C_1$–$C_{10}$ straight chain alkyl, (1-methyl)butyl, —$CH_2C_6H_5$, butyroyl, (1-hydroxy)butyl, and (1-chloro)butyl;

$R_{16}$ and $R_{17}$ are —H; and m is an integer ranging from 1 to 5;

with the proviso that the compound of Formula (I) is not: metacycloprodigiosin.

For use in the methods for treating or preventing cancer or neoplastic disease, a third preferred subclass of the compounds of Formula (I) is that wherein, in the compound of Formula (I):

each $R_1$ is —H;

$R_2$ is selected from the group consisting of —$CH_3$ and —$CH_2C_6H_5$;

$R_3$ is selected from the group consisting of —H, $C_1$–$C_{10}$ straight chain alkyl, and —$CH_2C_6H_5$;

$R_{16}$ and $R_{17}$ are —H; and m is an integer ranging from 1 to 5;

with the proviso that the compound of Formula (I) is not: metacycloprodigiosin.

For use in the methods for treating or preventing cancer or neoplastic disease, a fourth preferred subclass of the compounds of Formula (I) is that wherein, in the compounds of Formula (I):

each $R_1$ is independently selected from the group consisting of —H, and —$CH_3$;

$R_2$ is selected from the group consisting of —$CH_3$ and —$CH_2C_6H_5$;

$R_3$ is selected from the group consisting of —H, $C_1$–$C_{10}$ straight chain alkyl, —$CH_2C_6H_5$ butyroyl, (1-hydroxy)butyl, and (1-chloro)butyl;

$R_{16}$ and $R_{17}$ are —H; and m is an integer ranging from 1 to 5;

with the proviso that when m is 3, $R_3$ is not —$CH_2CH_3$ and when m is 1, $R_3$ is not —($CH_2$)$_3CH_3$.

For use in the present methods for treating or preventing cancer or neoplastic disease, a fifth preferred subclass of the compounds of Formula (I) is that wherein, in the compounds of Formula (I):

each $R_1$ is independently selected from the group consisting of —H and —$CH_3$;

$R_2$ is selected from the group consisting of —$CH_3$, and —$CH_2C_6H_5$;

$R_3$ is selected from the group consisting of —H, $C_1$–$C_{10}$ straight chain alkyl, (1-methyl)butyl, —$CH_2C_6H_5$, butyroyl, (1-hydroxy)butyl, and (1-chloro)butyl;

$R_{16}$ and $R_{17}$ are —H; and m is an integer ranging from 1 to 5.

For use in the present methods for treating or preventing cancer or neoplastic disease, a sixth preferred subclass of the compounds of Formula (I) is that wherein, in the compound of Formula (I):

each $R_1$ is independently selected from the group consisting of —H and —$CH_3$;

$R_2$ is selected from the group consisting of —$CH_3$ and —$CH_2C_6H_5$;

$R_3$ is selected from the group consisting of —H, $C_1$–$C_{11}$ straight chain alkyl, —$CH_2C_6H_5$, butyroyl, (1-hydroxy)butyl, and (1-chloro)butyl;

$R_{16}$ and $R_{17}$ are —H; and m is 2, 4, or 5.

For use in the present methods for treating or preventing cancer or neoplastic disease, a seventh preferred subclass of the compounds of Formula (I) is that wherein, in the compound of Formula (I):

each $R_1$ is independently selected from the group consisting of —H and —$CH_3$;

$R_2$ is selected from the group consisting of —$CH_3$, —$CH_2CH_3$, —($CH_2$)$_2CH_3$, and —$CH_2C_6H_5$;

$R_3$ is selected from the group consisting of —H, $C_1$–$C_{10}$ straight chain alkyl, —$CH_2C_6H_5$, butyroyl, (1-hydxoxy)butyl, and (1-chloro)butyl;

m is an integer ranging from 1 to 5;

when m is 3 and $R_2$ is —$CH_3$, then $R_{16}$ is selected from the group consisting of —H and —$CH_3$ and $R_{17}$ is selected from the group consisting of —H and —COOEt; and when m is other than 3 and $R_2$ is other than —$CH_3$ or —$CH_2CH_3$, then $R_{16}$ and $R_{17}$ are —H only; and with the proviso that the compound of Formula (I) is not: metacycloprodigio sin.

The invention further provides methods for inhibiting the growth of a cancer cell or neoplastic cell comprising a contacting a cancer cell or neoplastic cell with an effective amount of a composition comprising a pharmaceutically acceptable carrier and a compound having the general Formula (I) or a pharmaceutically acceptable salt thereof, wherein, in the compound of Formula (I):

each $R_1$ is independently selected from the group consisting of —H, —$CH_3$, —$CH_2CH_3$, —$CH_2C_6H_5$, —C(O)OC($CH_3$)$_3$, —C(O)O$CH_2C_6H_5$, and —C(O)$CH_3$;

$R_2$ is selected from the group consisting of —H, $C_1$–$C_{12}$ straight chain alkyl, —$CH_2C_6H_5$, —$SiR_{10}R_{11}R_{12}$, —C(O)$CH_3$, —C(O)$C_6H_5$, -2-tetrahydropyranyl, —$OCH_2OCH_3$, and —C(O)O$CH_2CCl_3$;

$R_3$ is selected from the group consisting of —H, $C_1$–$C_{12}$ straight chain alkyl, —CH($R_{14}$)($R_{15}$) wherein $R_{14}$ and $R_{15}$ are independently C$_1$–C$_{12}$ straight chain alkyl, —C(O)
C$_1$–C$_9$ straight chain alkyl, —CH(OH)C$_1$–C$_9$ straight chain
alkyl, —CH(Cl)C$_1$–C$_9$ straight chain alkyl, -(2-pyridyl)
methyl, -(3-pyridyl)methyl, -(4-pyridyl)methyl, and
—CH$_2$C$_6$H$_5$, the —CH$_2$C$_6$H$_5$ being unsubstituted or substituted on phenyl with one cyano or one or more halo, methoxyl, or trifluoromethyl groups;

R$_{10}$ is selected from the group consisting of C$_1$–C$_4$ straight or branched chain alkyl and —C$_6$H$_5$;

R$_{11}$ and R$_{12}$ are independently C$_1$–C$_3$ straight or branched chain alkyl;

m is an integer ranging from 1 to 5;

when m is 3 and R$_2$ is —CH$_2$CH$_3$, then R$_{16}$ is —H or —CH$_3$ and R$_{17}$ is —H;

when m is 3 and R$_2$ is —CH$_3$, then R$_{16}$ is —H or —CH$_3$ and R$_{17}$ is —H or —COOEt; and when m is other than 3 and R$_2$ is other than —CH$_3$ or —CH$_2$CH$_3$, then R$_{16}$ and R$_{17}$ are —H only;

with the proviso that the compound of Formnula (I) is not: metacycloprodigiosin.

A preferred compound for use in the method is butyl-meta-cycloheptylprodiginine or a pharmaceutically acceptable salt thereof.

Other preferred compounds for use in the method are selected from the group consisting of:

2-Ethyl-1-((3-methoxy-5-(1H-pyrrol-2-yl)-2H-pyrrol-2-ylidene)methyl)-10-azabicyclo[7.2.1]dodeca-9(12),11-diene;

11-((3-Methoxy-5-(1H-pyrrol-2-yl)-2H-pyrrol-2-ylidene)methyl)-10-azabicyclo[7.2.1]dodeca-9(12),11-diene;

2-Methyl-11-((3-methoxy-5-(1H-pyrrol-2-yl)-2H-pyrrol-2-ylidene)methyl)-10-azabicyclo[7.2.1]dodeca-9(12),11-diene;

2-n-Propyl-11-((3-methoxy-5-(1H-pyrrol-2-yl)-2H-pyrrol-2-ylidene)methyl)-10-azabicyclo[7.2.1]dodeca-9(12),11-diene;

2-n-Pentyl-11-((3-methoxy-5-(1H-pyrrol-2-yl)-2H-pyrrol-2-ylidene)methyl)-10-azabicyclo[7.2.1]dodeca-9(12),11-diene;

2-Benzyl-11-((3-methoxy-5-(1H-pyrrol-2-yl)-2H-pyrrol-2-ylidene)methyl)-10-azabicyclo[7.2.1]dodeca-9(12),11-diene;

(S)-2-n-Pentyl-11-((3-methoxy-5-(1H-pyrrol-2-yl)-2H-pyrrol-2-ylidene)methyl)-10-azabicyclo[7.2.1]dodeca-9(12),11-diene;

(R)-2-n-Pentyl-11-((3-methoxy-5-(1H-pyrrol-2-yl)-2H-pyrrol-2-ylidene)methyl)-10-azabicyclo[7.2.1]dodeca-9(12),11-diene;

(S)-2-n-Butyl-11-((3-methoxy-5-(1H-pyrrol-2-yl)-2H-pyrrol-2-ylidene)methyl)-10-azabicyclo[7.2.1]dodeca-9(12),11-diene;

(R)-2-n-Butyl-11-((3-methoxy-5-(1H-pyrrol-2-yl)-2H-pyrrol-2-ylidene)methyl)-10-azabicyclo[7.2.1]dodeca-9(12),11-diene;

(S)-2-Ethyl-11-((3-methoxy-5-(1H-pyrrol-2-yl)-2H-pyrrol-2-ylidene)methyl)-10-azabicyclo[7.2.1]dodeca-9(12),11-diene;

(R)-2-Ethyl-11-((3-methoxy-5-(1H-pyrrol-2-yl)-2H-pyrrol-2-ylidene)methyl)-10-azabicyclo[7.2.1]dodeca-9(12),11-diene;

(S)-2-Methyl-11-((3-methoxy-5-(1H-pyrrol-2-yl)-2H-pyrrol-2-ylidene)methyl)-10-azabicyclo[7.2.1]dodeca-9(12),11-diene;

(R)-2-Methyl-11-((3-methoxy-5-(1H-pyrrol-2-yl)-2H-pyrrol-2-ylidene)methyl)-10-azabicyclo[7.2.1]dodeca-9(12),11-diene;

(S)-2-n-Propyl-11-((3-methoxy-5-(1H-pyrrol-2-yl)-2H-pyrrol-2-ylidene)methyl)-10-azabicyclo[7.2.1]dodeca-9(12),11-diene;

(R)-2-n-Propyl-11-((3-methoxy-5-(1H-pyrrol-2-yl)-2H-pyrrol-2-ylidene)methyl)-10-azabicyclo[7.2.1]dodeca-9(12),11-diene;

2-Methyl-12-((3-methoxy-5-(1H-pyrrol-2-yl)-2H-pyrrol-2-ylidene)methyl)-1-azabicyclo[8.2.1]trideca-10(13),12-diene;

2-Ethyl-12-((3-methoxy-5-(1H-pyrrol-2-yl)-2H-pyrrol-2-ylidene)methyl)-11-azabicyclo[8.2.1]trideca-10(13),12-diene;

2-n-Propyl-12-((3-methoxy-5-(1H-pyrrol-2-yl)-2H-pyrrol-2-ylidene)methyl)-11-azabicyclo[8.2.1]trideca-10(13),12-diene;

2-n-Butyl-12-((3-methoxy-5-(1H-pyrrol-2-yl)-2H-pyrrol-2-ylidene)methyl)-11-azabicyclo[8.2.1]trideca-10(13),12-diene;

2-n-Pentyl-12-((3-methoxy-5-(1H-pyrrol-2-yl)-2H-pyrrol-2-ylidene)methyl)-11-azabicyclo[8.2.1]trideca-10(13),12-diene;

12-((3-Methoxy-5-(1H-pyrrol-2-yl)-2H-pyrrol-2-ylidene)methyl)-11-azabicyclo[8.2.1]trideca-10(13),12-diene;

2-Methyl-13-((3-methoxy-5-(1H-pyrrol-2-yl)-2H-pyrrol-2-ylidene)methyl)-12-azabicyclo[9.2.1]tetradeca-11(14),13-diene;

13-((3-Methoxy-5-(1H-pyrrol-2-yl)-2H-pyrrol-2-ylidene)methyl)-12-azabicyclo[9.2.1]tetradeca-11(14),13-diene;

2-Ethyl-12-methyl-13-((3-methoxy-5-(1-methyl-1H-pyrrol-2-yl)-2H-pyrrol-2-ylidene)methyl)-12-azabicyclo[9.2.1]tetradeca-11(14),13-diene;

2-Ethyl-12-methyl-13-((3-methoxy-5-(1H-pyrrol-2-yl)-2H-pyrrol-2-ylidene)methyl)-12-azabicyclo[9.2.1]tetradeca-11(14),13-diene;

2-n-Propyl-13-((3-methoxy-5-(1H-pyrrol-2-yl)-2H-pyrrol-2-ylidene)methyl)-12-azabicyclo[9.2.1]tetradeca-11(14),13-diene;

2-n-Butyl-13-((3-methoxy-5-(1H-pyrrol-2-yl)-2H-pyrrol-2-ylidene)methyl)-12-azabicyclo[9.2.1]tetradeca-11(14),13-diene;

14-((3-Methoxy-5-(1H-pyrrol-2-yl)-2H-pyrrol-2-ylidene)methyl)-13-azabicyclo[10.2.1]pentadeca-12(15),14-diene;

2-Butyl-11-((3-methoxy-5-(1-methyl-1H-pyrrol-2-yl)-2H-pyrrol-2-ylidene)methyl)-10-azabicyclo[7.2.1]dodeca-9(12),11-diene;

2-Butyl-11-((3-methoxy-5-(1-methyl-1H-pyrrol-2-yl)-2H-pyrrol-2-ylidene)methyl)-10-methyl-10-azabicyclo[7.2.1]dodeca-9(12),11-diene;

2-Butyl-11-((3-methoxy-5-(1H-pyrrol-2-yl)-2H-pyrrol-2-ylidene)methyl)-10-methyl-10-azabicyclo[7.2.1]dodeca-9(12),11-diene;

2-Ethyl-11-((3-benzyloxy-5-(1H-pyrrol-2-yl)-2H-pyrrol-2-ylidene)methyl)-10-azabicyclo[7.2.1]dodeca-9(12),11-diene;

2-Butyl-11-((3-hydroxy-5-(1H-pyrrol-2-yl)-2H-pyrrol-2-ylidene)methyl)-10-azabicyclo[7.2.1]dodeca-9(12),11-diene;

2-Butyl-11-((3-benzyloxy-5-(1H-pyrrol-2-yl)-2H-pyrrol-2-ylidene)methyl)-10-azabicyclo[7.2.1]dodeca-9(12),11-diene;

11-((3-Benzyloxy-5-(1H-pyrrol-2-yl)-2H-pyrrol-2-ylidene)methyl)-10-azabicyclo[7.2.1]dodeca-9(12),11-diene;

2-Methyl-11-((3-benzyloxy-5-(1H-pyrrol-2-yl)-2H-pyrrol-2-ylidene)methyl)-10-azabicyclo[7.2.1]dodeca-9(12),11-diene;

2-n-Propyl-11-((3-benzyloxy-5-(1H-pyrrol-2-yl)-2H-pyrrol-2-ylidene)methyl)-10-azabicyclo[7.2.1]dodeca-9(12),11-diene;

2-n-Pentyl-11-((3-benzyloxy-5-(1H-pyrrol-2-yl)-2H-pyrrol-2-ylidene)methyl)-10-azabicyclo[7.2.1]dodeca-9(12),11-diene;

2-Benzyl-11-((3-benzyloxy-5-(1H-pyrrol-2-yl)-2H-pyrrol-2-ylidene)methyl)-10-azabicyclo[7.2.1]dodeca-9 (12),11-diene;

2-Methyl-14-((3-methoxy-5-(1H-pyrrol-2-yl)-2H-pyrrol-2-ylidene)methyl)-13-azabicyclo[10.2.1]pentadeca-12(15), 14-diene;

15-((3-Methoxy-5-(1H-pyrrol-2-yl)-2H-pyrrol-2-ylidene) methyl)-14-azabicyclo[11.2.1]pentadeca-13(16),15-diene;

2-Methyl-5-((3-methoxy-5-(1H-pyrrol-2-yl)-2H-pyrrol-2-ylidene)methyl)-14-azabicyclo[11.2.1]pentadeca-13(16), 15-diene;

2-(2-Hydroxy-n-butyl)-11-((3-methoxy-5-(1H-pyrrol-2-yl)-2H-pyrrol-2-ylidene)methyl)-10-azabicyclo[7.2.1]dodeca-9(12),11-diene;

2-(2-Chloro-n-butyl)-11-((3-methoxy-5-(1H-pyrrol-2-yl)-2H-pyrrol-2-ylidene)methyl)-10-azabicyclo[7.2.1]dodeca-9(12),11-diene;

2-Butyl-11-((3-ethoxy-5-(1H-pyrrol-2-yl)-2H-pyrrol-2-ylidene)methyl)-10-azabicyclo[7.2.1]dodeca-9(12),11-diene;

11-((3-Ethoxy-5-(1H-pyrrol-2-yl)-2H-pyrrol-2-ylidene) methyl)-10-azabicyclo[7.2.1]dodeca-9(12),11-diene;

2-Methyl-1-((3-ethoxy-5-(1H-pyrrol-2-yl)-2H-pyrrol-2-ylidene)methyl)-10-azabicyclo[7.2.1]dodeca-9(12),11-diene;

2-n-Propyl-11-((3-ethoxy-5-(1H-pyrrol-2-yl)-2H-pyrrol-2-ylidene)methyl)-10-azabicyclo[7.2.1]dodeca-9(12),11-diene;

2-n-Pentyl-11-((3-ethoxy-5-(1H-pyrrol-2-yl)-2H-pyrrol-2-ylidene)methyl)-10-azabicyclo[7.2.1]dodeca-9(12),11-diene;

2-Benzyl-11-((3-ethoxy-5-(1H-pyrrol-2-yl)-2H-pyrrol-2-ylidene)methyl)-10-azabicyclo[7.2.1]dodeca-9(12),11-diene;

2-Ethyl-11-((3-ethoxy-5-(1H-pyrrol-2-yl)-2H-pyrrol-2-ylidene)methyl)-10-azabicyclo[7.2.1]dodeca-9(12),11-diene;

2-Methyl-13-((3-benzyloxy-5-(1H-pyrrol-2-yl)-2H-pyrrol-2-ylidene)methyl)-12-azabicyclo[9.2.1]tetradeca-11 (14),13-diene;

13-((3-Benzyloxy-5-(1H-pyrrol-2-yl)-2H-pyrrol-2-ylidene)methyl)-12-azabicyclo[9.2.1]tetradeca-11(14),13-diene;

2-Ethyl-12-methyl-13-((3-benzyloxy-5-(1-methyl-1H-pyrrol-2-yl)-2H-pyrrol-2-ylidene)methyl)-12-azabicyclo [9.2.1]tetradeca-11(14),13-diene;

2-Ethyl-12-methyl-13-((3-benzyloxy-5-(1H-pyrrol-2-yl)-2H-pyrrol-2-ylidene)methyl)-12-azabicyclo[9.2.1] tetradeca-11(14),13-diene;

2-n-Propyl-13-((3-benzyloxy-5-(1H-pyrrol-2-yl)-2H-pyrrol-2-ylidene)methyl)-12-azabicyclo[9.2.1]tetradeca-11 (14),13-diene; and 2-n-Butyl-13-((3-benzyloxy-5-(1H-pyrrol-2-yl)-2H-pyrrol-2-ylidene)methyl)-12-azabicyclo[9.2.1]tetradeca-11 (14),13-diene or a pharmaceutically acceptable salt thereof.

For use in the methods for inhibiting the growth of a cancer or neoplastic cell, a second preferred subclass of the compounds of Formula (I) is that wherein, in the compound of Formula (I):

each $R_1$ is independently selected from the group consisting of —H, —$CH_3$, —$CH_2CH_3$, —$CH_2C_6H_5$, —C(O)OC($CH_3$), —C(O)OCH$_2$C$_6$H$_5$, and —C(O)CH$_3$;

$R_2$ is selected from the group consisting of —H, $C_1$–$C_{12}$ straight chain alkyl, —$CH_2C_6H_5$, —$SiR_{10}R_{11}R_{12}$, —C(O)CH$_3$, —C(O)C$_6$H$_5$, -2-tetrahydropyranyl, —OCH$_2$OCH$_3$, and —C(O)OCH$_2$CCl$_3$;

$R_3$ is selected from the group consisting of —H, $C_1$–$C_{12}$ straight chain alkyl, —CH($R_{14}$)($R_{15}$) wherein $R_{14}$ and $R_{15}$ are independently $C_1$–$C_{12}$ straight chain alkyl, —C(O) $C_1$–$C_9$ straight chain alkyl, —CH(OH)$C_1$–$C_9$ straight chain alkyl, —CH(Cl)$C_1$–$C_9$ straight chain alkyl, -(2-pyridyl)methyl, -(3-pyridyl)methyl, -(4-pyridyl)methyl, and —$CH_2C_6H_5$, the —$CH_2C_6H_5$ being unsubstituted or substituted on phenyl with one cyano or one or more halo, methoxyl, or trifluoromethyl groups;

$R_{10}$ is selected from the group consisting of $C_1$–$C_4$ straight or branched chain alkyl and —$C_6H_5$;

$R_{11}$ and $R_{12}$ are independently $C_1$–$C_3$ straight or branched chain alkyl; and $R_{16}$ and $R_{17}$ are —H; and m is an integer ranging from 1 to 5;

with the proviso that the compound of Formula (I) is not: metacycloprodigiosin.

For use in the methods for inhibiting the growth of a cancer or neoplastic cell, a third preferred subclass of the compounds of Formula (I) is that wherein, in the compound of Formula (I):

each $R_1$ is independently selected from the group consisting of —H and —$CH_3$;

$R_2$ is selected from the group consisting of —$CH_3$, —$CH_2CH_3$, and —$CH_2C_6H_5$;

$R_3$ is selected from the group consisting of —H, $C_1$–$C_{10}$ straight chain alkyl, (1-methyl)butyl, —$CH_2C_6H_5$, butyroyl, (1-hydroxy)butyl, and (1-chloro)butyl;

m is an integer ranging from 1 to 5;

with the proviso that the compound of Formula (I) is not: metacycloprodigiosin.

For use in the methods for inhibiting the growth of a cancer or neoplastic cell, a fourth preferred subclass of the compounds of Formula (I) is that wherein, in the compound of Formula (I):

each $R_1$ is —H;

$R_2$ is selected from the group consisting of —$CH_3$ and —$CH_2C_6H_5$;

$R_3$ is selected from the group consisting of —H, $C_1$–$C_{10}$ straight chain alkyl, and —$CH_2C_6H_5$;

$R_{16}$ and $R_{17}$ are —H; and m is an integer ranging from 1 to 5;

with the proviso that the compound of Formula (I) is not: metacycloprodigiosin.

For use in the methods for inhibiting the growth of a cancer or neoplastic cell, a fifth preferred subclass of the compounds of Formula (I) is that wherein, in the compound of Formula (I):

each $R_1$ is independently selected from the group consisting of —H and —$CH_3$;

$R_2$ is selected from the group consisting of —$CH_3$ and —$CH_2C_6H_5$;

$R_3$ is selected from the group consisting of —H, $C_1$–$C_{10}$ straight chain alkyl, —$CH_2C_6H_5$, butyroyl, (1-hydroxy) butyl, and (1-chloro)butyl;

$R_{16}$ and $R_{17}$ are —H; and m is an integer ranging from 1 to 5;

with the proviso that when m is 3, $R_3$ is not —$CH_2CH_3$ and when m is 1, $R_3$ is not —$(CH_2)_3CH_3$.

For use in the methods for inhibiting the growth of a cancer or neoplastic cell, a sixth preferred subclass of the compounds of Formula (I) is that wherein, in the compound of Formula (I):

each $R_1$ is independently selected from the group consisting of —H and —$CH_3$;

$R_2$ is selected from the group consisting of —$CH_3$ and —$CH_2C_6H_5$;

$R_3$ is selected from the group consisting of —H, $C_1$–$C_{10}$ straight chain alkyl, (1-methyl)butyl, —$CH_2C_6H_5$ butyroyl, (1-hydroxy)butyl, and (1-chloro)butyl;

$R_{16}$ and $R_{17}$ are —H; and m is an integer ranging from 1 to 5.

For use in the methods for inhibiting the growth of a cancer or neoplastic cell, a seventh preferred subclass of the compounds of Formula (I) is that wherein, in the compound of Formula (I):

each $R_1$ is independently selected from the group consisting of —H and —CH₃;

$R_2$ is selected from the group consisting of —CH₃ and —CH₂C₆H₅;

$R_3$ is selected from the group consisting of —H, $C_1$–$C_{10}$ straight chain alkyl, —CH₂C₆H₅, butyroyl, (1-hydroxy)butyl, and (1-chloro)butyl;

$R_{16}$ and $R_{17}$ are —H; and m is 2, 4, or 5.

For use in the methods for inhibiting the growth of a cancer or neoplastic cell, an eighth preferred subclass of the compounds of Formula (I) is that wherein, in the compound of Formula (I):

each $R_1$ is independently selected from the group consisting of —H and —CH₃;

$R_2$ is selected from the group consisting of —CH₃, —CH₂CH₃, —(CH₂)₂CH₃, and —CH₂C₆H₅;

$R_3$ is selected from the group consisting of —H, $C_1$–$C_{10}$ straight chain alkyl, —CH₂C₆H₅, butyroyl, (1-hydxoxy)butyl, and (1-chloro)butyl;

m is an integer ranging from 1 to 5;

when m is 3 and $R_2$ is —CH₃, then $R_{16}$ is selected from the group consisting of —H and —CH₃ and $R_{17}$ is selected from the group consisting of —H and —COOEt; and when m is other than 3 and $R_2$ is other than —CH₃ or —CH₂CH₃, then $R_{16}$ and $R_{17}$ are —H only; and with the proviso that the compound of Formula (I) is not: metacycloprodigiosin.

The invention further provides methods for treating or preventing a viral infection in a patient comprising administering to a patient in need of such treatment or prevention a therapeutically effective amount of a composition comprising a pharmaceutically acceptable carrier and a compound of Formula (I) or a pharmaceutically acceptable salt thereof, wherein, in the compound of Formula (I):

each $R_1$ is independently selected from the group consisting of —H, —CH₃, —CH₂CH₃, —CH₂C₆H₅, —C(O)OC(CH₃)₃, —C(O)OCH₂C₆H₅, and —C(O)CH₃;

$R_2$ is selected from the group consisting of —H, $C_1$–$C_{12}$ straight chain alkyl, —CH₂C₆H₅, —SiR₁₀R₁₁R₁₂, —C(O)CH₃, —C(O)C₆H₅, -2-tetrahydropyranyl, —OCH₂OCH₃, and —C(O)OCH₂CCl₃;

$R_3$ is selected from the group consisting of —H, $C_1$–$C_{12}$ straight chain alkyl, —CH($R_{14}$)($R_{15}$) wherein $R_{14}$ and $R_{15}$ are independently $C_1$–$C_{12}$ straight chain alkyl, —C(O)$C_1$–$C_9$ straight chain alkyl, —CH(OH)$C_1$–$C_9$ straight chain alkyl, —CH(Cl)$C_1$–$C_9$ straight chain alkyl, -(2-pyridyl)methyl, -(3-pyridyl)methyl, -(4-pyridyl)methyl, and —CH₂C₆H₅, the —CH₂C₆H₅ being unsubstituted or substituted on phenyl with one cyano or one or more halo, methoxyl, or trifluoromethyl groups;

$R_{10}$ is selected from the group consisting of $C_1$–$C_4$ straight or branched chain alkyl and —C₆H₅;

$R_{11}$ and $R_{12}$ are independently $C_1$–$C_3$ straight or branched chain alkyl;

m is an integer ranging from 1 to 5; and when m is 3 and $R_2$ is —CH₂CH₃, then $R_{16}$ is —H or —CH₃ and $R_{17}$ is —H;

when m is 3 and $R_2$ is —CH₃, then $R_{16}$ is —H or —CH₃ and $R_{17}$ is —H or —COOEt; and when m is other than 3 and $R_2$ is other than —CH₃ or —CH₂CH₃, then $R_{16}$ and $R_{17}$ are —H only.

A preferred compound for use in the methods for treating or preventing a viral infection is butyl-meta-cycloheptylprodiginine or a pharmaceutically acceptable salt thereof.

Another preferred compound for use in the method for treating or preventing a viral infection is metacycloprodigiosine or a pharmaceutically acceptable salt thereof.

Other preferred compounds for use in the method are selected from the group consisting of:

2-Ethyl-11-((3-methoxy-5-(1H-pyrrol-2-yl)-2H-pyrrol-2-ylidene)methyl)-10-azabicyclo[7.2.1]dodeca-9(12),11-diene;

11-((3-Methoxy-5-(1H-pyrrol-2-yl)-2H-pyrrol-2-ylidene)methyl)-10-azabicyclo[7.2.1]dodeca-9(12),11-diene;

2-Methyl-11-((3-methoxy-5-(1H-pyrrol-2-yl)-2H-pyrrol-2-ylidene)methyl)-10-azabicyclo[7.2.1]dodeca-9(12),11-diene;

2-n-Propyl-11-((3-methoxy-5-(1H-pyrrol-2-yl)-2H-pyrrol-2-ylidene)methyl)-10-azabicyclo[7.2.1]dodeca-9(12),11-diene;

2-n-Pentyl-11-((3-methoxy-5-(1H-pyrrol-2-yl)-2H-pyrrol-2-ylidene)methyl)-10-azabicyclo[7.2.1]dodeca-9(12),11-diene;

2-Benzyl-11-((3-methoxy-5-(1H-pyrrol-2-yl)-2H-pyrrol-2-ylidene)methyl)-10-azabicyclo[7.2.1]dodeca-9(12),11-diene;

(S)-2-n-Pentyl-11-((3-methoxy-5-(1H-pyrrol-2-yl)-2H-pyrrol-2-ylidene)methyl)-10-azabicyclo[7.2.1]dodeca-9(12),11-diene;

(R)-2-n-Pentyl-11-((3-methoxy-5-(1H-pyrrol-2-yl)-2H-pyrrol-2-ylidene)methyl)-10-azabicyclo[7.2.1]dodeca-9(12),11-diene;

(S)-2-n-Butyl-11-((3-methoxy-5-(1H-pyrrol-2-yl)-2H-pyrrol-2-ylidene)methyl)-10-azabicyclo[7.2.1]dodeca-9(12),11-diene;

(R)-2-n-Butyl-11-((3-methoxy-5-(1H-pyrrol-2-yl)-2H-pyrrol-2-ylidene)methyl)-10-azabicyclo[7.2.1]dodeca-9(12),11-diene;

(S)-2-Ethyl-11-((3-methoxy-5-(1H-pyrrol-2-yl)-2H-pyrrol-2-ylidene)methyl)-10-azabicyclo[7.2.1]dodeca-9(12),11-diene;

(R)-2-Ethyl-11-((3-methoxy-5-(1H-pyrrol-2-yl)-2H-pyrrol-2-ylidene)methyl)-10-azabicyclo[7.2.1]dodeca-9(12),11-diene;

(S)-2-Methyl-11-((3-methoxy-5-(1H-pyrrol-2-yl)-2H-pyrrol-2-ylidene)methyl)-10-azabicyclo[7.2.1]dodeca-9(12),11-diene;

(R)-2-Methyl-11-((3-methoxy-5-(1H-pyrrol-2-yl)-2H-pyrrol-2-ylidene)methyl)-10-azabicyclo[7.2.1]dodeca-9(12),11-diene;

(S)-2-n-Propyl-11-((3-methoxy-5-(1H-pyrrol-2-yl)-2H-pyrrol-2-ylidene)methyl)-10-azabicyclo[7.2.1]dodeca-9(12),11-diene;

(R)-2-n-Propyl-11-((3-methoxy-5-(1H-pyrrol-2-yl)-2H-pyrrol-2-ylidene)methyl)-10-azabicyclo[7.2.1]dodeca-9(12),11-diene;

2-Methyl-12-((3-methoxy-5-(1H-pyrrol-2-yl)-2H-pyrrol-2-ylidene)methyl)-11-azabicyclo[8.2.1]trideca-10(13),12-diene;

2-Ethyl-12-((3-methoxy-5-(1H-pyrrol-2-yl)-2H-pyrrol-2-ylidene)methyl)-11-azabicyclo[8.2.1]trideca-10(13),12-diene;

2-n-Propyl-12-((3-methoxy-5-(1H-pyrrol-2-yl)-2H-pyrrol-2-ylidene)methyl)-11-azabicyclo[8.2.1]trideca-10(13),12-diene;

2-n-Butyl-12-((3-methoxy-5-(1H-pyrrol-2-yl)-2H-pyrrol-2-ylidene)methyl)-11-azabicyclo[8.2.1]trideca-10(13),12-diene;

2-n-Pentyl-12-((3-methoxy-5-(1H-pyrrol-2-yl)-2H-pyrrol-2-ylidene)methyl)-11-azabicyclo[8.2.1]trideca-10(13),12-diene;

12-((3-Methoxy-5-(1H-pyrrol-2-yl)-2H-pyrrol-2-ylidene)methyl)-11-azabicyclo[8.2.1]trideca-10(13),12-diene;

2-Methyl-13-((3-methoxy-5-(1H-pyrrol-2-yl)-2H-pyrrol-2-ylidene)methyl)-12-azabicyclo[9.2.1]tetradeca-11(14),13-diene;

13-((3-Methoxy-5-(1H-pyrrol-2-yl)-2H-pyrrol-2-ylidene)methyl)-12-azabicyclo[9.2.1]tetradeca-11(14),13-diene;

2-Ethyl-12-methyl-13-((3-methoxy-5-(1-methyl-1H-pyrrol-2-yl)-2H-pyrrol-2-ylidene)methyl)-12-azabicyclo[9.2.1]tetradeca-11(14),13-diene;

2-Ethyl-12-methyl-13-((3-methoxy-5-(1H-pyrrol-2-yl)-2H-pyrrol-2-ylidene)methyl)-12-azabicyclo[9.2.1]tetradeca-11(14),13-diene;

2-n-Propyl-13-((3-methoxy-5-(1H-pyrrol-2-yl)-2H-pyrrol-2-ylidene)methyl)-12-azabicyclo[9.2.1]tetradeca-11(14),13-diene;

2-n-Butyl-13-((3-methoxy-5-(1H-pyrrol-2-yl)-2H-pyrrol-2-ylidene)methyl)-12-azabicyclo[9.2.1]tetradeca-11(14),13-diene;

14-((3-Methoxy-5-(1H-pyrrol-2-yl)-2H-pyrrol-2-ylidene)methyl)-13-azabicyclo[10.2.1]pentadeca-12(15),14-diene;

2-Butyl-11-((3-methoxy-5-(1-methyl-1H-pyrrol-2-yl)-2H-pyrrol-2-ylidene)methyl)-10-azabicyclo[7.2.1]dodeca-9(12),11-diene;

2-Butyl-11-((3-methoxy-5-(1-methyl-1H-pyrrol-2-yl)-2H-pyrrol-2-ylidene)methyl)-10-methyl-10-azabicyclo[7.2.1]dodeca-9(12),11-diene;

2-Butyl-11-((3-methoxy-5-(1H-pyrrol-2-yl)-2H-pyrrol-2-ylidene)methyl)-10-methyl-10-azabicyclo[7.2.1]dodeca-9(12),11-diene;

2-Ethyl-11-((3-benzyloxy-5-(1H-pyrrol-2-yl)-2H-pyrrol-2-ylidene)methyl)-10-azabicyclo[7.2.1]dodeca-9(12),11-diene;

2-Butyl-11-((3-hydroxy-5-(1H-pyrrol-2-yl)-2H-pyrrol-2-ylidene)methyl)-10-azabicyclo[7.2.1]dodeca-9(12),11-diene;

2-Butyl-11-((3-benzyloxy-5-(1H-pyrrol-2-yl)-2H-pyrrol-2-ylidene)methyl)-10-azabicyclo[7.2.1]dodeca-9(12),11-diene;

11-((3-Benzyloxy-5-(1H-pyrrol-2-yl)-2H-pyrrol-2-ylidene)methyl)-10-azabicyclo[7.2.1]dodeca-9(12),11-diene;

2-Methyl-11-((3-benzyloxy-5-(1H-pyrrol-2-yl)-2H-pyrrol-2-ylidene)methyl)-10-azabicyclo[7.2.1]dodeca-9(12),11-diene;

2-n-Propyl-11-((3-benzyloxy-5-(1H-pyrrol-2-yl)-2H-pyrrol-2-ylidene)methyl)-10-azabicyclo[7.2.1]dodeca-9(12),11-diene;

2-n-Pentyl-11-((3-benzyloxy-5-(1H-pyrrol-2-yl)-2H-pyrrol-2-ylidene)methyl)-10-azabicyclo[7.2.1]dodeca-9(12),11-diene;

2-Benzyl-11-((3-benzyloxy-5-(1H-pyrrol-2-yl)-2H-pyrrol-2-ylidene)methyl)-10-azabicyclo[7.2.1]dodeca-9(12),11-diene;

2-Methyl-14-((3-methoxy-5-(1H-pyrrol-2-yl)-2H-pyrrol-2-ylidene)methyl)-13-azabicyclo[10.2.1]pentadeca-12(15),14-diene;

15-((3-Methoxy-5-(1H-pyrrol-2-yl)-2H-pyrrol-2-ylidene)methyl)-14-azabicyclo[11.2.1]pentadeca-13(16),15-diene;

2-Methyl-15-((3-methoxy-5-(1H-pyrrol-2-yl)-2H-pyrrol-2-ylidene)methyl)-14-azabicyclo[11.2.1]pentadeca-13(16),15-diene;

2-(2-Hydroxy-n-butyl)-11-((3-methoxy-5-(1H-pyrrol-2-yl)-2H-pyrrol-2-ylidene)methyl)-10-azabicyclo[7.2.1]dodeca-9(12),11-diene;

2-(2-Chloro-n-butyl)-11-((3-methoxy-5-(1H-pyrrol-2-yl)-2H-pyrrol-2-ylidene)methyl)-10-azabicyclo[7.2.1]dodeca-9(12),11-diene;

2-Butyl-11-((3-ethoxy-5-(1H-pyrrol-2-yl)-2H-pyrrol-2-ylidene)methyl)-10-azabicyclo[7.2.1]dodeca-9(12),11-diene;

11-((3-Ethoxy-5-(1H-pyrrol-2-yl)-2H-pyrrol-2-ylidene)methyl)-10-azabicyclo[7.2.1]dodeca-9(12),11-diene;

2-Methyl-1-((3-ethoxy-5-(1H-pyrrol-2-yl)-2H-pyrrol-2-ylidene)methyl)-10-azabicyclo[7.2.1]dodeca-9(12),11-diene;

2-n-Propyl-11-((3-ethoxy-5-(1H-pyrrol-2-yl)-2H-pyrrol-2-ylidene)methyl)-10-azabicyclo[7.2.1]dodeca-9(12),11-diene;

2-n-Pentyl-11-((3-ethoxy-5-(1H-pyrrol-2-yl)-2H-pyrrol-2-ylidene)methyl)-10-azabicyclo[7.2.1]dodeca-9(12),11-diene;

2-Benzyl-11-((3-ethoxy-5-(1H-pyrrol-2-yl)-2H-pyrrol-2-ylidene)methyl)-10-azabicyclo[7.2.1]dodeca-9(12),11-diene;

2-Ethyl-11-((3-ethoxy-5-(1H-pyrrol-2-yl)-2H-pyrrol-2-ylidene)methyl)-10-azabicyclo[7.2.1]dodeca-9(12),11-diene;

2-Methyl-13-((3-benzyloxy-5-(1H-pyrrol-2-yl)-2H-pyrrol-2-ylidene)methyl)-12-azabicyclo[9.2.1]tetradeca-11(14),13-diene;

13-((3-Benzyloxy-5-(1H-pyrrol-2-yl)-2H-pyrrol-2-ylidene)methyl)-12-azabicyclo[9.2.1]tetradeca-11(14),13-diene;

2-Ethyl-12-methyl-13-((3-benzyloxy-5-(1-methyl-1H-pyrrol-2-yl)-2H-pyrrol-2-ylidene)methyl)-12-azabicyclo[9.2.1]tetradeca-11(14),13-diene;

2-Ethyl-12-methyl-13-((3-benzyloxy-5-(1H-pyrrol-2-yl)-2H-pyrrol-2-ylidene)methyl)-12-azabicyclo[9.2.1]tetradeca-11(14),13-diene;

2-n-Propyl-13-((3-benzyloxy-5-(1H-pyrrol-2-yl)-2H-pyrrol-2-ylidene)methyl)-12-azabicyclo[9.2.1]tetradeca-11(14),13-diene; and 2-n-Butyl-13-((3-benzyloxy-5-(1H-pyrrol-2-yl)-2H-pyrrol-2-ylidene)methyl)-12-azabicyclo[9.2.1]tetradeca-11(14),13-diene or a pharmaceutically acceptable salt thereof.

For use in the present methods for treating or preventing a viral infection, a preferred subclass of the compounds of Formula (I) is that wherein, in the compound of Formula (I):

each $R_1$ is independently selected from the group consisting of —H, —CH$_3$, —CH$_2$CH$_3$, —CH$_2$C$_6$H$_5$, —C(O)OC(CH$_3$)$_3$, —C(O)OCH$_2$C$_6$H$_5$, and —C(O)CH$_3$;

$R_2$ is selected from the group consisting of —H, $C_1$–$C_{12}$ straight chain alkyl, —CH$_2$C$_6$H$_5$, —SiR$_{10}$R$_{11}$R$_{12}$, —C(O)CH$_3$, —C(O)C$_6$H$_5$, -2-tetrahydropyranyl, —OCH$_2$OCH$_3$, and —C(O)OCH$_2$CCl$_3$;

$R_3$ is selected from the group consisting of —H, $C_1$–$C_{12}$ straight chain alkyl, —CH(R$_{14}$)(R$_{15}$) wherein $R_{14}$ and $R_{15}$ are independently $C_1$–$C_{12}$ straight chain alkyl, —C(O)$C_1$–$C_9$ straight chain alkyl, —CH(OH)$C_1$–$C_9$ straight chain alkyl, —CH(Cl)$C_1$–$C_9$ straight chain alkyl, -(2-pyridyl)methyl, -(3-pyridyl)methyl, -(4-pyridyl)methyl, and —CH$_2$C$_6$H$_5$, the —CH$_2$C$_6$H$_5$ being unsubstituted or substituted on phenyl with one cyano or one or more halo, methoxyl, or trifluoromethyl groups;

$R_{10}$ is selected from the group consisting of $C_1$–$C_4$ straight or branched chain alkyl and —C$_6$H$_5$;

$R_{11}$ and $R_{12}$ are independently $C_1$–$C_3$ straight or branched chain alkyl; and $R_{16}$ and $R_{17}$ are —H; and m is an integer ranging from 1 to 5.

For use in the present methods for treating or preventing a viral infection, a second preferred subclass of the compounds of Formula (D is that wherein, in the compound of Formula (I):

each $R_1$ is independently selected from the group consisting of —H and —$CH_3$;

$R_2$ is selected from the group consisting of —$CH_3$, —$CH_2CH_3$, and —$CH_2C_6H_5$;

$R_3$ is selected from the group consisting of —H, $C_1$–$C_{10}$ straight chain alkyl, (1-methyl)butyl, —$CH_2C_6H_5$, butyroyl, (1-hydroxy)butyl, and (1-chloro)butyl;

$R_{16}$ and $R_{17}$ are —H; and m is an integer ranging from 1 to 5.

For use in the present methods for treating or preventing a viral infection, a third preferred subclass of the compounds of Formula (I) is that wherein, in the compound of Formula (I):

each $R_1$ is —H;

$R_2$ is selected from the group consisting of —$CH_3$ and —$CH_2C_6H_5$;

$R_3$ is selected from the group consisting of —H, $C_1$–$C_{10}$ straight chain alkyl, and —$CH_2C_6H_5$;

$R_{16}$ and $R_{17}$ are —H; and m is an integer ranging from 1 to 5.

For use in the present methods for treating or preventing a viral infection, a fourth preferred subclass of the compounds of Formula (I) is that wherein, in the compound of Formula (I):

each $R_1$ is independently selected from the group consisting of —H and —$CH_3$;

$R_2$ is selected from the group consisting of —$CH_3$ and —$CH_2C_6H_5$;

$R_3$ is selected from the group consisting of —H, $C_1$–$C_{10}$ straight chain alkyl, —$CH_2C_6H_5$, butyroyl, (1-hydroxy)butyl, and (1-chloro)butyl;

—$R_{16}$ and $R_{17}$ are —H; and m is an integer ranging from 1 to 5;

with the proviso that when m is 3, $R_3$ is not —$CH_2CH_3$ and when m is 1, $R_3$ is not —$(CH_2)_3CH_3$.

For use in the methods for treating or preventing a viral infection, a fifth preferred subclass of the compounds of Formula (I) is that wherein, in the compound of Formula (I):

each $R_1$ is independently selected from the group consisting of —H and —$CH_3$;

$R_2$ is selected from the group consisting of —$CH_3$ and —$CH_2C_6H_5$;

$R_3$ is selected from the group consisting of —H, $C_1$–$C_{10}$ straight chain alkyl, (1-methyl)butyl, —$CH_2C_6H_5$, butyroyl, (1-hydroxy)butyl, and (1-chloro)butyl;

$R_{16}$ and $R_{17}$ are —H; and m is an integer ranging from 1 to 5.

For use in the methods for treating or preventing a viral infection, a sixth preferred subclass of the compounds of Formula (I) is that wherein, in the compound of Formula (I):

each $R_1$ is independently selected from the group consisting of —H and —$CH_3$;

$R_2$ is selected from the group consisting of —$CH_3$ and —$CH_2C_6H_5$;

$R_3$ is selected from the group consisting of —H, $C_1$–$C_{10}$ straight chain alkyl, —$CH_2C_6H_5$, butyroyl, (1-hydroxy)butyl, and (1-chloro)butyl;

$R_{16}$ and $R_{17}$ are —H; and m is 2, 4, or 5.

For use in the present methods for treating or preventing a viral infection, a seventh preferred subclass of the compounds of Formula (I) is that wherein, in the compound of Formula (I):

each $R_1$ is independently selected from the group consisting of —H and —$CH_3$;

$R_1$ is selected from the group consisting of —$CH_3$, —$CH_2CH_3$, —$(CH_2)_2CH_3$, and —$CH_2C_6H_5$;

$R_3$ is selected from the group consisting of —H, $C_1$–$C_{10}$ straight chain alkyl, —$CH_2C_6H_5$, butyroyl, (1-hydxoxy)butyl, and (1-chloro)butyl;

m is an integer ranging from 1 to 5;

when m is 3 and $R_2$ is —$CH_3$, then $R_{16}$ is selected from the group consisting of —H and —$CH_3$ and $R_{17}$ is selected from the group consisting of —H and —COOEt; and when m is other than 3 and $R_2$ is other than —$CH_3$ or —$CH_2CH_3$, then $R_{16}$ and $R_{17}$ are —H only.

The invention further provides methods for inhibiting the replication or infectivity of a virus comprising a contacting a virus or a virus-infected cell with an effective amount of a composition comprising a pharmaceutically acceptable carrier and a compound having the general Formula (I) or a pharmaceutically acceptable salt thereof, wherein, in the compound of Formula (I):

each $R_1$ is independently selected from the group consisting of —H, —$CH_3$, —$CH_2CH_3$, —$CH_2C_6H_5$, —C(O)OC($CH_3$)$_3$, —C(O)O$CH_2C_6H_5$, and —C(O)$CH_3$;

$R_2$ is selected from the group consisting of —H, $C_1$–$C_{12}$ straight chain alkyl, —$CH_2C_6H_5$, —Si$R_{10}R_{11}R_{12}$, —C(O)$CH_3$, —C(O)$C_6H_5$, -2-tetrahydropyranyl, —$OCH_2OCH_3$, and —C(O)O$CH_2CCl_3$;

$R_3$ is selected from the group consisting of —H, $C_1$–$C_{12}$ straight chain alkyl, —CH($R_{14}$)($R_{15}$) wherein $R_{14}$ and $R_{15}$ are independently $C_1$–$C_{12}$ straight chain alkyl, —C(O)$C_1$–$C_9$ straight chain alkyl, —CH(OH)$C_1$–$C_9$ straight chain alkyl, —CH(Cl)$C_1$–$C_9$ straight chain alkyl, -(2-pyridyl)methyl, -(3-pyridyl)methyl, -(4-pyridyl)methyl, and —$CH_2C_6H_5$, the —$CH_2C_6H_5$ being unsubstituted or substituted on phenyl with one cyano or one or more halo, methoxyl, or trifluoromethyl groups;

$R_{10}$ is selected from the group consisting of $C_1$–$C_4$ straight or branched chain alkyl and —$C_6H_5$;

$R_{11}$ and $R_{12}$ are independently $C_1$–$C_3$ straight or branched chain alkyl;

m is an integer ranging from 1 to 5; and when m is 3 and $R_2$ is —$CH_2CH_3$, then $R_{16}$ is —H or —$CH_3$ and $R_{17}$ is —H;

when m is 3 and $R_2$ is —$CH_3$, then $R_{16}$ is —H or —$CH_3$ and $R_{17}$ is —H or —COOEt; and when m is other than 3 and $R_2$ is other than —$CH_3$ or —$CH_2CH_3$, then $R_{16}$ and $R_{17}$ are —H only.

A preferred compound for use in the methods for inhibiting the replication or infectivity of a virus is butyl-meta-cycloheptylprodiginine or a pharmaceutically acceptable salt thereof.

A preferred compound for use in the methods for inhibiting the replication or infectivity of a virus is metacycloprodigiosin or a pharmaceutically acceptable salt thereof.

Other preferred compounds for use in the method are selected from the group consisting of:

2-Ethyl-11-((3-methoxy-5-(1H-pyrrol-2-yl)-2H-pyrrol-2-ylidene)methyl)-10-azabicyclo[7.2.1]dodeca-9(12),11-diene;

11-((3-Methoxy-5-(1H-pyrrol-2-yl)-2H-pyrrol-2-ylidene) methyl)-10-azabicyclo[7.2.1]dodeca-9(12),11-diene;

2-Methyl-1-((3-methoxy-5-(1H-pyrrol-2-yl)-2H-pyrrol-2-ylidene)methyl)-10-azabicyclo[7.2.1]dodeca-9(12),11-diene;

2-n-Propyl-11-((3-methoxy-5-(1H-pyrrol-2-yl)-2H-pyrrol-2-ylidene)methyl)-10-azabicyclo[7.2.1]dodeca-9 (12),11-diene;

2-n-Pentyl-11-((3-methoxy-5-(1H-pyrrol-2-yl)-2H-pyrrol-2-ylidene)methyl)-10-azabicyclo[7.2.1]dodeca-9(12),11-diene;

2-Benzyl-11-((3-methoxy-5-(1H-pyrrol-2-yl)-2H-pyrrol-2-ylidene)methyl)-10-azabicyclo[7.2.1]dodeca-9(12),11-diene;

(S)-2-n-Pentyl-11-((3-methoxy-5-(1H-pyrrol-2-yl)-2H-pyrrol-2-ylidene)methyl)-10-azabicyclo[7.2.1]dodeca-9(12),11-diene;

(R)-2-n-Pentyl-11-((3-methoxy-5-(1H-pyrrol-2-yl)-2H-pyrrol-2-ylidene)methyl)-10-azabicyclo[7.2.1]dodeca-9(12),11-diene;

2-(S)-2-n-Butyl-11-((3-methoxy-5-(1H-pyrrol-2-yl)-2H-pyrrol-ylidene)methyl)-10-azabicyclo[7.2.1]dodeca-9(12),11-diene;

(R)-2-n-Butyl-11-((3-methoxy-5-(1H-pyrrol-2-yl)-2H-pyrrol-2-ylidene)methyl)-10-azabicyclo[7.2.1]dodeca-9(12),11-diene;

(S)-2-Ethyl-11-((3-methoxy-5-(1H-pyrrol-2-yl)-2H-pyrrol-2-ylidene)methyl)-10-azabicyclo[7.2.1]dodeca-9(12),11-diene;

(R)-2-Ethyl-11-((3-methoxy-5-(1H-pyrrol-2-yl)-2H-pyrrol-2-ylidene)methyl)-10-azabicyclo[7.2.1]dodeca-9(12),11-diene;

(S)-2-Methyl-11-((3-methoxy-5-(1H-pyrrol-2-yl)-2H-pyrrol-2-ylidene)methyl)-10-azabicyclo[7.2.1]dodeca-9(12),11-diene;

(R)-2-Methyl-11-((3-methoxy-5-(1H-pyrrol-2-yl)-2H-pyrrol-2-ylidene)methyl)-10-azabicyclo[7.2.1]dodeca-9(12),11-diene;

(S)-2-n-Propyl-11-((3-methoxy-5-(1H-pyrrol-2-yl)-2H-pyrrol-2-ylidene)methyl)-10-azabicyclo[7.2.1]dodeca-9(12),11-diene;

(R)-2-n-Propyl-11-((3-methoxy-5-(1H-pyrrol-2-yl)-2H-pyrrol-2-ylidene)methyl)-10-azabicyclo[7.2.1]dodeca-9(12),11-diene;

2-Methyl-12-((3-methoxy-5-(1H-pyrrol-2-yl)-2H-pyrrol-2-ylidene)methyl)-1-azabicyclo[8.2.1]trideca-10(13),12-diene;

2-Ethyl-12-((3-methoxy-5-(1H-pyrrol-2-yl)-2H-pyrrol-2-ylidene)methyl)-11-azabicyclo[8.2.1]trideca-10(13),12-diene;

2-n-Propyl-12-((3-methoxy-5-(1H-pyrrol-2-yl)-2H-pyrrol-2-ylidene)methyl)-11-azabicyclo[8.2.1]trideca-10(13),12-diene;

2-n-Butyl-12-((3-methoxy-5-(1H-pyrrol-2-yl)-2H-pyrrol-2-ylidene)methyl)-11-azabicyclo[8.2.1]trideca-10(13),12-diene;

2-n-Pentyl-12-((3-methoxy-5-(1H-pyrrol-2-yl)-2H-pyrrol-2-ylidene)methyl)-11-azabicyclo[8.2.1]trideca-10(13),12-diene;

12-((3-Methoxy-5-(1H-pyrrol-2-yl)-2H-pyrrol-2-ylidene)methyl)-11-azabicyclo[8.2.1]trideca-10(13),12-diene;

2-Methyl-13-((3-methoxy-5-(1H-pyrrol-2-yl)-2H-pyrrol-2-ylidene)methyl)-12-azabicyclo[9.2.1]tetradeca-11(14),13-diene;

13-((3-Methoxy-5-(1H-pyrrol-2-yl)-2H-pyrrol-2-ylidene)methyl)-12-azabicyclo[9.2.1]tetradeca-11(14),13-diene;

2-Ethyl-12-methyl-13-((3-methoxy-5-(1-methyl-1H-pyrrol-2-yl)-2H-pyrrol-2-ylidene)methyl)-12-azabicyclo[9.2.1]tetradeca-11(14),13-diene;

2-Ethyl-12-methyl-13-((3-methoxy-5-(1H-pyrrol-2-yl)-2H-pyrrol-2-ylidene)methyl)-12-azabicyclo[9.2.1]tetradeca-11(14),13-diene;

2-n-Propyl-13-((3-methoxy-5-(1H-pyrrol-2-yl)-2H-pyrrol-2-ylidene)methyl)-12-azabicyclo[9.2.1]tetradeca-11(14),13-diene;

2-n-Butyl-13-((3-methoxy-5-(1H-pyrrol-2-yl)-2H-pyrrol-2-ylidene)methyl)-12-azabicyclo[9.2.1]tetradeca-11(14),13-diene;

14-((3-Methoxy-5-(1H-pyrrol-2-yl)-2H-pyrrol-2-ylidene)methyl)-13-azabicyclo[10.2.1]pentadeca-12(15),14-diene;

2-Butyl-11-((3-methoxy-5-(1-methyl-1H-pyrrol-2-yl)-2H-pyrrol-2-ylidene)methyl)-10-azabicyclo[7.2.1]dodeca-9(12),11-diene;

2-Butyl-11-((3-methoxy-5-(1-methyl-1H-pyrrol-2-yl)-2H-pyrrol-2-ylidene)methyl)-10-methyl-10-azabicyclo[7.2.1]dodeca-9(12),11-diene;

2-Butyl-11-((3-methoxy-5-(1H-pyrrol-2-yl)-2H-pyrrol-2-ylidene)methyl)-10-methyl-10-azabicyclo[7.2.1]dodeca-9(12),11-diene;

2-Ethyl-11-((3-benzyloxy-5-(1H-pyrrol-2-yl)-2H-pyrrol-2-ylidene)methyl)-10-azabicyclo[7.2.1]dodeca-9(12),11-diene;

2-Butyl-11-((3-hydroxy-5-(1H-pyrrol-2-yl)-2H-pyrrol-2-ylidene)methyl)-10-azabicyclo[7.2.1]dodeca-9(12),11-diene;

2-Butyl-11-((3-benzyloxy-5-(1H-pyrrol-2-yl)-2H-pyrrol-2-ylidene)methyl)-10-azabicyclo[7.2.1]dodeca-9(12),11-diene;

11-((3-Benzyloxy-5-(1H-pyrrol-2-yl)-2H-pyrrol-2-ylidene)methyl)-10-azabicyclo[7.2.1]dodeca-9(12),11-diene;

2-Methyl-11-((3-benzyloxy-5-(1H-pyrrol-2-yl)-2H-pyrrol-2-ylidene)methyl)-10-azabicyclo[7.2.1]dodeca-9(12),11-diene;

2-n-Propyl-11-((3-benzyloxy-5-(1H-pyrrol-2-yl)-2H-pyrrol-2-ylidene)methyl)-10-azabicyclo[7.2.1]dodeca-9(12),11-diene;

2-n-Pentyl-11-((3-benzyloxy-5-(1H-pyrrol-2-yl)-2H-pyrrol-2-ylidene)methyl)-10-azabicyclo[7.2.1]dodeca-9(12),11-diene;

2-Benzyl-11-((3-benzyloxy-5-(1H-pyrrol-2-yl)-2H-pyrrol-2-ylidene)methyl)-10-azabicyclo[7.2.1]dodeca-9(12),11-diene;

2-Methyl-14-((3-methoxy-5-(1H-pyrrol-2-yl)-2H-pyrrol-2-ylidene)methyl)-13-azabicyclo[10.2.1]pentadeca-12(15),14-diene;

15-((3-Methoxy-5-(1H-pyrrol-2-yl)-2H-pyrrol-2-ylidene)methyl)-14-azabicyclo[11.2.1]pentadeca-13(16),15-diene;

2-Methyl-15-((3-methoxy-5-(1H-pyrrol-2-yl)-2H-pyrrol-2-ylidene)methyl)-14-azabicyclo[11.2.1]pentadeca-13(16),15-diene;

2-(2-Hydroxy-n-butyl)-11-((3-methoxy-5-(1H-pyrrol-2-yl)-2H-pyrrol-2-ylidene)methyl)-10-azabicyclo[7.2.1]dodeca-9(12),11-diene;

2-(2-Chloro-n-butyl)-11-((3-methoxy-5-(1H-pyrrol-2-yl)-2H-pyrrol-2-ylidene)methyl)-10-azabicyclo[7.2.1]dodeca-9(12),11-diene;

2-Butyl-11-((3-ethoxy-5-(1H-pyrrol-2-yl)-2H-pyrrol-2-ylidene)methyl)-10-azabicyclo[7.2.1]dodeca-9(12),11-diene;

11-((3-Ethoxy-5-(1H-pyrrol-2-yl)-2H-pyrrol-2-ylidene)methyl)-10-azabicyclo[7.2.1]dodeca-9(12),11-diene;

2-Methyl-11-((3-ethoxy-5-(1H-pyrrol-2-yl)-2H-pyrrol-2-ylidene)methyl)-10-azabicyclo[7.2.1]dodeca-9(12),11-diene;

2-n-Propyl-11-((3-ethoxy-5-(1H-pyrrol-2-yl)-2H-pyrrol-2-ylidene)methyl)-10-azabicyclo[7.2.1]dodeca-9(12),11-diene;

2-n-Pentyl-11-((3-ethoxy-5-(1H-pyrrol-2-yl)-2H-pyrrol-2-ylidene)methyl)-10-azabicyclo[7.2.1]dodeca-9(12),11-diene;

2-Benzyl-11-((3-ethoxy-5-(1H-pyrrol-2-yl)-2H-pyrrol-2-ylidene)methyl)-10-azabicyclo[7.2.1]dodeca-9(12),11-diene;

2-Ethyl-11-((3-ethoxy-5-(1H-pyrrol-2-yl)-2H-pyrrol-2-ylidene)methyl)-10-azabicyclo[7.2.1]dodeca-9(12),11-diene;

2-Methyl-13-((3-benzyloxy-5-(1H-pyrrol-2-yl)-2H-pyrrol-2-ylidene)methyl)-12-azabicyclo[9.2.1]tetradeca-11(14),13-diene;

13-((3-Benzyloxy-5-(1H-pyrrol-2-yl)-2H-pyrrol-2-ylidene)methyl)-12-azabicyclo[9.2.1]tetradeca-11(14),13-diene;

2-Ethyl-12-methyl-13-((3-benzyloxy-5-(1-methyl-1H-pyrrol-2-yl)-2H-pyrrol-2-ylidene)methyl)-12-azabicyclo[9.2.1]tetradeca-11(14),13-diene;

2-Ethyl-12-methyl-13-((3-benzyloxy-5-(1H-pyrrol-2-yl)-2H-pyrrol-2-ylidene)methyl)-12-azabicyclo[9.2.1]tetradeca-11(14),13-diene;

2-n-Propyl-13-((3-benzyloxy-5-(1H-pyrrol-2-yl)-2H-pyrrol-2-ylidene)methyl)-12-azabicyclo[9.2.1]tetradeca-11(14),13-diene; and 2-n-Butyl-13-((3-benzyloxy-5-(1H-pyrrol-2-yl)-2H-pyrrol-2-ylidene)methyl)-12-azabicyclo[9.2.1]tetradeca-11(14),13-diene or a pharmaceutically acceptable salt thereof.

For use in the methods for inhibiting the replication or infectivity of a virus, a preferred subclass of the compounds of Formula (1) are those wherein:

each $R_1$ is independently selected from the group consisting of —H, —$CH_3$, —$CH_2CH_3$, —$CH_2C_6H_5$, —$C(O)C(CH_3)_3$, —$C(O)OCH_2C_6H_5$, and —$C(O)CH_3$;

$R_2$ is selected from the group consisting of —H, $C_1$–$C_{12}$ straight chain alkyl, —$CH_2C_6H_5$, —$SiR_{10}R_{11}R_{12}$, —$C(O)CH_3$, —$C(O)C_6H_5$, -2-tetrahydropyranyl, —$OCH_2OCH_3$, and —$C(O)OCH_2CCl_3$;

$R_3$ is selected from the group consisting of —H, $C_1$–$C_{12}$ straight chain alkyl, —$CH(R_{14})(R_{15})$ wherein $R_{14}$ and $R_{15}$ are independently $C_1$–$C_{12}$ straight chain alkyl, —$C(O)C_1$–$C_9$ straight chain alkyl, —$CH(OH)C_1$–$C_9$ straight chain alkyl, —$CH(Cl)C_1$–$C_9$ straight chain alkyl, -(2-pyridyl)methyl, -(3-pyridyl)methyl, -(4-pyridyl)methyl, and —$CH_2C_6H_5$, the —$CH_2C_6H_5$ being unsubstituted or substituted on phenyl with one cyano or one or more halo, methoxyl, or trifluoromethyl groups;

$R_{10}$ is selected from the group consisting of $C_1$–$C_4$ straight or branched chain alkyl, and —$C_6H_5$;

$R_{11}$ and $R_{12}$ are independently $C_1$–$C_3$ straight or branched chain alkyl; and $R_{16}$ and $R_{17}$ are —H; and m is an integer ranging from 1 to 5.

For use in the methods for inhibiting the replication or infectivity of a virus, a second preferred subclass of the compounds of Formula (I) is that wherein, in the compound of Formula (I):

each $R_1$ is independently selected from the group consisting of —H and —$CH_3$;

$R_2$ is selected from the group consisting of —$CH_3$, —$CH_2CH_3$, and —$CH_2C_6H_5$;

$R_3$ is selected from the group consisting of —H, $C_1$–$C_{10}$ straight chain alkyl, (1-methyl)butyl, —$CH_2C_6H_5$, butyroyl, (1-hydroxy)butyl, and (1-chloro)butyl;

$R_{16}$ and $R_{17}$ are —H; and m is an integer ranging from 1 to 5.

For use in the methods for inhibiting the replication or infectivity of a virus, a third preferred subclass of the compounds of Formula (I) is that wherein, in the compound of Formula (I):

each $R_1$ is —H;

$R_2$ is selected from the group consisting of —$CH_3$ and —$CH_2C_6H_5$;

$R_3$ is selected from the group consisting of —H, $C_1$–$C_{10}$ straight chain alkyl, and —$CH_2C_6H_5$;

$R_{16}$ and $R_{17}$ are —H; and m is an integer ranging from 1 to 5.

For use in the methods for inhibiting the replication or infectivity of a virus, a fourth preferred subclass of the compounds of Formula (I) is that wherein, in the compound of Formula (I):

each $R_1$ is independently selected from the group consisting of —H and —$CH_3$;

$R_2$ is selected from the group consisting of —$CH_3$ and —$CH_2C_6H_5$;

$R_3$ is selected from the group consisting of —H, $C_1$–$C_{10}$ straight chain alkyl, —$CH_2C_6H_5$ butyroyl, (1-hydroxy)butyl, and (1-chloro)butyl;

$R_{16}$ and $R_{17}$ are —H; and m is an integer ranging from 1 to 5;

with the proviso that when m is 3, $R_3$ is not —$CH_2CH_3$ and when m is 1, $R_3$ is not —$(CH_2)_3CH_3$.

For use in the methods for inhibiting the replication or infectivity of a virus, a fifth preferred subclass of the compounds of Formula (I) is that wherein, in the compound of Formula (I):

each $R_1$ is independently selected from the group consisting of —H and —$CH_3$;

$R_2$ is selected from the group consisting of —$CH_3$ and —$CH_2C_6H_5$;

$R_3$ is selected from the group consisting of —H, $C_1$–$C_{10}$ straight chain alkyl, (1-methyl)butyl, —$CH_2C_6H_5$, butyroyl, (1-hydroxy)butyl, and (1-chloro)butyl;

$R_{16}$ and $R_{17}$ are —H; and m is an integer ranging from 1 to 5.

For use in the methods for inhibiting the replication or infectivity of a virus, a sixth preferred subclass of the compounds of Formula (I) is that wherein, in the compound of Formula (I):

each $R_1$ is independently selected from the group consisting of —H and —$CH_3$;

$R_2$ is selected from the group consisting of —$CH_3$ and —$CH_2C_6H_5$;

$R_3$ is selected from the group consisting of —H, $C_1$–$C_{10}$ straight chain alkyl, —$CH_2C_6H_5$, butyroyl, (1-hydroxy)butyl, and (1-chloro)butyl;

$R_{16}$ and $R_{17}$ are —H; and m is 2, 4, or 5.

For use in the methods for inhibiting the replication or infectivity of a virus, a seventh preferred subclass of the compounds of Formula (I) is that wherein, in the compound of Formula (I):

each $R_1$ is independently selected from the group consisting of —H and —$CH_3$;

$R_2$ is selected from the group consisting of —$CH_3$, —$CH_2CH_3$, —$(CH_2)_2CH_3$, and —$CH_2C_6H_5$;

$R_3$ is selected from the group consisting of —H, $C_1$–$C_{10}$ straight chain alkyl, —$CH_2C_6H_5$, butyroyl, (1-hydxoxy)butyl, and (1-chloro)butyl;

m is an integer ranging from 1 to 5;

when m is 3 and $R_2$ is —$CH_3$, then $R_{16}$ is selected from the group consisting of —H and —$CH_3$ and $R_{17}$ is selected from the group consisting of —H and —COOEt; and when m is other than 3 and $R_2$ is other than —$CH_3$ or —$CH_2CH_3$, then $R_{16}$ and $R_{17}$ are —H only.

4.2. FORMULA II

The present invention still further provides novel compounds having the general Formula (II):

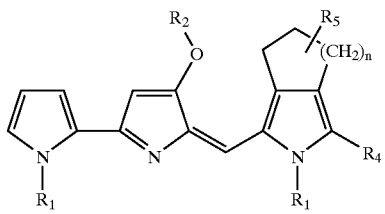

II and pharmaceutically acceptable salts thereof, wherein:

each $R_1$ is independently selected from the group consisting of —H, —$CH_3$, —$CH_2CH_3$, —$CH_2C_6H_5$, —$C(O)OC(CH_3)_3$, —$C(O)OCH_2C_6H_5$ and —$C(O)CH_3$;

$R_2$ is selected from the group consisting of —H, $C_1$–$C_{12}$ straight chain alkyl, —$CH_2C_6H_5$, —$SiR_{10}R_{11}R_{12}$, —$C(O)CH_3$, —$C(O)C_6H_5$, -2-tetrahydropyranyl, —$OCH_2OCH_3$, and —$C(O)OCH_2CCl_3$;

$R_4$ is selected from the group consisting of —H and $C_1$–$C_{12}$ straight chain alkyl;

$R_5$ is selected from the group consisting of —H, $C_1$–$C_4$ straight chain alkyl and —$C_6H_5$;

$R_{10}$ is selected from the group consisting of —$C_1$–$C_4$, straight or branched chain alkyl and —$C_6H_5$;

$R_{11}$ and $R_{12}$ are independently $C_1$–$C_3$ straight or branched chained alkyl; and n is an integer ranging from 1 to 6;

with the proviso that the compound of Formula (II) is not:
cycloprodigiosin, or
4-ethyl-2,4,5,6-tetrahydro-3-((3-methoxy-5-(1H-pyrrol-2-yl-)-2H-pyrrol-2-ylidene)methyl)-1-methyl-cyclopenta(c)pyrrole.

The compounds of Formula (II) and pharmaceutically acceptable salts thereof are useful for treating or preventing cancer or neoplastic disease in a patient in need of such treatment or prevention. The compounds of Formula (II) and pharmaceutically acceptable salts thereof are also useful for inhibiting the growth of a cancer cell or neoplastic cell. The compounds of Formula (II) and pharmaceutically acceptable salts thereof are useful for treating or preventing a viral infection in a patient in need of such treatment or prevention. The compounds of Formula (II) and pharmaceutically acceptable salts thereof are also useful for inhibiting the replication or infectivity of a virus.

A preferred subclass of the compounds of Formula (II) is that wherein:

$R_1$ is selected from the group consisting of —H and —$CH_3$;

$R_2$ is selected from the group consisting of —$CH_3$, —$CH_2CH_3$, and —$CH_2C_6H_5$;

$R_4$ and $R_5$ are independently selected from the group consisting of —H, —$CH_3$, and —$CH_2CH_3$; and n is an integer ranging from 1 to 3.

with the proviso that the compound of Formula (II) is not:
cycloprodigiosin or
4-ethyl-2,4,5,6-tetrahydro-3-((3-methoxy-5-(1H-pyrrol-2-yl-)-2H-pyrrol-2-ylidene)methyl)-1-methyl-cyclopenta(c)pyrrole.

A preferred second subclass of the compounds of Formula (II) is that wherein:

$R_1$ is selected from the group consisting of —H and —$CH_3$;

$R_2$ is selected from the group consisting of —$CH_3$, —$CH_2CH_3$, and —$CH_2C_6H_5$;

$R_4$ is selected from the group consisting of —H and $C_1$–$C_{12}$ straight chain alkyl;

$R_5$ is —H; and n is an integer ranging from 1 to 3.

A third preferred subclass of the compounds of Formula (II) is that wherein:

$R_1$ is selected from the group consisting of —H and —$CH_3$;

$R_2$ is selected from the group consisting of —$CH_3$, —$CH_2CH_3$, and —$CH_2C_6H_5$;

$R_4$ is —H;

$R_5$ is selected from the group consisting of —H, —$CH_3$, —$CH_2CH_3$, —$C_3H_7$, -n-$C_4H_9$, and —$C_6H_5$; and n is an integer ranging from 1 to 3.

In a preferred embodiment, the compounds of Formula (II) are selected from the group consisting of:

4,5,6,7-Tetrahydro-3-((3-benzyloxy-5-(1-methyl-1H-pyrrol-2-yl)-2H-pyrrol-2-ylidene)methyl)-1,4-dimethyl-2H-isoindole;

4,5,6,7-Tetrahydro-3-((3-methoxy-5-(1H-pyrrol-2-yl)-2H-pyrrol-2-ylidene)methyl)-4-ethyl-2H-isoindole; 4,5,6,7-Tetrahydro-3-((3-methoxy-5-(1H-pyrrol-2-yl)-2H-pyrrol-2-ylidene)methyl)-4-ethyl-1-methyl-2H-isoindole;

4,5,6,7-Tetrahydro-3-((3-methoxy-5-(1H-pyrrol-2-yl)-2H-pyrrol-2-ylidene)methyl)-1,4-diethyl-2H-isoindole;

4,5,6,7-Tetrahydro-3-((3-methoxy-5-(1H-pyrrol-2-yl)-2H-pyrrol-2-ylidene)methyl)-1-ethyl-4-methyl-2H-isoindole; and 4,5,6,7-Tetrahydro-3-((3-methoxy-5-(1H-pyrrol-2-yl)-2H-pyrrol-2-ylidene)methyl)-1-ethyl-2H-isoindole or a pharmaceutically acceptable salt thereof.

The present invention further provides compositions comprising a pharmaceutically acceptable carrier and a therapeutically effective amount of a compound of Formula (II) or a pharmaceutically acceptable salt thereof, wherein, in the compound of Formula (II):

each $R_1$ is independently selected from the group consisting of —H, —$CH_3$, —$CH_2CH_3$, —$CH_2C_6H_5$, —$C(O)OC(CH_3)_3$, —$C(O)OCH_2C_6H_5$, and —$C(O)CH_3$;

$R_1$ is selected from the group consisting of —H, $C_1$–$C_{12}$ straight chain alkyl, —$CH_2C_6H_5$, —$SiR_{10}R_1 R_{12}$, —$C(O)CH_3$, —$C(O)C_6H_5$, -2-tetrahydropyranyl, —$OCH_2OCH_3$, and —$C(O)OCH_2CCl_3$;

$R_4$ is selected from the group consisting of —H and $C_1$–$C_{12}$ straight chain alkyl;

$R_5$ is selected from the group consisting of —H, $C_1$–$C_4$ straight chain alkyl and —$C_6H_5$;

$R_{10}$ is selected from the group consisting of $C_1$–$C_4$ straight or branched chain alkyl, and —$C_6H_5$;

$R_{11}$ and $R_{12}$ are independently selected from the group consisting of —$CH_3$, —$CH_2CH_3$, and —$C_3H_7$; and n is an integer ranging from 1 to 6;

with the proviso that the compound of Formula (II) is not:
cycloprodigiosin, or
4-ethyl-2,4,5,6-tetrahydro-3-((3-methoxy-5-(1H-pyrrol-2-yl-)-2H-pyrrol-2-ylidene)methyl)-1-methyl-cyclopenta(c)pyrrole.

The compositions comprising a pharmaceutically acceptable carrier and a compound of Formula (II) or a pharmaceutically acceptable salt thereof are useful for treating or preventing cancer or neoplastic disease in a patient in need of such treatment or prevention. These compositions are also useful for inhibiting the growth of a cancer cell or neoplastic cell. The compositions comprising a pharmaceutically acceptable carrier and a compound of Formula (II) or a pharmaceutically acceptable salt thereof are useful for treating or preventing a viral infection in a patient in need of such treatment or prevention. These compositions are also useful for inhibiting the replication and/or infectivity of a virus. A preferred subclass of the compositions comprising a pharmaceutically acceptable carrier and a compound of Formula (II) or a pharmaceutically acceptable salt thereof is that wherein, in the compound of Formula (II):

$R_1$ is selected from the group consisting of —H and —$CH_3$;

$R_2$ is selected from the group consisting of —$CH_3$, —$CH_2CH_3$, and —$CH_2C_6H_5$;

$R_4$ and $R_5$ are independently selected from the group consisting of —H, —$CH_3$, and —$CH_2CH_3$;

n is an integer ranging from 1 to 3.

with the proviso that the compound of Formula (II) is not:
cycloprodigiosin or
4-ethyl-2,4,5,6-tetrahydro-3-((3-methoxy-5-(1H-pyrrol-2-yl-)-2H-pyrrol-2-ylidene)methyl)-1-methyl-cyclopenta(c)pyrrole.

A second preferred subclass of the compositions comprising a pharmaceutically acceptable carrier and a compound of Formula (II) or a pharmaceutically acceptable salt thereof is that wherein, in the compound of Formula (II):

$R_1$ is selected from the group consisting of —H and —$CH_3$;

$R_2$ is selected from the group consisting of —$CH_3$, —$CH_2CH_3$, and —$CH_2C_6H_5$, $R_4$ is selected from the group consisting of —H, —$CH_3$, —$CH_2CH_3$, and a $C_3$–$C_{12}$ straight chain alkyl;

$R_5$ is —H; and n is an integer ranging from 1 to 3.

A third preferred subclass of the compositions comprising a pharmaceutically acceptable carrier and a compound of Formula (II) or a pharmaceutically acceptable salt thereof is that wherein, in the compound of Formula (II):

$R_1$ is selected from the group consisting of —H and —$CH_3$;

$R_2$ is selected from the group consisting of —$CH_3$, —$CH_2CH_3$, and —$CH_2C_6H_5$;

$R_4$ is —H;

$R_5$ is selected from the group consisting of —H, —$CH_3$, —$CH_2CH_3$, —$C_3H_7$, -n-$C_4H_9$, and —$C_6H_5$; and n is an integer ranging from 1 to 3.

In preferred embodiments, the compositions comprising a pharmaceutically acceptable carrier and a compound of Formula (II) or a pharmaceutically acceptable salt thereof is that, in the compound of Formula (II) is selected from the group consisting of:

4,5,6,7-Tetrahydro-3-((3-benzyloxy-5-(1-methyl-1H-pyrrol-2-yl)-2H-pyrrol-2-ylidene)methyl)-1,4-dimethyl-2H-isoindole;

4,5,6,7-Tetrahydro-3-((3-methoxy-5-(1H-pyrrol-2-yl)-2H-pyrrol-2-ylidene)methyl)-4-ethyl-2H-isoindole;

4,5,6,7-Tetrahydro-3-((3-methoxy-5-(1H-pyrrol-2-yl)-2H-pyrrol-2-ylidene)methyl)-4-ethyl-1-methyl-2H-isoindole;

4,5,6,7-Tetrahydro-3-((3-methoxy-5-(1H-pyrrol-2-yl)-2H-pyrrol-2-ylidene)methyl)-1,4-diethyl-2H-isoindole;

4,5,6,7-Tetrahydro-3-((3-methoxy-5-(1H-pyrrol-2-yl)-2H-pyrrol-2-ylidene)methyl)-1-ethyl-4-methyl-2H-isoindole; and 4,5,6,7-Tetrahydro-3-((3-methoxy-5-(1H-pyrrol-2-yl)-2H-pyrrol-2-ylidene)methyl)-1-ethyl-2H-isoindole or a pharmaceutically acceptable salt thereof.

The invention provides methods for treating or preventing cancer or a neoplastic disease comprising administering to a patient in need of such treatment or prevention a composition comprising a therapeutically effective amount of a compound of Formula (II) or a pharmaceutically acceptable salt thereof, wherein:

each $R_1$ is independently selected from the group consisting of —H, —$CH_3$, —$CH_2CH_3$, —$CH_2C_6H_5$, —C(O)OC($CH_3$)$_3$, —C(O)O$CH_2C_6H_5$, and —C(O)$CH_3$;

$R_2$ is selected from the group consisting of —H, $C_1$–$C_{12}$ straight chain alkyl, —$CH_2C_6H$, —$SiR_{10}R_{11}R_{12}$, —C(O)$CH_3$, —C(O)$C_6H_5$, -2-tetrahydropyranyl, —$OCH_2OCH_3$, and —C(O)O$CH_2CCl_3$;

$R_4$ is selected from the group consisting of —H and $C_1$–$C_{12}$ straight chain alkyl;

$R_5$ is selected from the group consisting of —H, $C_1$–$C_4$ straight chain alkyl and —$C_6H_5$;

$R_{10}$ is selected from the group consisting of $C_1$–$C_4$ straight or branched chain alkyl, and —$C_6H_5$;

$R_{11}$ and $R_{12}$ are independently selected from the group consisting of $C_1$–$C_3$ straight or branched chain alkyl; and n is an integer ranging from 1 to 6;

with the proviso that the compound of Formula (II) is not:
cycloprodigiosin.

A preferred compound for use in treating or preventing cancer or a neoplastic disease is:
4-ethyl-2,4,5,6-tetrahydro-3-((3-methoxy-5-(1H-pyrrol-2-yl-)-2H-pyrrol-2-ylidene)methyl)-1-methyl-cyclopenta(c)pyrrole or a pharmaceutically acceptable salt thereof.

Other preferred compounds for the method are selected from the group consisting of:

4,5,6,7-Tetrahydro-3-((3-benzyloxy-5-(1-methyl-1H-pyrrol-2-yl)-2H-pyrrol-2-ylidene)methyl)-1,4-dimethyl-2H-isoindole;

4,5,6,7-Tetrahydro-3-((3-methoxy-5-(1H-pyrrol-2-yl)-2H-pyrrol-2-ylidene)methyl)-4-ethyl-2H-isoindole;

4,5,6,7-Tetrahydro-3-((3-methoxy-5-(1H-pyrrol-2-yl)-2H-pyrrol-2-ylidene)methyl)-4-ethyl-1-methyl-2H-isoindole;

4,5,6,7-Tetrahydro-3-((3-methoxy-5-(1H-pyrrol-2-yl)-2H-pyrrol-2-ylidene)methyl)-1,4-diethyl-2H-isoindole;

4,5,6,7-Tetrahydro-3-((3-methoxy-5-(1H-pyrrol-2-yl)-2H-pyrrol-2-ylidene)methyl)-1-ethyl-4-methyl-2H-isoindole; and 4,5,6,7-Tetrahydro-3-((3-methoxy-5-(1H-pyrrol-2-yl)-2H-pyrrol-2-ylidene)methyl)-1-ethyl-2H-isoindole or a pharmaceutically acceptable salt thereof.

For use in treating or preventing cancer or a neoplastic disease, a preferred subclass of the compounds of Formula (II) are those wherein, in the compound of Formula (II):

$R_1$ is selected from the group consisting of —H and —$CH_3$;

$R_2$ is selected from the group consisting of —$CH_3$, —$CH_2CH_3$, and —$CH_2C_6H_5$;

$R_4$ and $R_5$ are independently selected from the group consisting of —H, —$CH_3$, and —$CH_2CH_3$;

n is an integer ranging from 1 to 3.

with the proviso that the compound of Formula (II) is not:
cycloprodigiosin.

For use in treating or preventing cancer or a neoplastic disease, a second preferred subclass of the compounds of Formula (II) is that wherein, in the compound of Formula (II):

$R_1$ is selected from the group consisting of —H and —$CH_3$;

$R_2$ is selected from the group consisting of —$CH_3$, —$CH_2CH_3$, and —$CH_2C_6H_5$;

$R_4$ is selected from the group consisting of —H, —$CH_3$, —$CH_2CH_3$, and a $C_3$–$C_{12}$ straight chain alkyl;

R is —H; and n is an integer ranging from 1 to 3.

For use in treating or preventing cancer or a neoplastic disease, a third preferred subclass of the compounds of Formula (II) is that wherein, in the compound of Formula (II):

$R_1$ is selected from the group consisting of —H, and —$CH_3$;

$R_2$ is selected from the group consisting of —$CH_3$, —$CH_2CH_3$, and —$CH_2C_6H_5$; $R_4$ is —H;

R is selected from the group consisting of —H, —$CH_3$, —$CH_2CH_3$, —$C_3H_7$, -n-$C_4H_9$, and —$C_6H_5$; and n is an integer ranging from 1 to 3.

For use in treating or preventing cancer or a neoplastic disease, a fourth preferred subclass of the compounds of Formula (II) is that wherein, in the compound of Formula (II):

$R_1$ is selected from the group consisting of —H and —$CH_3$;

$R_2$ is selected from the group consisting of —$CH_3$, —$CH_2CH_3$, and —$CH_2C_6H_5$;

$R_4$ is selected from the group consisting of —H, —$CH_3$, —$CH_2CH_3$, and a $C_3$–$C_{12}$ straight chain alkyl;

$R_5$ is selected from the group consisting of —H, —$CH_3$, —$CH_2CH_3$, —$C_3H_7$, -n-$C_4H_9$, and —$C_6H_5$; and n is an integer ranging from 1 to 3;

with the proviso that the compound of Formula (II) is not: cycloprodigiosin.

The invention provides methods for inhibiting the growth of a cancer cell or neoplastic cell comprising a contacting a cancer cell or neoplastic cell with an effective amount of a composition comprising a pharmaceutically acceptable carrier and a compound having the general Formula (II) or a pharmaceutically acceptable salt thereof, wherein:

each $R_1$ is independently selected from the group consisting of —H, —$CH_3$, —$CH_2CH_3$, —$CH_2C_6H_5$, —$C(O)OC(CH_3)_3$, —$C(O)OCH_2C_6H_5$ and —$C(O)CH_3$;

$R_2$ is selected from the group consisting of —H, $C_1$–$C_{12}$ straight chain alkyl, —$CH_2C_6H_5$, —$SiR_{10}R_{11}R_{12}$, —$C(O)CH_3$, —$C(O)C_6H_5$, -2-tetrahydropyranyl, —$OCH_2OCH_3$, and —$C(O)OCH_2CCl_3$;

$R_4$ is selected from the group consisting of —H and $C_1$–$C_{12}$ straight chain alkyl;

$R_1$ is selected from the group consisting of —H, $C_1$–$C_4$ straight chain alkyl and —$C_6H_5$;

$R_{10}$ is selected from the group consisting of $C_1$–$C_4$ straight or branched chain alkyl and —$C_6H_5$;

$R_{11}$ and $R_{12}$ are independently $C_1$–$C_3$ straight or branched chain alkyl; and n is a integer from 1 to 6;

with the proviso that the compound of Formula (II) is not: cycloprodigiosin.

A preferred compound for use in the methods for inhibiting the growth of a cancer or neoplastic cell is:

4-ethyl-2,4,5,6-tetrahydro-3-((3-methoxy-5-(1H-pyrrol-2-yl-)-2H-pyrrol-2-ylidene)methyl)-1-methyl-cyclopenta(c)pyrrole or a pharmaceutically acceptable salt thereof.

Other preferred compounds for the method are selected from the group consisting of:

4,5,6,7-Tetrahydro-3-((3-benzyloxy-5-(1-methyl-1H-pyrrol-2-yl)-2H-pyrrol-2-ylidene)methyl)-1,4-dimethyl-2H-isoindole;

4,5,6,7-Tetrahydro-3-((3-methoxy-5-(1H-pyrrol-2-yl)-2H-pyrrol-2-ylidene)methyl)-4-ethyl-2H-isoindole;

4,5,6,7-Tetrahydro-3-((3-methoxy-5-(1H-pyrrol-2-yl)-2H-pyrrol-2-ylidene)methyl)-4-ethyl-1-methyl-2H-isoindole;

4,5,6,7-Tetrahydro-3-((3-methoxy-5-(1H-pyrrol-2-yl)-2H-pyrrol-2-ylidene)methyl)-1,4-diethyl-2H-isoindole;

4,5,6,7-Tetrahydro-3-((3-methoxy-5-(1H-pyrrol-2-yl)-2H-pyrrol-2-ylidene)methyl)-1-ethyl-4-methyl-2H-isoindole; and 4,5,6,7-Tetrahydro-3-((3-methoxy-5-(1H-pyrrol-2-yl)-2H-pyrrol-2-ylidene)methyl)-1-ethyl-2H-isoindole or a pharmaceutically acceptable salt thereof.

For use in the present methods for inhibiting the growth of a cancer or neoplastic cell, a preferred subclass of the compounds of Formula (II) is that wherein, in the compound of Formula (II):

$R_1$ is selected from the group consisting of —H and —$CH_3$;

$R_2$ is selected from the group consisting of —$CH_3$, —$CH_2CH_3$, and —$CH_2C_6H_5$;

$R_4$ and $R_5$ are independently selected from the group consisting of —H, —$CH_3$, and —$CH_2CH_3$; and n is an integer ranging from 1 to 3;

with the proviso that the compound of Formula (II) is not: cycloprodigiosin.

For use in the present methods for inhibiting the growth of a cancer or neoplastic cell, a second preferred subclass of the compounds of Formula (II) is that wherein, in the compound of Formula (II):

$R_1$ is selected from the group consisting of —H and —$CH_3$;

$R_2$ is selected from the group consisting of —$CH_3$, —$CH_2CH_3$, and —$CH_2C_6H_5$;

$R_4$ is selected from the group consisting of —H, —$CH_3$, —$CH_2CH_3$, and a $C_3$–$C_{12}$ straight chain alkyl;

$R_5$ is —H; and n is an integer ranging from 1 to 3.

For use in the present methods for inhibiting the growth of a cancer or neoplastic cell, a third preferred subclass of the compounds of Formula (II) is that wherein, in the compound of Formula (II):

$R_1$ is selected from the group consisting of —H and —$CH_3$;

$R_2$ is selected from the group consisting of —$CH_3$, —$CH_2CH_3$, and —$CH_2C_6H_5$;

$R_4$ is —H;

$R_1$ is selected from the group consisting of —H, —$CH_3$, —$CH_2CH_3$, —$C_3H_7$, -n-$C_4H_9$, and —$C_6H_5$;

n is a integer from 1 to 3.

For use in the present methods for inhibiting the growth of a cancer or neoplastic cell, a fourth preferred subclass of the compounds of Formula (1H) is that wherein, in the compound of Formula (II):

$R_1$ is selected from the group consisting of —H and —$CH_3$;

$R_2$ is selected from the group consisting of —$CH_3$, —$CH_2CH_3$, and —$CH_2C_6H_5$;

$R_4$ is selected from the group consisting of —H, —$CH_3$, —$CH_2CH_3$, and a $C_3$–$C_{12}$ straight chain alkyl;

$R_5$ is selected from the group consisting of —H, —$CH_3$, —$CH_2CH_3$, —$C_3H_7$, -n-$C_4H_9$, and —$C_6H_5$; and n is an integer ranging from 1 to 3;

with the proviso that the compound of Formula (II) is not: cycloprodigiosin.

The invention provides methods for treating or preventing a viral infection comprising administering to a patient in need of such treatment or prevention a therapeutically effective amount of a composition comprising a pharmaceutically acceptable carrier and a compound of Formula (II) or a pharmaceutically acceptable salt thereof, wherein:

each $R_1$ is independently selected from the group consisting of —H, —$CH_3$, —$CH_2CH_3$, —$CH_2C_6H_5$, —$C(O)OC(CH_3)_3$, —$C(O)OCH_2C_6H_5$, and —$C(O)CH_3$;

$R_2$ is selected from the group consisting of —H, $C_1$–$C_{12}$ straight chain alkyl, —$CH_2C_6H_5$, —$SiR_{10}R_{11}R_{12}$, —C(O)$CH_3$, —C(O)$C_6H_5$, -2-tetrahydropyranyl, —$OCH_2OCH_3$, and —C(O)$OCH_2CCl_3$;

$R_4$ is selected from the group consisting of —H and $C_1$–$C_{12}$ straight chain alkyl;

$R_5$ is selected from the group consisting of —H, $C_1$–$C_4$ straight chain alkyl and —$C_6H_5$;

$R_{10}$ is selected from the group consisting of $C_1$–$C_4$ straight or branched chain alkyl, and —$C_6H_5$;

$R_{11}$ and $R_{12}$ are independently $C_1$–$C_3$ straight or branched chain alkyl; and n is a integer from 1 to 6.

Preferred compounds for use in the method for treating or preventing a viral infection are:

cycloprodigiosin and 4-ethyl-2,4,5,6-tetrahydro-3-((3-methoxy-5-(1H-pyrrol-2-yl-)-2H-pyrrol-2-ylidene)methyl)-1-methyl-cyclopenta(c) pyrrole, or pharmaceutically acceptable salts thereof.

Other preferred compounds for the method are selected from the group consisting of:

4,5,6,7-Tetrahydro-3-((3-benzyloxy-5-(1-methyl-1H-pyrrol-2-yl)-2H-pyrrol-2-ylidene)methyl)-1,4-dimethyl-2H-isoindole;

4,5,6,7-Tetrahydro-3-((3-methoxy-5-(1H-pyrrol-2-yl)-2H-pyrrol-2-ylidene)methyl)-4-ethyl-2H-isoindole;

4,5,6,7-Tetrahydro-3-((3-methoxy-5-(1H-pyrrol-2-yl)-2H-pyrrol-2-ylidene)methyl)-4-ethyl-1-methyl-2H-isoindole;

4,5,6,7-Tetrahydro-3-((3-methoxy-5-(1H-pyrrol-2-yl)-2H-pyrrol-2-ylidene)methyl)-1,4-diethyl-2H-isoindole;

4,5,6,7-Tetrahydro-3-((3-methoxy-5-(1H-pyrrol-2-yl)-2H-pyrrol-2-ylidene)methyl)-1-ethyl-4-methyl-2H-isoindole; and 4,5,6,7-Tetrahydro-3-((3-methoxy-5-(1H-pyrrol-2-yl)-2H-pyrrol-2-ylidene)methyl)-1-ethyl-2H-isoindole or a pharmaceutically acceptable salt thereof.

For use in the present methods for treating or preventing a viral infection, a preferred subclass of the compounds of Formula (II) is that wherein, in the compound of Formula (II):

$R_1$ is selected from the group consisting of —H and —$CH_3$;

$R_2$ is selected from the group consisting of —$CH_3$, —$CH_2CH_3$, and —$CH_2C_6H_5$;

$R_4$ and $R_5$ are independently selected from the group consisting of —H, —$CH_3$, and —$CH_2CH_3$; and n is an integer ranging from 1 to 3.

For use in the present methods for treating or preventing a viral infection, a second preferred subclass of the compounds of Formula (II) is that wherein, in the compound of Formula (II):

$R_1$ is selected from the group consisting of —H and —$CH_3$;

$R_2$ is selected from the group consisting of —$CH_3$, —$CH_2CH_3$, and —$CH_2C_6H_5$;

$R_4$ is selected from the group consisting of —H, —$CH_3$, —$CH_2CH_3$, and a $C_3$–$C_{12}$ straight chain alkyl;

$R_1$ is —H; and n is an integer ranging from 1 to 3.

For use in the present methods for treating or preventing a viral infection, a third referred subclass of the compounds of Formula (II) is that wherein, in the compound of Formula (II):

$R_1$ is selected from the group consisting of —H and —$CH_3$;

$R_2$ is selected from the group consisting of —$CH_3$, —$CH_2CH_3$, and —$CH_2C_6H_5$;

$R_4$ is —H;

$R_5$ is selected from the group consisting of —H, —$CH_3$, —$CH_2CH_3$, —$C_3H_7$, -n-$C_4H_9$, and —$C_6H_5$; and n is an integer ranging from 1 to 3.

For use in the present methods for treating or preventing a viral infection, a fourth referred subclass of the compounds of Formula (II) is that wherein, in the compound of Formula (II):

$R_1$ is selected from the group consisting of —H and —$CH_3$;

$R_2$ is selected from the group consisting of —$CH_3$, —$CH_2CH_3$, and —$CH_2C_6H_5$;

$R_4$ is selected from the group consisting of —H, —$CH_3$, —$CH_2CH_3$, and a $C_3$–$C_{12}$ straight chain alkyl;

$R_5$ is selected from the group consisting of —H, —$CH_3$, —$CH_2CH_3$, —$C_3H_7$, -n-$C_4H_9$, and —$C_6H_5$; and n is an integer ranging from 1 to 3.

The invention provides methods for inhibiting the replication or infectivity of a virus comprising contacting a virus or a virus-infected cell with an effective amount of a composition comprising a pharmaceutically acceptable carrier and a compound having the general Formula (II) or a pharmaceutically acceptable salt thereof, wherein:

each $R_1$ is independently selected from the group consisting of —H, —$CH_3$, —$CH_2CH_3$, —$CH_2C_6H_5$, —C(O)OC($CH_3$)$_3$, —C(O)$OCH_2C_6H_5$, and —C(O)$CH_3$;

$R_2$ is selected from the group consisting of —H, $C_1$–$C_{12}$ straight chain alkyl, —$CH_2C_6H_5$, —$SiR_{10}R_{11}R_{12}$, —C(O)$CH_3$, —C(O)$C_6H_5$, -2-tetrahydropyranyl, —$OCH_2OCH_3$, and —C(O)$OCH_2CCl_3$;

$R_4$ is selected from the group consisting of —H and $C_1$–$C_{12}$ straight chain alkyl;

$R_5$ is selected from the group consisting of —H, $C_1$–$C_4$ straight chain alkyl and —$C_6H_5$;

$R_{10}$ is selected from the group consisting of $C_1$–$C_4$ straight or branched chain alkyl, and —$C_6H_5$;

$R_{11}$ and $R_{12}$ are independently $C_1$–$C_3$ straight or branched chain alkyl; and n is a integer from 1 to 6.

Preferred compounds for use in the methods for treating or preventing a viral infection are:

cycloprodigiosin and 4-ethyl-2,4,5,6-tetrahydro-3-((3-methoxy-5-(1H-pyrrol-2-yl-)-2H-pyrrol-2-ylidene)methyl)-1-methyl-cyclopenta(c) pyrrole, or pharmaceutically acceptable salts thereof.

Other preferred compounds for the method are selected from the group consisting of:

4,5,6,7-Tetrahydro-3-((3-benzyloxy-5-(1-methyl-1H-pyrrol-2-yl)-2H-pyrrol-2-ylidene)methyl)-1,4-dimethyl-2H-isoindole;

4,5,6,7-Tetrahydro-3-((3-methoxy-5-(1H-pyrrol-2-yl)-2H-pyrrol-2-ylidene)methyl)-4-ethyl-2H-isoindole;

4,5,6,7-Tetrahydro-3-((3-methoxy-5-(1H-pyrrol-2-yl)-2H-pyrrol-2-ylidene)methyl)-4-ethyl-1-methyl-2H-isoindole;

4,5,6,7-Tetrahydro-3-((3-methoxy-5-(1H-pyrrol-2-yl)-2H-pyrrol-2-ylidene)methyl)-1,4-diethyl-2H-isoindole;

4,5,6,7-Tetrahydro-3-((3-methoxy-5-(1H-pyrrol-2-yl)-2H-pyrrol-2-ylidene)methyl)-1-ethyl-4-methyl-2H-isoindole; and 4,5,6,7-Tetrahydro-3-((3-methoxy-5-(1H-pyrrol-2-yl)-2H-pyrrol-2-ylidene)methyl)-1-ethyl-2H-isoindole or a pharmaceutically acceptable salt thereof.

For use in the present methods for treating or preventing a viral infection, a preferred subclass of the compounds of Formula (II) is that wherein, in the compound of Formula (II):

$R_1$ is selected from the group consisting of —H and —CH$_3$;

$R_2$ is selected from the group consisting of —CH$_3$, —CH$_2$CH$_3$, and —CH$_2$C$_6$H$_5$;

$R_4$ and $R_5$ are independently selected from the group consisting of —H, —CH$_3$, and —CH$_2$CH$_3$; and n is an integer ranging from 1 to 3.

For use in the present methods for treating or preventing a viral infection, a second preferred subclass of the compounds of Formula (II) is that wherein, in the compound of Formula (II):

$R_1$ is selected from the group consisting of —H and —CH$_3$;

$R_2$ is selected from the group consisting of —CH$_3$, —CH$_2$CH$_3$, and —CH$_2$C$_6$H$_5$, $R_4$ is selected from the group consisting of —H, —CH$_3$, —CH$_2$CH$_3$, and a C$_3$–C$_{12}$ straight chain alkyl;

$R_5$ is —H; and n is an integer ranging from 1 to 3.

For use in the present methods for treating or preventing a viral infection, a third preferred subclass of the compounds of Formula (II) is that wherein, in the compound of Formula (II):

$R_1$ is selected from the group consisting of —H and —CH$_3$;

$R_2$ is selected from the group consisting of —CH$_3$, —CH$_2$CH$_3$, and —CH$_2$C$_6$H$_5$;

$R_4$ is —H;

$R_5$ is selected from the group consisting of —H, —CH$_3$, —CH$_2$CH$_3$, —C$_3$H$_7$,-n-C$_4$H$_9$, and C$_6$H$_5$; and n is an integer ranging from 1 to 3.

For use in the present methods for treating or preventing a viral infection, a fourth preferred subclass of the compounds of Formula (If) is that wherein, in the compound of Formula (II):

$R_1$ is selected from the group consisting of —H and —CH$_3$;

$R_2$ is selected from the group consisting of —CH$_3$, —CH$_2$CH$_3$, and —CH$_2$C$_6$H$_5$;

$R_4$ is selected from the group consisting of —H, —CH$_3$, —CH$_2$CH$_3$, and a C$_3$–C$_{12}$ straight chain alkyl;

$R_5$ is selected from the group consisting of —H, —CH$_3$, —CH$_2$CH$_3$, —C$_3$H$_7$, -n-C$_4$H$_9$ and R$_6$H$_5$; and n is an integer ranging from 1 to 3.

4.3. FORMULA III

The present invention still further provides novel compounds having the general Formula (III):

III and pharmaceutically acceptable salts thereof, wherein:

each $R_1$ is independently selected from the group consisting of —H, —CH$_3$, —CH$_2$CH$_3$, —CH$_2$C$_6$H$_5$, —C(O)OC(CH$_3$)$_3$, —C(O)OCH$_2$C$_6$H$_5$, and —C(O)CH$_3$;

$R_2$ is selected from the group consisting of —H, C$_1$–C$_{12}$ straight chain alkyl, —CH$_2$C$_6$H$_5$, —SiR$_{10}$R$_{11}$R$_{12}$, —C(O)CH$_3$, —C(O)C$_6$H$_5$, -2-tetrahydropyranyl, —OCH$_2$OCH$_3$, and —C(O)OCH$_2$CCl$_3$;

$R_5$ is selected from the group consisting of —H, C$_1$–C$_6$ straight chain alkyl and —C$_6$H$_5$;

$R_{10}$ is selected from the group consisting of C$_1$–C$_6$ straight or branched chain alkyl and —C$_6$H$_5$;

$R_{11}$ and $R_{12}$ are independently C$_1$–C$_3$ straight or branched chain alkyl; and n is an integer ranging from 1 to 6;

with the proviso that the compound of Formula (III) is not:
orthobutylcycloheptylprodiginine,
4-methoxy-5-((4,5,6,7-tetrahydro-2H-indol-2-ylidene)methyl)-2,2'-bi-1H-pyrrole),
4-methoxy-5-(4-hexyl-(4,5,6,7-tetrahydro-2H-indol-2-ylidene)methyl)-2,2'-bi-1H-pyrrole),
4-ethoxy-5-(4-hexyl-(4,5,6,7-tetrahydro-2H-indol-2-ylidene)methyl)-2,2'-bi-1H-pyrrole), or
4-propoxy-5-(4-hexyl-(4,5,6,7-tetrahydro-2H-indol-2-ylidene)methyl)-2,2'-bi-1H-pyrrole).

The compounds of Formula (III) and pharmaceutically acceptable salts thereof are useful for treating or preventing cancer or neoplastic disease in a patient in need of such treatment or prevention. The compounds of Formula (III) and pharmaceutically acceptable salts thereof are also useful for inhibiting the growth of a cancer cell or neoplastic cell. The compounds of Formula (III) and pharmaceutically acceptable salts thereof are useful for treating or preventing a viral infection in a patient in need of such treatment or prevention. The compounds of Formula (III) and pharmaceutically acceptable salts thereof are also useful for inhibiting the replication or infectivity of a virus.

A preferred subclass of the compounds of Formula (III) is that wherein:

each $R_1$ is independently selected from the group consisting of —H and —CH$_3$;

$R_2$ is selected from the group consisting of —CH$_3$, —CH$_2$CH$_3$, and —CH$_2$C$_6$H$_5$;

$R_5$ is selected from the group consisting of —CH$_3$ and —CH$_2$CH$_3$; and n is an integer ranging from 1 to 3.

In a preferred embodiment, the compounds of Formula (III) are selected from the group consisting of 4,5,6,7-Tetrahydro-3-((3-methoxy-5-(1H-pyrrol-2-yl)-2H-pyrrol-2-ylidene)methyl)-5-methyl-1H-indole, and 4,5,6,7-Tetrahydro-3-((3-methoxy-5-(1H-pyrrol-2-yl)-2H-pyrrol-2-ylidene)methyl)-1H-indole or a pharmaceutically acceptable salt thereof.

The present invention further provides compositions comprising a pharmaceutically acceptable carrier and a therapeutically effective amount of a compound of Formula (III) or a pharmaceutically acceptable salt thereof, wherein:

each $R_1$ is independently selected from the group consisting of —H, —CH$_3$, —CH$_2$CH$_3$, —CH$_2$C$_6$H$_5$, —C(O)OC(CH$_3$)$_3$, —C(O)OCH$_2$C$_6$H$_5$, and —C(O)CH$_3$;

$R_2$ is selected from the group consisting of —H, C$_1$–C$_{12}$ straight chain alkyl, —CH$_2$C$_6$H$_5$, —SiR$_{10}$R$_{11}$R$_{12}$, —C(O)CH$_3$, —C(O)C$_6$H$_5$, -2-tetrahydropyranyl, —OCH$_2$OCH$_3$, and —C(O)OCH$_2$CCl$_3$;

$R_5$ is selected from the group consisting of —H, C$_1$–C$_6$ straight chain alkyl and —C$_6$H$_5$;

$R_{10}$ is selected from the group consisting of C$_1$–C$_4$ straight or branched chain alkyl and —C$_6$H$_5$;

$R_{11}$ and $R_{12}$ are independently C$_1$–C$_3$ straight or branched chain alkyl; and n is an integer ranging from 1 to 6;

with the proviso that the compound of Formula (III) is not:
orthobutylcycloheptylprodiginine;
4-methoxy-5-((4,5,6,7-tetrahydro-2H-indol-2-ylidene)methyl)-2,2'-bi-1H-pyrrole), 4-methoxy-5-(4-hexyl-(4,5,6,7-tetrahydro-2H-indol-2-ylidene)methyl)-2,2'-bi-1H-pyrrole), 4-ethoxy-5-(4-hexyl-(4,5,6,7-tetrahydro-2H-indol-2-ylidene)methyl)-2,2'-bi-1H-pyrrole), or 4-propoxy-5-(4-hexyl-(4,5,6,7-tetrahydro-2H-indol-2-ylidene)methyl)-2,2'-bi-1H-pyrrole).

The compositions comprising a pharmaceutically acceptable carrier and a compound of Formula (III) or a pharmaceutically acceptable salt thereof are useful for treating or preventing cancer or neoplastic disease in a patient in need of such treatment or prevention. These compositions are also useful for inhibiting the growth of a cancer cell or neoplastic cell. The compositions comprising a pharmaceutically acceptable carrier and a compound of Formula (III) or a pharmaceutically acceptable salt thereof are useful for treating or preventing a viral infection in a patient in need of such treatment or prevention. These compositions are also useful for inhibiting the replication or infectivity of a virus.

A preferred subclass of the compositions comprising a pharmaceutically acceptable carrier and a compound of Formula (III) or a pharmaceutically acceptable salt thereof are those wherein, in the compound of Formula (III):

each $R_1$ is independently selected from the group consisting of —H and —$CH_3$;

$R_2$ is selected from the group consisting of —$CH_3$, —$CH_2CH_3$, and —$CH_2C_6H_5$;

$R_5$ is selected from the group consisting of —$CH_3$ and —$CH_2CH_3$; and n is an integer ranging from 1 to 3.

In preferred embodiments, the compositions comprise a pharmaceutically acceptable carrier and a compound of Formula (III) selected from the group consisting of selected from the group consisting of 4,5,6,7-Tetrahydro-3-((3-methoxy-5-(1H-pyrrol-2-yl)-2H-pyrrol-2-ylidene)methyl)-5-methyl-1H-indole, and 4,5,6,7-Tetrahydro-3-((3-methoxy-5-(1H-pyrrol-2-yl)-2H-pyrrol-2-ylidene)methyl)-1H-indole, or a pharmaceutically acceptable salt thereof.

The invention further provides methods for treating or preventing cancer or a neoplastic disease comprising administering to a patient in need of such treatment or prevention a composition comprising a therapeutically effective amount of a compound of Formula (III) or a pharmaceutically acceptable salt thereof, wherein:

each $R_1$ is independently selected from the group consisting of —H, —$CH_3$, —$CH_2CH_3$, —$CH_2C_6H_5$, —C(O)OC($CH_3$)$_3$, —C(O)O$CH_2C_6H_5$ and —C(O)$CH_3$;

$R_2$ is selected from the group consisting of —H, $C_1$–$C_{12}$ straight chain alkyl, —$CH_2C_6H_5$, —Si$R_{10}R_{11}R_{12}$, —C(O)$CH_3$, —C(O)$C_6H_5$, -2-tetrahydropyranyl, —$OCH_2OCH_3$, and —C(O)$OCH_2CCl_3$;

$R_5$ is selected from the group consisting of —H, $C_1$–$C_6$ straight chain alkyl and —$C_6H_5$;

$R_{10}$ is selected from the group consisting of $C_1$–$C_4$ straight or branched chain alkyl and —$C_6H_5$;

$R_{11}$ and $R_{12}$ are independently $C_1$–$C_3$ straight or branched chain alkyl; and n is an integer ranging from 1 to 6.

Preferred compounds for use in the methods for treating or preventing cancer or a neoplastic disease are:

4-methoxy-5-((4,5,6,7-tetrahydro-2H-indol-2-ylidene)methyl)-2,2'-bi-1H-pyrrole), 4-methoxy-5-(4-hexyl-(4,5,6,7-tetrahydro-2H-indol-2-ylidene)methyl)-2,2'-bi-1H-pyrrole), 4-ethoxy-5-(4-hexyl-(4,5,6,7-tetrahydro-2H-indol-2-ylidene)methyl)-2,2'-bi-1H-pyrrole), and 4-propoxy-5-(4-hexyl-(4,5,6,7-tetrahydro-2H-indol-2-ylidene)methyl)-2,2'-bi-1H-pyrrole), or pharmaceutically acceptable salts thereof.

Other preferred compounds for the method are selected from the group consisting of 4,5,6,7-Tetrahydro-3-((3-methoxy-5-(1H-pyrrol-2-yl)-2H-pyrrol-2-ylidene)methyl)-5-methyl-1H-indole and 4,5,6,7-Tetrahydro-3-((3-methoxy-5-(1H-pyrrol-2-yl)-2H-pyrrol-2-ylidene)methyl)-1H-indole, or a pharmaceutically acceptable salt thereof.

For use in the present methods for treating or preventing cancer or a neoplastic disease, a preferred subclass of the compounds of Formula (III) is that wherein, in the compound of Formula (III):

each $R_1$ is independently selected from the group consisting of —H and —$CH_3$;

$R_2$ is selected from the group consisting of —$CH_3$, —$CH_2CH_3$, and —$CH_2C_6H_5$;

$R_5$ is selected from the group consisting of —$CH_3$, and —$CH_2CH_3$; and n is an integer ranging from 1 to 3.

For use in the present methods for treating or preventing cancer or a neoplastic disease, a second preferred subclass of the compounds of Formula (III) is that wherein, in the compound of Formula (III):

each $R_1$ is independently selected from the group consisting of —H and —$CH_3$;

$R_2$ is selected from the group consisting of —$CH_3$, —$CH_2CH_3$, and —$CH_2C_6H_5$;

$R_5$ is selected from the group consisting of —H, —$CH_3$, —$CH_2CH_3$, —$C_3H_7$, -n-$C_4H_9$, —$(CH_2)_5CH_3$, and —$C_6H_5$; and n is an integer ranging from 1 to 3.

The invention further provides methods for inhibiting the growth of a cancer cell or neoplastic cell comprising a contacting a cancer cell or neoplastic cell with an effective amount of a composition comprising a pharmaceutically acceptable carrier and a compound having the general Formula (III) or a pharmaceutically acceptable salt thereof, wherein:

each $R_1$ is independently selected from the group consisting of —H, —$CH_3$, —$CH_2CH_3$, —$CH_2C_6H_5$, —C(O)OC($CH_3$)$_3$, —C(O)O$CH_2C_6H_5$, and —C(O)$CH_3$;

$R_2$ is selected from the group consisting of —H, $C_1$–$C_{12}$ straight chain alkyl, —$CH_2C_6H_5$, —Si$R_{10}R_{11}R_{12}$, —C(O)$CH_3$, —C(O)$C_6H_5$, -2-tetrahydropyranyl, —$OCH_2OCH_3$, and —C(O)$OCH_2CCl_3$;

$R_5$ is selected from the group consisting of —H, $C_1$–$C_6$ straight chain alkyl and —$C_6H_5$;

$R_{10}$ is selected from the group consisting of $C_1$–$C_4$ straight or branched chain alkyl, and —$C_6H_5$;

$R_{11}$ and $R_{12}$ are independently $C_1$–$C_3$ straight or branched chain alkyl; and n is an integer ranging from 1 to 6.

Preferred compounds for use in the methods for inhibiting the growth of a cancer or neoplastic cell are:

4-methoxy-5-((4,5,6,7-tetrahydro-2H-indol-2-ylidene)methyl)-2,2'-bi-1H-pyrrole), 4-methoxy-5-(4-hexyl-(4,5,6,7-tetrahydro-2H-indol-2-ylidene)methyl)-2,2'-bi-1H-pyrrole), 4-ethoxy-5-(4-hexyl-(4,5,6,7-tetrahydro-2H-indol-2-ylidene)methyl)-2,2'-bi-1H-pyrrole), and 4-propoxy-5-(4-hexyl-(4,5,6,7-tetrahydro-2H-indol-2-ylidene)methyl)-2,2'-bi-1H-pyrrole), or a pharmaceutically acceptable salt thereof.

Other preferred compounds for use in the method are selected from the group consisting of 4,5,6,7-Tetrahydro-3-((3-methoxy-5-(1H-pyrrol-2-yl)-2H-pyrrol-2-ylidene)methyl)-5-methyl-1H-indole and 4,5,6,7-Tetrahydro-3-((3-methoxy-5-(1H-pyrrol-2-yl)-2H-pyrrol-2-ylidene)methyl)-1H-indole, or a pharmaceutically acceptable salt thereof.

For use in the present methods for inhibiting the growth of a cancer or neoplastic cell, a preferred subclass of the compounds of Formula (III) are those wherein, in the compound of Formula (III):

each $R_1$ is independently selected from the group consisting of —H and —$CH_3$;

$R_2$ is selected from the group consisting of —$CH_3$, —$CH_2CH_3$, and —$CH_2C_6H_5$;

$R_5$ is selected from the group consisting of —$CH_3$ and —$CH_2CH_3$; and n is an integer ranging from 1 to 3.

For use in the present methods for inhibiting the growth of a cancer or neoplastic cell, a second preferred subclass of the compounds of Formula (III) is that wherein, in the compound of Formula (III):

each $R_1$ is independently selected from the group consisting of —H and —$CH_3$;

$R_2$ is selected from the group consisting of —$CH_3$, —$CH_2CH_3$, and —$CH_2C_6H_5$;

$R_5$ is selected from the group consisting of —H, —$CH_3$, —$CH_2CH_3$, —$C_3H_7$, -n-$C_4H_9$, —$(CH_2)_5CH_3$, and —$C_6H_5$; and n is an integer ranging from 1 to 3.

The invention further provides methods for treating or preventing a viral infection in a patient comprising administering to a patient in need of such treatment or prevention a therapeutically effective amount of a composition comprising a pharmaceutically acceptable carrier and a compound of Formula (III) and pharmaceutically acceptable salts thereof, wherein:

each $R_1$ is independently selected from the group consisting of —H, —$CH_3$, —$CH_2CH_3$, —$CH_2C_6H_5$, —$C(O)OC(CH_3)_3$, —$C(O)OCH_2C_6H_5$, and —$C(O)CH_3$;

$R_2$ is selected from the group consisting of —H, $C_1$–$C_{12}$ straight chain alkyl, —$CH_2C_6H_5$, —$SiR_{10}R_{11}R_{12}$, —$C(O)CH_3$, —$C(O)C_6H_5$, -2-tetrahydropyranyl, —$OCH_2OCH_3$, and —$C(O)OCH_2CCl_3$;

$R_5$ is selected from the group consisting of —H, $C_1$–$C_6$ straight chain alkyl and —$C_6H_5$;

$R_{10}$ is selected from the group consisting of $C_1$–$C_4$ straight or branched chain alkyl and —$C_6H_5$;

$R_{11}$ and $R_{12}$ are independently $C_1$–$C_3$ straight or branched chain alkyl; and n is an integer ranging from 1 to 6.

Preferred compounds for use in the methods for treating or preventing a viral infection are:

4-methoxy-5-((4,5,6,7-tetrahydro-2H-indol-2-ylidene)methyl)-2,2'-bi-1H-pyrrole), 4-methoxy-5-(4-hexyl-(4,5,6,7-tetrahydro-2H-indol-2-ylidene)methyl)-2,2'-bi-1H-pyrrole), 4-ethoxy-5-(4-hexyl-(4,5,6,7-tetrahydro-2H-indol-2-ylidene)methyl)-2,2'-bi-1H-pyrrole), and 4-propoxy-5-(4-hexyl-(4,5,6,7-tetrahydro-2H-indol-2-ylidene)methyl)-2,2'-bi-1H-pyrrole), or a pharmaceutically acceptable salt thereof Other preferred compounds for use in the method are selected from the group consisting of 4,5,6,7-Tetrahydro-3-((3-methoxy-5-(1H-pyrrol-2-yl)-2H-pyrrol-2-ylidene)methyl)-5-methyl-1H-indole and 4,5,6,7-Tetrahydro-3-((3-methoxy-5-(1H-pyrrol-2-yl)-2H-pyrrol-2-ylidene)methyl)-1H-indole, or a pharmaceutically acceptable salt thereof.

For use in the present methods for treating or preventing a viral infection, a preferred subclass of the compounds of Formula (III) is that wherein, in the compound of Formula (III):

each $R_1$ is independently selected from the group consisting of —H and —$CH_3$;

$R_2$ is selected from the group consisting of —$CH_3$, —$CH_2CH_3$, and —$CH_2C_6H_5$;

$R_5$ is selected from the group consisting of —$CH_3$ and —$CH_2CH_3$; and n an integer ranging from 1 to 3.

For use in the present methods for treating or preventing a viral infection, a second preferred subclass of the compounds of Formula (III) is that wherein, in the compound of Formula (III):

each $R_1$ is independently selected from the group consisting of —H, and —$CH_3$;

$R_2$ is selected from the group consisting of —$CH_3$, —$CH_2CH_3$, and —$CH_2C_6H_5$;

$R_5$ is selected from the group consisting of —H, —$CH_3$, —$CH_2CH_3$, —$C_3H_7$, -n-$C_4H_9$, —$(CH_2)_5CH_3$, and —$C_6H_5$; and n is an integer ranging from 1 to 3.

The invention further provides methods for inhibiting the replication or infectivity of a virus comprising contacting a virus or a virus-infected cell with an effective amount of a composition comprising a pharmaceutically acceptable carrier and a compound having the general Formula (III) or a pharmaceutically acceptable salt thereof, wherein:

each $R_1$ is independently selected from the group consisting of —H, —$CH_3$, —$CH_2CH_3$, —$CH_2C_6H_5$, —$C(O)OC(CH_3)_3$, —$C(O)OCH_2C_6H_5$ and —$C(O)CH_3$;

$R_2$ is selected from the group consisting of —H, $C_1$–$C_{12}$ straight chain alkyl, —$CH_2C_6H_5$, —$SiR_{10}R_{11}R_{12}$, —$C(O)CH_3$, —$C(O)C_6H_5$, -2-tetrahydropyranyl, —$OCH_2OCH_3$, and —$C(O)OCH_2CCl_3$;

$R_5$ is selected from the group consisting of —H, $C_1$–$C_6$ straight chain alkyl and —$C_6H_5$;

$R_{10}$ is selected from the group consisting of $C_1$–$C_6$ straight or branched chain alkyl and —$C_6H_5$;

$R_{11}$ and $R_{12}$ are independently $C_1$–$C_3$ straight or branched chain alkyl; and n is an integer ranging from 1 to 6.

Preferred compounds for use in the method for inhibiting the replication or infectivity of a virus are:

4-methoxy-5-((4,5,6,7-tetrahydro-2H-indol-2-ylidene)methyl)-2,2'-bi-1H-pyrrole), 4-methoxy-5-(4-hexyl-(4,5,6,7-tetrahydro-2H-indol-2-ylidene)methyl)-2,2'-bi-1H-pyrrole), 4-ethoxy-5-(4-hexyl-(4,5,6,7-tetrahydro-2H-indol-2-ylidene)methyl)-2,2'-bi-1H-pyrrole), and, 4-propoxy-5-(4-hexyl-(4,5,6,7-tetrahydro-2H-indol-2-ylidene)methyl)-2,2'-bi-1H-pyrrole) or a pharmaceutically acceptable salt thereof.

Other preferred compounds for use in the method are selected from the group consisting of 4,5,6,7-Tetrahydro-3-((3-methoxy-5-(1H-pyrrol-2-yl)-2H-pyrrol-2-ylidene)methyl)-5-methyl-1H-indole and 4,5,6,7-Tetrahydro-3-((3-methoxy-5-(1H-pyrrol-2-yl)-2H-pyrrol-2-ylidene)methyl)-1H-indole, or a pharmaceutically acceptable salt thereof.

For use in the present methods for inhibiting the replication or infectivity of a virus, a preferred subclass of the compounds of Formula (III) is that wherein, in the compound of Formula (III):

each $R_1$ is independently selected from the group consisting of —H and —$CH_3$;

$R_2$ is selected from the group consisting of —$CH_3$, —$CH_2CH_3$, and —$CH_2C_6H_5$;

$R_5$ is selected from the group consisting of —$CH_3$ and —$CH_2CH_3$; and n is an integer ranging from 1 to 3.

For use in the present methods for inhibiting the replication or infectivity of a virus, a second preferred subclass of the compounds of Formula (III) is that wherein, in the compound of Formula (III):

each $R_1$ is independently selected from the group consisting of —H and —$CH_3$;

$R_2$ is selected from the group consisting of —$CH_3$, —$CH_2CH_3$, and —$CH_2C_6H_5$;

$R_5$ is selected from the group consisting of —H, —$CH_3$, —$CH_2CH_3$, —$C_3H_7$, -n-$C_4H_9$, —$(CH_2)_5CH_3$, and —$C_6H_5$; and n is an integer ranging from 1 to 3.

4.4. FORMULA IV

The present invention encompasses novel compounds having the general Formula (IV):

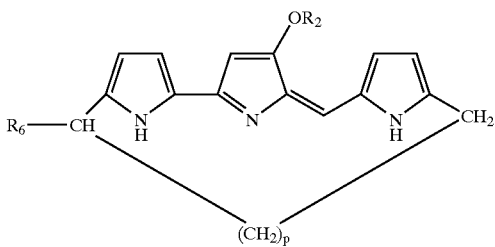

IV and pharmaceutically acceptable salts thereof, wherein:

$R_2$ is selected from the group consisting of —H, $C_1$–$C_{12}$ straight chain alkyl, —$CH_2C_6H_5$, —$SiR_{10}R_{11}R_{12}$, —$C(O)CH_3$, —$C(O)C_6H_5$, -2-tetrahydropyranyl, —$OCH_2OCH_3$, and —$C(O)OCH_2CCl_3$;

$R_6$ is selected from the group consisting of —H, —$CH_3$, and —$CH_2CH_3$;

$R_{10}$ is selected from the group consisting of $C_1$–$C_4$ straight or branched chain alkyl and —$C_6H_5$;

$R_{11}$ and $R_{12}$ are independently $C_1$–$C_3$ straight or branched chain alkyl; and p is as integer from 6 to 8;

with the proviso that the compound of Formula (IV) is not:
cyclononylprodiginine,
methylcyclooctylprodiginine,
methylcyclodecylprodiginine,
ethylcyclononylprodiginine,
R39FF,
R39MF,
R39SF,
610FF, or
610MF.

The compounds of Formula (IV) and pharmaceutically acceptable salts thereof are useful for treating or preventing cancer or neoplastic disease in a patient in need of such treatment or prevention. The compounds of Formula (IV) and pharmaceutically acceptable salts thereof are also useful for inhibiting the growth of a cancer cell or neoplastic cell. The compounds of Formula (IV) and pharmaceutically acceptable salts thereof are useful for treating or preventing a viral infection in a patient in need of such treatment or prevention. The compounds of Formula (IV) and pharmaceutically acceptable salts thereof are also useful for inhibiting the replication or infectivity of a virus.

A preferred subclass of the compounds of Formula (IV) is that wherein:

$R_2$ is selected from the group consisting of —$CH_3$, —$CH_2CH_3$, and —$CH_2C_6H_5$;

$R_6$ is selected from the group consisting of —H, —$CH_3$, and —$CH_2CH_3$; and p is an integer ranging from 6 to 8;

with the proviso that the compound of Formula (IV) is not:
cyclononylprodiginine,
methylcyclooctylprodiginine,
methylcyclodecylprodiginine,
ethylcyclononylprodiginine,
R39FF,
R39MF,
R39SF,
610FF, or
610MF.

A second preferred subclass of the compounds of Formula (IV) is that wherein:

$R_2$ is selected from the group consisting of —$CH_3$, —$CH_2CH_3$, and —$CH_2C_6H_5$;

$R_6$ is —H; and p is an integer of 6 or 8.

A third preferred subclass of the compounds of Formula (IV) is that wherein:

$R_2$ is selected from the group consisting of —$CH_2CH_3$, and —$CH_2C_6H_5$;

$R_6$ is selected from the group consisting of —H, —$CH_3$, and —$CH_2CH_3$; and p is an integer ranging from 6 to 8.

In one embodiment, preferred compounds of Formula (IV) are selected from the group consisting of 4-Methoxy-23,24,25-triazatetracyclo(18.2.1.1$^{2,5}$.1$^{7,10}$)pentacosa-2(25),3,5,7,9,20,22-heptaene, and 4-Methoxy-24,25,26-triazatetracyclo(19.2.1.1$^{2,5}$.1$^{7,10}$)hexacosa-2(26),3,5,7,9,21,23-heptaene or a pharmaceutically acceptable salt thereof.

The present invention further provides compositions comprising a pharmaceutically acceptable carrier and a therapeutically effective amount of a compound of Formula (IV) or a pharmaceutically acceptable salt thereof, wherein:

$R_2$ is selected from the group consisting of —H, $C_1$–$C_{12}$ straight chain alkyl, —$CH_2C_6H_5$, —$SiR_{10}R_{11}R_{12}$, —$C(O)CH_3$, —$C(O)C_6H_5$, -2-tetrahydropyranyl, —$OCH_2OCH_3$, and —$C(O)OCH_2CCl_3$;

$R_6$ is selected from the group consisting of —H, —$CH_3$, and —$CH_2CH_3$;

$R_{10}$ is selected from the group consisting of $C_1$–$C_4$ straight or branched chain alkyl and —$C_6H_5$;

$R_{11}$ and $R_{12}$ are independently $C_1$–$C_3$ straight or branched chain alkyl; and p is an integer ranging from 6 to 8;

with the proviso that the compound of Formula (IV) is not:
cyclononylprodiginine,
methylcyclooctylprodiginine,
methylcyclodecylprodiginine,
ethylcyclononylprodiginine,
R39FF,
R39MF,
R39SF,
610FF, or
610MF.

The compositions comprising a pharmaceutically acceptable carrier and a compound of Formula (IV) or a pharmaceutically acceptable salt thereof are useful for treating or preventing cancer or neoplastic disease in a patient in need of such treatment or prevention. These compositions are also useful for inhibiting the growth of a cancer cell or neoplastic cell. The compositions comprising a pharmaceutically acceptable carrier and a compound of Formula (IV) or a pharmaceutically acceptable salt thereof are useful for treating or preventing a viral infection in a patient in need of such treatment or prevention. These compositions are also useful for inhibiting the replication or infectivity of a virus.

A preferred subclass of the compositions comprising a pharmaceutically acceptable carrier and compound of Formula (IV) or a pharmaceutically acceptable salt thereof is that wherein, in the compound of Formula (IV):

$R_2$ is selected from the group consisting of —$CH_3$, —$CH_2CH_3$, and —$CH_2C_6H_5$;

$R_6$ is selected from the group consisting of —H, —$CH_3$, and —$CH_2CH_3$; and p is an integer ranging from 6 to 8;

with the proviso that the compound of Formula (IV) is not:
cyclononylprodiginine,
methylcyclooctylprodiginine,
methylcyclodecylprodiginine,
ethylcyclononylprodiginine,
R39FF,
R39MF,
R39SF,
610FF, or
610MF.

A second preferred subclass of the compositions comprising a pharmaceutically acceptable carrier and a compound of Formula (IV) or a pharmaceutically acceptable salt thereof is that wherein, in the compound of Formula (IV):

$R_2$ is selected from the group consisting of —$CH_3$, —$CH_2CH_3$, and —$CH_2C_6H_5$;

$R_6$ is —H;

p is 6 or 8.

A third preferred subclass of the compositions comprising a pharmaceutically acceptable carrier and a compound of Formula (IV) or a pharmaceutically acceptable salt thereof is that wherein, in the compound of Formula (IV):

$R_2$ is selected from the group consisting of —$CH_2CH_3$, and —$CH_2C_6H_5$;

$R_6$ is selected from the group consisting of —H, —$CH_3$, and —$CH_2CH_3$;

p is an integer ranging from 6 to 8.

In preferred embodiments, the compositions comprise a pharmaceutically acceptable carrier and a compound of Formula (IV) selected from the group consisting of 4-Methoxy-23,24,25-triazatetracyclo($18.2.1.1^{2,5}.1^{7,10}$)pentacosa-2(25),3,5,7,9,20,22-heptaene and 4-Methoxy-24,25,26-triazatetracyclo($19.2.1.1^{2,5}.1^{7,10}$)hexacosa-2(26),3,5,7,9,21,23-heptaene, or a pharmaceutically acceptable salt thereof.

The invention further provides methods for treating or preventing cancer or a neoplastic disease comprising administering to a patient in need of such treatment or prevention a composition comprising a therapeutically effective amount of a compound of Formula (IV) or a pharmaceutically acceptable salt thereof, wherein:

$R_2$ is selected from the group consisting of —H, $C_1$–$C_{12}$ straight chain alkyl, —$CH_2C_6H_5$, —$SiR_{10}R_{11}R_{12}$, —C(O)$CH_3$, —C(O)$C_6H_5$, -2-tetrahydropyranyl, —$OCH_2OCH_3$, and —C(O)$OCH_2CCl_3$;

$R_6$ is selected from the group consisting of —H, —$CH_3$, and —$CH_2CH_3$;

$R_{10}$ is selected from the group consisting of $C_1$–$C_4$ straight or branched chain alkyl and —$C_6H_5$;

$R_{11}$ and $R_{12}$ are independently $C_1$–$C_3$ straight or branched chain alkyl; and p is an integer ranging from 6 to 8.

Preferred compounds for use in the method for treating or preventing cancer are:
cyclononylprodiginine,
methylcyclooctylprodiginine,
methylcyclodecylprodiginine,
ethylcyclononylprodiginine,
R39FF,
R39MF,
R39SF,
610FF, and
610MF, or a pharmaceutically acceptable salt thereof.

Other preferred compounds for use in the method are selected from the group consisting of 4-Methoxy-23,24,25-triazatetracyclo($18.2.1.1^{2,5}.1^{7,10}$)pentacosa-2(25),3,5,7,9,20,22-heptaene and 4-Methoxy-24,25,26-triazatetracyclo($19.2.1.1^{2,5}.1^{7,10}$)hexacosa-2(26),3,5,7,9,21,23-heptaene, or a pharmaceutically acceptable salt thereof.

For use in the present methods for treating or preventing cancer, a preferred subclass of the compounds of Formula (IV) is that wherein, in the compound of Formula (IV):

$R_2$ is selected from the group consisting of —$CH_3$, —$CH_2CH_3$, and —$CH_2C_6H_5$;

$R_6$ is selected from the group consisting of —H, —$CH_3$, and —$CH_2CH_3$; and p is an integer ranging from 6 to 8.

For use in the present methods for treating or preventing cancer, a second preferred subclass of the compounds of Formula (IV) is that wherein, in the compound of Formula (IV):

$R_2$ is selected from the group consisting of —$CH_3$, —$CH_2CH_3$, and —$CH_2C_6H_5$;

R is —H; and p is 6 or 8.

For use in the present methods for treating or preventing cancer, a third preferred subclass of the compounds of Formula (IV) is that wherein, in the compound of Formula (IV):

$R_2$ is selected from the group consisting of —$CH_2CH_3$, and —$CH_2C_6H_5$;

$R_6$ is selected from the group consisting of —H, —$CH_3$, and —$CH_2CH_3$; and p is an integer ranging from 6 to 8.

For use in the present methods for treating or preventing cancer, a fourth preferred subclass of the compounds of Formula (IV) is that wherein, in the compound of Formula (IV):

$R_2$ is selected from the group consisting of —$CH_3$, —$CH_2CH_3$, and —$CH_2C_6H_5$;

$R_6$ is selected from the group consisting of —H, —$CH_3$, and —$CH_2CH_3$; and p is an integer ranging from 6 to 8.

The invention further provides methods for inhibiting the growth of a cancer cell or neoplastic cell comprising a contacting a cancer cell or neoplastic cell with an effective amount of a composition comprising a pharmaceutically acceptable carrier and a compound having the general Formula (IV) or a pharmaceutically acceptable salt thereof, wherein:

$R_2$ is selected from the group consisting of —H, $C_1$–$C_{12}$ straight chain alkyl, —$CH_2C_6H_5$, —$SiR_{10}R_{11}R_{12}$, —C(O)$CH_3$, —C(O)$C_6H_5$, -2-tetrahydropyranyl, —$OCH_2OCH_3$, and —C(O)$OCH_2CCl_3$;

$R_6$ is selected from the group consisting of —H, —$CH_3$, and —$CH_2CH_3$;

$R_{10}$ is selected from the group consisting of $C_1$–$C_4$ straight or branched chain alkyl and —$C_6H_5$;

$R_{11}$ and $R_{12}$ are independently $C_1$–$C_3$ straight or branched chain alkyl; and p is an integer ranging from 6 to 8.

Preferred compounds for use in the method for inhibiting the growth of a cancer or neoplastic cell are:
cyclononylprodiginine,
methylcyclooctylprodiginine, methylcyclodecylprodiginine,
ethylcyclononylprodiginine,
R39FF,
R39MF,
R39SF,
610FF, and
610MF, or a pharmaceutically acceptable salt thereof.

Other preferred compounds for use in the method are selected from the group consisting of 4-Methoxy-23,24,25-triazatetracyclo(18.2.1.1$^{2,5}$.1$^{7,10}$)pentacosa-2(25),3,5,7,9,20,22-heptaene and 4-Methoxy-24,25,26-triazatetracyclo(19.2.1.1$^{2,5}$.1$^{7,10}$)hexacosa-2(26),3,5,7,9,21,23-heptaene, or a pharmaceutically acceptable salt thereof.

For use in the present methods for inhibiting the growth of a cancer or neoplastic cell, a preferred subclass of the compounds of Formula (IV) is that wherein, in the compound of Formula (IV):

$R_2$ is selected from the group consisting of —CH$_3$, —CH$_2$CH$_3$, and —CH$_2$C$_6$H$_5$;

$R_6$ is selected from the group consisting of —H, —CH$_3$, and —CH$_2$CH$_3$; and p is an integer ranging from 6 to 8.

For use in the present methods for inhibiting the growth of a cancer or neoplastic cell, a second preferred subclass of the compounds of Formula (IV) is that wherein, in the compound of Formula (IV):

$R_2$ is selected from the group consisting of —CH$_3$, —CH$_2$CH$_3$, and —CH$_2$C$_6$H$_5$;

$R_6$ is —H;

p is an integer of 6 or 8.

For use in the present methods for inhibiting the growth of a cancer or neoplastic cell, a third preferred subclass of the compounds of Formula (IV) is that wherein, in the compound of Formula (IV):

$R_2$ is selected from the group consisting of —CH$_2$CH$_3$, and —CH$_2$C$_6$H$_5$;

$R_6$ is selected from the group consisting of —H, —CH$_3$, and —CH$_2$CH$_3$;

p is an integer ranging from 6 to 8.

For use in the present methods for inhibiting the growth of a cancer or neoplastic cell, a fourth preferred subclass of the compounds of Formula (IV) is that wherein, in the compound of Formula (IV):

$R_2$ is selected from the group consisting of —CH$_3$, —CH$_2$CH$_3$, and —CH$_2$C$_6$H$_5$;

$R_6$ is selected from the group consisting of —H, —CH$_3$, and —CH$_2$CH$_3$; and p is an integer ranging from 6 to 8.

The invention further provides methods for treating or preventing a viral infection in a patient comprising administering to a patient in need of such treatment or prevention a therapeutically effective amount of a composition comprising a pharmaceutically acceptable carrier and a compound of Formula (IV) or a pharmaceutically acceptable salt thereof, wherein:

$R_2$ is selected from the group consisting of —H, $C_1$–$C_{12}$ straight chain alkyl, —CH$_2$C$_6$H$_5$, —SiR$_{10}$R$_{11}$R$_{12}$, —C(O)CH$_3$, —C(O)C$_6$H$_5$, -2-tetrahydropyranyl, —OCH$_2$OCH$_3$, and —C(O)OCH$_2$CCl$_3$;

$R_6$ is selected from the group consisting of —H, —CH$_3$, and —CH$_2$CH$_3$;

$R_{10}$ is selected from the group consisting of $C_1$–$C_4$ straight or branched chain alkyl, and —C$_6$H$_5$;

$R_{11}$ and $R_{12}$ are independently $C_1$–$C_3$ straight or branched chain alkyl; and p is an integer ranging from 6 to 8.

Preferred compounds for use in the methods for treating or preventing a viral infection are:

cyclononylprodiginine,
methylcyclooctylprodiginine,
methylcyclodecylprodiginine,
ethylcyclononylprodiginine,
R39FF,
R39MF,
R39SF,
610FF, and
610MF, or pharmaceutically acceptable salts thereof.

Other preferred compounds for use in the method are selected from the group consisting of 4-Methoxy-23,24,25-triazatetracyclo(18.2.1.1$^{2,5}$.1$^{7,10}$)pentacosa-2(25),3,5,7,9,20,22-heptaene and 4-Methoxy-24,25,26-triazatetracyclo(19.2.1.1$^{7,10}$)hexacosa-2(26),3,5,7,9,21,23-heptaene, or a pharmaceutically acceptable salt thereof For use in the present methods for treating or preventing a viral infection, a preferred subclass of the compounds of Formula (IV) is that wherein, in the compound of Formula (IV):

$R_2$ is selected from the group consisting of —CH$_3$, —CH$_2$CH$_3$, and —CH$_2$C$_6$H$_5$;

$R_6$ is selected from the group consisting of —H, —CH$_3$, and —CH$_2$CH$_3$;

p is an integer ranging from 6 to 8.

For use in the present methods for treating or preventing a viral infection, a second preferred subclass of the compounds of Formula (IV) is that wherein, in the compound of Formula (IV):

$R_2$ is selected from the group consisting of —CH$_3$, —CH$_2$CH$_3$, and —CH$_2$C$_6$H$_5$;

$R_6$ is —H;

p is an integer of 6 or 8.

For use in the present methods for treating or preventing a viral infection, a third preferred subclass of the compounds of Formula (IV) is that wherein, in the compound of Formula (IV):

$R_2$ is selected from the group consisting of —CH$_2$CH$_3$, and —CH$_2$C$_6$H$_5$;

$R_6$ is selected from the group consisting of —H, —CH$_3$, and —CH$_2$CH$_3$;

p is an integer ranging from 6 to 8.

For use in the present methods for treating or preventing a viral infection, a fourth preferred subclass of the compounds of Formula (IV) is that wherein, in the compound of Formula (IV):

$R_2$ is selected from the group consisting of —CH$_3$, —CH$_2$CH$_3$, and —CH$_2$C$_6$H$_5$;

$R_6$ is selected from the group consisting of —H, —CH$_3$, and —CH$_2$CH$_3$; and p is an integer ranging from 6 to 8.

The invention further provides methods for inhibiting the replication or infectivity of a virus comprising a contacting a virus or a virus-infected cell with an effective amount of a composition comprising a pharmaceutically acceptable carrier and a compound having the general Formula (IV) or a pharmaceutically acceptable salt thereof, wherein:

$R_2$ is selected from the group consisting of —H, $C_1$–$C_{12}$ straight chain alkyl, —CH$_2$C$_6$H$_5$, —SiR$_{10}$R$_{11}$R$_{12}$, —C(O)CH$_3$, —C(O)C$_6$H$_5$, -2-tetrahydropyranyl, —OCH$_2$OCH$_3$, and —C(O)OCH$_2$CCl$_3$;

$R_6$ is selected from the group consisting of —H, —CH$_3$, and —CH$_2$CH$_3$;

$R_{10}$ is selected from the group consisting of $C_1$–$C_4$ straight or branched chain alkyl and —C$_6$H$_5$;

$R_{11}$ and $R_{12}$ are independently $C_1$–$C_3$ straight or branched chain alkyl; and p is an integer ranging from 6 to 8.

Preferred compounds for use in the methods for inhibiting the replication or infectivity of a virus are:

cyclononylprodiginine,
methylcyclooctylprodiginine,
methylcyclodecylprodiginine,
ethylcyclononylprodiginine,
$R_{39}FF$,
$R_{39}MF$,
$R_{39}SF$,
610FF, and
610MF, or a pharmaceutically acceptable salt thereof.

Other preferred compounds for use in the method are selected from the group consisting of 4-Methoxy-23,24,25-triazatetracyclo(18.2.1.1$^{2,5}$.1$^{7,10}$)pentacosa-2(25),3,5,7,9,20,22-heptaene and 4-Methoxy-24,25,26-triazatetracyclo(19.2.1.1$^{2,5}$.1$^{7,10}$)hexacosa-2(26),3,5,7,9,21,23-heptaene, or a pharmaceutically acceptable salt thereof.

For use in the present methods for inhibiting the replication or infectivity of a virus, a preferred subclass of the compounds of Formula (IV) is that wherein, in the compound of Formula (IV):

$R_2$ is selected from the group consisting of —$CH_3$, —$CH_2CH_3$, and —$CH_2C_6H_5$;

$R_6$ is selected from the group consisting of —H, —$CH_3$, and —$CH_2CH_3$; and p is an integer ranging from 6 to 8.

For use in the present methods for inhibiting the replication or infectivity of a virus, a second preferred subclass of the compounds of Formula (IV) is that wherein, in the compound of Formula (IV):

$R_2$ is selected from the group consisting of —$CH_3$, —$CH_2CH_3$, and —$CH_2C_6H_5$;

$R_6$ is —H; and p is an integer of 6 or 8.

For use in the present methods for inhibiting the replication or infectivity of a virus, a third preferred subclass of the compounds of Formula (IV) is that wherein, in the compound of Formula (IV):

$R_2$ is selected from the group consisting of —$CH_2CH_3$, and —$CH_2C_6H_5$;

$R_6$ is selected from the group consisting of —H, —$CH_3$, and —$CH_2CH_3$; and p is an integer ranging from 6 to 8.

For use in the present methods for inhibiting the replication or infectivity of a virus, a fourth preferred subclass of the compounds of Formula (IV) is that wherein, in the compound of Formula (IV):

$R_2$ is selected from the group consisting of —$CH_3$, —$CH_2CH_3$, and —$CH_2C_6H_5$;

$R_6$ is selected from the group consisting of —H, —$CH_3$, and —$CH_2CH_3$; and p is an integer ranging from 6 to 8.

4.5. FORMULA V

The present invention provides methods for treating or preventing cancer or a neoplastic disease comprising administering to a patient in need of such treatment or prevention a composition comprising a therapeutically effective amount of a compound of Formula (V):

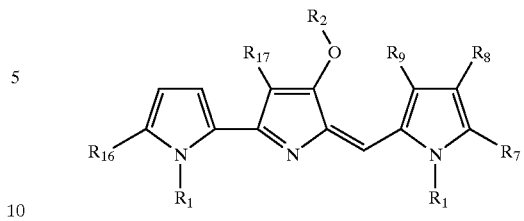

or a pharmaceutically acceptable salt thereof, wherein:

$R_1$ is selected from the group consisting of —H, —$CH_3$, —$CH_2CH_3$, —$CH_2C_6H_5$, —$C(O)OC(CH_3)_3$, —$C(O)OCH_2C_6H_5$, and —$C(O)CH_3$;

$R_2$ is selected from the group consisting of —H, $C_1$-$C_{12}$ straight chain alkyl, —$CH_2C_6H_5$, —$SiR_{10}R_{11}R_{12}$, —$C(O)CH_3$, —$C(O)C_6H_5$, -2-tetrahydropyranyl, —$OCH_2OCH_3$, and —$C(O)OCH_2CCl_3$;

$R_7$ is selected from the group consisting of —H, $C_1$-$C_{15}$ straight chain alkyl, —$(CH_2)_9CH=CH_2$, —$(CH_2)_6F$, —$(CH_2)_5OC_6H_5$, —$(CH_2)_6OH$, —$(CH_2)_7CN$, —$CH_2CH_2C_6H_5$, —$(CH_2)_4COOH$, —$(CH_2)$, COOH, —$(CH_2)_5COOMe$, —$(CH_2)_{11}COOH$, —$(CH_2)_{12}COOH$, —$(CH_2)_{12}OH$, —$(CH_2)_{13}OH$, —$(CH_2)_{11}CN$, —$(CH_2)_{11}OC(O)NH_2$, —$(CH_2)_{11}COOEt$, —$C(O)(CH_2)_9CH_3$, —$(CH_2)_5C(O)N(CH_2CH_2)_2O$, $C_3$-$C_7$ cycloalkyl, —$C_6H_5$,2-pyrrolyl, -3-pyrrolyl, 2-pyridyl, 3-pyridyl, 4-pyridyl, 2-furanyl, and 3-furanyl, the phenyl being substituted with one or more halo, methyl, methoxyl, hydroxyl, methoxycarbonyl or trifluoromethyl groups;

$R_8$ is selected from the group consisting of —H, $C_1$-$C_{11}$, straight chain alkyl, —$(CH_2)_4COOEt$, and —$C_6H_5$;

when $R_7$ is other than 2-pyrrolyl, then $R_9$ is selected from the group consisting of —H, —$CH_3$, —$CH_2CH_3$, and —$CH_2CH_2CH_3$;

when $R_7$ is 2-pyrrolyl, then $R_9$ is selected from the group consisting of —H, —$CH_3$, —$CH_2CH_3$, —$CH_2CH_2CH_3$, and —$OCH_3$;

$R_{10}$ is selected from the group consisting of $C_1$-$C_4$ straight or branched chain alkyl and —$C_6H_5$;

$R_{11}$ and $R_{12}$ are independently selected from the group consisting of —$CH_3$, —$CH_2CH_3$, and —$C_3H_7$;

$R_{16}$ is selected from the group consisting of —H, —$CH_3$, —$CH_2CH_2CH_3$, and —$(CH_2)_6CH_3$; and $R_{17}$ is selected from the group consisting of —H, —CN, —COOMe, —COOEt, and —COOH;

with the proviso that the compound of Formula (V) is not:
prodigiosin,
undecylprodigiosin,
norprodigiosin, or
nonylprodigiosin.

Where $R_7$ is phenyl substituted with one or more halo, —$CH_3$, —$OCH_3$, —OH, —$COOCH_3$, or —$CF_3$ groups, $R_7$ is preferably 4-methylphenyl, 4-methoxyphenyl, 4-hydroxyphenyl, 4-(methoxycarbonyl)phenyl, 4-(trifluoromethyl)phenyl, 4-fluorophenyl, 4-chlorophenyl, 4-bromophenyl, 2,4-dimethoxyphenyl, 2,4-dichlorophenyl, and 2-chloro-4-fluorophenyl.

Preferred compounds for use in the methods for treating or preventing cancer or a neoplastic disease are:
6-methoxy-2-methyl-3-heptylprodigeosene,
4-methoxy-5-((3-methoxy-5-(1H-pyrrol-2-yl)-2H-pyrrol-2-ylidene)methyl)-2,2'-bi-1H-pyrrol, nonylprodigiosin, and 3-heptyl-5-((3-methoxy-5-pyrrol-2-yl-2H-pyrrol-2-ylidene)methyl)-2-methyl-4-propylpyrrole, or pharmaceutically acceptable salts thereof.

For use in the present methods for treating or preventing cancer or a neoplastic disease, a preferred subclass of the compounds of Formula (V) is that wherein, in the compound of Formula (V):

$R_1$ is —H;

$R_2$ is selected from the group consisting of —H, $C_1$–$C_{12}$ straight chain alkyl, —CH(CH$_3$)$_2$, and —CH$_2$C$_6$H$_5$;

$R_7$ is selected from the group consisting of —H, —C$_1$—C$_5$ straight chain alkyl, —(CH$_2$)$_9$C=CH$_2$, —(CH$_2$)$_5$CH$_2$F, —(CH$_2$)$_5$OC$_5$H$_6$, —(CH$_2$)$_6$OH, —(CH$_2$)$_7$CN, —CH$_2$CH$_2$C$_5$H$_6$, —(CH$_2$)$_4$COOH, —(CH$_2$)$_5$COOH, —(CH$_2$)$_5$COOMe, —(CH$_2$)$_{11}$COOH, —(CH$_2$)$_{12}$COOH, —(CH$_2$)$_{12}$OH, —(CH$_2$)$_{13}$OH, —(CH$_2$)$_{11}$CN, —(CH$_2$)$_{11}$OC(O)NH$_2$, —(CH$_2$)$_{11}$COOEt —C(O)(CH$_2$)$_9$CH$_3$, —(CH$_2$)$_5$C(O)N(CH$_2$CH$_2$)$_2$O, and 2-pyrrolyl;

$R_8$ is selected from the group consisting of —H, $C_1$–$C_{11}$ straight chain alkyl, —(CH$_2$)$_4$COOEt, and —C$_6$H$_5$;

when $R_7$ is other than 2-pyrrolyl, then $R_9$ is selected from the group consisting of —H, —CH$_3$, —CH$_2$CH$_3$, and —CH$_2$CH$_2$CH$_3$;

when $R_7$ is 2-pyrrolyl, then $R_9$ is selected from the group consisting of —H, —CH$_3$, —CH$_2$CH$_3$, —CH$_2$CH$_2$CH$_3$, and —OCH$_3$;

$R_{16}$ is selected from the group consisting of —H, —CH$_3$, —CH$_2$CH$_2$CH$_3$, and —(CH$_2$)$_6$CH$_3$; and $R_{17}$ is selected from the group consisting of —H, —CN, —COOMe, —COOEt, and —COOH;

with the proviso that the compound of Formula (V) is not:
prodigiosin,
undecylprodigiosin,
norprodigiosin, or
nonylprodigiosin.

For use in the present methods for treating or preventing cancer or a neoplastic disease, a second preferred subclass of the compounds of Fonnula (V) is that wherein, in the compound of Formula (V):

$R_1$ is —H;

$R_2$ is selected from the group consisting of $C_1$—$C_{12}$ straight chain alkyl, —CH(CH$_3$)$_2$, and —CH$_2$C$_6$H$_5$;

$R_7$ is selected from the group consisting of —H, —CH$_3$, —CH$_2$CH$_3$, $C_8$–$C_{15}$ straight chain alkyl, —(CH$_2$)$_9$C=CH$_2$, —(CH$_2$)$_5$CH$_2$F, —(CH$_2$)$_5$OC$_5$H$_6$, —(CH$_2$)$_6$OH, —(CH$_2$)$_7$CN, —CH$_2$CH$_2$C$_5$H$_6$, —(CH$_2$)$_4$COOH, —(CH$_2$)$_5$COOH, —(CH$_2$)$_5$COOMe, —(CH$_2$)$_{11}$COOH, —(CH$_2$)$_{12}$COOH, —(CH$_2$)$_{12}$OH, —(CH$_2$)$_{13}$OH, —(CH$_2$)$_{11}$CN, —(CH$_2$)$_{11}$OC(O)NH$_2$, —(CH$_2$)$_{11}$COOEt —C(O)(CH$_2$)$_9$CH$_3$, —(CH$_2$)$_5$C(O)N(CH$_2$CH$_2$)$_2$O, and 2-pyrrolyl;

$R_8$ is selected from the group consisting of —H, —CH$_3$, —CH$_2$CH$_3$, $C_6$–$C_{11}$ straight chain alkyl, —(CH$_2$)$_4$COOEt, and —C$_6$H$_5$;

when $R_7$ is other than 2-pyrrolyl, $R_9$ is selected from the group consisting of —H, —CH$_3$, —CH$_2$CH$_3$, and —CH$_2$CH$_2$CH$_3$;

when $R_7$ is 2-pyrrolyl, then $R_9$ is selected from the group consisting of —H, —CH$_3$, —CH$_2$CH$_3$, —CH$_2$CH$_2$CH$_3$, and —OCH$_3$;

$R_{16}$ is selected from the group consisting of —H, —CH$_3$, —CH$_2$CH$_2$CH$_3$, and —(CH$_2$)$_6$CH$_3$; and $R_{17}$ is selected from the group consisting of —H, —CN, —COOMe, —COOEt, and —COOH;

with the proviso that the compound of Formula (V) is not:
prodigiosin, or
undecylprodiginine.

The present invention provides methods for inhibiting the growth of a cancer cell or neoplastic cell comprising a contacting a cancer cell or neoplastic cell with an effective amount of a composition comprising a pharmaceutically acceptable carrier and a compound having the general Formula (V) or a pharmaceutically acceptable salt thereof, wherein:

$R_1$ is selected from the group consisting of —H, —CH$_3$, —CH$_2$CH$_3$, —CH$_2$C$_6$H$_5$, —C(O)OC(CH$_3$)$_3$, —C(O)OCH$_2$C$_6$H$_5$, and —C(O)CH$_3$;

$R_2$ is selected from the group consisting of —H, $C_1$–$C_{12}$ straight chain alkyl, —CH$_2$C$_6$H$_5$, —SiR$_{10}$R$_{11}$R$_{12}$ —C(O)CH$_3$, —C(O)C$_6$H$_5$, -2-tetrahydropyranyl, —OCH$_2$OCH$_3$, and —C(O)OCH$_2$CCl$_3$;

$R_7$ is selected from the group consisting of —H, $C_1$–$C_{15}$ straight chain alkyl, —(CH$_2$)$_9$CH=CH$_2$, —(CH$_2$)$_6$F, —(CH$_2$)$_5$OC$_6$H$_5$, —(CH$_2$)$_6$OH, —(CH$_2$)$_7$CN, —CH$_2$CH$_2$C$_6$H$_5$, —(CH$_2$)$_4$COOH, —(CH$_2$)$_5$COOH, —(CH$_2$)$_5$COOMe, —(CH$_2$)$_{11}$COOH, —(CH$_2$)$_{12}$COOH, —(CH$_2$)$_{12}$OH, —(CH$_2$)$_{13}$OH, —(CH$_2$)$_{11}$CN, —(CH$_2$)$_{11}$OC(O)NH$_2$, —(CH$_2$)$_{11}$COOEt, —C(O)(CH$_2$)$_9$CH$_3$, —(CH$_2$)$_5$C(O)N(CH$_2$CH$_2$)$_2$O, $C_3$–$C_7$ cycloalkyl, —C$_6$H$_5$, 2-pyrrolyl, -3-pyrrolyl, 2-pyridyl, 3-pyridyl, 4-pyridyl, 2-furanyl, and 3-furanyl, the phenyl being substituted with one or more halo, methyl, methoxyl, hydroxyl, methoxycarbonyl or the trifluoromethyl groups;

$R_8$ is selected from the group consisting of —H, $C_1$–$C_{11}$ straight chain alkyl, —(CH$_2$)$_4$COOEt, and —C$_6$H$_5$;

when $R_7$ is other than 2-pyrrolyl, $R_9$ is selected from the group consisting of —H, —CH$_3$, —CH$_2$CH$_3$, and —CH$_2$CH$_2$CH$_3$;

when $R_7$ is 2-pyrrolyl, then $R_9$ is selected from the group consisting of —H, —CH$_3$, —CH$_2$CH$_3$, —CH$_2$CH$_2$CH$_3$, and —OCH$_3$;

$R_{10}$ is selected from the group consisting of $C_1$–$C_4$ straight or branched chain alkyl and —C$_6$H$_5$;

$R_{11}$ and $R_{12}$ are independently selected from the group consisting of —CH$_3$, —CH$_2$CH$_3$, and —C$_3$H$_7$;

$R_{16}$ is selected from the group consisting of —H, —CH$_3$, —CH$_2$CH$_2$CH$_3$, and —(CH$_2$)$_6$CH$_3$; and $R_{17}$ is selected from the group consisting of —H, —CN, —COOMe, —COOEt, and —COOH;

with the proviso that the compound of Formula (V) is not:
prodigiosin,
undecylprodigiosin,
norprodigiosin, or
nonylprodigiosin.

Preferred compounds for use in the method for inhibiting the growth of a cancer or neoplastic cell are:

6-methoxy-2-methyl-3-heptylprodigeosene, 4-methoxy-5-((3-methoxy-5-(1H-pyrrol-2-yl)-2H-pyrrol-2-ylidene)methyl)-2,2'-bi-1H-pyrrol, nonylprodigiosin, and 3-heptyl-5-((3-methoxy-5-pyrrol-2-yl-2H-pyrrol-2-ylidene)methyl)-2-methyl-4-propyl-pyrrole, or a pharmaceutically acceptable salt thereof.

For use in the present methods for inhibiting the growth of a cancer or neoplastic cell, a preferred subclass of the compounds of Formula (V) is that wherein, in the compound of Formula (V):

$R_1$ is —H;

$R_2$ is selected from the group consisting of —H, $C_1$–$C_{12}$ straight chain alkyl, —CH(CH$_3$)$_2$, and —CH$_2$C$_6$H$_5$;

$R_7$ is selected from the group consisting of —H, —CH$_3$, —CH$_2$CH$_3$, $C_3$–$C_{15}$ straight chain alkyl, —(CH$_2$)$_9$CH=CH$_2$, —(CH$_2$)$_5$CH$_2$F, —(CH$_2$)$_5$OC$_6$H$_5$, —(CH$_2$)$_6$OH, —(CH$_2$)$_7$CN, —CH$_2$CH$_2$C$_6$H$_5$—(CH$_2$)$_4$COOH, —(CH$_2$)$_5$COOH, —(CH$_2$)$_5$COOMe, —(CH$_2$)$_{11}$COOH, —(CH$_2$)$_{12}$COOH, —(CH$_2$)$_{12}$OH, —(CH$_2$)$_{13}$OH, —(CH$_2$)$_{11}$CN, —(CH$_2$)$_{11}$OC(O)NH$_2$, —(CH$_2$)$_{11}$COOEt —C(O)(CH$_2$)$_9$CH$_3$, —(CH$_2$)$_5$C(O)N(CH$_2$CH$_2$)$_2$O, and 2-pyrrolyl;

$R_1$ is selected from the group consisting of —H, $C_1$–$C_{11}$ straight chain alkyl, —(CH$_2$)$_4$COOEt, and —C$_6$H$_5$;

when $R_7$ is other than 2-pyrrolyl, $R_9$ is selected from the group consisting of —H, —$CH_3$, —$CH_2CH_3$, and —$CH_2CH_2CH_3$;

when $R_7$ is 2-pyrrolyl, then $R_9$ is selected from the group consisting of —H, —$CH_3$, —$CH_2CH_3$, —$CH_2CH_2CH_3$, and —$OCH_3$;

$R_{16}$ is selected from the group consisting of —H, —$CH_3$, —$CH_2CH_2CH_3$, and —$(CH_2)_6CH_3$; and $R_{17}$ is selected from the group consisting of —H, —CN, —COOMe, —COOEt, and —COOH;

with the proviso that the compound of Formula (V) is not:
prodigiosin,
undecylprodigiosin,
norprodigiosin, or
nonylprodigiosin.

For use in the present methods for inhibiting the growth of a cancer or neoplastic cell, a second preferred subclass of the compounds of Formula (V) is that wherein, in the compound of Formula (V):

$R_1$ is —H;

$R_2$ is selected from the group consisting of —$CH_3$, $C_1$—$C_{12}$ straight chain alkyl, —$CH(CH_3)_2$, and —$CH_2C_6H_5$;

$R_7$ is selected from the group consisting of —H, —$CH_3$, —$CH_2CH_3$, $C_8$–$C_{15}$ straight chain alkyl, —$(CH_2)_9$CH=$CH_2$, —$(CH_2)_5CH_2F$, —$(CH_2)_5OC_6H_5$, —$(CH_2)_6$OH, —$(CH_2)_7CN$, —$CH_2CH_2C_6H_5$, —$(CH_2)_4COOH$, —$(CH_2)_5COOH$, —$(CH_2)_5COOMe$, —$(CH_2)_{11}COOH$, —$(CH_2)_{12}COOH$, —$(CH_2)_{12}OH$, —$(CH_2)_{13}OH$, —$(CH_2)_{11}CN$, —$(CH_2)_{11}OC(O)NH_2$, —$(CH_2)_{11}COOEt$ —$C(O)(CH_2)_9CH_3$, —$(CH_2)_5C(O)N(CH_2CH_2)_2O$, and 2-pyrrolyl;

$R_8$ is selected from the group consisting of —H, —$CH_3$, —$CH_2CH_3$, $C_6$–$C_{11}$ straight chain alkyl, —$(CH_2)_4COOEt$, and —$C_6H_5$;

when $R_7$ is other than 2-pyrrolyl, $R_9$ is selected from the group consisting of —H, —$CH_3$, —$CH_2CH_3$, and —$CH_2CH_2CH_3$;

when $R_7$ is 2-pyrrolyl, then $R_9$ is selected from the group consisting of —H, —$CH_3$, —$CH_2CH_3$, —$CH_2CH_2CH_3$, and —$OCH_3$;

$R_{16}$ is selected from the group consisting of —H, —$CH_3$, —$CH_2CH_2CH_3$, and —$(CH_2)_6CH_3$;

$R_{17}$ is selected from the group consisting of —H, —CN, —COOMe, —COOEt, and —COOH;

with the proviso that the compound of Formula (V) is not:
prodigiosin, or
undecylprodiginine.

The present invention provides methods for treating or preventing a viral infection in a patient comprising administering to a patient in need of such treatment or prevention a therapeutically effective amount of a composition comprising a pharmaceutically acceptable carrier and a compound of Formula (V) or a pharmaceutically acceptable salt thereof, wherein:

$R_1$ is selected from the group consisting of —H, —$CH_3$, —$CH_2CH_3$, —$CH_2C_6H_5$, —$C(O)OC(CH_3)_3$, —$C(O)OCH_2C_6H_5$, and —$C(O)CH_3$;

$R_2$ is selected from the group consisting of —H, $C_1$–$C_{12}$ straight chain alkyl, —$CH_2C_6H_5$, —$SiR_{10}R_{11}R_{12}$, —$C(O)CH_3$, —$C(O)C_6H_5$, -2-tetrahydropyranyl, —$OCH_2OCH_3$, and —$C(O)OCH_2CCl_3$;

$R_7$ is selected from the group consisting of —H, $C_1$–$C_5$ straight chain alkyl, —$(CH_2)_9CH$=$CH_2$, —$(CH_2)_6F$, —$(CH_2)_5OC_6H_5$, —$(CH_2)_6OH$, —$(CH_2)_7CN$, —$CH_2CH_2C_6H_5$, —$(CH_2)_4COOH$, —$(CH_2)_5COOH$, —$(CH_2)_5COOMe$, —$(CH_2)_{11}COOH$, —$(CH_2)_{12}COOH$, —$(CH_2)_{12}OH$, —$(CH_2)_{13}OH$, —$(CH_2)_{11}CN$, —$(CH_2)_{11}OC(O)NH_2$, —$(CH_2)_{11}COOEt$, —$C(O)(CH_2)_9CH_3$, —$(CH_2)_5C(O)N(CH_2CH_2)_2O$, $C_3$–$C_7$ cycloalkyl, —$C_6H_5$, 2-pyrrolyl, -3-pyrrolyl, 2-pyridyl, 3-pyridyl, 4-pyridyl, 2-furanyl, and 3-furanyl, the phenyl being substituted with one or more halo, methyl, methoxyl, hydroxyl, methoxycarbonyl or trifluoromethyl groups;

$R_8$ is selected from the group consisting of —H, $C_1$–$C_{11}$ straight chain alkyl, —$(CH_2)_4COOEt$, and —$C_6H_5$;

when $R_7$ is other than 2-pyrrolyl, $R_9$ is selected from the group consisting of —H, —$CH_3$, —$CH_2CH_3$, and —$CH_2CH_2CH_3$;

when $R_7$ is 2-pyrrolyl, then $R_9$ is selected from the group consisting of —H, —$CH_3$, —$CH_2CH_3$, —$CH_2CH_2CH_3$, and —$OCH_3$;

$R_{10}$ is selected from the group consisting of $C_1$–$C_4$ straight or branched chain alkyl and —$C_6H_5$;

$R_{11}$ and $R_{12}$ are independently selected from the group consisting of —$CH_3$, —$CH_2CH_3$, and —$C_3H_7$;

$R_{16}$ is selected from the group consisting of —H, —$CH_3$, —$CH_2CH_2CH_3$, and —$(CH_2)_6CH_3$; and $R_{17}$ is selected from the group consisting of —H, —CN, —COOMe, —COOEt, and —COOH.

Preferred compounds for use in the methods for treating or preventing a viral infection are:
6-methoxy-2-methyl-3-heptylprodigeosene,
4-methoxy-5-((3-methoxy-5-(1H-pyrrol-2-yl)-2H-pyrrol-2-ylidene)methyl)2,2'-bi-1H-pyrrol,
nonylprodigiosin,
3-heptyl-5-((3-methoxy-5-pyrrol-2-yl-2H-pyrrol-2-ylidene)methyl)-2-methyl-4-propyl-pyrrole,
prodigiosin,
undecylprodigiosin,
norprodigiosin, and
nonylprodigiosin, or pharmaceutically acceptable salts thereof.

For use in the present methods for treating or preventing a viral infection, a preferred subclass of the compounds of Formula (V) is that wherein, in the compound of Formula (V):

$R_1$ is —H;

$R_2$ is selected from the group consisting of —H, $C_1$–$C_{12}$ straight chain alkyl, —$CH(CH_3)_2$, and —$CH_2C_6H_5$;

$R_7$ is selected from the group consisting of —H, —$CH_3$, —$CH_2CH_3$, $C_3$–$C_5$ straight chain alkyl, —$(CH_2)_9$CH=$CH_2$, —$(CH_2)_5CH_2F$, —$(CH_2)_5OC_6H_5$, —$(CH_2)_6$OH, —$(CH_2)_7CN$, —$CH_2CH_2C_6H_5$, —$(CH_2)_4COOH$, —$(CH_2)_5COOH$, —$(CH_2)_5COOMe$, —$(CH_2)_{11}COOH$, —$(CH_2)_{12}COOH$, —$(CH_2)_{12}OH$, —$(CH_2)_{13}OH$, —$(CH_2)_{11}CN$, —$(CH_2)_{11}OC(O)NH_2$, —$(CH_2)_{11}COOEt$ —$C(O)(CH_2)_9$ $CH_3$, —$(CH_2)_5C(O)N(CH_2CH_2)_2O$, and 2-pyrrolyl;

$R_8$ is selected from the group consisting of —H, $C_1$–$C_{11}$ straight chain alkyl, —$(CH_2)_4COOEt$, and —$C_6H_5$;

when $R_7$ is other than 2-pyrrolyl, $R_9$ is selected from the group consisting of —H, —$CH_3$, —$CH_2CH_3$, and —$CH_2CH_2CH_3$;

when $R_7$ is 2-pyrrolyl, then $R_9$ is selected from the group consisting of —H, —$CH_3$, —$CH_2CH_3$, —$CH_2CH_2CH_3$, and —$OCH_3$;

$R_{16}$ is selected from the group consisting of —H, —$CH_3$, —$CH_2CH_2CH_3$, and —$(CH_2)_6CH_3$; and $R_{17}$ is selected from the group consisting of —H, —CN, —COOMe, —COOEt, and —COOH.

For use in the present methods for treating or preventing a viral infection, a second preferred subclass of the compounds of Formula (V) is that wherein, in the compound of Formula (V):

$R_1$ is —H;

$R_2$ is selected from the group consisting of $C_1$–$C_{12}$ straight chain alkyl, —CH(CH$_3$)$_2$, and —CH$_2$C$_6$H$_5$;

$R_7$ is selected from the group consisting of —H, —CH$_3$, —CH$_2$CH$_3$, $C_8$–$C_{15}$ straight chain alkyl, —(CH$_2$)$_9$CH=CH$_2$, —(CH$_2$)$_5$CH$_2$F, —(CH$_2$)$_5$OC$_6$H$_5$, —(CH$_2$)$_6$OH, —(CH$_2$)$_7$CN, —CH$_2$CH$_2$C$_6$H$_5$, —(CH$_2$)$_4$COOH, —(CH$_2$)$_5$COOH, —(CH$_2$)$_5$COOMe, —(CH$_2$)$_{11}$COOH, —(CH$_2$)$_{12}$COOH, —(CH$_2$)$_{12}$OH, —(CH$_2$)$_{13}$OH, —(CH$_2$)$_{11}$CN, —(CH$_2$)$_{11}$OC(O)NH$_2$, —(CH$_2$)$_{11}$COOEt —C(O)(CH$_2$)$_9$CH$_3$, —(CH$_2$)$_5$C(O)N(CH$_2$CH$_2$)$_2$O, and 2-pyrrolyl;

$R_8$ is selected from the group consisting of —H, —CH$_3$, —CH$_2$CH$_3$, $C_6$–$C_{11}$ straight chain alkyl, —(CH$_2$)$_4$COOEt, and —C$_6$H$_5$;

when $R_7$ is other than 2-pyrrolyl, then $R_9$ is selected from the group consisting of —H, —CH$_3$, —CH$_2$CH$_3$, and —CH$_2$CH$_2$CH$_3$;

when $R_7$ is 2-pyrrolyl, then $R_9$ is selected from the group consisting of —H, —CH$_3$, —CH$_2$CH$_3$, —CH$_2$CH$_2$CH$_3$, and —OCH$_3$;

$R_{16}$ is selected from the group consisting of —H, —CH$_3$, —CH$_2$CH$_2$CH$_3$, and —(CH$_2$)$_6$CH$_3$; and $R_{17}$ is selected from the group consisting of —H, —CN, —COOMe, —COOEt, and —COOH.

The present invention provides methods for inhibiting the replication or infectivity of a virus comprising a contacting a virus or a virus-infected cell with an effective amount of a composition comprising a pharmaceutically acceptable carrier and a compound having the general Formula (V) or a pharmaceutically acceptable salt thereof, wherein:

$R_1$ is selected from the group consisting of —H, —CH$_3$, —CH$_2$CH$_3$, —CH$_2$C$_6$H$_5$, —C(O)OC(CH$_3$)$_3$, —C(O)OCH$_2$C$_6$H$_5$, and —C(O)CH$_3$;

$R_2$ is selected from the group consisting of —H, $C_1$–$C_{12}$ straight chain alkyl, —CH$_2$C$_6$H$_5$, —SiR$_{10}$R$_{11}$R$_{12}$, —C(O)CH$_3$, —C(O)C$_6$H$_5$, -2-tetrahydropyranyl, —OCH$_2$OCH$_3$, and —C(O)OCH$_2$CCl$_3$;

$R_7$ is selected from the group consisting of —H, $C_1$–$C_{15}$ straight chain alkyl, —(CH$_2$)$_9$CH=CH$_2$, —(CH$_2$)$_6$F, —(CH$_2$)$_5$OC$_6$H$_5$, —(CH$_2$)$_6$OH, —(CH$_2$)$_7$CN, —CH$_2$CH$_2$C$_6$H$_5$, —(CH$_2$)$_4$COOH, —(CH$_2$)$_5$COOH, —(CH$_2$)$_5$COOMe, —(CH$_2$)$_5$COOH, —(CH$_2$)$_{12}$COOH, —(CH$_2$)$_{12}$OH, —(CH$_2$)$_{13}$OH, —(CH$_2$)$_{11}$CN, —(CH$_2$)$_{11}$OC(O)NH$_2$, —(CH$_2$)$_{11}$COOEt, —C(O)(CH$_2$)$_9$CH$_3$, —(CH$_2$)$_5$C(O)N(CH$_2$CH$_2$)$_2$O, $C_3$–$C_7$ cycloalkyl, —C$_6$H$_5$, 2-pyrrolyl, -3-pyrrolyl, 2-pyridyl, 3-pyridyl, 4-pyridyl, 2-furanyl, and 3-furanyl, the phenyl being substituted with one or more halo, methyl, methoxyl, hydroxyl, methoxycarbonyl or trifluoromethyl groups;

$R_8$ is selected from the group consisting of —H, $C_1$–$C_{11}$ straight chain alkyl, —(CH$_2$)$_4$COOEt, and —C$_6$H$_5$;

when $R_7$ is other than 2-pyrrolyl, $R_9$ is selected from the group consisting of —H, —CH$_3$, —CH$_2$CH$_3$, and —CH$_2$CH$_2$CH$_3$;

when $R_7$ is 2-pyrrolyl, then $R_9$ is selected from the group consisting of —H, —CH$_3$, —CH$_2$CH$_3$, —CH$_2$CH$_2$CH$_3$, and —OCH$_3$;

$R_{10}$ is selected from the group consisting of $C_1$–$C_4$ straight or branched chain alkyl and —C$_6$H$_5$;

$R_{11}$ and $R_{12}$ are independently selected from the group consisting of —CH$_3$, —CH$_2$CH$_3$, and —C$_3$H$_7$;

$R_{16}$ is selected from the group consisting of —H, —CH$_3$, —CH$_2$CH$_2$CH$_3$, and —(CH$_2$)$_6$CH$_3$; and $R_{17}$ is selected from the group consisting of —H, —CN, —COOMe, —COOEt, and —COOH.

Preferred compounds for use in the method for inhibiting the replication or infectivity of a virus are:

6-methoxy-2-methyl-3-heptylprodigeosene, 4-methoxy-5-((3-methoxy-5-(1H-pyrrol-2-yl)-2H-pyrrol-2-ylidene)methyl)-2,2'-bi-1H-pyrrol, nonylprodigiosin, 3-heptyl-5-((3-methoxy-5-pyrrol-2-yl-2H-pyrrol-2-ylidene)methyl)-2-methyl-4-propyl-pyrrole prodigiosin, undecylprodigiosin, norprodigiosin, and nonylprodigiosin, or pharmaceutically acceptable salts thereof.

For use in the present methods for inhibiting the replication or infectivity of a virus, a preferred subclass of the compounds of Formula (V) is that wherein, in the compound of Formula (V):

$R_1$ is —H;

$R_2$ is selected from the group consisting of —H, $C_1$–$C_{12}$ straight chain alkyl, —CH(CH$_3$)$_2$, and —CH$_2$C$_6$H$_5$;

$R_7$ is selected from the group consisting of —H, —CH$_3$, —CH$_2$CH$_3$, $C_3$–$C_{15}$ straight chain alkyl, —(CH$_2$)$_9$C=CH$_2$, —(CH$_2$)$_5$CH$_2$F, —(CH$_2$)$_5$OC$_5$H$_6$, —(CH$_2$)$_6$OH, —(CH$_2$)$_7$CN, —CH$_2$CH$_2$C$_5$H$_6$, —(CH$_2$)$_4$COOH, —(CH$_2$)$_5$COOH, —(CH$_2$)$_5$COOMe, —(CH$_2$)$_{11}$COOH, —(CH$_2$)$_{12}$COOH, —(CH$_2$)$_{12}$OH, —(CH$_2$)$_{13}$OH, —(CH$_2$)$_{11}$CN, —(CH$_2$)$_{11}$OC(O)NH$_2$, —(CH$_2$)$_{11}$COOEt, —C(O)(CH$_2$)$_9$CH$_3$, —(CH$_2$)$_5$C(O)N(CH$_2$CH$_2$)$_2$O, and 2-pyrrolyl;

$R_8$ is selected from the group consisting of —H, $C_1$–$C_{11}$ straight chain alkyl, —(CH$_2$)$_4$COOEt, and —C$_6$H$_5$;

when $R_7$ is other than 2-pyrrolyl, $R_9$ is selected from the group consisting of —H, —CH$_3$, —CH$_2$CH$_3$, and —CH$_2$CH$_2$CH$_3$;

when $R_7$ is 2-pyrrolyl, then $R_9$ is selected from the group consisting of —H, —CH$_3$, —CH$_2$CH$_3$, —CH$_2$CH$_2$CH$_3$, and —OCH$_3$;

$R_{16}$ is selected from the group consisting of —H, —CH$_3$, —CH$_2$CH$_2$CH$_3$, and —(CH$_2$)$_6$CH$_3$; and $R_{17}$ is selected from the group consisting of —H, —CN, —COOMe, —COOEt, and —COOH.

For use in the present methods for inhibiting the replication or infectivity of a virus, a second preferred subclass of the compounds of Formula (V) is that wherein, in the compound of Formula (V):

$R_1$ is —H;

$R_2$ is selected from the group consisting of $C_1$–$C_{12}$ straight chain alkyl, —CH(CH$_3$)$_2$, and —CH$_2$C$_6$H$_5$;

$R_7$ is selected from the group consisting of —H, —CH$_3$, —CH$_2$CH$_3$, $C_8$–$C_{15}$ straight chain alkyl, —(CH$_2$)$_9$C=CH$_2$, —(CH$_2$)$_5$CH$_2$F, —(CH$_2$)$_5$OC$_5$H$_6$, —(CH$_2$)$_6$OH, —(CH$_2$)$_7$CN, —CH$_2$CH$_2$C$_5$H$_6$, —(CH$_2$)$_4$COOH, —(CH$_2$)$_5$COOH, —(CH$_2$)$_5$COOMe, —(CH$_2$)$_5$COOH, —(CH$_2$)$_{12}$COOH, —(CH$_2$)$_{12}$OH, —(CH$_2$)$_{13}$OH, —(CH$_2$)$_{11}$CN, —(CH$_2$)$_{11}$OC(O)NH$_2$, —(CH$_2$)$_{11}$COOEt —C(O)(CH$_2$)$_9$CH$_3$, —(CH$_2$)$_5$C(O)N(CH$_2$CH$_2$)$_2$O, and 2-pyrrolyl;

$R_8$ is selected from the group consisting of —H, —CH$_3$, —CH$_2$CH$_3$, $C_6$–$C_{11}$ straight chain alkyl, —(CH$_2$)$_4$COOEt, and —C$_6$H$_5$;

when $R_7$ is other than 2-pyrrolyl, $R_9$ is selected from the group consisting of —H, —CH$_3$, —CH$_2$CH$_3$, and —CH$_2$CH$_2$CH$_3$;

when $R_7$ is 2-pyrrolyl, then $R_9$ is selected from the group consisting of —H, —CH$_3$, —CH$_2$CH$_3$, —CH$_2$CH$_2$CH$_3$, and —OCH$_3$;

$R_{16}$ is selected from the group consisting of —H, —CH$_3$, —CH$_2$CH$_2$CH$_3$, and —(CH$_2$)$_6$CH$_3$; and $R_{17}$ is selected from the group consisting of —H, —CN, —COOMe, —COOEt, and —COOH.

4.6. Racemates and Enantiomers of Formula (I–V) Compounds

As used herein, the term "Pyrrole-Type compounds" means, collectively, the compounds of Formulas (I–V) and racemates and/or enantiomers thereof, and pharmaceutically acceptable salts thereof

4.7. Synthesis of the Pyrrole-Type Compounds

The compounds of the invention can be obtained via conventional organic syntheses, e.g., as described below. Schemes A–I indicate methods by which compounds of the invention may be obtained. In several sections herein and within Schemes A–I, chemical classes are indicated by numerical labeling in bold text.

4.7.1. The Compounds of Formula (I)

The compounds of Formula (I) can be obtained using conventional organic synthesis or by the following illustrative methods:

The compounds of Formula (I) wherein $R_1$ is H, $R_2$ is Me, $R_3$ is straight chain alkyl, benzyl or substituted benzyl, and m is 1–5 can be prepared by the methods shown in Scheme A.

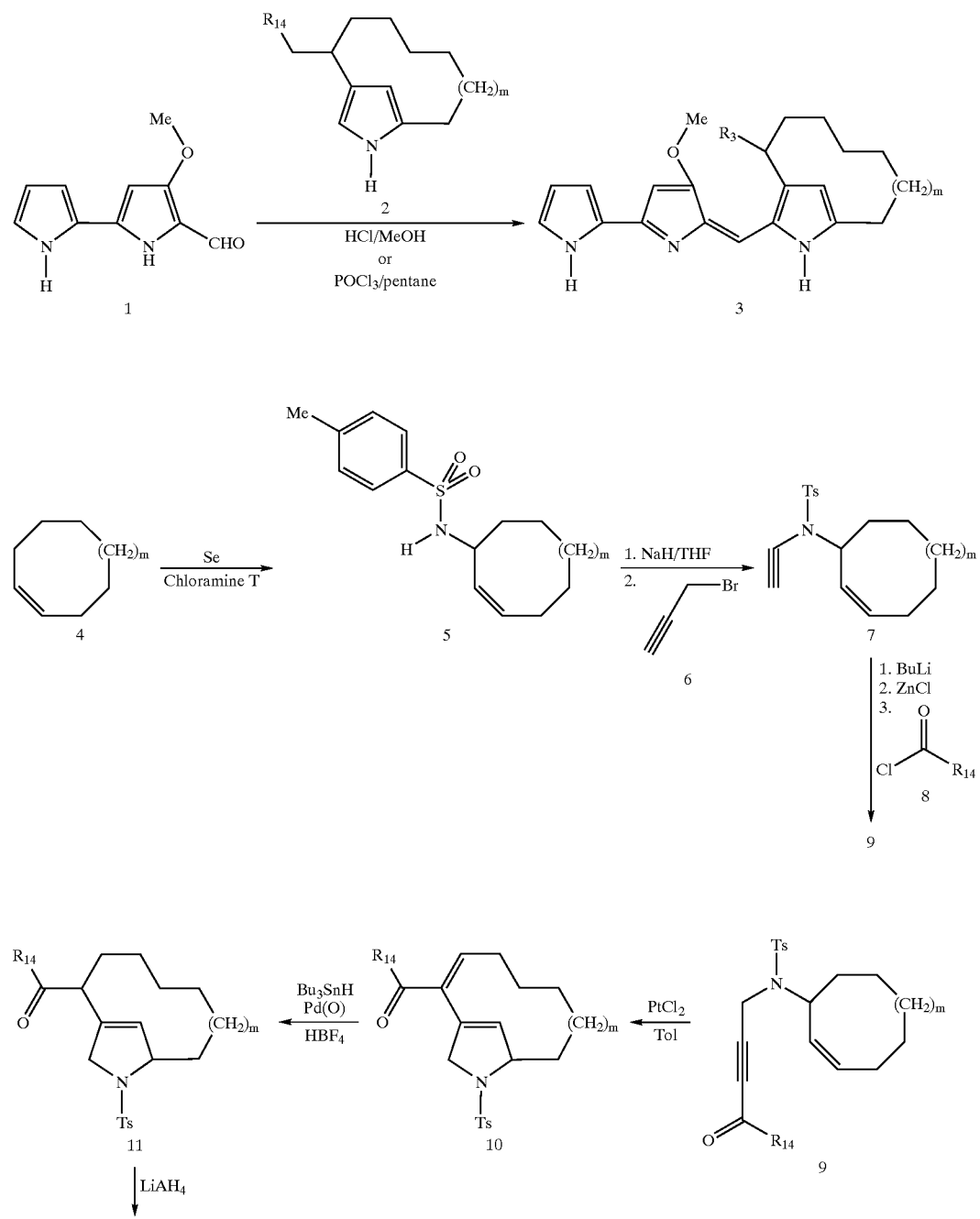

Scheme A

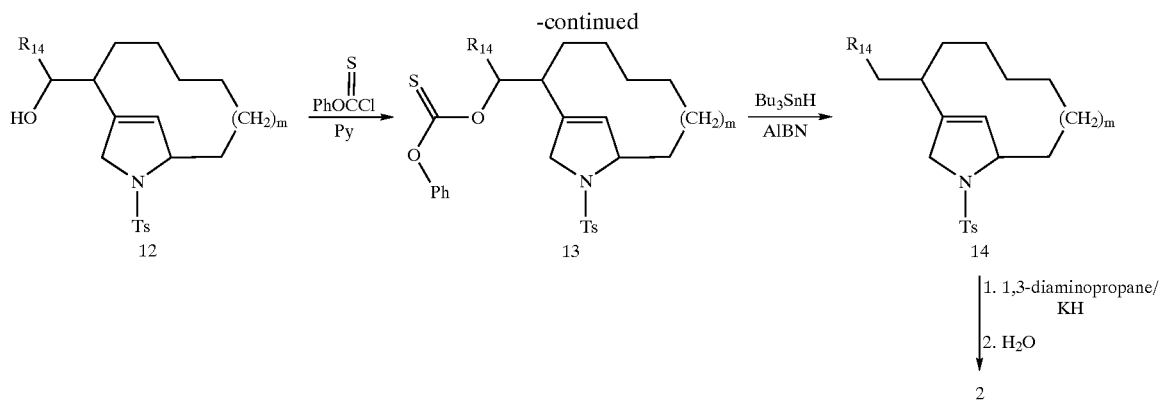

Specifically, the dipyrrole aldehyde 1 (D. L. Boger and M. Patel, J. Org. Chem. 53, 1405–1415, 1988) reacts under acid catalysis with the pyrrole 2, giving the prodigiosene 3. The reaction of 1 with pyrroles, such as 2, is also carried out with phosphorous oxychloride in solvents such as pentane. (J. A. van Koeveringe and J. Lugtenburg, Recl. Trav. Chim. Pays-Bas 96, 55–58, 1977.)

The methods used for the synthesis of pyrroles of structure 2 are outlined in Scheme A. $R_{14}$ is $R_3$ less its α-carbon. These methods have been described by A. Fürstner et al., J. Am. Chem. Soc. 120, 8305–8314, 1998; when m is 1 and $R_{14}$ is n-$C_3H_7$, the structure 3 compound produced is butyl-cycloheptylprodigiosin (also know as streptorubin B or butyl-meta-cycloheptylprodigiosin). Compounds 2 where m is 2–5 are prepared by replacing cis-cyclooctene (4, m=1) with cis-cyclononene, cis-cyclodecene, cis-cycloundecene, and cis-cyclododecene (m=2, 3, 4, and 5, respectively). The structure of the $R_3$ group (straight chain alkyl, benzyl, substituted benzyl, or 2-, 3-, or 4-pyridyl) in compounds 2 is determined by the choice of the acid chloride 8 used in the reaction with compound 7. Thus, for example, the compound 2 in which m is 1 and $R_{14}$ is $C_6H_5$ is produced when cis-cyclooctene (4, m is 1) and benzoyl chloride (8, $R_{14}$ is $C_6H_5$) are used at the appropriate points of the synthesis. Acid chlorides are prepared from their corresponding carboxylic acids by using thionyl chloride, oxalyl chloride, and/or other methods known in the art.

Compounds of Formula (I) wherein $R_1$ is H, $R_2$ is Me, and $R_3$ is an acyl group as defined above can be prepared by the methods shown in Scheme B.

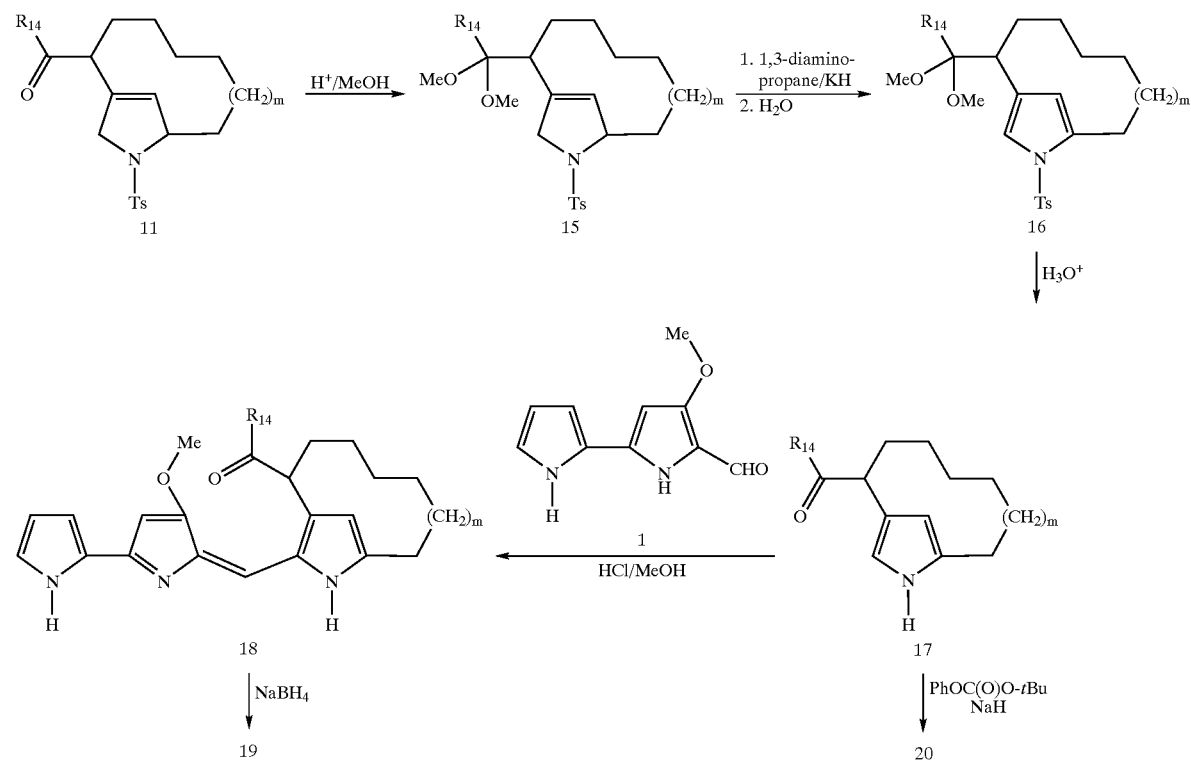

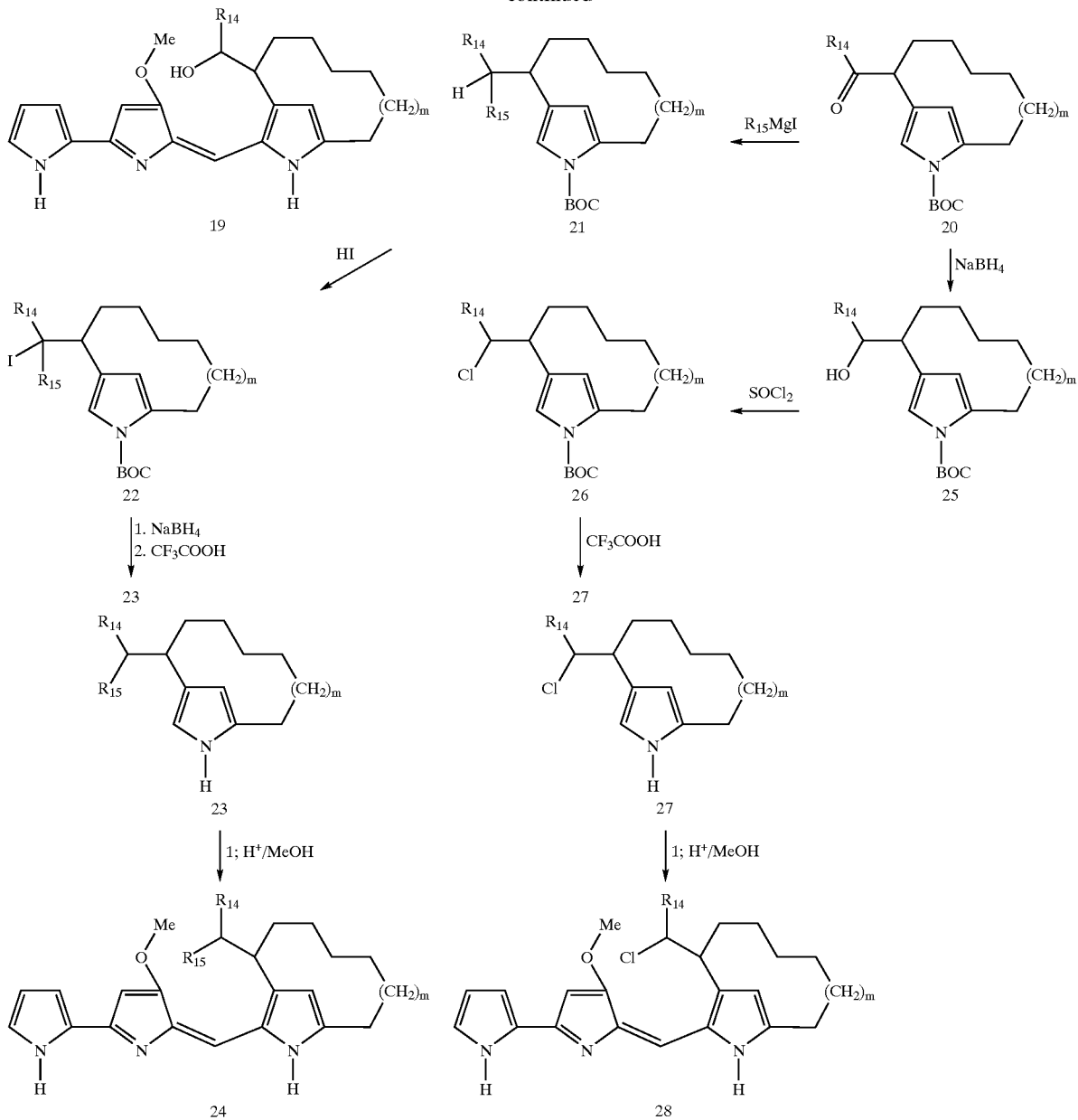

Variations of m and $R_{14}$ are introduced as described above. The ketone functionality of compound 11 is converted to the dimethyl ketal by methods well known in the art (see, for example, T. W. Greene and P. G. M. Wuts, "Protective Groups in Organic Synthesis," 2$^{nd}$ Ed., Wiley, New York, 1991, pp 178–183. ("Greene and Wuts."). The N-Ts-dihydropyrrole ring of is converted to the pyrrole 16 by the method of Fürstner et al., cited above. The ketone carbonyl group is regenerated by standard methods, giving the acyl compound 17. The compound 17 reacts with 1 under conditions given above to produce the acylprodigiosene 18.

Compounds of Formula (I) wherein $R_1$ is H, $R_2$ is Me, and $R_3$ is a 1-hydroxyalkyl group are prepared from 18 as shown in Scheme B. Using standard hydride reduction methods, such as sodium borohydride, 19 is obtained from 18.

Compounds of Formula (I) wherein $R_1$ is H, $R_2$ is Me, and $R_3$ is a branched alkyl are prepared by the methods shown in Scheme B. $R_{15}$ is the branch of the branched chain alkyl. The ketopyrrole 17 reacts with sodium hydride and phenyl t-butylcarbonate (Greene and Wuts, p. 387), giving the N-BOC-pyrrole 20. Compound is reacted with an alkyl ($R_{15}$) magnesium iodide in a Grignard reaction, giving tertiary alcohol 21. In a series of well-known reaction steps, 21 is converted to the branched alkyl pyrrole derivative 23. First the hydroxyl group of 21 is replaced with iodide by reaction with hydrogen iodide. The iodine atom is removed from 22 by hydride reduction, for example, with sodium borohydride. The N-BOC protecting group is removed using trifluoroacetic acid and the resulting pyrrole 23 reacts with 1 under conditions given above, giving the branched alkyl compound 24. Thus, for example, the compound 24 in which m is 1 and $R_{14}$ and $R_{15}$ are Me is produced when 8 is acetyl chloride (Scheme A) and $R_{15}$ MgI is methyl magnesium iodide.

Compounds of Formula (I) wherein $R_1$ is H, $R_2$ is Me, and $R_3$ is a 1-chloroalkyl group are prepared by the methods shown in Scheme B. The ketone carbonyl of is reduced with, for example, sodium borohydride, giving the hydroxyl compound 25. Reaction of 25 with thionyl chloride replaces the hydroxyl group with a chlorine atom as shown in 26. The N-BOC protecting group is removed as described above to give the pyrrole 27, which reacts with 1 to give 28.

Compounds of Formula (I) wherein $R_1$ is H, $R_2$ is Me, and $R_3$ is a hydrogen atom are prepared by the methods shown in Scheme C.

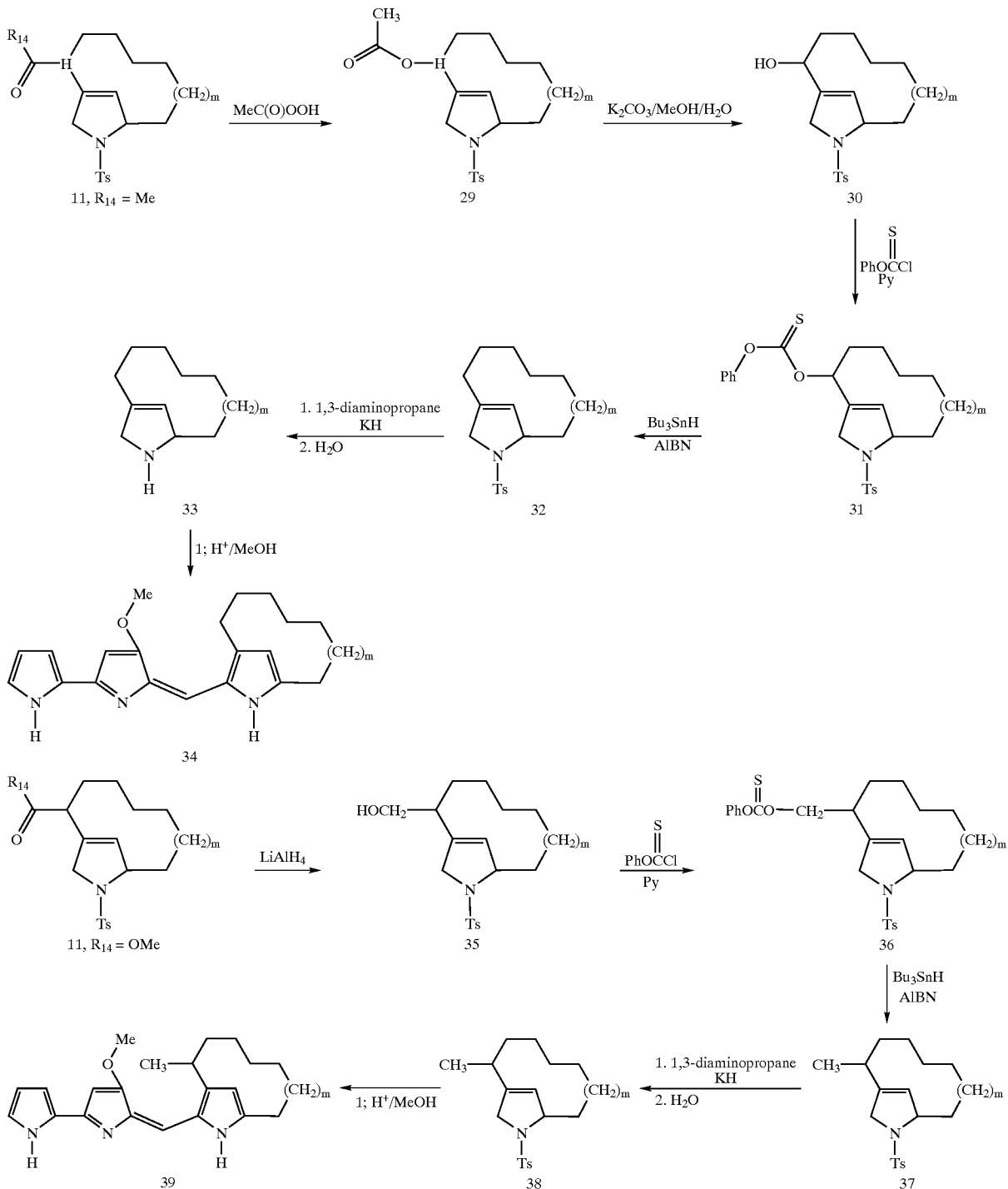

Compound 11 where $R_{14}$ is Me, undergoes a Baeyer-Villiger reaction and thereby is converted to the acetoxy derivative 29. The acetoxy group is saponified by methods known to the art, giving the hydroxyl derivative 30. Using methodology of Fürstner et al., outlined above, the hydroxyl group of 30 is removed in the series of reactions shown in Scheme C leading to 33 via 31 and 32. Finally, the reaction of 33 with 1 under acid catalysis as described above gives 34.

Compounds of Formula (I) wherein $R_1$ is H, $R_2$ is Me, and $R_3$ is a methyl group are prepared by the methods shown in Schemes A and C. Using ethyl chloroformate (in compound 8, $R_{14}$ is OEt) in reaction with 7 (Scheme A), one obtains 9, which is converted to 11 using the reaction conditions outlined in Scheme A. The compound 11 is reduced with, for example, lithium aluminum hydride, giving the hydroxymethyl derivative (Scheme C). Using the same series of reactions described above, is transformed into the methyl-substituted pyrrole 38 via 36 and 37 which, in turn, reacts with 1 under acid catalysis, furnishing 39.

Once the compounds of Formula (I) have been synthesized, they can be purified or substantially purified, using conventional chromatography, recrystallization or other purification techniques known to those skilled in the art.

In certain embodiments of the invention, the compounds of the invention are indicated by chemical name. The structures of these compounds are indicated in Table 3, below, which describes the structure as shown in the corresponding synthesis Schemes.

TABLE 3

FORMULA I

| Compound | Structure |
|---|---|
| 2-Ethyl-11-((3-methoxy-5-(1H-pyrrol-2-yl)-2H-pyrrol-2-ylidene)methyl)-10-azabicyclo[7.2.1]dodeca-9(12),11-diene | chemical class 3 as depicted in Scheme A; $R_3$ is Et, m is 1 |
| 11-((3-Methoxy-5-(1H-pyrrol-2-yl)-2H-pyrrol-2-ylidene)methyl)-10-azabicyclo[7.2.1]dodeca-9(12),11-diene | chemical class 34 as depicted in Scheme C; m is 1 |
| 2-Methyl-11-((3-methoxy-5-(1H-pyrrol-2-yl)-2H-pyrrol-2-ylidene)methyl)-10-azabicyclo[7.2.1]dodeca-9(12),11-diene | chemical class 39 as depicted in Scheme C; m is 1 |
| 2-n-Propyl-11-((3-methoxy-5-(1H-pyrrol-2-yl)-2H-pyrrol-2-ylidene)methyl)-10-azabicyclo[7.2.1]dodeca-9(12),11-diene | chemical class 3 as depicted in Scheme A; $R_3$ is —$CH_2CH_2CH_3$, m is 1 |
| 2-n-Pentyl-11-((3-methoxy-5-(1H-pyrrol-2-yl)-2H-pyrrol-2-ylidene)methyl)-10-azabicyclo[7.2.1]dodeca-9(12),11-diene | chemical class 3 as depicted in Scheme A; $R_3$ is —$CH_2CH_2CH_2CH_2CH_3$, m is 1 |
| 2-Benzyl-11-((3-methoxy-5-(1H-pyrrol-2-yl)-2H-pyrrol-2-ylidene)methyl)-10-azabicyclo[7.2.1]dodeca-9(12),11-diene | chemical class 3 as depicted in Scheme A; $R_3$ is —$CH_2C_6H_5$, m is 1 |
| (R)-2-n-Pentyl-11-((3-methoxy-5-(1H-pyrrol-2-yl)-2H-pyrrol-2-ylidene)methyl)-10-azabicyclo[7.2.1]dodeca-9(12),11-diene | chemical class 3 as depicted in Scheme A; $R_3$ is —$CH_2CH_2CH_2CH_2CH_3$, m is 1 |
| (S)-2-n-Butyl-11-((3-methoxy-5-(1H-pyrrol-2-yl)-2H-pyrrol-2-ylidene)methyl)-10-azabicyclo[7.2.1]dodeca-9(12),11-diene | chemical class 3 as depicted in Scheme A; $R_3$ is —$CH_2CH_2CH_2CH_3$, m is 1 |
| (R)-2-n-Butyl-11-((3-methoxy-5-(1H-pyrrol-2-yl)-2H-pyrrol-2-ylidene)methyl)-10-azabicyclo[7.2.1]dodeca-9(12),11-diene | chemical class 3 as depicted in Scheme A; $R_3$ is —$CH_2CH_2CH_2CH_3$, m is 1 |
| (S)-2-Ethyl-11-((3-methoxy-5-(1H-pyrrol-2-yl)-2H-pyrrol-2-ylidene)methyl)-10-azabicyclo[7.2.1]dodeca-9(12),11-diene | chemical class 3 as depicted in Scheme A; $R_3$ is Et, m is 1 |
| (R)-2-Ethyl-11-((3-methoxy-5-(1H-pyrrol-2-yl)-2H-pyrrol-2-ylidene)methyl)-10-azabicyclo[7.2.1]dodeca-9(12),11-diene | chemical class 3 as depicted in Scheme A; $R_3$ is Et, m is 1 |
| (S)-2-Methyl-11-((3-methoxy-5-(1H-pyrrol-2-yl)-2H-pyrrol-2-ylidene)methyl)-10-azabicyclo[7.2.1]dodeca-9(12),11-diene | chemical class 3 as depicted in Scheme A; $R_3$ is Me, m is 1 |
| (R)-2-Methyl-11-((3-methoxy-5-(1H-pyrrol-2-yl)-2H-pyrrol-2-ylidene)methyl)-10-azabicyclo[7.2.1]dodeca-9(12),11-diene | chemical class 3 as depicted in Scheme A; $R_3$ is Me, m is 1 |
| (S)-2-n-Propyl-11-((3-methoxy-5-(1H-pyrrol-2-yl)-2H-pyrrol-2-ylidene)methyl)-10-azabicyclo[7.2.1]dodeca-9(12),11-diene | chemical class 3 as depicted in Scheme A; $R_3$ is —$CH_2CH_2CH_3$, m is 1 |
| (R)-2-n-Propyl-11-((3-methoxy-5-(1H-pyrrol-2-yl)-2H-pyrrol-2-ylidene)methyl)-10-azabicyclo[7.2.1]dodeca-9(12),11-diene | chemical class 3 as depicted in Scheme A; $R_3$ is —$CH_2CH_2CH_3$, m is 1 |
| 2-Methyl-12-((3-methoxy-5-(1H-pyrrol-2-yl)-2H-pyrrol-2-ylidene)methyl)-11-azabicyclo[8.2.1]trideca-10(13),12-diene | chemical class 39 as depicted in Scheme C; m is 2 |
| 2-Ethyl-12-((3-methoxy-5-(1H-pyrrol-2-yl)-2H-pyrrol-2-ylidene)methyl)-11-azabicyclo[8.2.1]trideca-10(13),12-diene | chemical class 3 as depicted in Scheme A; $R_3$ is Et, m is 2 |
| 2-n-Propyl-12-((3-methoxy-5-(1H-pyrrol-2-yl)-2H-pyrrol-2-ylidene)methyl)-11-azabicyclo[8.2.1]trideca-10(13),12-diene | chemical class 3 as depicted in Scheme A; $R_3$ is —$CH_2CH_2CH_3$, m is 2 |
| 2-n-Butyl-12-((3-methoxy-5-(1H-pyrrol-2-yl)-2H-pyrrol-2-ylidene)methyl)-11-azabicyclo[8.2.1]trideca-10(13),12-diene | chemical class 3 as depicted in Scheme A; $R_3$ is —$CH_2CH_2CH_2CH_3$, m is 2 |
| 2-n-Pentyl-12-((3-methoxy-5-(1H-pyrrol- | chemical class 3 as depicted in Scheme A; |

TABLE 3-continued

FORMULA I

| Compound | Structure |
|---|---|
| 2-yl)-2H-pyrrol-2-ylidene)methyl)-11-azabicyclo[8.2.1]trideca-10(13),12-diene | $R_3$ is —$CH_2CH_2CH_2CH_2CH_3$, m is 2 |
| 12-((3-Methoxy-5-(1H-pyrrol-2-yl)-2H-pyrrol-2-ylidene)methyl)-11-azabicyclo[8.2.1]trideca-10(13),12-diene | chemical class 34 as depicted in Scheme C; m is 2 |
| 2-Methyl-13-((3-methoxy-5-(1H-pyrrol-2-yl)-2H-pyrrol-2-ylidene)methyl)-12-azabicyclo[9.2.1]tetradeca-11(14),13-diene | chemical class 39 as depicted in Scheme C; m is 3 |
| 13-((3-Methoxy-5-(1H-pyrrol-2-yl)-2H-pyrrol-2-ylidene)methyl)-12-azabicyclo[9.2.1]tetradeca-11(14),13-diene | chemical class 34 as depicted in Scheme C; m is 3 |
| 2-Ethyl-12-methyl-13-((3-methoxy-5-(1-methyl-1H-pyrrol-2-yl)-2H-pyrrol-2-ylidene)methyl)-12-azabicyclo[9.2.1]tetradeca-11(14),13-diene | chemical class 108 as depicted in Scheme H; $R_3$ is —$CH_2CH_3$, m is 3 |
| 2-Ethyl-12-methyl-13-((3-methoxy-5-(1H-pyrrol-2-yl)-2H-pyrrol-2-ylidene)methyl)-12-azabicyclo[9.2.1]tetradeca-11(14),13-diene | chemical class 109 as depicted in Scheme H; $R_3$ is —$CH_2CH_3$, m is 3 |
| 2-n-Propyl-13-((3-methoxy-5-(1H-pyrrol-2-yl)-2H-pyrrol-2-ylidene)methyl)-12-azabicyclo[9.2.1]tetradeca-11(14),13-diene | chemical class 3 as depicted in Scheme A; $R_3$ is —$CH_2CH_2CH_3$, m is 3 |
| 2-n-Butyl-13-((3-methoxy-5-(1H-pyrrol-2-yl)-2H-pyrrol-2-ylidene)methyl)-12-azabicyclo[9.2.1]tetradeca-11(14),13-diene | chemical class 3 as depicted in Scheme A; $R_3$ is —$CH_2CH_2CH_2CH_3$, m is 3 |
| 14-((3-Methoxy-5-(1H-pyrrol-2-yl)-2H-pyrrol-2-ylidene)methyl)-13-azabicyclo[10.2.1]pentadeca-12(15),14-diene | chemical class 34 as depicted in Scheme C; m is 4 |
| 2-Butyl-11-((3-methoxy-5-(1-methyl-1H-pyrrol-2-yl)-2H-pyrrol-2-ylidene)methyl)-10-azabicyclo[7.2.1]dodeca-9(12),11-diene | chemical class 106 as depicted in Scheme H |
| 2-Butyl-11-((3-methoxy-5-(1-methyl-1H-pyrrol-2-yl)-2H-pyrrol-2-ylidene)methyl)-10-methyl-10-azabicyclo[7.2.1]dodeca-9(12),11-diene | chemical class 108 as depicted in Scheme H; $R_3$ is —$CH_2CH_2CH_2CH_3$, m is 1 |
| 2-Butyl-11-((3-methoxy-5-(1H-pyrrol-2-yl)-2H-pyrrol-2-ylidene)methyl)-10-methyl-10-azabicyclo[7.2.1]dodeca-9(12),11-diene | chemical class 109 as depicted in Scheme H; $R_3$ is —$CH_2CH_2CH_2CH_3$, m is 1 |
| 2-Ethyl-11-((3-benzyloxy-5-(1H-pyrrol-2-yl)-2H-pyrrol-2-ylidene)methyl)-10-azabicyclo[7.2.1]dodeca-9(12),11-diene | chemical class 119 as depicted in Scheme I; $R_2$ is —$CH_2C_6H_5$ |
| 2-Butyl-11-((3-hydroxy-5-(1H-pyrrol-2-yl)-2H-pyrrol-2-ylidene)methyl)-10-azabicyclo[7.2.1]dodeca-9(12),11-diene | chemical class 137 as depicted in Scheme I; $R_3$ is —$CH_2CH_2CH_2CH_3$, m is 1 |
| 2-Butyl-11-((3-benzyloxy-5-(1H-pyrrol-2-yl)-2H-pyrrol-2-ylidene)methyl)-10-azabicyclo[7.2.1]dodeca-9(12),11-diene | Formula I; $R_1$ is —H, $R_2$ is —$CH_2C_6H_5$, $R_3$ is —$(CH_2)_3CH_3$, $R_{16}$ is —H, $R_{17}$ is —H, m is 1 |
| 11-((3-Benzyloxy-5-(1H-pyrrol-2-yl)-2H-pyrrol-2-ylidene)methyl)-10-azabicyclo[7.2.1]dodeca-9(12),11-diene | Formula I; $R_1$ is —H, $R_2$ is —$CH_2C_6H_5$, $R_3$ is —H, $R_{16}$ is —H, $R_{17}$ is —H, m is 1 |
| 2-Methyl-11-((3-benzyloxy-5-(1H-pyrrol-2-yl)-2H-pyrrol-2-ylidene)methyl)-10-azabicyclo[7.2.1]dodeca-9(12),11-diene | Formula I; $R_1$ is —H, $R_2$ is —$CH_2C_6H_5$, $R_3$ is —$CH_3$, $R_{16}$ is —H, $R_{17}$ is —H, m is 1 |
| 2-n-Propyl-11-((3-benzyloxy-5-(1H-pyrrol-2-yl)-2H-pyrrol-2-ylidene)methyl)-10-azabicyclo[7.2.1]dodeca-9(12),11-diene | Formula I; $R_1$ is —H, $R_2$ is —$CH_2C_6H_5$, $R_3$ is —$(CH_2)_2CH_3$, $R_{16}$ is —H, $R_{17}$ is —H, m is 1 |
| 2-n-Pentyl-11-((3-benzyloxy-5-(1H-pyrrol-2-yl)-2H-pyrrol-2-ylidene)methyl)-10-azabicyclo[7.2.1]dodeca-9(12),11-diene | Formula I; $R_1$ is —H, $R_2$ is —$CH_2C_6H_5$, $R_3$ is —$(CH_2)_4CH_3$, $R_{16}$ is —H, $R_{17}$ is —H, m is 1 |
| 2-Benzyl-11-((3-benzyloxy-5-(1H-pyrrol-2-yl)-2H-pyrrol-2-ylidene)methyl)-10-azabicyclo[7.2.1]dodeca-9(12),11-diene | Formula I; $R_1$ is —H, $R_2$ is —$CH_2C_6H_5$, $R_3$ is —$CH_2C_6H_5$, $R_{16}$ is —H, $R_{17}$ is —H, m is 1 |
| 2-Methyl-14-((3-methoxy-5-(1H-pyrrol-2-yl)-2H-pyrrol-2-ylidene)methyl)-13-azabicyclo[10.2.1]pentadeca-12(15),14-diene | chemical class 39 as depicted in Scheme C; m is 4 |
| 15-((3-Methoxy-5-(1H-pyrrol-2-yl)-2H-pyrrol-2-ylidene)methyl)-14-azabicyclo[11.2.1]pentadeca-13(16),15-diene | chemical class 34 as depicted in Scheme C; m is 5 |
| 2-Methyl-15-((3-methoxy-5-(1H-pyrrol-2-yl)-2H-pyrrol-2-ylidene)methyl)-14-azabicyclo[11.2.1]pentadeca-13(16),15-diene | chemical class 39 as depicted in Scheme C; m is 5 |
| 2-(2-Hydroxy-n-butyl)-11-((3-methoxy-5-(1H-pyrrol-2-yl)-2H-pyrrol-2-ylidene)methyl)-10-azabicyclo[7.2.1]dodeca-9(12),11-diene | chemical class 19 as depicted in Scheme B; $R_{14}$ is —$CH_2CH_2CH_3$, m is 1 |

TABLE 3-continued

FORMULA I

| Compound | Structure |
|---|---|
| 2-(2-Chloro-n-butyl)-11-((3-methoxy-5-(1H-pyrrol-2-yl)-2H-pyrrol-2-ylidene)methyl)-10-azabicyclo[7.2.1]dodeca-9(12),11-diene | chemical class 24 as depicted in Scheme B; $R_{14}$ is —$CH_2CH_2CH_3$, m is 1 |
| 2-Butyl-11-((3-ethoxy-5-(1H-pyrrol-2-yl)-2H-pyrrol-2-ylidene)methyl)-10-azabicyclo[7.2.1]dodeca-9(12),11-diene | Formula I; $R_1$ is —H, $R_2$ is —$CH_2CH_3$, $R_3$ is —$(CH_2)_3CH_3$, $R_{16}$ is —H, $R_{17}$ is —H, m is 1 |
| 11-((3-Ethoxy-5-(1H-pyrrol-2-yl)-2H-pyrrol-2-ylidene)methyl)-10-azabicyclo[7.2.1]dodeca-9(12),11-diene | Formula I; $R_1$ is —H, $R_2$ is —$CH_2CH_3$, $R_3$ is —H, $R_{16}$ is —H, $R_{17}$ is —H, m is 1 |
| 2-Methyl-11-((3-ethoxy-5-(1H-pyrrol-2-yl)-2H-pyrrol-2-ylidene)methyl)-10-azabicyclo[7.2.1]dodeca-9(12),11-diene | Formula I; $R_1$ is —H, $R_2$ is —$CH_2CH_3$, $R_3$ is $CH_3$, $R_{16}$ is —H, $R_{17}$ is —H, m is 1 |
| 2-n-Propyl-11-((3-ethoxy-5-(1H-pyrrol-2-yl)-2H-pyrrol-2-ylidene)methyl)-10-azabicyclo[7.2.1]dodeca-9(12),11-diene | Formula I; $R_1$ is —H, $R_2$ is —$CH_2CH_3$, $R_3$ is —$(CH_2)_2CH_3$, $R_{16}$ is —H, $R_{17}$ is —H, m is 1 |
| 2-n-Pentyl-11-((3-ethoxy-5-(1H-pyrrol-2-yl)-2H-pyrrol-2-ylidene)methyl)-10-azabicyclo[7.2.1]dodeca-9(12),11-diene | Formula I; $R_1$ is —H, $R_2$ is —$CH_2CH_3$, $R_3$ is —$(CH_2)_4CH_3$, $R_{16}$ is —H, $R_{17}$ is —H, m is 1 |
| 2-Benzyl-11-((3-ethoxy-5-(1H-pyrrol-2-yl)-2H-pyrrol-2-ylidene)methyl)-10-azabicyclo[7.2.1]dodeca-9(12),11-diene | Formula I; $R_1$ is —H, $R_2$ is —$CH_2CH_3$, $R_3$ is —$CH_2C_6H_5$, $R_{16}$ is —H, $R_{17}$ is —H, m is 1 |
| 2-Ethyl-11-((3-ethoxy-5-(1H-pyrrol-2-yl)-2H-pyrrol-2-ylidene)methyl)-10-azabicyclo[7.2.1]dodeca-9(12),11-diene | Formula I; $R_1$ is —H, $R_2$ is —$CH_2CH_3$, $R_3$ is —$CH_2CH_3$, $R_{16}$ is —H, $R_{17}$ is —H, m is 1 |
| 2-Methyl-13-((3-benzyloxy-5-(1H-pyrrol-2-yl)-2H-pyrrol-2-ylidene)methyl)-12-azabicyclo[9.2.1]tetradeca-11(14),13-diene | Formula I; $R_1$ is —H, $R_2$ is —$CH_2C_6H_5$, $R_3$ is —$CH_3$, $R_{16}$ is —H, $R_{17}$ is —H, m is 3 |
| 13-((3-Benzyloxy-5-(1H-pyrrol-2-yl)-2H-pyrrol-2-ylidene)methyl)-12-azabicyclo[9.2.1]tetradeca-11(14),13-diene | Formula I; $R_1$ is —H, $R_2$ is —$CH_2C_6H_5$, $R_3$ is —H, $R_{16}$ is —H, $R_{17}$ is —H, m is 3 |
| 2-Ethyl-12-methyl-13-((3-benzyloxy-5-(1-methyl-1H-pyrrol-2-yl)-2H-pyrrol-2-ylidene)methyl)-12-azabicyclo[9.2.1]tetradeca-11(14),13-diene | Formula I; $R_1$ is —$CH_3$, $R_2$ is —$CH_2C_6H_5$, $R_3$ is —$CH_2CH_3$, $R_{16}$ is —H, $R_{17}$ is —H, m is 3 |
| 2-Ethyl-12-methyl-13-((3-benzyloxy-5-(1H-pyrrol-2-yl)-2H-pyrrol-2-ylidene)methyl)-12-azabicyclo[9.2.1]tetradeca-11(14),13-diene | Formula I; $R_1$ (ring A) is —H, $R_1$ (ring C) is —$CH_3$, $R_2$ is —$CH_2C_6H_5$, $R_3$ is —$CH_2CH_3$, $R_{16}$ is —H, $R_{17}$ is —H, m is 3 |
| 2-n-Propyl-13-((3-benzyloxy-5-(1H-pyrrol-2-yl)-2H-pyrrol-2-ylidene)methyl)-12-azabicyclo[9.2.1]tetradeca-11(14),13-diene | Formula I; $R_1$ is —H, $R_2$ is —$CH_2C_6H_5$, $R_3$ is —$(CH_2)_2CH_3$, $R_{16}$ is —H, $R_{17}$ is —H, m is 3 |
| 2-n-Butyl-13-((3-benzyloxy-5-(1H-pyrrol-2-yl)-2H-pyrrol-2-ylidene)methyl)-12-azabicyclo[9.2.1]tetradeca-11(14),13-diene | Formula I; $R_1$ is —H, $R_2$ is —$CH_2C_6H_5$, $R_3$ is —$(CH_2)_3CH_3$, $R_{16}$ is —H, $R_{17}$ is —H, m is 3 |

4.7.2. The Compounds of Formula (II)

The compounds of Formula (II) can be obtained using conventional organic synthesis or by the following illustrative methods:

Compounds of Formula (II) where $R_1$ is H and $R_2$ is Me can be prepared by the methods shown in Scheme D.

Scheme D

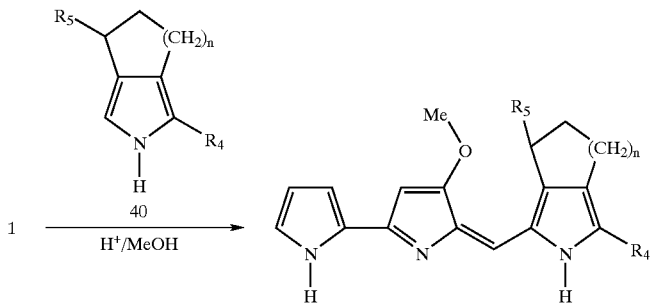

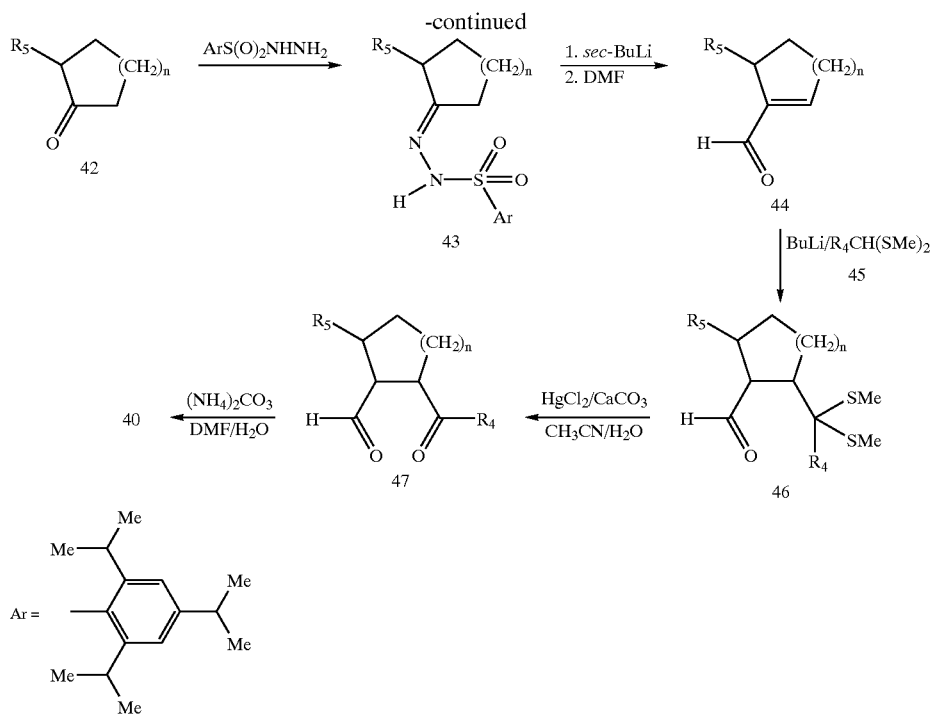
-continued

The dipyrrole aldehyde 1 reacts under acid catalysis with the pyrrole of structure 40 giving the prodigiosene 41. Pyrroles of structure 40 are prepared starting with the appropriate α-substituted cycloalkanone 42. The reaction of 42 with 2,4,6-tri-i-propylphenylsulfonylhydrazine gives the corresponding hydrazone 43. Compound 43 reacts with sec-butyllithium and N,N-dimethylformamide (DMF) to give the α,β-unsaturated aldehyde 44. The anion of the dimethylthioacetaldehyde reagent 45 is generated using n-butyllithium and adds to the conjugated system of 44, producing 46. The group $R_4$ in 45 may be hydrogen or $C_1$–$C_{12}$ alkyl. Reaction of 46 with mercury(II) chloride and calcium carbonate converts the dimethylthiocarbonyl into a carbonyl group, generating 47. Compound 47 reacts with ammonium carbonate in DMF giving the pyrrole 40. The methods shown in Scheme D for the chemical transformation of compound 42 into compound 40 have been described by H. H. Wasserman and J. M. Fukuyama, Tetrahedron Lett. 25, 1387–1388, 1984. When in compound 42, n is 2 and $R_5$ is Me, and when in compound 45, $R_4$ is Me, then the structure 40 is cycloprodigiosin as described by Wasserman and Fukuyama. Compounds of structure 42 useful in the reaction sequence of Scheme D include, but are not limited to, cyclopentanone, cyclohexanone, cycloheptanone, cyclooctanone, cyclononanone, cyclodecanone and the 2-methyl and 2-ethyl derivatives of each of these cyclic ketones. The dimethylthioacetals 45 are prepared from their corresponding aldehydes by methods well known in the art and are chosen to give the range of alkyl substituents specified above.

Once the compounds of Formula (II) have been synthesized, they can be purified or substantially purified, using conventional chromatography, recrystallization or other purification techniques known to those skilled in the art.

In certain embodiments of the invention, the compounds of the invention are indicated by chemical name. The structures of these compounds are indicated in Table 4, below, which describes the structure as shown in the corresponding synthesis Schemes.

TABLE 4

FORMULA II

| Compound | Structure |
| --- | --- |
| 4,5,6,7-Tetrahydro-3-((3-benzyloxy-5-(1-methyl-1H-pyrrol-2-yl)-2H-pyrrol-2-ylidene)methyl)-1,4-dimethyl-2H-isoindole | chemical class 125 as depicted in Scheme I; $R_2$ is —$CH_2C_6H_5$ |
| 4,5,6,7-Tetrahydro-3-((3-methoxy-5-(1H-pyrrol-2-yl)-2H-pyrrol-2-ylidene)methyl)-4-ethyl-2H-isoindole | chemical class 41 as depicted in Scheme D; $R_4$ is H, $R_5$ is Et, n is 2 |
| 4,5,6,7-Tetrahydro-3-((3-methoxy-5-(1H-pyrrol-2-yl)-2H-pyrrol-2-ylidene)methyl)-4-ethyl-1-methyl-2H-isoindole | chemical class 41 as depicted in Scheme D; $R_4$ is Me, $R_5$ is Et, n is 2 |
| 4,5,6,7-Tetrahydro-3-((3-methoxy-5-(1H-pyrrol-2-yl)-2H-pyrrol-2-ylidene)methyl)- | chemical class 41 as depicted in Scheme D; $R_4$ is Et, $R_5$ is Et, n is 2 |

TABLE 4-continued

FORMULA II

| Compound | Structure |
|---|---|
| 1,4-diethyl-2H-isoindole | |
| 4,5,6,7-Tetrahydro-3-((3-methoxy-5-(1H-pyrrol-2-yl)-2H-pyrrol-2-ylidene)methyl)-1-ethyl-4-methyl-2H-isoindole | chemical class 41 as depicted in Scheme D; $R_4$ is Et, $R_5$ is Me, n is 2 |
| 4,5,6,7-Tetrahydro-3-((3-methoxy-5-(1H-pyrrol-2-yl)-2H-pyrrol-2-ylidene)methyl)-1-ethyl-2H-isoindole | chemical class 41 as depicted in Scheme D; $R_4$ is Et, $R_5$ is H, n is 2 |

4.7.3. The Compounds of Formula (III)

The compounds of Formula (III) can be obtained using conventional organic synthesis or by the following illustrative methods:

Compounds of Formula (III) where $R_1$ is H and $R_2$ is Me can be prepared by the methods shown in Scheme E.

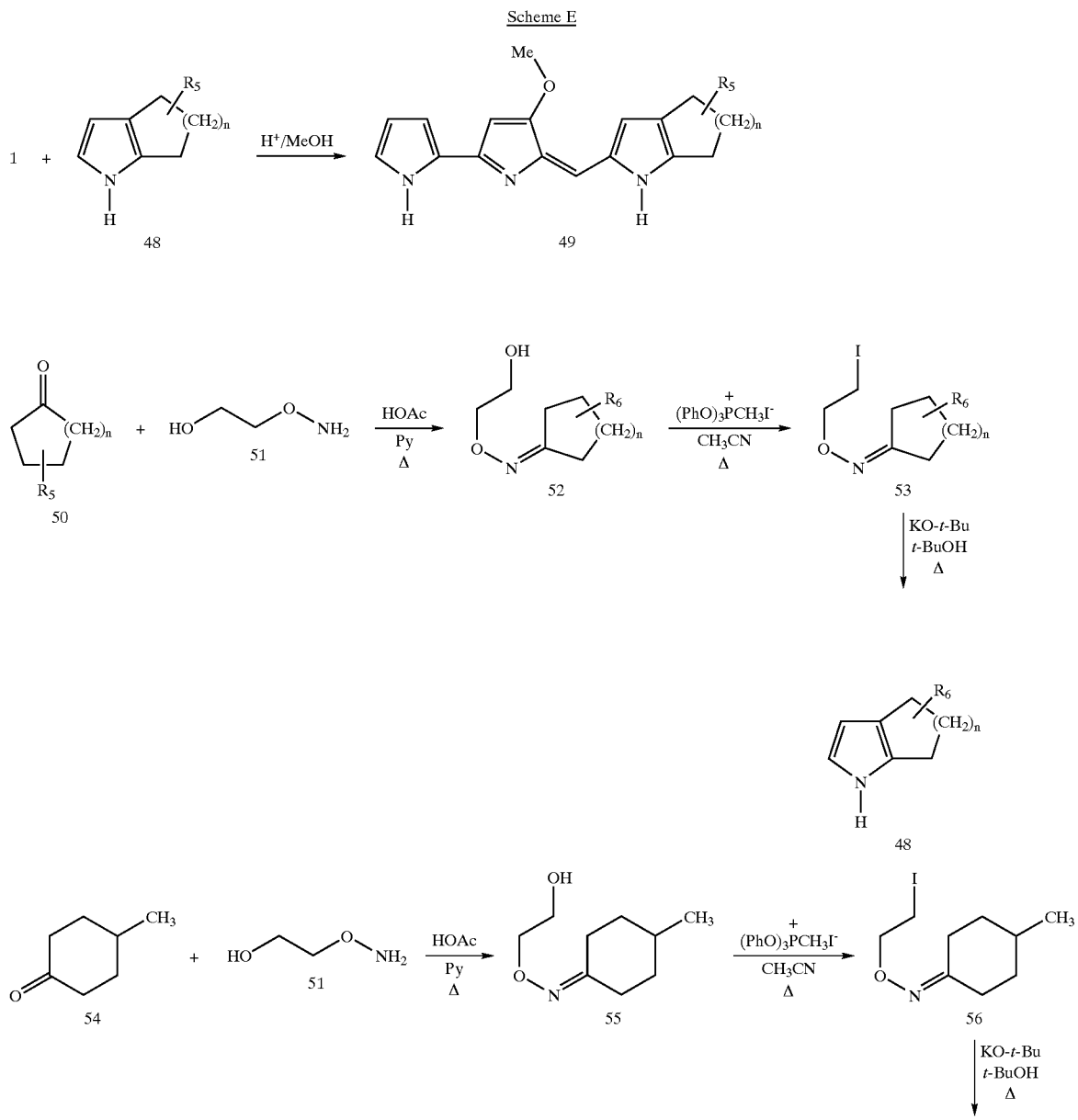

-continued

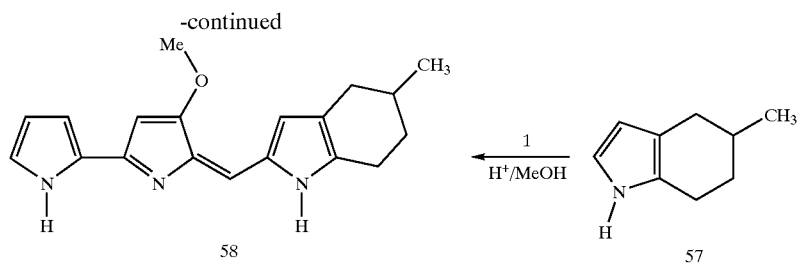

The dipyrrole aldehyde 1 reacts under acid catalysis with the pyrrole of structure 48 giving the prodigiosene 49. Pyrroles of structure 48 are prepared starting with the appropriate cyclic ketone 50 as outlined in Scheme E. The cyclic ketone 50 reacts with O-(2-hydroxyethyl)-hydroxylamine 51 (D. Dhanak et al., J. Chem. Soc., Chem. Commun. 903–904, 1986) forming the O-(2-hydroxyethyl)-oxime 52. The hydroxyl group of 52 is replaced with iodine by reaction with methyltriphenoxyphosphonium iodide, giving 53. Cyclization of 53 occurs upon heating with potassium t-butoxide in t-butyl alcohol and affords the pyrrole 48. Compounds of structure 50 that are used to prepare compounds of structure 48 include, but are not limited to, cyclopentanone; cyclohexanone; 2-methyl-, 2-ethyl-, 4-methyl-, 4-ethyl-, 4-propyl-, 4-n-butyl, and 4-phenylcyclohexanone; cycloheptanone; 2-methyl- and 2-ethylcycloheptanone; cyclooctanone; 2-methyl-, 2-ethyl-, 5-methyl-, and 5-ethylcyclooctanone; cyclononanone; 2-methyl- and 2-ethylcyclononanone; cyclodecanone; 2-methyl-,2-ethyl-,6-methyl-, and 6-ethylcyclodecanone. When, for example, 4-methylcyclohexanone 54 is used in this series of reactions, the oxime 55 is first formed. From 55 the iodide 56 is prepared and is cyclized to the pyrrole 57. Reaction of 57 with 1 gives the prodigiosene 58.

Once the compounds of Formula (III) have been synthesized, they can be purified or substantially purified, using conventional chromatography, recrystallization or other purification techniques known to those skilled in the art.

In certain embodiments of the invention, the compounds of the invention are indicated by chemical name. The structures of these compounds are indicated in Table 5, below, which describes the structure as shown in the corresponding synthesis Schemes.

TABLE 5

| FORMULA III | |
|---|---|
| Compound | Structure |
| 4,5,6,7-Tetrahydro-3-((3-methoxy-5-(1H-pyrrol-2-yl)-2H-pyrrol-2-ylidene)methyl)-5-methyl-1H-indole | chemical class 58 as depicted in Scheme E |
| 4,5,6,7-Tetrahydro-3-((3-methoxy-5-(1H-pyrrol-2-yl)-2H-pyrrol-2-ylidene)methyl)-1H-indole | chemical class 49 as depicted in Scheme E; $R_5$ is H, n is 2 |

4.7.4. The Compounds of Formula (IV)

The compounds of Formula (IV) can be obtained using conventional organic synthesis or by the following illustrative methods:

Compounds of Formula (IV) where $R_1$ is H and $R_2$ is Me can be prepared by the methods shown in Scheme F.

Scheme F

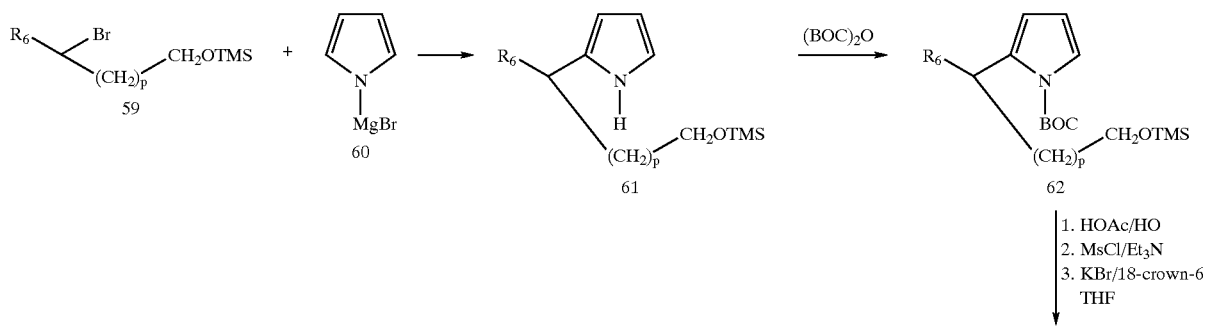

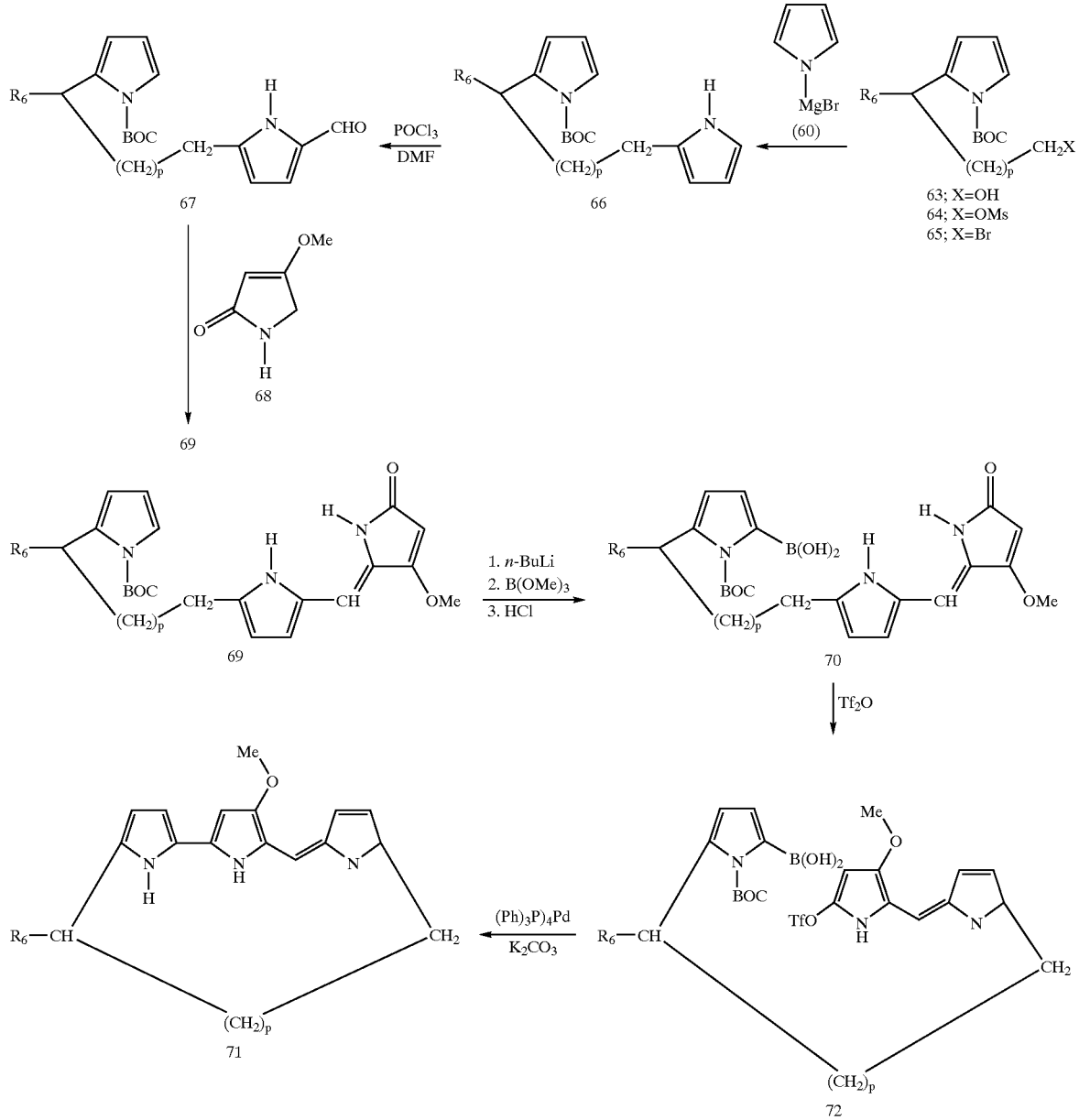

The O-TMS-bromoalcohol 59 reacts with pyrrylmagnesium bromide 60 giving the 2-substituted pyrrole 61. The pyrrole 61 reacts with t-butyloxycarbonyl anhydride (BOC anhydride) to give the N-BOC-pyrrole 62. The O-TMS protecting group is removed in acetic acid-water, giving the alcohol 63. The alcohol 63 is converted to the O-mesylate 64, and the mesylate group is replaced with bromine, giving 65. The alkyl bromide 65 reacts with 60, giving 66. A Vilsmeier reaction with 66 introduces a carboxaldehyde group into the α-position of the pyrrole ring that is not N-BOC protected. The carboxaldehyde 67 reacts (R. D'Alessio and A. Rossi, SYNLETT 513–514, 1996) with 5H-4-methoxypyrrol-2(1H)-one 68 (L. Duc, et. al., Synthesis 391–394, 1992) under alkaline conditions. The N-BOC group lost in this reaction is replaced, giving 69. The boronic acid group of 70 is introduced (D'Alessio and Rossi) and the carbonyl group of the pyrrol-2-one functionality is converted to an O-triflate group, giving 71. Reaction of 71 in the presence of Pd(0) generates the prodigiosene 72. The bromoalcohols used for the preparation of compounds of structure 59 include, but are not limited to, 8-bromononan-1-ol, 8-bromodecan-1-ol, 9-bromodecan-1-ol, 9-bromoundecan-1-ol, 10-bromoundecan-1-ol, and 10-bromododecan-1-ol. The O-TMS derivatives, obtained from bromoalcohols, are prepared by methods known to the art. Compounds of Formula (IV) are also prepared by adaptations of methods described by Futrstner et al., 1999 J. Org. Chem. 64:8275–8280.

Once the compounds of Formula (IV) have been synthesized, they can be purified or substantially purified, using conventional chromatography, recrystallization or other purification techniques known to those skilled in the art.

In certain embodiments of the invention, the compounds of the invention are indicated by chemical name. The structures of these compounds are indicated in Table 6, below, which describes the structure as shown in the corresponding synthesis Schemes.

TABLE 6

FORMULA IV

| Compound | Structure |
| --- | --- |
| 4-Methoxy-23,24,25-triazatetracyclo[18.2.1.1$^{2,5}$.1$^{7,10}$]pentacosa-2(25),3,5,7,9,20,22-heptaene | chemical class 72 as depicted in Scheme F; R6 is H, p is 7 |
| 4-Methoxy-24,25,26-triazatetracyclo[19.2.1.1$^{2,5}$.1$^{7,10}$]hexacosa-2(26),3,5,7,9,21,23-heptaene | chemical class 72 as depicted in Scheme F; R$_6$ is H, p is 8 |

4.7.5. The Compounds of Formula (V)

The compounds of Formula (V) can be obtained using conventional organic synthesis or by the following illustrative methods:

Compounds of Formula V where $R_1$ is H and $R_2$ is Me can be prepared by the methods shown in Scheme G.

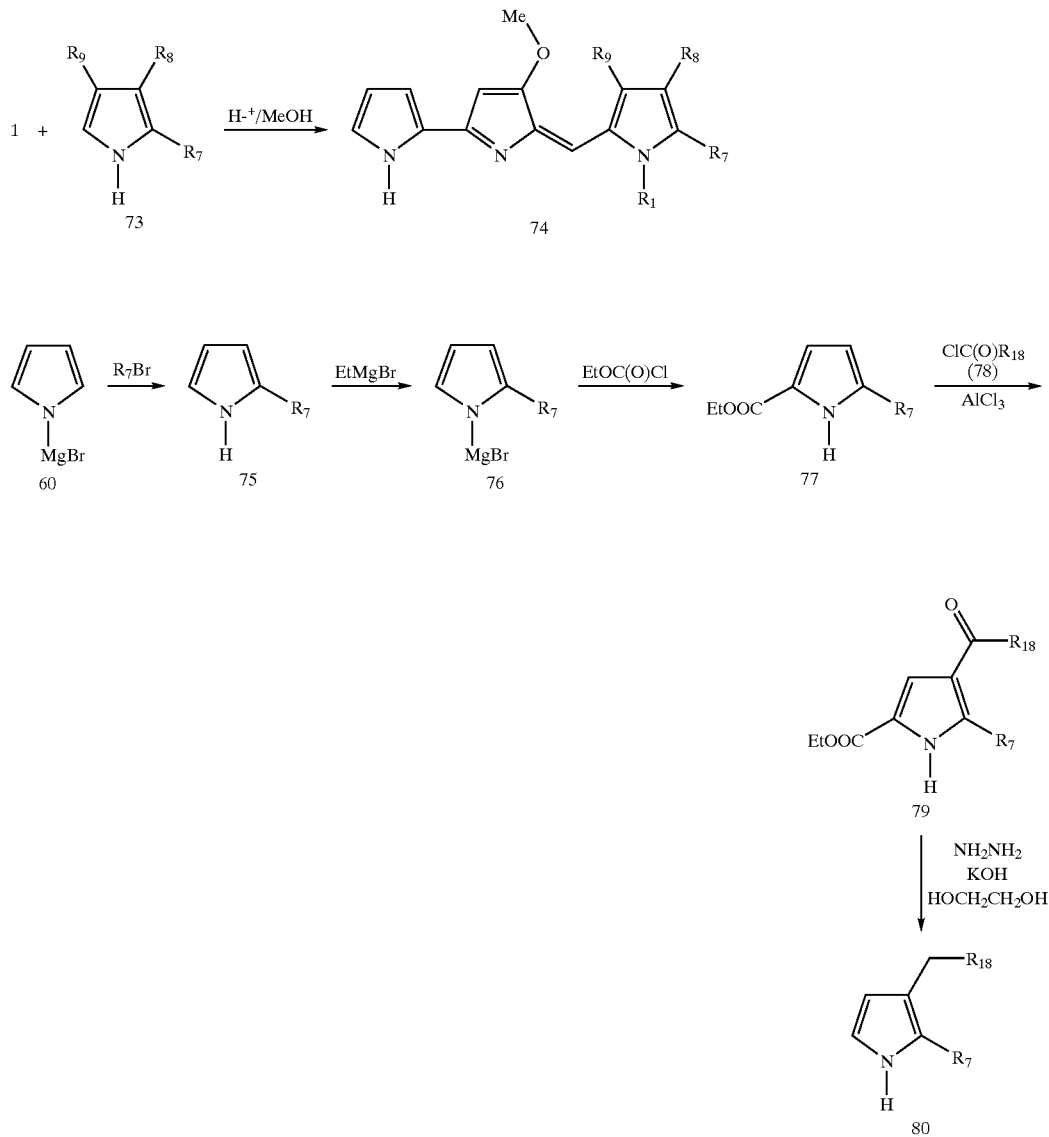

-continued
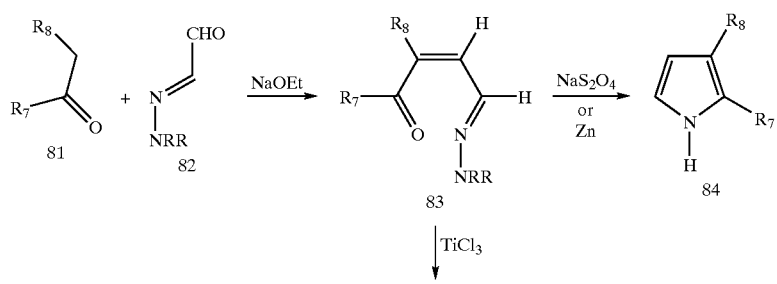
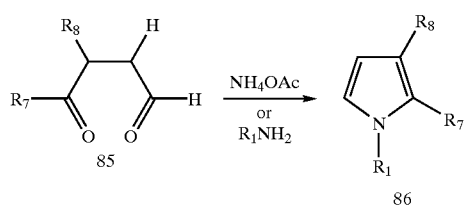
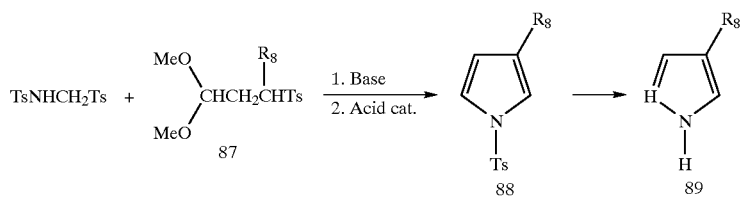
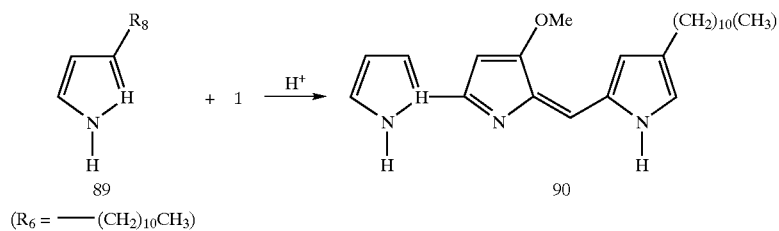
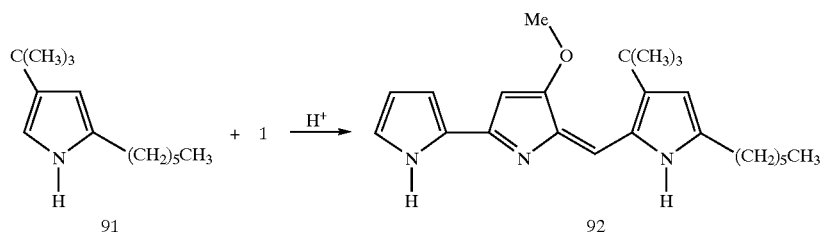
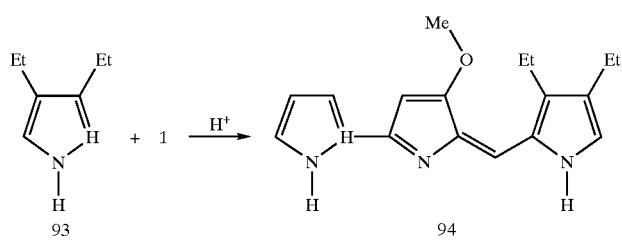

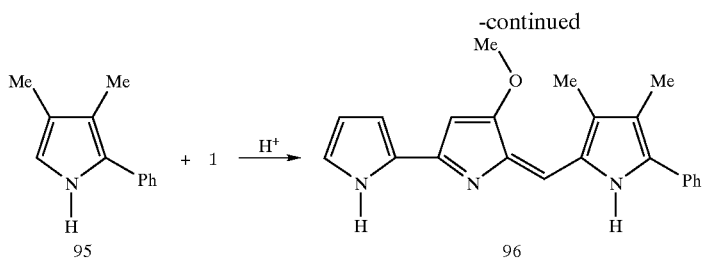

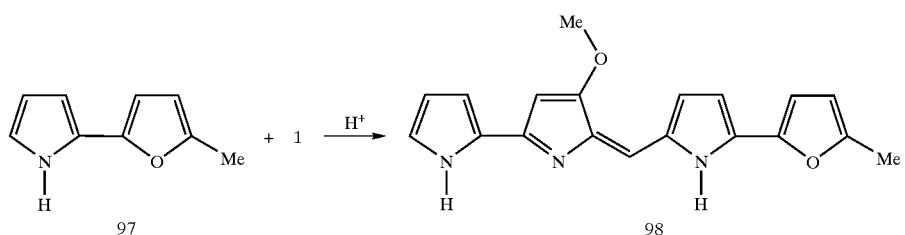

The dipyrrole aldehyde 1 reacts under acid catalysis with the pyrrole of structure 73 giving the prodigiosene 74. Numerous methods have been described for the synthesis of pyrroles of structure 73 (e.g., G. P. Bear, "The Synthesis of 1H-Pyrroles" in "Pyrroles," Vol. 1, R. A. Jones, ed., Wiley, N.Y., 1990; pp 105–294). For pyrroles 73 where $R_7$ is alkyl or cycloalkyl and $R_8$ is $R_9$ is H, reaction of the pyrrole Grignard reagent 60 with an alkyl halide or cycloalkyl halide gives the desired 2-substituted pyrrole 75. The 2-substituted pyrroles 75 are further substituted in the 3-position by the sequence of reactions showing the transformation of 75 into 80 in Scheme G and adapted from the report by A. J. Castro et. al., J. Org. Chem. 28, 857–860, 1963. In this reaction sequence, the reagent 78 is chosen so that $R_{16}$ is one methylene group shorter than $R_7$ of the final pyrrole. The two steps shown in Scheme G by which 77 is converted to 80, i.e., acylation of the pyrrole ring—in this case by a Friedel-Crafts type process—followed by a Wolff-Kishner type reduction, are of general use for the introduction of acyl and/or alkyl and aralkyl groups onto the pyrrole nucleus. Another acylation method widely used with pyrroles is the Vilsmeier process, described above and illustrated in Scheme F in the conversion of compound 66 to 67 (e.g., D.O.A. Garrido et al., J. Org. Chem. 49, 2619–2622, 1984). Replacement of dimethylformamide by other dimethylalkyl or arylamides in the Vilsmeier process introduces an acyl group into the pyrrole. The method of Dhanak et al., described above, is also useful for the synthesis of pyrroles of structure 73 in which $R_7$ is one carbon length shorter than $R_8$ and $R_9$ is H when symmetrical alkyl ketones are used as a starting material. A large variety of 2,3-disubstituted pyrroles (where $R_7$ and $R_8$ are non-hydrogen substituents and $R_9$ is H) are prepared by methods reported by Severin and coworkers (see Pyrroles, Vol. 1; pp 159–161 and references cited therein). The ketone 81 and glyoxalhydrazone 82 condense, giving 83, which cyclizes to the pyrrole 84 when reacted with either sodium dithionite or zinc. The intermediate 83 also reacts with titanium trichloride to provide a 1,4-ketoaldehyde 85, which reacts with ammonium acetate or a primary amine to yield the pyrrole 86. Reaction of $TsNHCH_2Ts$ with 87 under alkaline conditions (H. Kinoshita et al., Chem. Lett. 1033–1036, 1986; C.A. 106:84139d) gives an intermediate addition product that under acidic conditions is converted to the N-tosylpyrrole 88. Removal of the tosyl group from 88 by standard methods affords the 3-substituted pyrrole 89 that is used in the synthesis of prodigiosenes. For example, in pyrrole 89, when $R_9$ is $—(CH_2)_{10}CH_3$, and $R_7$ and $R_9$ are H, reaction with 1 gives prodigiosene 90. Among the methods for preparation of 2,4-disubstituted, 3,4-disubstituted, and 2,3,4-trisubstituted pyrroles are those described by J. Tang above; J. G. Verkade, J. Org. Chem. 59, 7793–7802, 1994; B. Franck et al., Liebigs Ann. Chem. 503–510, 1994; D. Brown et al., J. Chem. Soc. Perkin Trans. 1, 455–463, 1986; D. Enders et al., Tetrahedron Lett. 36, 8007–8010, 1995; and K. Utimoto et al., Tetrahedron Lett. 22, 4277–4278, 1981. Reaction of, for example, the 2,4-disubstituted pyrrole 91 with 1 gives the prodigiosene 92. Reaction of the 3,4-disubstituted pyrrole 93 with 1 gives the prodigiosene 94. Reaction of the 2,3,4-trisubstituted pyrrole 95 with 1 gives the prodigiosene 96. The preparations of furyl-substituted pyrroles have been described in the literature, for example by Korostova et al., Zh. Org. Khim. 30, 905–908, 1994 (C.A. 122:290633k); I. G. Iovel et al., Khim. Geterotsikl. Soedin., 746–749, 1989 (C.A. 112:178533v); S. E. Korostova et al., Khim. Geterotsikl. Soedin., 901–906, 1989 (C.A. 112:178530s); A. M. Nadim et al., Khim. Geterotsikl. Soedin., 1141–1143, 1991 (C.A. 116:194084n); M. V. Sigalov et al., J. Org. Chem. 57,3943–3948,1992 and references cited therein. Furyl pyrroles, for example 97, react with 1, giving the prodigiosenes, in this case 98.

Once the compounds of Formula (V) have been synthesized, they can be purified or substantially purified, using conventional chromatography, recrystallization or other purification techniques known to those skilled in the art.

4.7.6. Other Compounds of Formula (I–V)
The compounds of Formulas I–III and V in which $R_1$ is not H are prepared using methods shown in Scheme H.
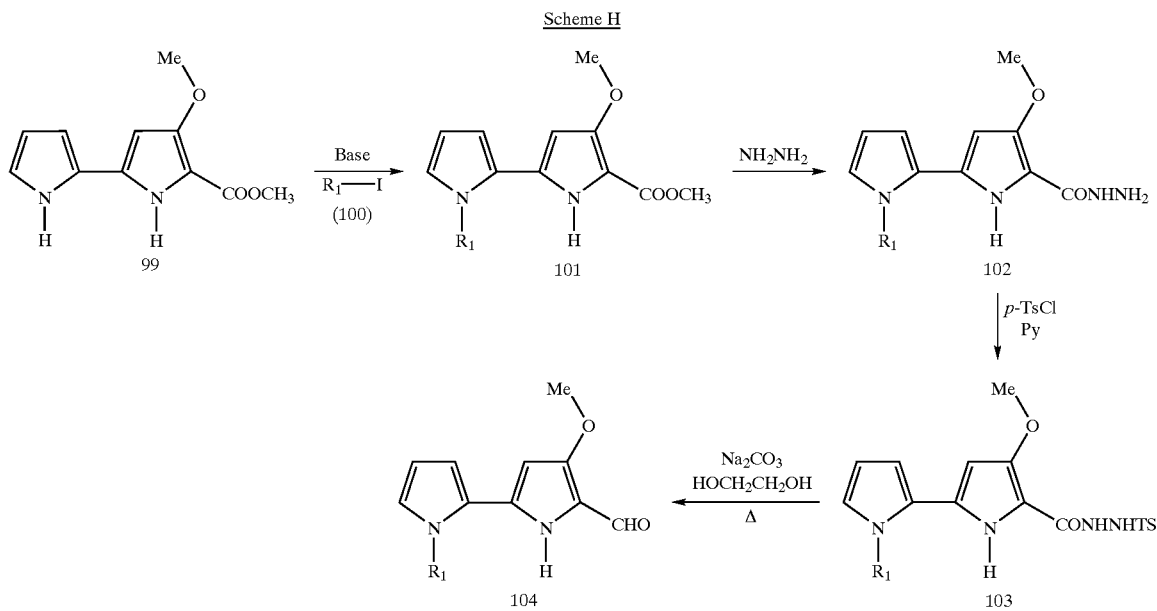
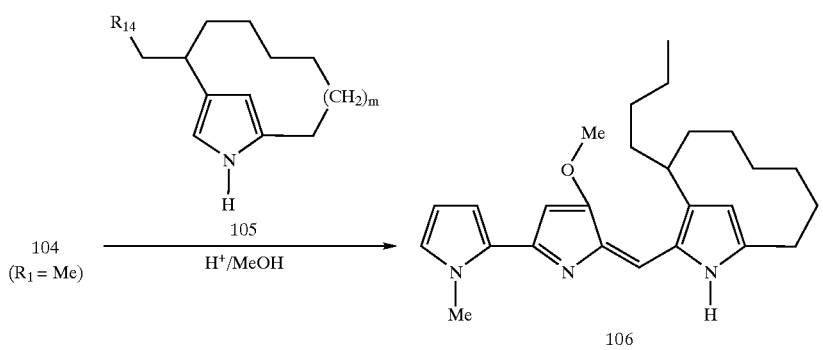
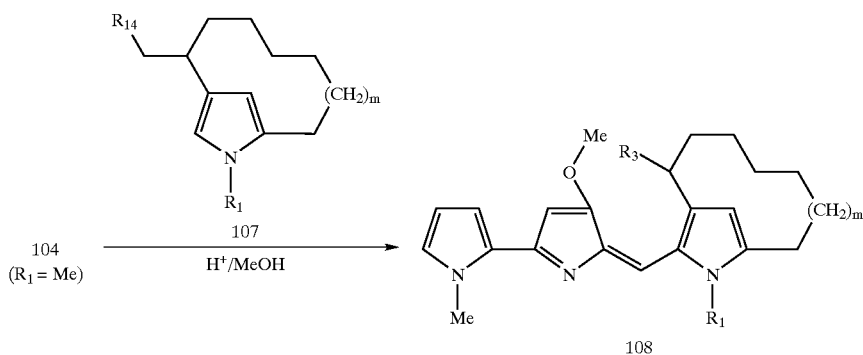

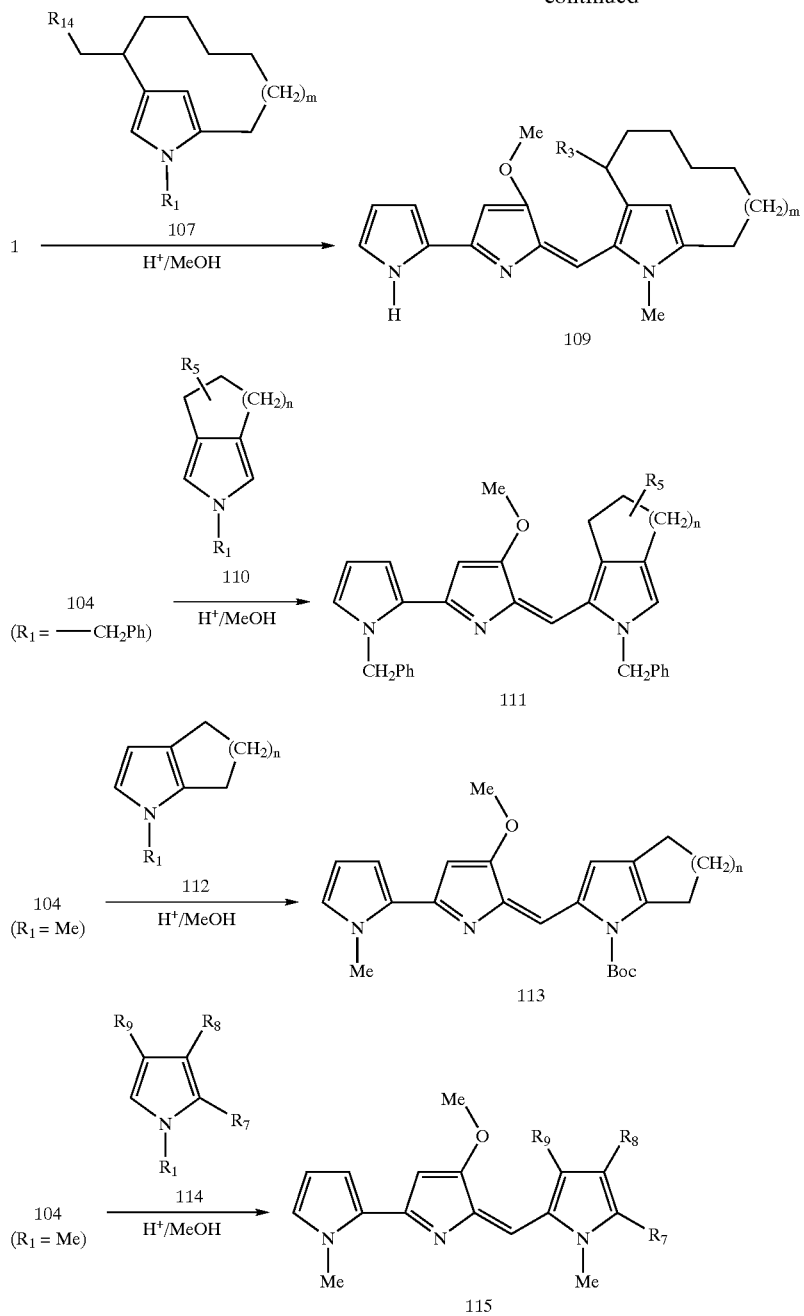

The bipyrrole carboxylic ester 99 reacts with iodides 100, such as methyl iodide, ethyl iodide and benzyl iodide, in the presence of a base such as pyridine, triethylamine, or sodium carbonate or in the presence of one equivalent of a base such as n-butyllithium or potassium t-butoxide, generating 101. Hydrazinolysis of 101 converts the carboxylic acid ester into the hydrazide 102. The hydrazide is tosylated with p-toluenesulfonyl chloride, giving 103, which reacts with sodium carbonate to give the aldehyde 104 ($R_1$ is Me). The synthesis of compound 99 has been described by Boger and Patel, cited above. The three-step reaction sequence used for conversion of carboxylate esters into aldehydes also is described by Boger and Patel and was originally reported by H. Rapoport and K. G. Holden, J. Am. Chem. Soc. 84, 635–642, 1962. The reaction of 104 ($R_1$ is Me) with, for example, 105 where m is 1 and $R_{14}$ is n-$C_3H_7$ under acid catalysis generates the prodigiosene 106 ($R_{14}$ is $R_3$ less its α-carbon). Pyrroles such as those described herein having no substituent on the nitrogen atom are N-alkylated or N-acylated by methods known to the art. The reaction of 104 ($R_1$ is Me) with the N-alkylated or acylated pyrrole 107 where, for example, $R_1$ is Me, gives the prodigiosene 108 under acidic conditions. The reaction of 1 with 107 likewise produces the prodigiosene 109 wherein the ring-A pyrrole has an unsubstituted N—H atom and the ring-C pyrrole is N—Me substituted. Other examples, which are intended to illustrate but not to limit the methods by which prodigiosenes with $R_2$ is not Me are prepared, are also shown in Scheme H. Reaction of 104 ($R_1$ is —$CH_2Ph$) with pyrrole 110 ($R_1$ is —$CH_2Ph$) gives the prodigiosene 111. The reaction of 104 ($R_1$ is Me) with the pyrrole 112 ($R_1$ is BOC) gives the prodigiosene 113. The reaction of 104 ($R_1$ is Me) with the pyrrole 114 ($R_1$ is Me) gives the prodigiosene 115.
The compounds of Formulas I–V in which $R_2$ is not Me can be prepared using methods shown in Scheme I.
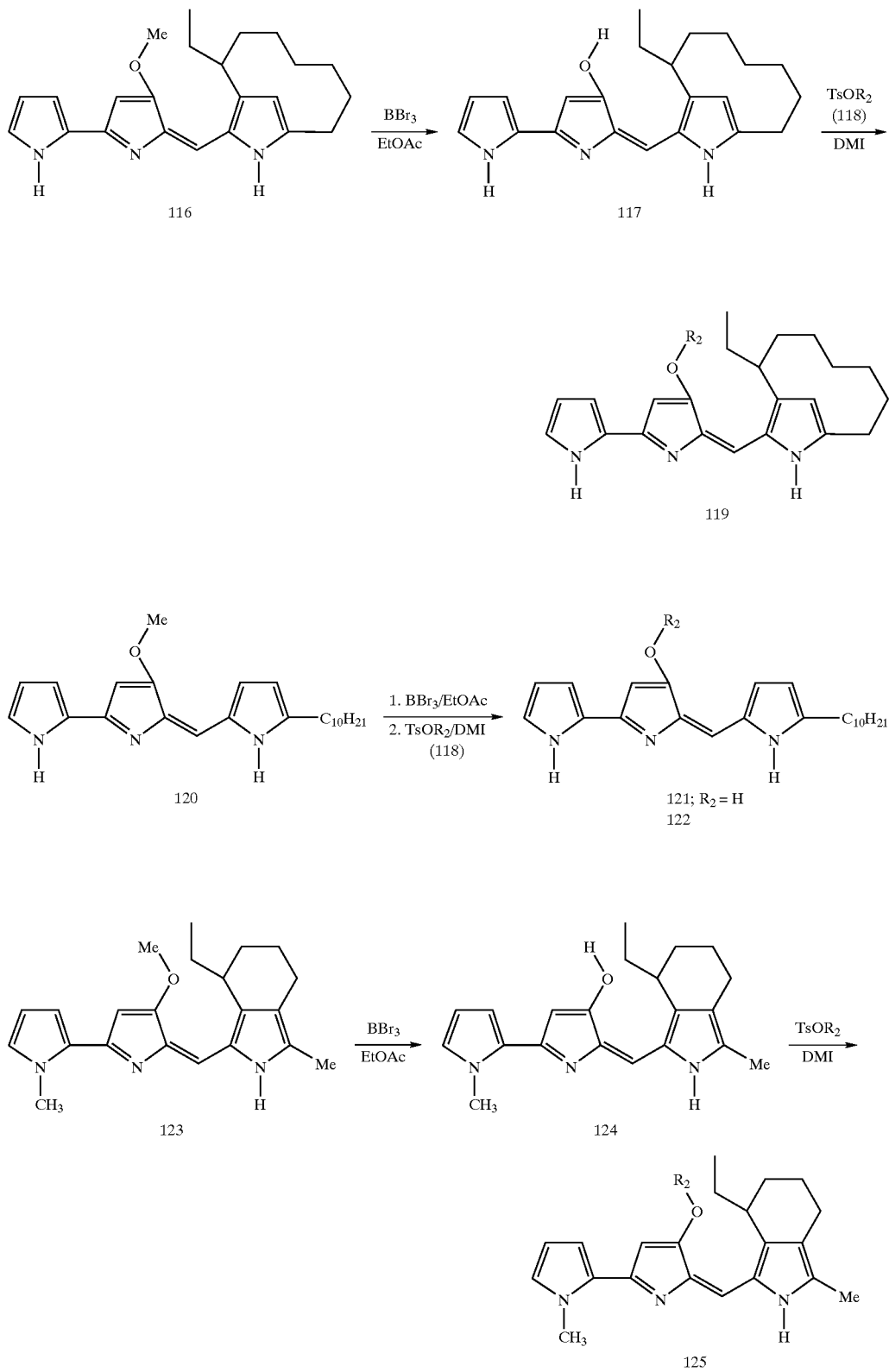

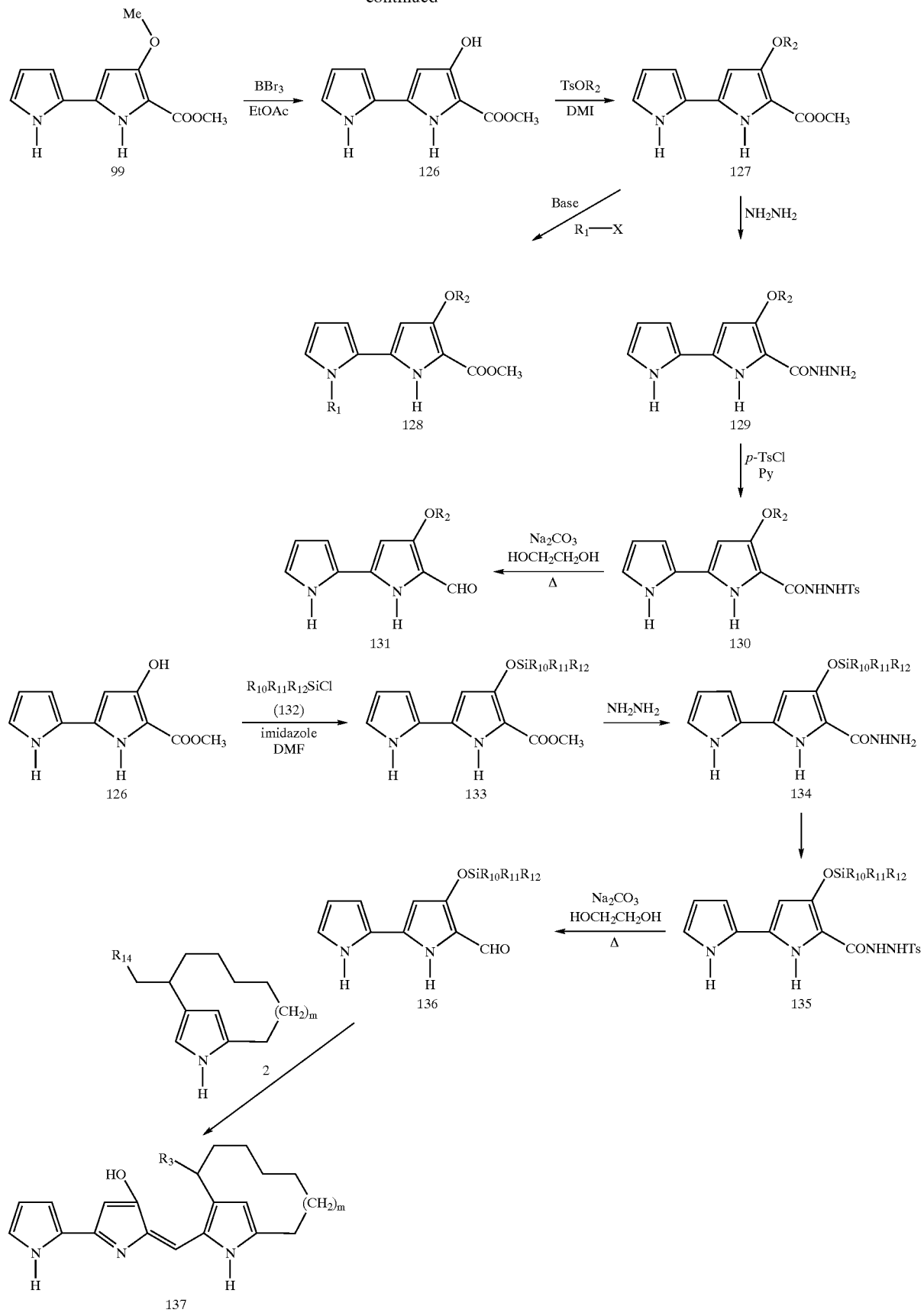

The methoxyl group (at $R_2$) of the compound of Formula I, II, III, IV, or V is demethylated with boron tribromide, iodotrimethylsilane, sodium ethylthiolate, or other reagents (Greene and Wuts, pp. 145–149). For example, reaction of the prodigiosene 116 with $BBr_3$ gives the hydroxy compound 117. Reaction of 117 with an alkyl p-toluenesulfonate such as ethyl p-toluenesulfonate, benzyl p-toluenesulfonate, or substituted benzyl p-toluenesulfonate in dimethylimidazolidinone (DMI) generates alkyl ether 119 (Pyrroles, Part 2, R. A. Jones, Ed., Wiley, N.Y., 1992; p. 557; G. A. Hunter, et. al., J. Chem. Soc. Perkin Trans. 1, 3245–3251, 1991). Another example is the cleavage of the methyl ether of prodigiosene 120 followed by re-etherification of the intermediate 121 with an alkyl p-toluenesulfonate, giving the new ether 122. Still another example is the cleavage of the methyl ether of the prodigiosene 123 followed by re-etherification of the hydroxy compound 124, giving the prodigiosene 125.

Another method useful for preparing prodigiosenes having a B-ring ether other than methoxyl begins with cleavage of the methoxyl group of the intermediate 99. The resulting hydroxy compound 126 is re-etherified using an alkyl tosylate reagent described above, giving 127. The more nucleophilic A-ring nitrogen of Compound 127 is alkylated, for example, with methyl iodide in the presence of a base, producing 128. The compound 127 can also be converted by the previously described series of reactions via 129 and 130 to the aldehyde 131. Aldehyde 131 can be used in coupling reactions with pyrroles generating prodigiosene compounds in same way that the coupling of 1 with pyrroles gives compounds of this class.

The preparations of Pyrrole-Type compounds I–V where $R_2$ is a trialkyl silyl ether, a tetrahydropyranyl ether, a methoxymethyl ether, a trichloroethyl carbonate, or an acyl group are carried out by methods known to the art (Greene and Wuts) and applied either to the prodigiosene alcohols such as 117 or dipyrroles such as 126. As shown in Scheme I, the dipyrrole alcohol 126 reacts with a chlorotrialkylsilane 132 (for example, chlorotrimethylsilane or chloro-t-butyldimethylsilane), giving the trialkylsilylether 133. Using the previously described series of reactions for conversion of a methoxycarbonyl group to an aldehyde group, 133 is converted to the aldehyde 136 via the hydrazide 134 and the tosylhydrazide 135. The reaction of 136 with a pyrrole, such as for example 2, gives the prodigiosene 137. The trialkylsilyl ether is cleaved under the acidic conditions of the reaction. Reaction of 137 under conditions used in formation of 133 from 126 gives a trialkylsilyl ether of 137.

Methods for the preparation of the two enantiomers of cyclobutylprodigiosin are outlined in Scheme J.

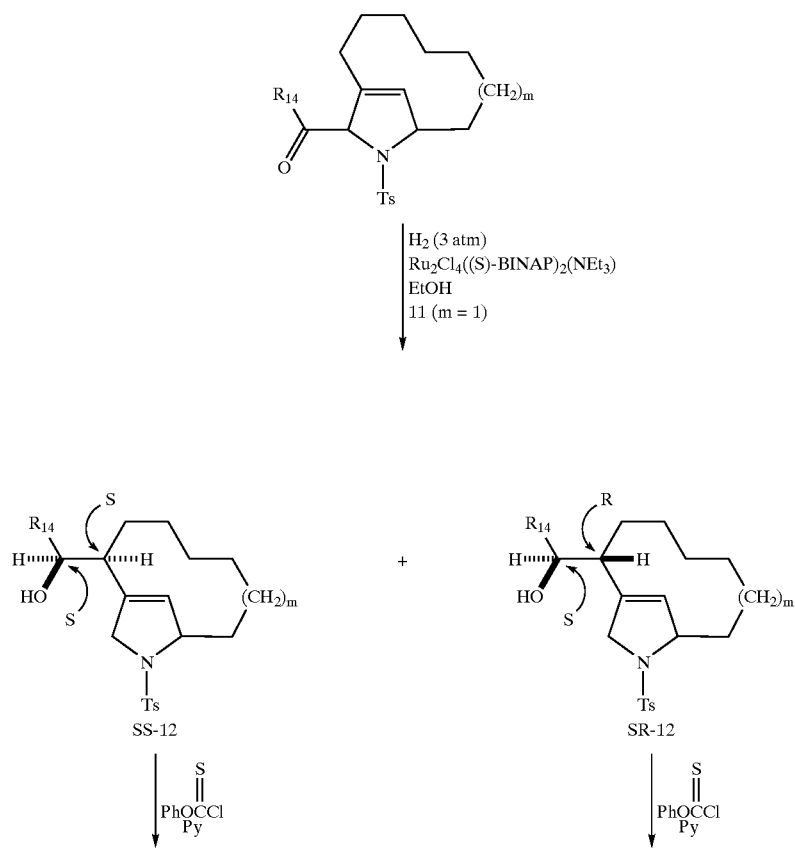

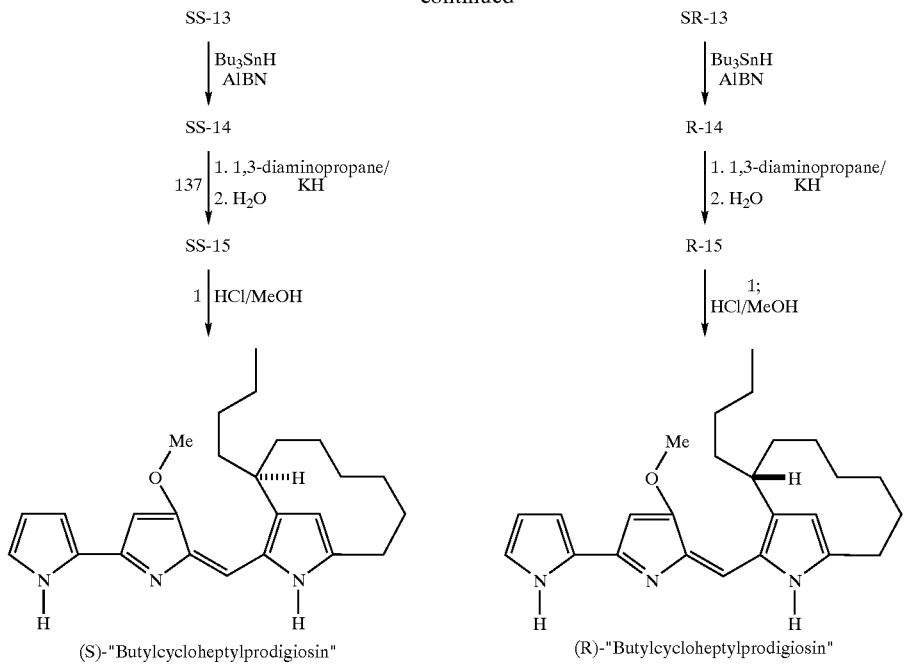

The catalyst used for the asymmetric reduction of ketone 11($R_{14}$ is n-propyl, m is 1) is described in "Catalytic Asymmetric Synthesis," I. Ojima, ed., VCH, N.Y., 1993; see chapter 1 by H. Takaya, T. Ohta, and R. Noyori. The diastereomeric pair SS-12 and SR-12, or SS-13 and SR-13, are easily separable using common chromatographic or recrystallization methods. These methods can also be used to obtain enantiomers of a compound of Formula (I) where $R_3$ is other than n-butyl.

4.8. Therapeutic/Prophylactic Administration and Compositions

As used herein, the novel compounds of the present invention, the compounds of the present compositions, and the compounds of the present methods are known collectively as "Pyrrole-Type compounds".

Due to the activity of the Pyrrole-Type compounds, the Pyrrole-Type compounds are advantageously useful in veterinary and human medicine. For example, the Pyrrole-Type compounds are useful for the treatment or prevention of cancer or neoplastic disease or inhibiting the growth of a cancer cell or neoplastic cell. The Pyrrole-Type compounds are also useful for the treatment or prevention of a viral infection or inhibiting the replication or infectivity of a virus.

When administered to a subject, e.g., an animal for veterinary use or to a human for clinical use, or when made to contact a cell or tissue, the Pyrrole-Type compounds are preferably in isolated form. By "isolated" it is meant that prior to administration or contacting, a Pyrrole-Type compound is separated from other components of a synthetic organic chemical reaction mixture or natural product source, e.g., plant matter, tissue culture, bacterial broth, etc. Preferably, the Pyrrole-Type compounds are isolated via conventional techniques, e.g., extraction followed by chromatography, recrystalization, or another conventional technique. When in isolated form, the Pyrrole-Type compounds are at least 90%, preferably at least 95%, of a single Pyrrole-Type compound by weight of that which is isolated. "Single Pyrrole-Type compound" means an enantiomer or a racemate of a Pyrrole-Type compound.

The invention provides methods of treatment and prophylaxis by administration to a subject of an effective amount of a Pyrrole-Type compound. The subject is preferably an animal, including, but not limited to, an animal such a cow, horse, sheep, pig, chicken, turkey, quail, cat, dog, mouse, rat, rabbit, guinea pig, etc., and is more preferably a mammal, and most preferably a human.

The present compositions, which comprise one or more Pyrrole-Type compounds, may be administered by any convenient route, for example by infusion or bolus injection, by absorption through epithelial or mucocutaneous linings (e.g., oral mucosa, rectal and intestinal mucosa, etc.) and may be administered together with another biologically active agent. Administration can be systemic or local. Various delivery systems are known, e.g., encapsulation in liposomes, microparticles, microcapsules, capsules, etc., and can be used to administer a Pyrrole-Type compound of the invention. In certain embodiments, more than one Pyrrole-Type compound of the invention is administered to a subject. Methods of administration include but are not limited to intradermal, intramuscular, intraperitoneal, intravenous, subcutaneous, intranasal, epidural, oral, sublingual, intranasal, intracerebral, intravaginal, transdermal, rectally, by inhalation, or topically to the ears, nose, eyes, or skin. The preferred mode of administration is left to the discretion of the practitioner, and will depend in-part upon the site of the medical condition (such as the site of cancer or viral infection).

In specific embodiments, it may be desirable to administer one or more Pyrrole-Type compounds of the invention locally to the area in need of treatment. This may be achieved, for example, and not by way of limitation, by local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. In one embodiment, administration can be by direct injection at the site (or former site) of a cancer, tumor or neoplastic or pre-neoplastic tissue. In another embodiment, administration can be by direct injection at the site (or former site) of a viral infection.

In certain embodiments, it may be desirable to introduce one or more Pyrrole-Type compounds of the invention into the central nervous system by any suitable route, including intraventricular and intrathecal injection. Intraventricular injection may be facilitated by an intraventricular catheter, for example, attached to a reservoir, such as an Ommaya reservoir.

Pulmonary administration can also be employed, e.g., by use of an inhaler or nebulizer, and formulation with an aerosolizing agent, or via perfusion in a fluorocarbon or synthetic pulmonary surfactant. In certain embodiments, the Pyrrole-Type compounds can be formulated as a suppository, with traditional binders and carriers such as triglycerides.

In another embodiment, the Pyrrole-Type compounds of the invention can be delivered in a vesicle, in particular a liposome (see Langer, Science 249:1527–1533 (1990); Treat et al., in Liposomes in the Therapy of Infectious Disease and Cancer, Lopez-Berestein and Fidler (eds.), Liss, New York, pp. 353–365 (1989); Lopez-Berestein, ibid., pp. 317–327; see generally ibid.)

In yet another embodiment, the Pyrrole-Type compounds can be delivered in a controlled release system. In one embodiment, a pump may be used (see Langer, supra; Sefton, CRC Crit. Ref. Biomed. Eng. 14:201 (1987); Buchwald et al., Surgery 88:507 (1980); Saudek et al., N. Engl. J. Med. 321:574 (1989)). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, J. Macromol. Sci. Rev. Macromol. Chem. 23:61 (1983); see also Levy et al., Science 228:190 (1985); During et al., Ann. Neurol. 25:351 (1989); Howard et al., J. Neurosurg. 71:105 (1989)). In yet another embodiment, a controlled-release system can be placed in proximity of the target of the Pyrrole-Type compounds, e.g., the brain, thus requiring only a fraction of the systemic dose (see, e.g., Goodson, in Medical Applications of Controlled Release, supra, vol. 2, pp. 115–138 (1984)). Other controlled-release systems discussed in the review by Langer (Science 249:1527–1533 (1990)) may be used.

The present compositions will contain a therapeutically effective amount of a Pyrrole-Type compound, preferably in purified form, together with a suitable amount of a pharmaceutically acceptable carrier so as to provide the form for proper administration to the patient.

In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which a Pyrrole-Type compound is administered. Such pharmaceutical carriers can be liquids, such as water and oils, including those of petroleum, animal, vegetable or synthetic origin, such as peanut oil, soybean oil, mineral oil, sesame oil and the like. The pharmaceutical carriers can be saline, gum acacia, gelatin, starch paste, talc, keratin, colloidal silica, urea, and the like. In addition, auxiliary, stabilizing, thickening, lubricating and coloring agents may be used. When administered to a subject, the Pyrrole-Type compounds and pharmaceutically acceptable carriers are preferably sterile. Water is a preferred carrier when the Pyrrole-Type compound is administered intravenously. Saline solutions and aqueous dextrose and glycerol solutions can also be employed as liquid carriers, particularly for injectable solutions. Suitable pharmaceutical carriers also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The present compositions, if desired, can also contain minor amounts of wetting or emulsifying agents, or pH buffering agents.

The present compositions can take the form of solutions, suspensions, emulsion, tablets, pills, pellets, capsules, capsules containing liquids, powders, sustained-release formulations, suppositories, emulsions, aerosols, sprays, suspensions, or any other form suitable for use. In one embodiment, the pharmaceutically acceptable carrier is a capsule (see e.g., U.S. Pat. No. 5,698,155). Other examples of suitable pharmaceutical carriers are described in "Remington's Pharmaceutical Sciences" by E. W. Martin.

The phrase "pharmaceutically acceptable salt(s)," as used herein includes but are not limited to salts of acidic or basic groups that may be present in compounds used in the present compositions. Compounds included in the present compositions that are basic in nature are capable of forming a wide variety of salts with various inorganic and organic acids. The acids that may be used to prepare pharmaceutically acceptable acid addition salts of such basic compounds are those that form non-toxic acid addition salts, i.e. salts containing pharmacologically acceptable anions, including but not limited to sulfuric, citric, maleic, acetic, oxalic, hydrochloride, hydrobromide, hydroiodide, nitrate, sulfate, bisulfate, phosphate, acid phosphate, isonicotinate, acetate, lactate, salicylate, citrate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate (i.e., 1,1'-methylene-bis-(2-hydroxy-3-naphthoate)) salts. Compounds included in the present compositions that include an amino moiety may form pharmaceutically or cosmetically acceptable salts with various amino acids, in addition to the acids mentioned above. Compounds, included in the present compositions, that are acidic in nature are capable of forming base salts with various pharmacologically or cosmetically acceptable cations. Examples of such salts include alkali metal or alkaline earth metal salts and, particularly, calcium, magnesium, sodium lithium, zinc, potassium, and iron salts.

In a preferred embodiment, the Pyrrole-Type compounds are formulated in accordance with routine procedures as a pharmaceutical composition adapted for intravenous administration to human beings. Typically, Pyrrole-Type compounds for intravenous administration are solutions in sterile isotonic aqueous buffer. Where necessary, the compositions may also include a solubilizing agent. Compositions for intravenous administration may optionally include a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the Pyrrole-Type compound is to be administered by infusion, it can be dispensed, for example, with an infusion bottle containing sterile pharmaceutical grade water or saline. Where the Pyrrole-Type compound is administered by injection, an ampoule of sterile water for injection or saline can be provided so that the ingredients may be mixed prior to administration. oily Compositions for oral delivery may be in the form of tablets, lozenges, aqueous or oily suspensions, granules, powders, emulsions, capsules, syrups, or elixirs, for example. Orally administered compositions may contain one or more optionally agents, for example, sweetening agents such as fructose, aspartame or saccharin; flavoring agents such as peppermint, oil of wintergreen, or cherry; coloring agents; and preserving agents, to provide a pharmaceutically palatable preparation. Moreover, where in tablet or pill form, the compositions may be coated to delay disintegration and absorption in the gastrointestinal tract thereby providing a sustained action over an extended period of time. Selectively permeable membranes surrounding an osmotically active driving compound are also suitable for orally administered Pyrrole-Type compounds. In these later platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time delay material such as glycerol monostearate or glycerol stearate may also be used. Oral compositions can include standard carriers such as mannitol, lactose, starch, magnesium stearate, sodium saccharine, cellulose, magnesium carbonate, etc. Such carriers are preferably of pharmaceutical grade.

The amount of the Pyrrole-Type compound that will be effective in the treatment of a particular disorder or condition will depend on the nature of the disorder or condition, and can be determined by standard clinical techniques. In addition, in vitro or in vivo assays may optionally be employed to help identify optimal dosage ranges. The precise dose to be employed in the compositions will also depend on the route of administration, and the seriousness of the disease or disorder, and should be decided according to the judgment of the practitioner and each patient's circumstances. However, suitable dosage ranges for intravenous administration are generally about 20–500 micrograms of Pyrrole-Type compound per kilogram body weight. In specific preferred embodiments of the invention, the i.v. dose is 10–40, 30–60, 60–100, or 100–200 micrograms per kilogram body weight. In other embodiments, the i.v. dose is 75–150, 150–250, 250–375 or 375–500 micrograms per kilogram body weight. Suitable dosage ranges for intranasal administration are generally about 0.01 pg/kg body weight to 1 mg/kg body weight. Suppositories generally contain active ingredient in the range of 0.5% to 10% by weight. Oral compositions preferably contain 10% to 95% active ingredient. In specific preferred embodiments of the invention, suitable dose ranges for oral administration are generally 1–500 micrograms of active compound per kilogram body weight. In specific preferred embodiments, the oral dose is 1–10, 10–30, 30–90, or 90–150 micrograms per kilogram body weight. In other embodiments, the oral dose is 150–250, 250–325, 325–450 or 450–1000 micrograms per kilogram body weight. Effective doses may be extrapolated from dose-response curves derived from in vitro or animal model test systems. Such animal models and systems are well known in the art.

The invention also provides pharmaceutical packs or kits comprising one or more containers filled with one or more Pyrrole-Type compounds of the invention. Optionally associated with such container(s) can be a notice in the form prescribed by a governmental agency regulating the manufacture, use or sale of pharmaceuticals or biological products, which notice reflects approval by the agency of manufacture, use or sale for human administration. In certain preferred embodiment, e.g., when administered for the treatment or prevention of cancer, the kit may also contain one or more chemotherapeutic agents useful for treating cancer or a neoplastic disease to be administered in combination with a Pyrrole-Type compound of the invention. In certain preferred embodiments, e.g., when administered for the treatment or prevention of viral disease, the kit may contain one or more Pyrrole-Type compound(s) of the invention and one or more anti-viral agents.

The Pyrrole-Type compounds of the invention are preferably assayed in vitro, and then in vivo, for the desired therapeutic or prophylactic activity, prior to use in humans. For example, in vitro assays can be used to determine whether administration of a specific Pyrrole-Type compound or combination of Pyrrole-Type compounds is preferred.

In one embodiment, a patient tissue sample is grown in culture, and contacted or otherwise administered with a Pyrrole-Type compound, and the effect of such Pyrrole-Type compound upon the tissue sample is observed and compared to a non-contacted tissue. In other embodiments, a cell culture model is used in which the cells of the cell culture are contacted or otherwise administered with a Pyrrole-Type compound, and the effect of such Pyrrole-Type compound upon the tissue sample is observed and compared to a non-contacted cell culture. Generally, a lower level of proliferation or survival of the contacted cells compared to the non-contracted cells indicates that the Pyrrole-Type compound is effective to treat a the patient. Such Pyrrole-Type compounds may also be demonstrated effective and safe using animal model systems.

Other methods will be known to the skilled artisan and are within the scope of the invention.

4.9. Inhibition of Cancer and Neoplastic Cells and Disease

The Pyrrole-Type compounds may be demonstrated to inhibit tumor cell proliferation, cell transformation and tumorigenesis in vitro and in vivo using a variety of assays known in the art, or described herein. Such assays may use cells of a cancer cell line, or cells from a patient. Many assays well-known in the art can be used to assess such survival and/or growth; for example, cell proliferation can be assayed by measuring ($^3$H)-thymidine incorporation, by direct cell count, by detecting changes in transcription, translation or activity of known genes such as proto-oncogenes (e.g., fos, myc) or cell cycle markers (Rb, cdc2, cyclin A, D1, D2, D3, E, etc). The levels of such protein and mRNA and activity can be determined by any method well known in the art. For example, protein can be quantitated by known immunodiagnostic methods such as Western blotting or immunoprecipitation using commercially available antibodies (for example, many cell cycle marker antibodies are from Santa Cruz Inc.). mRNA can be quantitated by methods that are well known and routine in the art, for example by northern analysis, RNase protection, the polymerase chain reaction in connection with the reverse transcription, etc. Cell viability can be assessed by using trypan-blue staining or other cell death or viability markers known in the art. Differentiation can be assessed visually based on changes in morphology, etc.

The present invention provides for cell cycle and cell proliferation analysis by a variety of techniques known in the art, including but not limited to the following:

As one example, bromodeoxyuridine (BRDU) incorporation may be used as an assay to identifyr proliferating cells. The BRDU assay identifies a cell population undergoing DNA synthesis by incorporation of BRDU into newly synthesized DNA. Newly synthesized DNA may then be detected using an anti-BRDU antibody (see Hoshino et al., 1986, Int. J. Cancer 38, 369; Campana et al.,1988, J. Immunol. Meth. 107, 79).

Cell proliferation may also be examined using ($^3$H)-thymidine incorporation (see e.g., Chen, J., 1996, Oncogene 13:1395–403; Jeoung, J., 1995, J. Biol. Chem. 270:18367–73). This assay allows for quantitative characterization of S-phase DNA synthesis. In this assay, cells synthesizing DNA will incorporate ($^3$H)-thymidine into newly synthesized DNA. Incorporation may then be measured by standard techniques in the art such as by counting of radioisotope in a Scintillation counter (e.g. Beckman LS 3800 Liquid Scintillation Counter).

Detection of proliferating cell nuclear antigen (PCNA) may also be used to measure cell proliferation. PCNA is a 36 kilodalton protein whose expression is elevated in proliferating cells, particularly in early G1 and S phases of the cell cycle and therefore may serve as a marker for proliferating cells. Positive cells are identified by immunostaining using an anti-PCNA antibody (see Li et al., 1996, Curr. Biol. 6:189–199; Vassilev et al., 1995, J. Cell Sci. 108:1205–15).

Cell proliferation may be measured by counting samples of a cell population over time (e.g. daily cell counts). Cells may be counted using a hemacytometer and light microscopy (e.g. HyLite hemacytometer, Hausser Scientific). Cell number may be plotted against time in order to obtain a growth curve for the population of interest. In a preferred embodiment, cells counted by this method are first mixed with the dye Trypan-blue (Sigma), such that living cells exclude the dye, and are counted as viable members of the population.

DNA content and/or mitotic index of the cells may be measured, for example, based on the DNA ploidy value of the cell. For example, cells in the G1 phase of the cell cycle generally contain a 2N DNA ploidy value. Cells in which DNA has been replicated but have not progressed through mitosis (e.g. cells in S-phase) will exhibit a ploidy value higher than 2N and up to 4N DNA content. Ploidy value and cell-cycle kinetics may be further measured using propidum iodide assay (see e.g. Turner, T., et al., 1998, Prostate 34:175–81). Alternatively, the DNA ploidy maybe determined by quantitation of DNA Feulgen staining (which binds to DNA in a stoichiometric manner) on a computerized microdensitometrystaining system (see e.g., Bacus, S., 1989, Am. J. Pathol. 135:783–92). In an another embodiment, DNA content may be analyzed by preparation of a chromosomal spread (Zabalou, S., 1994, Hereditas. 120:127–40; Pardue,1994, Meth. Cell Biol. 44:333–351).

The expression of cell-cycle proteins (e.g., CycA. CycB, CycE, CycD, cdc2, Cdk4/6, Rb, p21, p27, etc.) provide crucial information relating to the proliferative state of a cell or population of cells. For example, identification in an anti-proliferation signaling pathway may be indicated by the induction of p21$^{cip1}$. Increased levels of p21 expression in cells results in delayed entry into G1 of the cell cycle (Harper et al., 1993, Cell 75:805–816; Li et al., 1996, Curr. Biol. 6:189–199). p21 induction may be identified by immunostaining using a specific anti-p21 antibody available commercially (e.g. Santa Cruz). Similarly, cell-cycle proteins may be examined by Western blot analysis using commercially available antibodies. In another embodiment, cell populations are synchronized prior to detection of a cell cycle protein. Cell cycle proteins may also be detected by FACS (fluorescence-activated cell sorter) analysis using antibodies against the protein of interest.

Detection of changes in length of the cell cycle or speed of cell cycle may also be used to measure inhibition of cell proliferation by the Pyrrole-Type compounds of the invention. In one embodiment the length of the cell cycle is determined by the doubling time of a population of cells (e.g., using cells contacted or not contacted with one or more Pyrrole-Type compounds of the invention). In another embodiment, FACS analysis is used to analyze the phase of cell cycle progression, or purify G1, S, and G2/M fractions (see e.g., Delia, D. et al., 1997, Oncogene 14:2137–47).

Lapse of cell cycle checkpoint(s), and/or induction of cell cycle checkpoint(s), may be examined by the methods described herein, or by any method known in the art. Without limitation, a cell cycle checkpoint is a mechanism which ensures that a certain cellular events occur in a particular order. Checkpoint genes are defined by mutations that allow late events to occur without prior completion of an early event (Weinert, T., and Hartwell, L., 1993, Genetics, 134:63–80). Induction or inhibition of cell cycle checkpoint genes may be assayed, for example, by Western blot analysis, or by immunostaining, etc. Lapse of cell cycle checkpoints may be further assessed by the progression of a cell through the checkpoint without prior occurrence of specific events (e.g. progression into mitosis without complete replication of the genomic DNA).

In addition to the effects of expression of a particular cell cycle protein, activity and post-translational modifications of proteins involved in the cell cycle can play an integral role in the regulation and proliferative state of a cell. The invention provides for assays involved detected post-translational modifications (e.g. phosphorylation) by any method known in the art. For example, antibodies that detect phosphorylated tyrosine residues are commercially available, and may be used in Western blot analysis to detect proteins with such modifications. In another example, modifications such as myristylation, may be detected on thin layer chromatography or reverse phase h.p.l.c. (see e.g., Glover, C., 1988, Biochem. J. 250:485–91; Paige, L., 1988, Biochem J.; 250:485–91).

Activity of signaling and cell cycle proteins and/or protein complexes is often mediated by a kinase activity. The present invention provides for analysis of kinase activity by assays such as the histone Hi assay (see e.g., Delia, D. et al., 1997, Oncogene 14:2137–47).

The Pyrrole-Type compounds can also be demonstrated to alter cell proliferation in cultured cells in vitro using methods which are well known in the art. Specific examples of cell culture models include, but are not limited to, for lung cancer, primary rat lung tumor cells (Swafford et al., 1997, Mol. Cell. Biol., 17:1366–1374) and large-cell undifferentiated cancer cell lines (Mabry et al., 1991, Cancer Cells, 3:53–58); colorectal cell lines for colon cancer (Park and Gazdar,1996, J. Cell Biochem. Suppl. 24:131–141); multiple established cell lines for breast cancer (Hambly et al., 1997, Breast Cancer Res. Treat. 43:247–258; Gierthy et al., 1997, Chemosphere 34:1495–1505; Prasad and Church, 1997, Biochem. Biophys. Res. Commun. 232:14–19); a number of well-characterized cell models for prostate cancer (Webber et al., 1996, Prostate, Part 1, 29:386–394; Part 2, 30:58–64; and Part 3, 30:136–142; Boulikas, 1997, Anticancer Res. 17:1471–1505); for genitourinary cancers, continuous human bladder cancer cell lines (Ribeiro et al., 1997, Int. J. Radiat. Biol. 72:11–20); organ cultures of transitional cell carcinomas (Booth et al., 1997, Lab Invest. 76:843–857) and rat progression models (Vet et al., 1997, Biochim. Biophys Acta 1360:39–44); and established cell lines for leukemias and lymphomas (Drexler, 1994, Leuk. Res. 18:919–927, Tohyama, 1997, Int. J. Hematol. 65:309–317).

The Pyrrole-Type compounds can also be demonstrated to inhibit cell transformation (or progression to malignant phenotype) in vitro. In this embodiment, cells with a transformed cell phenotype are contacted with one or more Pyrrole-Type compounds, and examined for change in characteristics associated with a transformed phenotype (a set of in vitro characteristics associated with a tumorigenic ability in vivo), for example, but not limited to, colony formation in soft agar, a more rounded cell morphology, looser substratum attachment, loss of contact inhibition, loss of anchorage dependence, release of proteases such as plasminogen activator, increased sugar transport, decreased serum requirement, or expression of fetal antigens, etc. (see Luria et al., 1978, *General Virology,* 3d Ed., John Wiley & Sons, New York, pp. 436–446).

Loss of invasiveness or decreased adhesion may also be used to demonstrate the anti-cancer effects of the Pyrrole-Type compounds. For example, a critical aspect of the formation of a metastatic cancer is the ability of a precancerous or cancerous cell to detach from primary site of disease and establish a novel colony of growth at a secondary site. The ability of a cell to invade peripheral sites is reflective of a potential for a cancerous state. Loss of invasiveness may be measured by a variety of techniques known in the art including, for example, induction of E-cadherin-mediated cell—cell adhesion. Such E-cadherin-mediated adhesion can result in phenotypic reversion and loss of invasiveness (Hordijk et al., 1997, Science 278:1464–66).

Loss of invasiveness may further be examined by inhibition of cell migration. A variety of 2-dimensional and 3-dimensional cellular matrices are commercially available (Calbiochem-Novabiochem Corp. San Diego, Calif.). Cell migration across or into a matrix may be examined by microscopy, time-lapsed photography or videography, or by any method in the art allowing measurement of cellular migration. In a related embodiment, loss of invasiveness is examined by response to hepatocyte growth factor (HGF). HGF-induced cell scattering is correlated with invasiveness of cells such as Madin-Darby canine kidney (MDCK) cells. This assay identifies a cell population that has lost cell scattering activity in response to HGF (Hordijk et al., 1997, Science 278:1464–66).

Alternatively, loss of invasiveness may be measured by cell migration though a chemotaxis chamber (Neuroprobe/Precision Biochemicals Inc. Vancouver, BC). In such assay, a chemo-attractant agent is incubated on one side of the chamber (e.g., the bottom chamber) and cells are plated on a filter separating the opposite side (e.g., the top chamber). In order for cells to pass from the top chamber to the bottom chamber, the cells must actively migrate through small pores in the filter. Checkerboard analysis of the number of cells that have migrated may then be correlated with invasiveness (see e.g., Ohnishi, T., 1993, Biochem. Biophys. Res. Commun. 193:518–25).

The Pyrrole-Type compounds can also be demonstrated to inhibit tumor formation in vivo. A vast number of animal models of hyperproliferative disorders, including ftumorigenesis and metastatic spread, are known in the art (see Table 317-1, Chapter 317, "Principals of Neoplasia," in *Harrison's Principals of Internal Medicine,*13th Edition, Isselbacher et al., eds., McGraw-Hill, New York, p. 1814, and Lovejoy et al., 1997, J. Pathol. 181:130–135). Specific examples include for lung cancer, transplantation of tumor nodules into rats (Wang et al., 1997, Ann. Thorac. Surg. 64:216–219) or establishment of lung cancer metastases in SCID mice depleted of NK cells (Yono and Sone, 1997, Gan To Kagaku Ryoho 24:489–494); for colon cancer, colon cancer transplantation of human colon cancer cells into nude mice (Gutman and Fidler, 1995, World J. Surg. 19:226–234), the cotton top tamarin model of human ulcerative colitis (Warren,1996, Aliment. Pharmacol. Ther. Supp 12:45–47) and mouse models with mutations of the adenomatous polyposis tumor suppressor (Polakis,1997, Biochim. Biophys. Acta 1332:F127-F147); for breast cancer, transgenic models of breast cancer (Dankort and Muller, 1996, Cancer Treat. Res. 83:71–88; Amundadittir et al., 1996, Breast Cancer Res. Treat. 39:119–135) and chemical induction of tumors in rats (Russo and Russo, 1996, Breast Cancer Res. Treat. 39:7–20); for prostate cancer, chemically-induced and transgenic rodent models, and human xenograft models (Royai et al., 1996, Semin. Oncol. 23:35–40); for genitourinary cancers, induced bladder neoplasm in rats and mice (Oyasu, 1995, Food Chem. Toxicol 33:747–755) and xenografts of human transitional cell carcinomas into nude rats (Jarrett et al., 1995, J. Endourol. 9:1–7); and for hematopoietic cancers, transplanted allogeneic marrow in animals (Appelbaum, 1997, Leukemia 11(Suppl. 4):S15–S17). Further, general animal models applicable to many types of cancer have been described, including, but not restricted to, the p53-deficient mouse model (Donehower, 1996, Semin. Cancer Biol. 7:269–278), the Min mouse (Shoemaker et al., 1997, Biochem. Biophys. Acta, 1332:F25–F48), and immune responses to tumors in rat (Frey, 1997, Methods, 12:173–188).

For example, a Pyrrole-Type compound can be administered to a test animal, preferably a test animal predisposed to develop a type of tumor, and the test animal subsequently examined for an decreased incidence of tumor formation in comparison with controls not administered the Pyrrole-Type compound. Alternatively, a Pyrrole-Type compound can be administered to test animals having tumors (e.g., animals in which tumors have been induced by introduction of malignant, neoplastic, or transformed cells, or by administration of a carcinogen) and subsequently examining the tumors in the test animals for tumor regression in comparison to controls not administered the Pyrrole-Type compound.

4.9.1. Treatment or Prevention of Cancer or a Neonatal Disease in Combination with Chemotherapy or Radiotherapy Cancer or a neoplastic disease, including, but not limited to, neoplasms, tumors, metastases, or any disease or disorder characterized by uncontrolled cell growth, can be treated or prevented by administration of a composition comprising a pharmaceutically acceptable carrier and a Pyrrole-Type compound or a pharmaceutically acceptable salt thereof. The compositions can comprise one or more Pyrrole-Type compounds, or a pharmaceutically acceptable salt thereof.

In certain embodiments, one or more Pyrrole-Type compounds of the invention are used to treat or prevent cancer or neoplastic disease in combination with one or more anti-cancer, chemotherapeutic agents including, but not limited to, methotrexate, taxol, mercaptopurine, thioguanine, hydroxyurea, cytarabine, cyclophosphamide, ifosfamide, nitrosoureas, cisplatin, carboplatin, mitomycin, dacarbazine, procarbizine, etoposides, campathecins, bleomycin, doxorubicin, idarubicin, daunorubicin, dactinomycin, plicamycin, mitoxantrone, asparaginase, vinblastine, vincristine, vinorelbine, paclitaxel, and docetaxel. In a preferred embodiment, one or more Pyrrole-Type compound of the invention is used to treat or prevent cancer or neoplastic disease in combination with one or more chemotherapeutic or other anti-cancer agents including, but not limited to those presented in Table 7.

TABLE 7

CHEMOTHERAPEUTICS AND OTHER ANTI-CANCER AGENTS

| | |
|---|---|
| Radiation: | γ-radiation |
| Alkylating agents | |
| Nitrogen mustards: | cyclophosphamide |
| | Ifosfamide |
| | trofosfamide |
| | Chlorambucil |
| Nitrosoureas: | carmustine (BCNU) |
| | Lomustine (CCNU) |
| Alkylsulphonates | busulfan |
| | Treosulfan |
| Triazenes: | Dacarbazine |
| Platinum containing compounds: | Cisplatin |
| | carboplatin |
| Plant Alkaloids | |
| Vinca alkaloids: | vincristine |
| | Vinblastine |
| | Vindesine |
| | Vinorelbine |
| Taxoids: | paclitaxel |
| | Docetaxol |
| DNA Topoisomerase Inhibitors | |
| Epipodophyllins: | etoposide |
| | Teniposide |
| | Topotecan |
| | 9-aminocamptothecin |
| | campto irinotecan |
| | crisnatol |
| mytomycins: | |
| mytomycin C | Mytomycin C |
| Anti-metabolites | |
| Anti-folates: | |
| DHFR inhibitors: | methotrexate |
| | Trimetrexate |
| IMP dehydrogenase Inhibitors: | mycophenolic acid |
| | Tiazofurin |
| | Ribavirin |
| | EICAR |
| Ribonucleotide reductase Inhibitors: | hydroxyurea |
| | deferoxamine |
| Pyrimidine analogs: | |
| Uracil analogs | 5-Fluorouracil |
| | Floxuridine |
| | Doxifluridine |
| | Ratitrexed |
| Cytosine analogs | cytarabine (ara C) |
| | Cytosine arabinoside |
| | fludarabine |
| Purine analogs: | mercaptopurine |
| | Thioguanine |
| Hormonal therapies: | |

TABLE 7-continued

CHEMOTHERAPEUTICS AND OTHER ANTI-CANCER AGENTS

| | |
|---|---|
| Receptor antagonists: | |
| Anti-estrogens | Tamoxifen |
| | Raloxifene |
| | megestrol |
| LHRH agonists: | goscrclin |
| | Leuprolide acetate |
| Anti-androgens: | flutamide |
| | bicalutamide |
| Retinoids/Deltoids | |
| Vitamin D3 analogs: | EB 1089 |
| | CB 1093 |
| | KH 1060 |
| Photodyamic therapies: | vertoporfin (BPD-MA) |
| | Phthalocyanine |
| | photosensitizer Pc4 |
| | Demethoxy-hypocrellin A |
| | (2BA-2-DMHA) |
| Cytokines: | Interferon-α |
| | Interferon-γ |
| | Tumor necrosis factor |
| Others: | |
| Isoprenylation inhibitors: | Lovastatin |
| Dopaminergic neurotoxins: | 1-methyl-4-phenylpyridinium ion |
| Cell cycle inhibitors: | staurosporine |
| Actinomycins: | Actinomycin D |
| | Dactinomycin |
| Bleomycins: | bleomycin A2 |
| | Bleomycin B2 |
| | Peplomycin |
| Anthracyclines: | daunorubicin |
| | Doxorubicin (adriamycin) |
| | Idarubicin |
| | Epirubicin |
| | Pirarubicin |
| | Zorubicin |
| | Mitoxantrone |
| MDR inhibitors: | verapamil |
| $Ca^{2+}$ATPase inhibitors: | thapsigargin |

In other embodiments, a composition comprising one or more Pyrrole-Type compounds is administered along with radiation therapy and/or with one or a combination of chemotherapeutic agents, preferably with one or more chemotherapeutic agents with which treatment of the cancer has not been found to be refractory. The Pyrrole-Type compound can be administered to a patient that has also undergone surgery as treatment for the cancer.

In another specific embodiment, the invention provides a method to treat or prevent cancer that has shown to be refractory to treatment with a chemotherapy and/or radiation therapy.

In a specific embodiment, a composition comprising one or more Pyrrole-Type compounds is administered concurrently with chemotherapy or radiation therapy. In another specific embodiment, chemotherapy or radiation therapy is administered prior or subsequent to administration of a present composition, preferably at least an hour, five hours, 12 hours, a day, a week, a month, more preferably several months (e.g., up to three months), subsequent to administration of a therapeutic of the invention.

The chemotherapy or radiation therapy administered concurrently with, or prior or subsequent to, the administration of a present composition can be accomplished by any method known in the art. The chemotherapeutic agents are preferably administered in a series of sessions, any one or a combination of the chemotherapeutic agents listed above can be administered. With respect to radiation therapy, any radiation therapy protocol can be used depending upon the type of cancer to be treated. For example, but not by way of limitation, x-ray radiation can be administered; in particular, high-energy megavoltage (radiation of greater that 1 MeV energy) can be used for deep tumors, and electron beam and orthovoltage x-ray radiation can be used for skin cancers. Gamma-ray emitting radioisotopes, such as radioactive isotopes of radium, cobalt and other elements, may also be administered to expose tissues to radiation.

Additionally, the invention provides methods of treatment of cancer or neoplastic disease with a present composition as an alternative to chemotherapy or radiation therapy where the chemotherapy or the radiation therapy has proven or may prove too toxic, e.g., results in unacceptable or unbearable side effects, for the subject being treated. The subject being treated with the present compositions may, optionally, be treated with other cancer treatments such as surgery, radiation therapy or chemotherapy, depending on which treatment is found to be acceptable or bearable.

4.9.2. Cancer and Neoplastic Disease Treatable or Preventable

Cancers or neoplastic diseases and related disorders that can be treated or prevented by administration of the present compositions include but are not limited to those listed in Table 8 (for a review of such disorders, see Fishman et al., 1985, *Medicine*, 2d Ed., J. B. Lippincott Co., Philadelphia):

TABLE 8

CANCERS AND NEOPLASTIC DISORDERS

Leukemia
    acute leukemia
    acute lymphocytic leukemia
    acute myelocytic leukemia
        myeloblastic
        promyelocytic
        myelomonocytic
        monocytic
        erythroleukemia
    chronic leukemia
    chronic myelocytic (granulocytic) leukemia
    chronic lymphocytic leukemia
Polycythemia vera
Lymphoma
    Hodgkin's disease
    non-Hodgkin's disease
Multiple myeloma
Waldenström's macroglobulinemia
Heavy chain disease
Solid tumors
    sarcomas and carcinomas
        fibrosarcoma
        myxosarcoma
        liposarcoma
        chondrosarcoma
        osteogenic sarcoma
        chordoma
        angiosarcoma
        endotheliosarcoma
        lymphangiosarcoma
        lymphangioendotheliosarcoma
        synovioma
        mesothelioma
        Ewing's tumor
        leiomyosarcoma
        rhabdomyosarcoma
        colon carcinoma
        pancreatic cancer
        breast cancer
        ovarian cancer
        prostate cancer TABLE 8-continued

CANCERS AND NEOPLASTIC DISORDERS squamous cell carcinoma
        basal cell carcinoma
        adenocarcinoma
        sweat gland carcinoma
        sebaceous gland carcinoma
        papillary carcinoma
        papillary adenocarcinomas
        cystadenocarcinoma
        medullary carcinoma
        bronchogenic carcinoma
        renal cell carcinoma
        hepatoma
        bile duct carcinoma
        choriocarcinoma
        seminoma
        embryonal carcinoma
        Wilms' tumor
        cervical cancer
        uterine cancer
        testicular tumor
        lung carcinoma
        small cell lung carcinoma
        bladder carcinoma
        epithelial carcinoma
        glioma
        astrocytoma
        medulloblastoma
        craniopharyngioma
        ependymoma
        pinealoma
        hemangioblastoma
        acoustic neuroma
        oligodendroglioma
        meningioma
        melanoma
        neuroblastoma
        retinoblastoma In specific embodiments, cancer, malignancy or dysproliferative changes (such as metaplasias and dysplasias), or hyperproliferative disorders, are treated or prevented in the ovary, breast, colon, lung, skin, pancreas, prostate, bladder, or uterus. In other specific embodiments, sarcoma, melanoma, or leukemia is treated or prevented.

In a highly preferred embodiment, the present compositions are used to treat or prevent cancers including prostate (more preferably hormone-insensitive), Neuroblastoma, Lymphoma (preferably follicular or Diffuse Large B-cell), Breast (preferably Estrogen-receptor positive), Colorectal, Endometrial, Ovarian, Lymphoma (preferably non-Hodgkin's), Lung (preferably Small cell), or Testicular (preferably germ cell).

In a preferred embodiment, the present compositions are used to inhibit the growth of a cell derived from a cancer or neoplasm such as prostate (more preferably hormone-insensitive), Neuroblastoma, Lymphoma (preferably follicular or Diffuse Large B-cell), Breast (preferably Estrogen-receptor positive), Colorectal, Endometrial, Ovarian, Lymphoma (preferably non-Hodgkin's), Lung (preferably Small cell), or Testicular (preferably germ cell).

In specific embodiments of the invention, the present compositions are used to inhibit the growth of a cell, said cell being derived from a cancer or neoplasm in Table 8 or herein.

4.9.3. Demonstration of Inhibition of Viruses and Viral Infections

The Pyrrole-Type compounds may be demonstrated to inhibit the replication or infectivity of a virus or a virus-infected cell in vitro or in vivo using a variety of assays known in the art, or described herein. In certain embodiments, such assays may use cells of a cell line, or cells from a patient. In specific embodiments, the cells may be infected with a virus prior to the assay, or during the assay. The cells may be contacted with a virus. In certain other embodiments, the assays may employ cell-free viral cultures.

In one embodiment, a Pyrrole-Type compound is demonstrated to have activity in treating or preventing viral disease by contacting cultured cells that exhibit an indicator of a viral reaction (e.g., formation of inclusion bodies) in vitro with the Pyrrole-Type compound, and comparing the level of said indicator in the cells contacted with the Pyrrole-Type compound with said level of said indicator in cells not so contacted, wherein a lower level in said contacted cells indicates that the Pyrrole-Type compound has activity in treating or preventing viral disease. Cell models that can be used for such assays include, but are not limited to, viral infection of T lymphocytes (Selin et al., 1996, J. Exp. Med. 183:2489–2499); hepatitis B infection of dedifferentiated hepatoma cells (Raney et al., 1997, J. Virol. 35 71:1058–1071); viral infection of cultured salivary gland epithelial cells (Clark et al., 1994, Autoimmunity 18:7–14); synchronous HIV-1 infection of $CD^{4+}$ lymphocytic cell lines (Wainberg et al., 1997, Virology 233:364–373); viral infection of respiratory epithelial cells (Stark et al., 1996, Human Gene Ther. 7:1669–1681); and amphotrophic retroviral infection of NIH-3T3cells (Morgan et al., 1995, J. Virol. 69:6994–7000).

In another embodiment, a Pyrrole-Type compound can be demonstrated to have activity in treating or preventing viral disease by administering said Pyrrole-Type compound to a test animal having symptoms of a viral infection, such as characteristic respiratory symptoms in animal models, or which test animal does not exhibit a viral reaction and is subsequently challenged with an agent that elicits an viral reaction, and measuring the change in the viral reaction after the administration of said Pyrrole-Type compound, wherein a reduction in said viral reaction or a prevention of said viral reaction indicates that the Pyrrole-Type compound has activity in treating or preventing viral disease. Animal models that can be used for such assays include, but are not limited to, guinea pigs for respiratory viral infections (Kudlacz and Knippenberg, 1995, Inflamm. Res. 44:105–110); mice for influenza virus infection (Dobbs et al., 1996, J. Immunol. 157:1870–1877); lambs for respiratory syncitial virus infection (Masot et al., 1996, Zentralbl. Veterinarmed. 43:233–243); mice for neurotrophic virus infection (Barna et al., 1996, Virology 223:331–343); hamsters for measles infection (Fukuda et al., 1994, Acta Otolaryngol. Suppl (Stockh.) 514:111–116); mice for encephalomyocarditis infection (Hirasawa et al., 1997, J. Virol. 71:4024–4031); and mice for cytomegalovirus infection (Orange and Biron, 1996, J. Immunol. 156:1138–1142). In certain embodiments of the invention more than one Pyrrole-Type compound is administered to a test animal, virus, or viral-infected cell.

4.9.4. Viruses and Viral Infections

Viruses and viral infections that can be treated or prevented by administration of a composition of the invention include but are not limited to those listed in Table 9 including, but not limited to, DNA viruses such as hepatitis type B and hepatitis type C virus; parvoviruses, such as adeno-associated virus and cytomegalovirus; papovaviruses such as papilloma virus, polyoma viruses, and SV40; adenoviruses; herpes viruses such as herpes simplex type I (HSV-I), herpes simplex type II (HSV-II), and Epstein-Barr virus; poxviruses, such as variola (smallpox) and vaccinia virus; and RNA viruses, such as human immunodeficiency virus type I (HIV-I), human immunodeficiency virus type II (HIV-II), human T-cell lymphotropic virus type I (HTLV-I), human T-cell lymphotropic virus type II (HTLV-II), influenza virus, measles virus, rabies virus, Sendai virus, picornaviruses such as poliomyelitis virus, coxsackieviruses, rhinoviruses, reoviruses, togaviruses such as rubella virus (German measles) and Semliki forest virus, arboviruses, and hepatitis type A virus.

In a preferred embodiment of the invention, the compositions of the invention are sed to treat or prevent a viral infection associated with a virus as listed in Table 9. In another preferred embodiment, the compositions of the invention are used inhibit the replication or infectivity of a virus listed in Table 9. In yet another preferred embodiment, one or more Pyrrole-Type compounds of the invention are used inhibit the growth of a cell infected with a virus listed in Table 9.

TABLE 9

| | |
|---|---|
| Herpesviruses: | EBV |
| | HHV-8 (KSHV) |
| | Herpesvirus saimiri |
| Adenoviruses: | All strains |
| Retroviruses: | HIV-1 and 2 |
| | HTLV-I |
| Human Papillomaviruses: | HPV - all strains |
| Birnaviruses: | Infectious pancreatic necrosis virus |
| Other: | African Swine Fever virus (all strains) |

5. EXAMPLES

The following examples are set forth to assist in understanding the invention and should not, of course, be construed as specifically limiting the invention described and claimed herein. Such variations of the invention, including the substitution of all equivalents now known or later developed, which would be within the purview of those skilled in the art, and changes in Formulation or minor changes in experimental design, are to be considered to fall within the scope of the invention incorporated herein.

Example 1

2-Ethyl-11-((3-methoxy-5-(1H-pyrrol-2-yl)-2H-pyrrol-2-ylidene)methyl)-10-azabicyclo[7.2.1]dodeca-9(12),11-diene

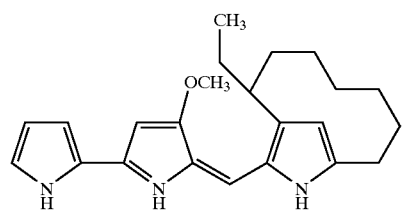

The pyrrole 2 ($R_{14}$ is Me, m is 1; 2-ethyl-10-azabicyclo[7.2.1]doceca-9(12),11-diene) (1.0 mmol) is added to a stirred solution of 1 (4-methoxy-2,2'-bipyrrole-5- carboxaldehyde) (Boger and Patel, 1988, J. Org. Chem. 53:1405) (1.0 mmol) in methanol (5 mL) under argon. The solution is warmed to near the boiling point of the solvent and while still warm, concentrated hydrochloric acid (drops) is added. The reaction mixture is left to stand at room temperature and progress of the reaction is monitored using thin-layer chromatography. When the reaction is complete, the solvent is removed under reduced pressure and the residue is purified using colunm chromatography (neutral alumina), providing the above-titled compound.

Example 2

2-Benzyl-11-((3-methoxy-5-(1H-pyrrol-2-yl)-2H-pyrrol-2-ylidene)methyl)-10-azabicyclo[7.2.1]dodeca-9(12),11-diene

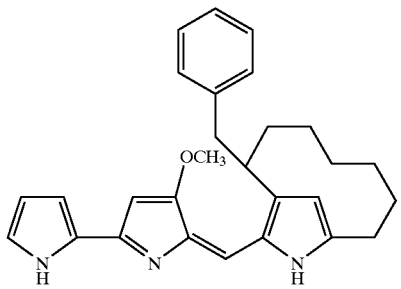

A solution of the pyrrole 2 ($R_{14}$ is Ph, m is 1; 2-benzyl-10-azabicyclo[7.2.1]doceca-9(12),11-diene) (1.0 mmol) in n-pentane (4 mL) is added to a solution of 1 (1.0 mmol) in pentane (5 mL) under argon. The resulting solution is stirred and cooled in an ice-water bath. Phosphorous oxychloride (1.0 mmol) is added and the resulting mixture is stirred until reaction is complete as determined by thin-layer chromatography. The resulting solid precipitate is collected by filtration, washed with cold pentane, and added to a suspension of excess moist calcium hydroxide in pentane (10 mL). The resulting mixture is mixed vigorously, and the pentane solution is separated, dried ($Na_2SO_4$), filtered and concentrated, giving a crude mixture of the above-titled compound. The crude mixture is purified using chromatography over neutral alumina to obtain the above-titled compound.

Example 3

4,5,6,7-Tetrahydro-3-((3-methoxy-5-(1H-pyrrol-2-yl)-2H-pyrrol-2-ylidene)methyl)-1-ethyl-2H-isoindole

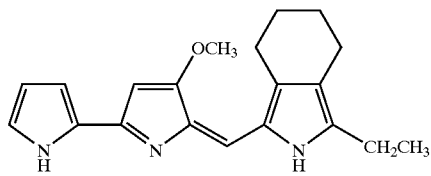

A solution of the pyrrole 40 ($R_2$ is Et, $R_5$ is H, n is 2; 2-ethyl-3,4-tetramethylenepyrrole) (1.0 mmol) in methanol (2 mL) is added to a stirred solution of 1 (4-methoxy-2,2'-bipyrrole-5-carboxaldehyde) (1.0 mmol) in methanol (3 mL) under argon. The solution is warmed to near the boiling point of the solvent and, while still warm, concentrated hydrochloric acid (drops) is added. The reaction mixture is left to stand at room temperature and progress of the reaction is followed using thin-layer chromatography. When the reaction appears complete, the solvent is removed under reduced pressure and the residue is purified using chromatography (neutral alumina) giving the above-titled compound.

Example 4

4,5,6,7-Tetrahydro-3-((3-methoxy-5-(1H-pyrrol-2-yl)-2H-pyrrol-2-ylidene)methyl)-5-methyl-1H-indole

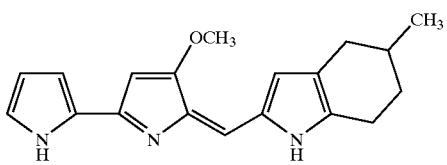

Following the procedures described in Example 1, pyrrole 57 and 1 react, giving the above-titled compound.

Example 5

Methoxy-5-((5-(2-(2-methyl)-furyl)-2H-pyrrol-2-ylidene)methyl)-2,2'-bi-1H-pyrrole

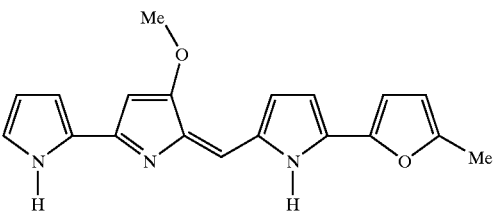

Following the procedures described in Example 1, 2-(2-(2-methyl)-furyl)-1H-pyrrole (97) and 1 react, providing the above-titled compound.

Example 6

Preparation of Two Diastereoisomers of 1-(10-(toluenesulfonyl)-10-azabicyclo[7.2.1]dodec-1(12)-en-2-yl)butan-1-ol

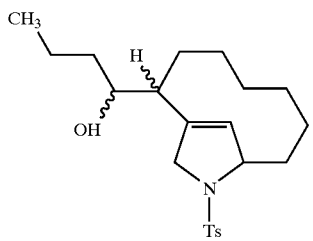

A solution of 11($R_{14}$ is n-propyl, m is 1; A. Fürstner et al., J. Am. Chem. Soc. 120, 8305–8314, 1998) (2.0 mmol) in ethanol (20 mL) containing $Ru_2Cl_4((S)\text{-BINAP})_2 \cdot NEt_3$ (0.1 mol) is hydrogenated under $H_2$ at 3 atmospheres of pressure. The resulting mixture is warmed until an equivalent of hydrogen is consumed. The reaction mixture is cooled to room temperature, the reaction vessel is flushed with nitrogen, and the solvent is removed under reduced pressure. The mixture of diastereoisomers of 12 ($R_{14}=Ch_3CH_2CH_2$, m=1) is separated using conventional chromatographic techniques.

Example 7

A Diastereoisomer of Thiocarbonic Acid O-phenyl ester O-(1-(10-(toluenesulfonyl)-10-azabicyclo[7.2.1]dodec-1(12)-en-2-yl)butyl) ester

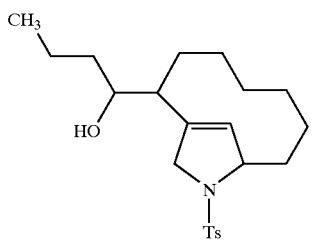

Phenylchlorothionoformate (3.0 mmol) and pyridine (2.0 mmol) are added in methylene chloride (10 mL) to a solution of one of the diastereomers obtained from Example 6 (1 mmol). The solution is stirred under argon at ice bath temperature. The solution is stirred at room temperature for hours, after which excess reagent is quenched with methanol. The resulting solution is concentrated, and the residue is purified using high-performance liquid chromatography, affording the above-titled compound.

Example 8

Preparation of an Enantiomer of 2-butyl-10-(toluenesulfonyl)-10-azabicyclo[7.2.1]dodec-1(12)-ene

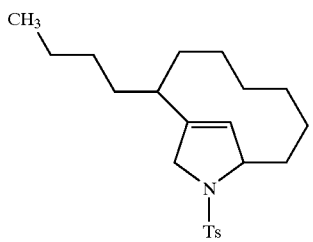

AIBN (0.20 mmol) and tri-n-butyltinhydride (2.0 mmol) are added to a solution of the product of Example 7 (1 mmol) in toluene (10 mL). The mixture is stirred at 75° C. until reaction is complete as detected by thin-layer chromatography. Solvent is removed under reduced pressure and the residue is purified using high-performance liquid chromatography, affording the above-titled compound.

Example 9

Preparation of an Enantiomer of 2-butyl-10-azabicyclo[7.2.1]dodeca-1(11),9(12)-diene

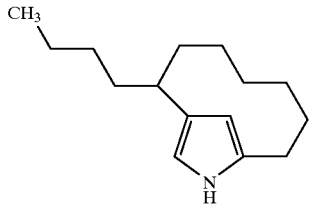

1,3-Diaminopropane (30 mL) is added to potassium hydride (10 mmol) under argon at room temperature. The mixture is stirred 3 hours. The resulting mixture is added dropwise at −15° C. over a period of an hour to a solution of the product of Example 8 (1 mmol) in 1,3-diaminopropane (15 mL). The resulting mixture is stirred at −15° C. for three hours and then is poured carefully into cold water. The aqueous phase is extracted with EtOAc, and the organic extracts are dried (Na$_2$SO$_4$), filtered and concentrated, affording a crude mixture of the above-titled compound. The crude mixture is purified using conventional chromatographic methods.

Example 10

An Enantiomer of 2-butyl-11-((3-methoxy-5-(1H-pyrrol-2-yl)-2H-pyrrol-2-ylidene)methyl)-10-azabicyclo[7.2.1]dodeca-9(12),11-diene

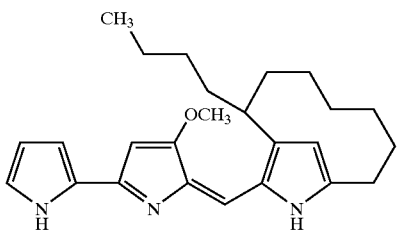

Using the procedure described in Example 1, the product of Example 9 and 1 react, affording the above-titled compound.

Example 11

The enantiomer of 2-butyl-11-((3-methoxy-5-(1H-pyrrol-2-yl)-2H-pyrrol-2-ylidene)methyl)-10-azabicyclo[7.2.1]dodeca-9(12),11-diene Opposite from that of Example 10.

The diastereomer obtained from the procedure of Example 6 but not used in Example 7 is reacted according to Examples 7–10 to afford the above-titled compound.

Example 12

Butyl-meta-cycloheptylprodiginine via Fermentation.

One Bennett's agar slant of *Streptoverticillium baldacci* (ATCC no. 25189) was inoculated into five 50 mL cultures of fermentation medium. The fermentation medium consisted of 10 g soybean meal (Central Soya, Bellevue, Ohio), 20 g glucose,10 g meat peptone 851C (Difco Laboratories, Detroit, Mich.) and 5 g sodium chloride in 1 liter of tap water, pH adjusted to 7.5 (*J. Heterocycl. Chem.* 10:925–929, 1973). The cultures were incubated at 28° C. for 4 days with ~220 rpm shaking. Twenty 500 mL cultures were then inoculated with 10 mL of the above culture and incubated at 28° C. for days with ~220 rpm shaking.

The bacterial cells were harvested after days by filtration, then mechanically homogenized in three, 1-liter aliquots of ethyl acetate. All of the extracts were pooled and separated from cell debris before evaporation under vacuum to near complete dryness. While the extract was drying, a 1 liter Partition-chromatography solvent system consisting of hexane: ethyl acetate: methanol: water (1:3:3:3 ratio) was prepared in a separating funnel.

The dried extract was dissolved in the upper solvent layer of the solvent system. The bottom layer of the solvent system was then added, and the resulting mixture was shaken in a separating funnel. The bottom layer was then discarded, and the upper, dark-red colored layer was completely dried under a vacuum. The resulting residue was dissolved in approximately 50 mL of toluene.

The toluene solution of the residue was applied to a 250 g hexane-packed alumina column. Fresh alumina was used for every batch and care was taken to not let the column dry out. The column was washed with 1–2 volumes of hexane to remove any toluene or lipids from the extract. Fractions of 10–15 mL each were collected as the extract was slowly eluted with 4-column volumes of hexane:ethyl acetate (9:1 ratio). The eluate containing a main red zone was evaporated and dissolved in 10–20 mL of dichloromethane. The dissolved eluate was then applied to a hexane-packed 200 g silica gel (60–200 mesh, Bayer, Pittsburgh, Pa.) column. The column was washed with 1–2 column volumes of hexane to remove any toluene or lipids from the extract. Fractions of 10–15 mL each were collected as the extract was slowly eluted with 4–5 column volumes of hexane:ethyl acetate (9:1 ratio). The eluate containing a red-pink color zone was then dried under a vacuum to provide the above-titled compound, which was >99% pure as shown by NMR and MS.

Example 13

In Vitro Assay Demonstrating Anti-Oncogenic Effects of Illustrative Pyrrole-Type Compounds Butyl-meta-Cycloheptylprodiginine and Ethyl-meta-Cyclononylprodiginine

TABLE 10

| | | | Cytoxicity (% Dead cells) | | |
| --- | --- | --- | --- | --- | --- |
| Compound | Concentration μM | Time of Exposure (h) | Normal Human Breast Epithelial Cells | MCF-7 Breast Cancer cells | MBA-MB231 Breast Cancer cells |
| Butyl-meta-cycloheptylprodiginine | 0 | 72 | 5 | 24 | 20 |
| | 0.25 | 72 | 5 | 70 | 64 |
| | 1.0 | 72 | 5 | 100 | 100 |
| | 2.0 | 72 | 15 | 100 | 100 |
| Ethyl-meta-cyclononylprodiginine | 0 | 24 | 17 | 14 | N.D. |
| | 0.2 | 24 | 10 | 45 | N.D. |
| | 1.0 | 24 | 9 | 62 | N.D. |
| | 2.0 | 24 | 15 | 65 | N.D. |

Methods

An in vitro cytotoxicity assay was used to demonstrate the selective toxicity of butyl-meta-cycloheptylprodiginine and ethyl-meta-cyclononylprodiginine to oncogenic cells, relative to that of normal cells. Normal and cancerous human breast cells were plated at a density of ~70,000–80,000 cells/well in 24 well plates. Each test compound was added to the cell media at the indicated concentration and incubated at 37° C. in a $CO_2$ incubator for the indicated time. Following incubation, cells were harvested and exposed to trypan blue dye; dead cells were stained exclusively (living cells remained unstained) and counted.

Results

The cytotoxicity assay showed that butyl-meta-cycloheptylprodiginine selectively killed the breast cancer cells, relative to normal human breast epithelial cells. As seen in Table 10, a 0.25 μm concentration of butyl-meta-cycloheptylprodiginine causes only 5% cell death in normal cells as compared to 70% and 64% cell death in cancer cells. Ethyl-meta-cyclononylprodiginine had similar effects. These results indicate that butyl-meta-cycloheptylprodiginine and ethyl-meta-cyclononylprodiginine, illustrative Pyrrole-Type compounds of the present invention, are selective anti-cancer agents.

The present invention is not to be limited in scope by the specific embodiments disclosed in the examples which are intended as illustrations of a few aspects of the invention and any embodiments which are functionally equivalent are within the scope of this invention. Indeed, various modifications of the invention in addition to those shown and described herein will become apparent to those skilled in the art and are intended to fall within the appended claims.

A number of references have been cited, the entire disclosures of which are incorporated herein by reference.

What is claimed is:

1. A method for treating prostate cancer comprising administering to a patient in need of such treatment a therapeutically effective amount of a compound of Formula (I):

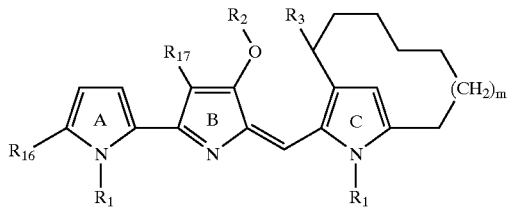

or a pharmaceutically acceptable salt thereof, wherein, in the compound of Formula (I):
each $R_1$ is independently selected from the group consisting of —H, —$CH_3$, —$CH_2CH_3$, —$CH_2C_6H_5$, C(O)OC($CH_3$)$_3$, —C(O)O$CH_2C_6H_5$, and —C(O)$CH_3$;
$R_2$ is selected from the group consisting of —H, $C_1$–$C_{12}$ straight chain alkyl, —$CH_2C_6H_5$, —$SiR_{10}R_{11}R_{12}$, —C(O)CH$_3$, —C(O)C$_6$H$_5$, -2-tetrahydropyranyl, —OCH$_2$OCH$_3$, and —C(O)OCH$_2$CCl$_3$;

R$_3$ is selected from the group consisting of —H, C$_1$–C$_{12}$ straight chain alkyl, —CH(R$_{14}$)(R$_{15}$) wherein R$_{14}$ and R$_{15}$ are independently C$_1$–C$_{12}$ straight chain alkyl, —C(O)C$_1$–C$_9$ straight chain alkyl, —CH(OH)C$_1$–C$_9$ straight chain alkyl, —CH(Cl)C$_1$–C$_9$ straight chain alkyl, -(2-pyridyl)methyl, -(3-pyridyl)methyl, -(4-pyridyl)methyl, and —CH$_2$C$_6$H$_5$, the —CH$_2$C$_6$H$_5$ being unsubstituted or substituted on phenyl with one cyano or one or more halo, methoxyl, or trifluoromethyl groups;

R$_{10}$ is selected from the group consisting of C$_1$–C$_4$ straight or branched chain alkyl and R$_{11}$ and R$_{12}$ are independently C$_1$–C$_3$ straight or branched chain alkyl;

m is an integer ranging from 1 to 5; and when m is 3 and R$_2$ is —CH$_2$CH$_3$, then R$_{16}$ is —H or —CH$_3$ and R$_{17}$ is —H;

when m is 3 and R$_2$ is —CH$_3$, then R$_{16}$ is —H or —CH$_3$ and R$_{17}$ is —H or —COOEt; and when m is other than 3 and R$_2$ is other than —CH$_3$ or —CH$_2$CH$_3$, then R$_{16}$ and R$_{17}$ are —H only;

with the proviso that the compound of Formula (I) is not metacycloprodigiosin.

2. A method for treating cervical cancer comprising administering to a patient in need of such treatment a therapeutically effective amount of a compound of Formula (I):

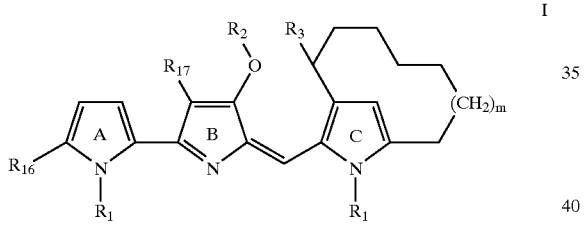

or a pharmaceutically acceptable salt thereof, wherein, in the compound of Formula (I):

each R$_1$ is independently selected from the group consisting of —H, —CH$_3$, —CH$_2$CH$_3$, —CH$_2$C$_6$H$_5$, —C(O)OC(CH$_3$)$_3$, —C(O)OCH$_2$C$_6$H$_5$, and —C(O)CH$_3$;

R$_2$ is selected from the group consisting of —H, C$_1$–C$_{12}$ straight chain alkyl, —CH$_2$C$_6$H$_5$, —SiR$_{10}$R$_{11}$R$_{12}$, —C(O)CH$_3$, —C(O)C$_6$H$_5$, -2-tetrahydropyranyl, —OCH$_2$OCH$_3$, and —C(O)OCH$_2$CCl$_3$;

R$_3$ is selected from the group consisting of —H, C$_1$–C$_{12}$ straight chain alkyl, —CH(R$_{14}$)(R$_{15}$) wherein R$_{14}$ and R$_{15}$ are independently C$_1$–C$_{12}$ straight chain alkyl, —C(O)C$_1$–C$_9$ straight chain alkyl, —CH(OH)C$_1$–C$_9$ straight chain alkyl, —CH(Cl)C$_1$–C$_9$ straight chain alkyl, -(2-pyridyl)methyl, -(3-pyridyl)methyl, -(4-pyridyl)methyl, and —CH$_2$C$_6$H$_5$, the —CH$_2$C$_6$H$_5$ being unsubstituted or substituted on phenyl with one cyano or one or more halo, methoxyl, or trifluoromethyl groups;

R$_{10}$ is selected from the group consisting of C$_1$–C$_4$ straight or branched chain alkyl and —C$_6$H$_5$;

R$_{11}$ and R$_{12}$ are independently C$_1$–C$_3$ straight or branched chain alkyl;

m is an integer ranging from 1 to 5; and when m is 3 and R$_2$ is —CH$_2$CH$_3$, then R$_{16}$ is —H or —CH$_3$ and R$_{17}$ is —H;

when m is 3 and R$_2$ is —CH$_3$, then R$_{16}$ is —H or —CH$_3$ and R$_{17}$ is —H or —COOEt; and when m is other than 3 and R$_2$ is other than —CH$_3$ or —CH$_2$CH$_3$, then R$_{16}$ and R$_{17}$ are —H only;

with the proviso that the compound of Formula (I) is not metacycloprodigiosin.

3. A method for inhibiting the growth of a prostate cancer cell comprising contacting a said cancer cell with an effective amount of a compound of Formula (I):

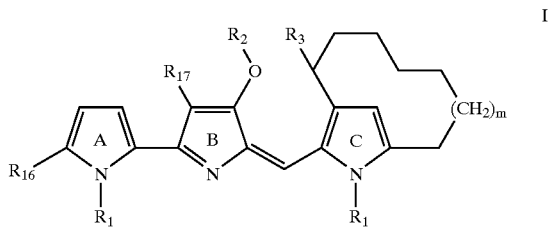

or a pharmaceutically acceptable salt thereof, wherein, in the compound of Formula (I):

each R$_1$ is independently selected from the group consisting of —H, —CH$_3$, —CH$_2$CH$_3$, —CH$_2$C$_6$H$_5$, —C(O)OC(CH$_3$)$_3$, —C(O)OCH$_2$C$_6$H$_5$, and —C(O)CH$_3$;

R$_2$ is selected from the group consisting of —H, C$_1$–C$_{12}$ straight chain alkyl, —CH$_2$C$_6$H$_5$, —SiR$_{10}$R$_{11}$R$_{12}$, —C(O)CH$_3$, —C(O)C$_6$H$_5$, -2-tetrahydropyranyl, —OCH$_2$OCH$_3$, and —C(O)OCH$_2$CCl$_3$;

R$_3$ is selected from the group consisting of —H, C$_1$–C$_{12}$ straight chain alkyl, —CH(R$_{14}$)(R$_{15}$) wherein R$_{14}$ and R$_{15}$ are independently C$_1$–C$_{12}$ straight chain alkyl, —C(O)C$_1$–C$_9$ straight chain alkyl, —CH(OH)C$_1$–C$_9$ straight chain alkyl, —CH(Cl)C$_1$–C$_9$ straight chain alkyl, -(2-pyridyl)methyl, -(3-pyridyl)methyl, -(4-pyridyl)methyl, and —CH$_2$C$_6$H$_5$, the —CH$_2$C$_6$H$_5$ being unsubstituted or substituted on phenyl with one cyano or one or more halo, methoxyl, or trifluoromethyl groups;

R$_{10}$ is selected from the group consisting of C$_1$–C$_4$ straight or branched chain alkyl and —C$_6$H$_5$;

R$_{11}$ and R$_{12}$ are independently C$_1$–C$_3$ straight or branched chain alkyl;

m is an integer ranging from 1 to 5;

when m is 3 and R$_2$ is —CH$_2$CH$_3$ then R$_{16}$ is —H or —CH$_3$ and R$_{17}$ is —H;

when m is 3 and R$_2$ is —CH$_3$, then R$_{16}$ is —H or —CH$_3$ and R$_{17}$ is —H or —COOEt; and when m is other than 3 and R$_2$ is other than —CH$_3$ or —CH$_2$CH$_3$, then R$_{16}$ and R$_{17}$ are —H only; with the proviso that the compound of Formula (I) is not metacycloprodigiosin.

4. A method for inhibiting the growth of a cervical cancer cell comprising contacting a said cancer cell with an effective amount of a compound of Formula (I):

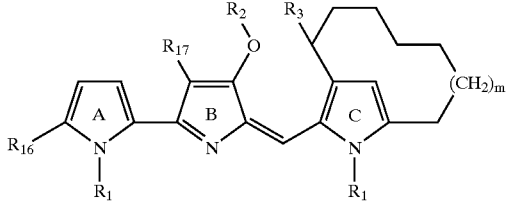

I or a pharmaceutically acceptable salt thereof wherein, in the compound of Formula (I):

each $R_1$ is independently selected from the group consisting of —H, —CH$_3$, —CH$_2$CH$_3$, —CH$_2$C$_6$H$_5$, —C(O)OC(CH$_3$)$_3$, —C(O)OCH$_2$C$_6$H$_5$, and —C(O)CH$_3$;

$R_2$ is selected from the group consisting of —H, C$_1$–C$_{12}$ straight chain alkyl, —CH$_2$C$_6$H$_5$, —SiR$_{10}$R$_{11}$R$_{12}$, —C(O)CH$_3$, —C(O)C$_6$H$_5$, -2-tetrahydropyranyl, —OCH$_2$OCH$_3$, and —C(O)OCH$_2$CCl$_3$;

$R_3$ is selected from the group consisting of —H, C$_1$–C$_{12}$ straight chain alkyl, —CH(R$_{14}$)(R$_{15}$) wherein $R_{14}$ and $R_{15}$ are independently C$_1$–C$_{12}$ straight chain alkyl, —C(O)C$_1$–C$_9$ straight chain alkyl, —CH(OH)C$_1$–C$_9$ straight chain alkyl, —CH(Cl)C$_1$–C$_9$ straight chain alkyl, -(2-pyridyl)methyl, -(3-pyridyl)methyl, -(4-pyridyl)methyl, and —CH$_2$C$_6$H$_5$, the —CH$_2$C$_6$H$_5$ being unsubstituted or substituted on phenyl with one cyano or one or more halo, methoxyl, or trifluoromethyl groups;

$R_{10}$ is selected from the group consisting of C$_1$–C$_4$ straight or branched chain alkyl and —C$_6$H$_5$;

$R_{11}$ and $R_{12}$ are independently C$_1$–C$_3$ straight or branched chain alkyl;

m is an integer ranging from 1 to 5;

when m is 3 and $R_2$ is —CH$_2$CH$_3$, then $R_{16}$ is —H or —CH$_3$ and $R_{17}$ is —H;

when m is 3 and $R_2$ is —CH$_3$, then $R_{16}$ is —H or —CH$_3$ and $R_{17}$ is —H or —COOEt; and when m is other than 3 and $R_2$ is other than —CH$_3$ or —CH$_2$CH$_3$, then $R_{16}$ and $R_{17}$ are —H only;

with the proviso that the compound of Formula (I) is not metacycloprodigiosin.

5. The method of claim 1, wherein the compound of Formula (I):

each $R_1$ is independently selected from the group consisting of —H, —CH$_3$, —CH$_2$CH$_3$, —CH$_2$C$_6$H$_5$, —C(O)OC(CH$_3$)$_3$, —C(O)OCH$_2$C$_6$H$_5$, and —C(O)CH$_3$;

$R_2$ is selected from the group consisting of —H, C$_1$–C$_{12}$ straight chain alkyl, —CH$_2$C$_6$H$_5$, —SiR$_{10}$R$_{11}$R$_{12}$, —C(O)CH$_3$, —C(O)C$_6$H$_5$, -2-tetrahydropyranyl, —OCH$_2$OCH$_3$, and —C(O)OCH$_2$CCl$_3$;

$R_3$ is selected from the group consisting of —H, C$_1$–C$_{12}$ straight chain alkyl, —CH(R$_{14}$)(R$_{15}$) wherein $R_{14}$ and $R_{15}$ are independently C$_1$–C$_{12}$ straight chain alkyl, —C(O)C$_1$–C$_9$ straight chain alkyl, —CH(OH)C$_1$–C$_9$ straight chain alkyl, —CH(Cl)C$_1$–C$_9$ straight chain alkyl, -(2-pyridyl)methyl, -(3-pyridyl)methyl, -(4-pyridyl)methyl, and —CH$_2$C$_6$H$_5$, the —CH$_2$C$_6$H$_5$ being unsubstituted or substituted on phenyl with one cyano or one or more halo, methoxyl, or trifluoromethyl groups;

$R_{10}$ is selected from the group consisting of C$_1$–C$_4$ straight or branched chain alkyl and $R_{11}$ and $R_{12}$ are independently C$_1$–C$_3$ straight or branched chain alkyl; and $R_{16}$ and $R_{17}$ are —H; and m is an integer ranging from 1 to 5;

with the proviso that the compound of Formula (I) is not: metacycloprodigiosin.

6. The method of claim 1, wherein the compound of Formula (I) is butyl-meta-cycloheptylprodiginine or a pharmaceutically acceptable salt thereof.

7. The method of claim 1, wherein, in the compound of Formula (I):

each $R_1$ is independently selected from the group consisting of —H, and —CH$_3$;

$R_2$ is selected from the group consisting of —CH$_3$, —CH$_2$CH$_3$, and —CH$_2$C$_6$H$_5$;

$R_3$ is selected from the group consisting of —H, C$_1$–C$_{10}$ straight chain alkyl, (1-methyl)butyl, —CH$_2$C$_6$H$_5$, butyroyl, (1-hydroxy)butyl, and (1-chloro)butyl;

$R_{16}$ and $R_{17}$ are —H; and m is an integer ranging from 1 to 5;

with the proviso that the compound of Formula (I) is not: metacycloprodigiosin.

8. The method of claim 1, wherein, in the compound of Formula (I):

each $R_1$ is —H $R_2$ is selected from the group consisting of —CH$_3$, and —CH$_2$C$_6$H$_5$;

$R_3$ is selected from the group consisting of —H, C$_1$–C$_{10}$ straight chain alkyl, and —CH$_2$C$_6$H$_5$;

$R_{16}$ and $R_{17}$ are —H; and m is an integer ranging from 1 to 5;

with the proviso that the compound of Formula (I) is not: metacycloprodigiosin.

9. The method of claim 1, wherein, in the compound of Formula (I):

each $R_1$ is independently selected from the group consisting of —H, and —CH$_3$;

$R_2$ is selected from the group consisting of —CH$_3$, and —CH$_2$C$_6$H$_5$;

$R_3$ is selected from the group consisting of —H, C$_1$–C$_{10}$ straight chain alkyl, —CH$_2$C$_6$H$_5$, butyroyl, (1-hydroxy)butyl, and (1-chloro)butyl;

$R_{16}$ and $R_{17}$ are —H; and m is an integer ranging from 1 to 5.

with the proviso that when m is 3, $R_3$ is not —CH$_2$CH$_3$ and when m is 1, $R_3$ is not —(CH$_2$)$_3$CH$_3$.

10. The method of claim 1, wherein, in the compound of Formula (I):

each $R_1$ is independently selected from the group consisting of —H, and —CH$_3$;

$R_2$ is selected from the group consisting of —CH$_3$, and —CH$_2$C$_6$H$_5$;

$R_3$ is selected from the group consisting of —H, C$_1$–C$_{10}$ straight chain alkyl, (1-methyl)butyl, —CH$_2$C$_6$H$_5$, butyroyl, (1-hydroxy)butyl, and (1-chloro)butyl;

$R_{16}$ and $R_{17}$ are —H; and m is an integer ranging from 1 to 5.

11. The method of claim 1, wherein, in the compound of Formula (I):

each $R_1$ is independently selected from the group consisting of —H, and —CH$_3$;

$R_2$ is selected from the group consisting of —CH$_3$, and —CH$_2$C$_6$H$_5$;

R$_3$ is selected from the group consisting of —H, C$_1$–C$_{10}$ straight chain alkyl, —CH$_2$C$_6$H$_5$, butyroyl, (1-hydroxy)butyl), and (1-chloro)butyl;

R$_{16}$ and R$_{17}$ are —H; and m is 2, 4 or 5.

12. The method of claim 1, wherein, in the compound of Formula (I):

each R$_1$ is independently selected from the group consisting of —H, and —CH$_3$;

R$_2$ is selected from the group consisting of —CH$_3$, —CH$_2$CH$_3$, —(CH$_2$)$_2$CH$_3$, and —CH$_2$C$_6$H$_5$;

R$_3$ is selected from the group consisting of —H, C$_1$–C$_{10}$ straight chain alkyl, —CH$_2$C$_6$H$_5$, butyroyl, (1-hydxoxy)butyl, and (1-chloro)butyl;

m is an integer ranging from 1 to 5;

when m is 3 and R$_2$ is —CH$_3$, then R$_{16}$ is selected from the group consisting of —H, and —CH$_3$ and R$_{17}$ is selected from the group consisting of —H, and —COOEt; and when m is other than 3 and R$_2$ is other than —CH$_3$ or —CH$_2$CH$_3$, then R$_{16}$ and R$_{17}$ are —H only;

with the proviso that the compound of Formula (I) is not: metacycloprodigiosin.

13. The method of claim 1, wherein the compound of Formula I is selected from the group consisting of:

butyl-meta-cycloheptylprodiginine;

2-Ethyl-11-((3-methoxy-5-(1H-pyrrol-2-yl)-2H-pyrrol-2-ylidene)methyl)-10-azabicyclo[7.2.1]dodeca-9(12),11-diene;

11-((3-Methoxy-5-(1H-pyrrol-2-yl)-2H-pyrrol-2-ylidene)methyl)-10-azabicyclo[7.2.1]dodeca-9(12),11-diene;

2-Methyl-11-((3-methoxy-5-(1H-pyrrol-2-yl)-2H-pyrrol-2-ylidene)methyl)-10-azabicyclo[7.2.1]dodeca-9(12),11-diene;

2-n-Propyl-11-((3-methoxy-5-(1H-pyrrol-2-yl)-2H-pyrrol-2-ylidene)methyl)-10-azabicyclo[7.2.1]dodeca-9(12),11-diene;

2-n-Pentyl-11-((3-methoxy-5-(1H-pyrrol-2-yl)-2H-pyrrol-2-ylidene)methyl)-10-azabicyclo[7.2.1]dodeca-9(12),11-diene;

2-Benzyl-11-((3-methoxy-5-(1H-pyrrol-2-yl)-2H-pyrrol-2-ylidene)methyl)-10-azabicyclo[7.2.1]dodeca-9(12),11-diene;

(S)-2-n-Pentyl-11-((3-methoxy-5-(1H-pyrrol-2-yl)-2H-pyrrol-2-ylidene)methyl)-10-azabicyclo[7.2.1]dodeca-9(12),11-diene;

(R)-2-n-Pentyl-11-((3-methoxy-5-(1H-pyrrol-2-yl)-2H-pyrrol-2-ylidene)methyl)-10-azabicyclo[7.2.1]dodeca-9(12),11-diene;

(S)-2-n-Butyl-11-((3-methoxy-5-(1H-pyrrol-2-yl)-2H-pyrrol-2-ylidene)methyl)-10-azabicyclo[7.2.1]dodeca-9(12),11-diene;

(R)-2-n-Butyl-11-((3-methoxy-5-(1H-pyrrol-2-yl)-2H-pyrrol-2-ylidene)methyl)-10-azabicyclo[7.2.1]dodeca-9(12),11-diene;

(S)-2-Ethyl-11-((3-methoxy-5-(1H-pyrrol-2-yl)-2H-pyrrol-2-ylidene)methyl-10-azabicyclo[7.2.1]dodeca-9(12),11-diene;

(R)-2-Ethyl-11-((3-methoxy-5-(1H-pyrrol-2-yl)-2H-pyrrol-2-ylidene)methyl)-10-azabicyclo[7.2.1]dodeca-9(12),11-diene;

(S)-2-Methyl-11-((3-methoxy-5-(1H-pyrrol-2-yl)-2H-pyrrol-2-ylidene)methyl)-10-azabicyclo[7.2.1]dodeca-9(12),11-diene;

(R)-2-Methyl-11-((3-methoxy-5-(1H-pyrrol-2-yl)-2H-pyrrol-2-ylidene)methyl)-10-azabicyclo[7.2.1]dodeca-9(12),11-diene;

(S)-2-n-Propyl-11-((3-methoxy-5-(1H-pyrrol-2-yl)-2H-pyrrol-2-ylidene)methyl)-10-azabicyclo[7.2.1]dodeca-9(12),11-diene;

(R)-2-n-Propyl-11-((3-methoxy-5-(1H-pyrrol-2-yl)-2H-pyrrol-2-ylidene)methyl)-10-azabicyclo[7.2.1]dodeca-9(12),11-diene;

2-Methyl-12-((3-methoxy-5-(1H-pyrrol-2-yl)-2H-pyrrol-2-ylidene)methyl)-11-azabicycio[8.2.1]trideca-10(13),12-diene;

2-Ethyl-12-((3-methoxy-5-(1H-pyrrol-2-yl)-2H-pyrrol-2-ylidene)methyl)-11-azabicyclo[8.2.1]trideca-10(13),12-diene;

2-n-Propyl-12-((3-methoxy-5-(1H-pyrrol-2-yl)-2H-pyrrol-2-ylidene)methyl)-11-azabicyclo[8.2.1]trideca-10(13),12-diene;

2-n-Butyl-12-((3-methoxy-5-(1H-pyrrol-2-yl)-2H-pyrrol-2-ylidene)methyl)-11-azabicycio[8.2.1]trideca-10(13),12-diene;

2-n-Pentyl-12-((3-methoxy-5-(1H-pyrrol-2-yl)-2H-pyrrol-2-ylidene)methyl)-11-azabicyclo[8.2.1]trideca-10(13),12-diene;

12-((3-Methoxy-5-(1H-pyrrol-2-yl)-2H-pyrrol-2-ylidene)methyl)-11-azabicyclo[8.2.1]trideca-10(13),12-diene;

2-Methyl-13-((3-methoxy-5-(1H-pyrrol-2-yl)-2H-pyrrol-2-ylidene)methyl)-12-azabicyclo[9.2.1]tetradeca-11(14),13-diene;

13-((3-Methoxy-5-(1H-pyrrol-2-yl)-2H-pyrrol-2-ylidene)methyl)-12-azabicycio[9.2.1]tetradeca-11(14),13-diene;

2-Ethyl-12-methyl-13-((3-methoxy-5-(1-methyl-1H-pyrrol-2-yl)-2H-pyrrol-2-ylidene)methyl)-12-azabicyclo[9.2.1]tetradeca-11(14),13-diene;

2-Ethyl-12-methyl-13-((3-methoxy-5-(1H-pyrrol-2-yl)-2H-pyrrol-2-ylidene)methyl)-12-azabicyclo [9.2.1] tetradeca-11(14),13-diene;

2-n-Propyl-13-((3-methoxy-5-(1H-pyrrol-2-yl)-2H-pyrrol-2-ylidene)methyl)-12-azabicyclo[9.2.1] tetradeca-11(14),13-diene;

2-n-Butyl-13-((3-methoxy-5-(1H-pyrrol-2-yl)-2H-pyrrol-2-ylidene)methyl)-12-azabicyclo[9.2.1]tetradeca-11(14),13-diene;

14-((3-Methoxy-5-(1H-pyrrol-2-yl)-2H-pyrrol-2-ylidene)methyl)13-azabicyclo[10.2.1]pentadeca-12(15),14-diene;

2-Butyl-11-((3-methoxy-5-(1-methyl-1H-pyrrol-2-yl)-2H-pyrrol-2-ylidene)methyl)-10-azabicyclo[7.2.1]dodeca-9(12),11-diene;

2-Butyl-11-((3-methoxy-5-(1-methyl-1H-pyrrol-2-yl)-2H-pyrrol-2-ylidene)methyl)-10-methyl-10-azabicyclo[7.2.1]dodeca-9(12),11-diene;

2-Butyl-11-((3-methoxy-5-(1H-pyrrol-2-yl)-2H-pyrrol-2-ylidene)methyl)-10-methyl-10-azabicyclo[7.2.1]dodeca-9(12),11-diene;

2-Ethyl-11-((3-benzyloxy-5-(1H-pyrrol-2-yl)-2H-pyrrol-2-ylidene)methyl)-10-azabicyclo[7.2.1]dodeca-9(12),11-diene;

2-Butyl-11-((3-hydroxy-5-(1H-pyrrol-2-yl)-2H-pyrrol-2-ylidene)methyl)-10-azabicyclo[7.2.1]dodeca-9(12),11-diene;

2-Butyl-11-((3-benzyloxy-5-(1H-pyrrol-2-yl)-2H-pyrrol-2-ylidene)methyl)-10-azabicyclo[7.2.1]dodeca-9(12),11-diene;

11-((3-Benzyloxy-5-(1H-pyrrol-2-yl)-2H-pyrrol-2-ylidene)methyl)-10-azabicyclo[7.2.1]dodeca-9(12),11-diene;

2-Methyl-11-((3-benzyloxy-5-(1H-pyrrol-2-yl)-2H-pyrrol-2-ylidene)methyl)-10-azabicyclo[7.2.1]dodeca-9(12),11-diene;

2-n-Propyl-11-((3-benzyloxy-5-(1H-pyrrol-2-yl)-2H-pyrrol-2-ylidene)methyl)-10-azabicyclo[7.2.1]dodeca-9(12),11-diene;

2-n-Pentyl-11-((3-benzyloxy-5-(1H-pyrrol-2-yl)-2H-pyrrol-2-ylidene)methyl)-10-azabicyclo[7.2.1]dodeca-9(12),11-diene;

2-Benzyl-11-((3-benzyloxy-5-(1H-pyrrol-2-yl)-2H-pyrrol-2-ylidene)methyl)-10-azabicyclo[7.2.1]dodeca-9(12),11-diene;

2-Methyl-14-((3-methoxy-5-(1H-pyrrol-2-yl)-2H-pyrrol-2-ylidene)methyl)-13-azabicyclo[10.2.1]pentadeca-12(15),14-diene;

15-((3-Methoxy-5-(1H-pyrrol-2-yl)-2H-pyrrol-2-ylidene)methyl)-14-azabicyclo[11.2.1]hexadeca-13(16),15-diene;

2-Methyl-15-((3-methoxy-5-(1H-pyrrol-2-yl)-2H-pyrrol-2-ylidene)methyl)-14-azabicyclo[11.2.1]hexadeca-13(16),15-diene;

2-(2-Hydroxy-n-butyl)-11-((3-methoxy-5-(1H-pyrrol-2-yl)-2H-pyrrol-2-ylidene)methyl)-10-azabicyclo[7.2.1]dodeca-9(12),11-diene;

2-(2-Chloro-n-butyl)-11-((3-methoxy-5-(1H-pyrrol-2-yl)-2H-pyrrol-2-ylidene)methyl)-10-azabicyclo[7.2.1]dodeca-9(12),11-diene;

2-Butyl-11-((3-ethoxy-5-(1H-pyrrol-2-yl)-2H-pyrrol-2-ylidene)methyl)-10-azabicyclo[7.2.1]dodeca-9(12),11-diene;

11-((3-Ethoxy-5-(1H-pyrrol-2-yl)-2H-pyrrol-2-ylidene)methyl)-10-azabicyclo[7.2.1]dodeca-9(12),11-diene;

2-Methyl-11-((3-ethoxy-5-(1H-pyrrol-2-yl)-2H-pyrrol-2-ylidene)methyl)-10-azabicyclo[7.2.1]dodeca-9(12),11-diene;

2-n-Propyl-11-((3-ethoxy-5-(1H-pyrrol-2-yl)-2H-pyrrol-2-ylidene)methyl)-10-azabicyclo[7.2.1]dodeca-9(12),11-diene;

2-n-Pentyl-11-((3-ethoxy-5-(1H-pyrrol-2-yl)-2H-pyrrol-2-ylidene)methyl)-10-azabicyclo[7.2.1]dodeca-9(12),11-diene;

2-Benzyl-11-((3-ethoxy-5-(1H-pyrrol-2-yl)-2H-pyrrol-2-ylidene)methyl)-10-azabicyclo[7.2.1]dodeca-9(12),11-diene;

2-Ethyl-11-((3-ethoxy-5-(1H-pyrrol-2-yl)-2H-pyrrol-2-ylidene)methyl)-10-azabicyclo[7.2.1]dodeca-9(12),11-diene;

2-Methyl-13-((3-benzyloxy-5-(1H-pyrrol-2-yl)-2H-pyrrol-2-ylidene)methyl)-12-azabicyclo[9.2.1]tetradeca-11(14),13-diene;

13-((3-Benzyloxy-5-(1H-Pyrrol-2-yl)-2H-pyrrol-2-ylidene)methyl)-12-azabicyclo[9.2.1]tetradeca-11(14),13-diene;

2-Ethyl-12-methyl-13-((3-benzyloxy-5-(1-methyl-1H-pyrrol-2-yl)-2H-pyrrol-2-ylidene)methyl)-12-azabicyclo[9.2.1]tetradeca-11(14),13-diene;

2-Ethyl-12-methyl-13-((3-benzyloxy-5-(1H-pyrrol-2-yl)-2H-pyrrol-2-ylidene)methyl)-12-azabicyclo[9.2.1]tetradeca-11(14),13-diene;

2-n-Propyl-13-((3-benzyloxy-5-(1H-pyrrol-2-yl)-2H-pyrrol-2-ylidene)methyl)-12-azabicyclo[9.2.1]tetradeca-11(14),13-diene; and 2-n-Butyl-13-((3-benzyloxy-5-(1H-pyrrol-2-yl)-2H-pyrrol-2-ylidene)methyl)-12-azabicyclo[9.2.1]tetradeca-11(14),13-diene;

and a pharmaceutically acceptable salt thereof.

14. The method of claim 2, wherein, in the compound of Formula (I):

each $R_1$ is independently selected from the group consisting of —H, —$CH_3$, —$CH_2CH_3$, —$CH_2C_6H_5$, —C(O)OC($CH_3$)$_3$, —C(O)O$CH_2C_6H_5$, and —C(O)$CH_3$;

$R_2$ is selected from the group consisting of —H, $C_1$–$C_{12}$ straight chain alkyl, —$CH_2C_6H_5$, —$SiR_{10}R_{11}R_{12}$, —C(O)$CH_3$, —C(O)$C_6H_5$, -2-tetrahydropyranyl, —O$CH_2$O$CH_3$, and —C(O)O$CH_2CCl_3$;

$R_3$ is selected from the group consisting of —H, $C_1$–$C_{12}$ straight chain alkyl, —CH($R_{14}$)($R_{15}$) wherein $R_{14}$ and $R_{15}$ are independently $C_1$–$C_{12}$ straight chain alkyl, —C(O)$C_1$–$C_9$ straight chain alkyl, —CH(OH)$C_1$–$C_9$ straight chain alkyl, —CH(Cl)$C_1$–$C_9$ straight chain alkyl, -(2-pyridyl)methyl, -(3-pyridyl)methyl, -(4-pyridyl)methyl, and —$CH_2C_6H_5$, the —$CH_2C_6H_5$ being unsubstituted or substituted on phenyl with one cyano or one or more halo, methoxyl, or trifluoromethyl groups;

$R_{10}$ is selected from the group consisting of $C_1$–$C_4$ straight or branched chain alkyl and —$C_6H_5$;

$R_{11}$ and $R_{12}$ are independently $C_1$–$C_3$ straight or branched chain alkyl; and $R_{16}$ and $R_{17}$ are —H; and m is an integer ranging from 1 to 5;

with the proviso that the compound of Formula (I) is not: metacycloprodigiosin.

15. The method of claim 2, wherein the compound of Formula (I) is butyl-meta-cycloheptyiprodiginine or a pharmaceutically acceptable salt thereof.

16. The method of claim 2, wherein the compound of Formula (I):

each $R_1$ is independently selected from the group consisting of —H, and —$CH_3$;

$R_2$ is selected from the group consisting of —$CH_3$, —$CH_2CH_3$, and —$CH_2C_6H_5$;

$R_3$ is selected from the group consisting of —H, $C_1$–$C_{10}$ straight chain alkyl, (1-methyl)butyl, —$CH_2C_6H_5$, butyroyl, (1-hydroxy)butyl, and (1-chloro)butyl;

$R_{16}$ and $R_{17}$ are —H; and m is an integer ranging from 1 to 5;

with the proviso that the compound of Formula (I) is not: metacycloprodigiosin.

17. The method of claim 2, wherein, in the compound of Formula (I):

each $R_1$ is —H;

$R_2$ is selected from the group consisting of —$CH_3$, and —$CH_2C_6H_5$;

$R_3$ is selected from the group consisting of —H, $C_1$–$C_{10}$ straight chain alkyl, and —$CH_2C_6H_5$;

$R_{16}$ and $R_{17}$ are —H; and m is an integer ranging from 1 to 5;

with the proviso that the compound of Formula (I) is not: metacycloprodigiosin.

18. The method of claim 2, wherein, in the compound of Formula (I):

each $R_1$ is independently selected from the group consisting of —H, and —$CH_3$;

R₂ is selected from the group consisting of —CH₃, and —CH₂C₆H₅;

R₃ is selected from the group consisting of —H, C₁–C₁₀ straight chain alkyl, —CH₂C₆H₅, butyroyl, (1-hydroxy)butyl, and (1-chloro)butyl;

R₁₆ and R₁₇ are —H; and m is an integer ranging from 1 to 5.

with the proviso that when m is 3, R₃ is not —CH₂CH₃ and when m is 1, R₃ is not —(CH₂)₃CH₃.

19. The method of claim 2, wherein, in the compound of Formula (I):

each R₁ is independently selected from the group consisting of —H, and —CH₃;

R₂ is selected from the group consisting of —CH₃, and —CH₂C₆H₅;

R₃ is selected from the group consisting of —H, C₁–C₁₀ straight chain alkyl, (1-methyl)butyl, —CH₂C₆H₅, butyroyl, (1-hydroxy)butyl, and (1-chloro)butyl;

R₁₆ and R₁₇ are —H; and m is an integer ranging from 1 to 5.

20. The method of claim 2, wherein, in the compound of Formula (I):

each R₁ is independently selected from the group consisting of —H, and —CH₃;

R₂ is selected from the group consisting of —CH₃, and —CH₂C₆H₅;

R₃ is selected from the group consisting of —H, C₁–C₁₀ straight chain alkyl, —CH₂C₆H₅, butyroyl, (1-hydroxy)butyl, and (1-chloro)butyl;

R₁₆ and R₁₇ are —H; and m is 2, 4 or 5.

21. The method of claim 2, wherein, in the compound of Formula (I):

each R₁ is independently selected from the group consisting of —H, and —CH₃;

R₂ is selected from the group consisting of —CH₃, —CH₂CH₃, —(CH₂)₂CH₃, and —CH₂C₆H₅;

R₃ is selected from the group consisting of —H, C₁–C₁₀ straight chain alkyl, —CH₂C₆H₅, butyroyl, (1-hydxoxy)butyl, and (1-chloro)butyl;

m is an integer ranging from 1 to 5;

when m is 3 and R₂ is —CH₃, then R₁₆ is selected from the group consisting of —H, and —CH₃ and R₁₇ is selected from the group consisting of —H, and —COOEt; and when m is other than 3 and R₂ is other than —CH₃ or —CH₂CH₃, then R₁₆ and R₁₇ are —H only;

with the proviso that the compound of Formula (I) is not: metacycloprodigiosin.

22. The method of claim 2, wherein the compound of Formula I is selected from the group consisting of: butyl-meta-cycloheptyiprodiginine;

2-Ethyl-11-((3-methoxy-5-(1H-pyrrol-2-yl)-2H-pyrrol-2-ylidene)methyl)-10-azabicyclo[7.2.1]dodeca-9(12),11-diene;

11-((3-Methoxy-5-(1H-pyrrol-2-yl)-2H-pyrrol-2-ylidene)methyl)-10-azabicyclo[7.2.1]dodeca-9(12),11-diene;

2-Methyl-11-((3-methoxy-5-(1H-pyrrol-2-yl)-2H-pyrrol-2-ylidene)methyl)-10-azabicyclo[7.2.1]dodeca-9(12),11-diene;

2-n-Propyl-11-((3-methoxy-5-(1H-pyrrol-2-yl)-2H-pyrrol-2-ylidene)methyl)-10-azabicyclo[7.2.1]dodeca-9(12),11-diene;

2-n-Pentyl-11-((3-methoxy-5-(1H-pyrrol-2-yl)-2H-pyrrol-2-ylidene)methyl)-10-azabicyclo[7.2.1]dodeca-9(12),11-diene;

2-Benzyl-11-((3-methoxy-5-(1H-pyrrol-2-yl)-2H-pyrrol-2-ylidene)methyl)-10-azabicyclo[7.2.1]dodeca-9(12),11-diene;

(S)-2-n-Pentyl-11-((3-methoxy-5-(1H-pyrrol-2-yl)-2H-pyrrol-2-ylidene)methyl)-10-azabicyclo[7.2.1]dodeca-9(12),11-diene;

(R)-2-n-Pentyl-11-((3-methoxy-5-(1H-pyrrol-2-yl)-2H-pyrrol-2-ylidene)methyl)-10-azabicyclo[7.2.1]dodeca-9(12),11-diene;

(S)-2-n-Butyl-11-((3-methoxy-5-(1H-pyrrol-2-yl)-2H-pyrrol-2-ylidene)methyl)-10-azabicyclo[7.2.1]dodeca-9(12),11-diene;

(R)-2-n-Butyl-11-((3-methoxy-5-(1H-pyrrol-2-yl)-2H-pyrrol-2-ylidene)methyl)-10-azabicyclo[7.2.1]dodeca-9(12),11-diene;

(S)-2-Ethyl-11-((3-methoxy-5-(1H-pyrrol-2-yl-)-2H-pyrrol-2-ylidene)methyl)-10-azabicyclo[7.2.1]dodeca-9(12),11-diene;

(R)-2-Ethyl-11-((3-methoxy-5-(1H-pyrrol-2-yl)-2H-pyrrol-2-ylidene)methyl)-10-azabicyclo[7.2.1]dodeca-9(12),11-diene;

(S)-2-Methyl-11-((3-methoxy-5-(1H-pyrrol-2-yl)-2H-pyrrol-2-ylidene)methyl)-10-azabicyclo [7.2.1]dodeca-9(12),11-diene;

(R)-2-Methyl-11-((3-methoxy-5-(1H-pyrrol-2-yl)-2H-pyrrol-2-ylidene)methyl)-10-azabicyclo[7.2.1]dodeca-9(12),11-diene;

(S)-2-n-Propyl-11-((3-methoxy-5-(1H-pyrrol-2-yl)-2H-pyrrol-2-ylidene)methyl)-10-azabicyclo[7.2.1]dodeca-9(12),11-diene;

(R)-2-n-Propyl-11-((3-methoxy-5-(1H-pyrrol-2-yl)-2H-pyrrol-2-ylidene)methyl)-10-azabicyclo[7.2.1]dodeca-9(12),11-diene;

2-Methyl-12-((3-methoxy-5-(1H-pyrrol-2-yl)-2H-pyrrol-2-ylidene)methyl)-11-azabicyclo[8.2.1]trideca-10(13),12-diene;

2-Ethyl-12-((3-methoxy-5-(1H-pyrrol-2-yl)-2H-pyrrol-2-ylidene)methyl)-11-azabicyclo[8.2.1]trideca-10(13),12-diene;

2-n-Propyl-12-((3-methoxy-5-(1H-pyrrol-2-yl)-2H-pyrrol-2-ylidene)methyl)-11-azabicyclo[8.2.1]trideca-10(13),12-diene;

2-n-Butyl-12-((3-methoxy-5-(1H-pyrrol-2-yl)-2H-pyrrol-2-ylidene)methyl)-11-azabicyclo[8.2.1]trideca-10(13),12-diene;

2-n-Pentyl-12-((3-methoxy-5-(1H-pyrrol-2-yl)-2H-pyrrol-2-ylidene)methyl)-11-azabicyclo[8.2.1]trideca-10(13),12-diene;

12-((3-Methoxy-5-(1H-pyrrol-2-yl)-2H-pyrrol-2-ylidene)methyl)-11-azabicyclo[8.2.1]trideca-10(13),12-diene;

2-Methyl-13-((3-methoxy-5-(1H-pyrrol-2-yl)-2H-pyrrol-2-ylidene)methyl)-12-azabicyclo[9.2.1]tetradeca-11(14),13-diene;

13-((3-Methoxy-5-(1H-pyrrol-2-yl)-2H-pyrrol-2-ylidene)methyl)-12-azabicyclo[9.2.1]tetradeca-11(14),13-diene;

2-Ethyl-12-methyl-13-((3-methoxy-5-(1-methyl-1H-pyrrol-2-yl)-2H-pyrrol-2-ylidene)methyl)-12-azabicyclo[9.2.1]tetradeca-11(14),13-diene;

2-Ethyl-12-methyl-13-((3-methoxy-5-(1H-pyrrol-2-yl)-2H-pyrrol-2-ylidene)methyl)-12-azabicyclo[9.2.1]tetradeca-11(14),13-diene;

2-n-Propyl-13-((3-methoxy-5-(1H-pyrrol-2-yl)-2H-pyrrol-2-ylidene)methyl)-12-azabicyclo[9.2.1]tetradeca-11(14),13-diene;

2-n-Butyl-13-((3-methoxy-5-(1H-pyrrol-2-yl)-2H-pyrrol-2-ylidene)methyl)-12-azabicyclo[9.2.1]tetradeca-11(14),13-diene;

14-((3-Methoxy-5-(1H-pyrrol-2-yl)-2H-pyrrol-2-ylidene)methyl)-13-azabicyclo[10.2.1]pentadeca-12(15),14-diene;

2-Butyl-11-((3-methoxy-5-(1-methyl-1H-pyrrol-2-yl)-2H-pyrrol-2-ylidene)methyl)-10-azabicyclo[7.2.1]dodeca-9(12),11-diene;

2-Butyl-11-((3-methoxy-5-(1-methyl-1H-pyrrol-2-yl)-2H-pyrrol-2-ylidene)methyl)-10-methyl-10-azabicyclo[7.2.1]dodeca-9(12),11-diene;

2-Butyl-11-((3-methoxy-5-(1H-pyrrol-2-yl)-2H-pyrrol-2-ylidene)methyl)-10-methyl-10-azabicyclo[7.2.1]dodeca-9(12),11-diene;

2-Ethyl-11-((3-benzyloxy-5-(1H-pyrrol-2-yl)-2H-pyrrol-2-ylidene)methyl)-10-azabicyclo[7.2.1]dodeca-9(12),11-diene;

2-Butyl-11-((3-hydroxy-5-(1H-pyrrol-2-yl)-2H-pyrrol-2-ylidene)methyl)-10-azabicyclo[7.2.1]dodeca-9(12),11-diene;

2-Butyl-11-((3-benzyloxy-5-(1H-pyrrol-2-yl)-2H-pyrrol-2-ylidene)methyl)-10-azabicyclo[7.2.1]dodeca-9(12),11-diene;

11-((3-Benzyloxy-5-(1H-pyrrol-2-yl)-2H-pyrrol-2-ylidene)methyl)-10-azabicyclo[7.2.1]dodeca-9(12),11-diene;

2-Methyl-11-((3-benzyloxy-5-(1H-pyrrol-2-yl)-2H-pyrrol-2-ylidene)methyl)-10-azabicyclo[7.2.1]dodeca-9(12),11-diene;

2-n-Propyl-11-((3-benzyloxy-5-(1H-pyrrol-2-yl)-2H-pyrrol-2-ylidene)methyl)-10-azabicyclo[7.2.1]dodeca-9(12),11-diene;

2-n-Pentyl-11-((3-benzyloxy-5-(1H-pyrrol-2-yl)-2H-pyrrol-2-ylidene)methyl)-10-azabicyclo[7.2.1]dodeca-9(12),11-diene;

2-Benzyl-11-((3-benzyloxy-5-(1H-pyrrol-2-yl)-2H-pyrrol-2-ylidene)methyl)-10-azabicyclo[7.2.1]dodeca-9(12),11-diene;

2-Methyl-14-((3-methoxy-5-(1H-pyrrol-2-yl)-2H-pyrrol-2-ylidene)methyl)-13-azabicyclo[10.2.1]pentadeca-12(15),14-diene;

15-((3-Methoxy-5-(1H-pyrrol-2-yl)-2H-pyrrol-2-ylidene)methyl)-14-azabicyclo[11.2.1]hexadeca-13(16),15-diene;

2-Methyl-15-((3-methoxy-5-(1H-pyrrol-2-yl)-2H-pyrrol-2-ylidene)methyl)-14-azabicyclo[11.2.1]hexadeca-13(16),15-diene;

2-(2-Hydroxy-n-butyl)-11-((3-methoxy-5-(1H-pyrrol-2-yl)-2H-pyrrol-2-ylidene)methyl)-10-azabicyclo[7.2.1]dodeca-9(12),11-diene;

2-(2-Chloro-n-butyl)-11-((3-methoxy-5-(1H-pyrrol-2-yl)-2H-pyrrol-2-ylidene)methyl)-10-azabicyclo[7.2.1]dodeca-9(12),11-diene;

2-Butyl-11-((3-ethoxy-5-(1H-pyrrol-2-yl)-2H-pyrrol-2-ylidene)methyl)-10-azabicyclo[7.2.1]dodeca-9(12),11-diene;

11-((3-Ethoxy-5-(1H-pyrrol-2-yl)-2H-pyrrol-2-ylidene)methyl)-10-azabicyclo[7.2.1]dodeca-9(12),11-diene;

2-Methyl-11-((3-ethoxy-5-(1H-pyrrol-2-yl)-2H-pyrrol-2-ylidene)methyl)-10-azabicyclo[7.2.1]dodeca-9(12),11-diene;

2-n-Propyl-11-((3-ethoxy-5-(1H-pyrrol-2-yl)-2H-pyrrol-2-ylidene)methyl)-10-azabicyclo[7.2.1]dodeca-9(12),11-diene;

2-n-Pentyl-11-((3-ethoxy-5-(1H-pyrrol-2-yl)-2H-pyrrol-2-ylidene)methyl)-10-azabicyclo[7.2.1]dodeca-9(12),11-diene;

2-Benzyl-11-((3-ethoxy-5-(1H-pyrrol-2-yl)-2H-pyrrol-2-ylidene)methyl)-10-azabicyclo[7.2.1]dodeca-9(12),11-diene;

2-Ethyl-11-((3-ethoxy-5-(1H-pyrrol-2-yl)-2H-pyrrol-2-ylidene)methyl)-10-azabicyclo[7.2.1]dodeca-9(12),11-diene;

2-Methyl-13-((3-benzyloxy-5-(1H-pyrrol-2-yl)-2H-pyrrol-2-ylidene)methyl)-12-azabicyclo[9.2.1]tetradeca-11(14),13-diene;

13-((3-Benzyloxy-5-(1H-pyrrol-2-yl)-2H-pyrrol-2-ylidene)methyl)-12-azabicyclo[9.2.1]tetradeca-11(14),13-diene;

2-Ethyl-12-methyl-13-((3-benzyloxy-5-(1-methyl-1H-pyrrol-2-yl)-2H-pyrrol-2-ylidene)methyl)-12-azabicyclo[9.2.1]tetradeca-11(14),13-diene;

2-Ethyl-12-methyl-13-((3-benzyloxy-5-(1H-pyrrol-2-yl)-2H-pyrrol-2-ylidene)methyl)-12-azabicyclo[9.2.1]tetradeca-11(14),13-diene;

2-n-Propyl-13-((3-benzyloxy-5-(1H-pyrrol-2-yl)-2H-pyrrol-2-ylidene)methyl)-12-azabicyclo[9.2.1]tetradeca-11(14),13-diene; and 2-n-Butyl-13-((3-benzyloxy-5-(1H-pyrrol-2-yl)-2H-pyrrol-2-ylidene)methyl)-12-azabicyclo[9.2.1]tetradeca-11(14),13-diene;

and a pharmaceutically acceptable salt thereof.

23. The method of claim 2, wherein the compound of Formula (I) is butyl-meta-cycloheptylprodiginine or a pharmaceutically acceptable salt thereof.

24. The method of claim 3, wherein the compound of Formula (I) is butyl-meta-cycloheptylprodiginine or a pharmaceutically acceptable salt thereof.

25. The method of claim 4, wherein the compound of Formula (I) is butyl-meta-cycloheptylprodiginine or a pharmaceutically acceptable salt thereof.

26. The method of claim 3, wherein the compound of Formula (I) is butyl-meta-cycloheptylprodiginine or a pharmaceutically acceptable salt thereof.

27. The method of claim 3, wherein, in the compound of Formula (I):

each $R_1$ is independently selected from the group consisting of —H, —CH$_3$, —CH$_2$CH$_3$, —CH$_2$C$_6$H$_5$, —C(O)OC(CH$_3$)$_3$, —C(O)OCH$_2$C$_6$H$_5$, and —C(O)CH$_3$;

$R_2$ is selected from the group consisting of —H, $C_1$–$C_{12}$ straight chain alkyl, —CH$_2$C$_6$H$_5$, —SiR$_{10}$R$_{11}$R$_{12}$, —C(O)CH$_3$, —C(O)C$_6$H$_5$, -2-tetrahydropyranyl, —OCH$_2$OCH$_3$, and —C(O)OCH$_2$CCl$_3$;

$R_3$ is selected from the group consisting of —H, $C_1$–$C_{12}$ straight chain alkyl, —CH(R$_{14}$)(R$_{15}$) wherein $R_{14}$ and $R_{15}$ are independently $C_1$–$C_{12}$ straight chain alkyl, —C(O)C$_1$–C$_9$ straight chain alkyl, —CH(OH)C$_1$–C$_9$ straight chain alkyl, —CH(Cl)C$_1$–C$_9$ straight chain alkyl, -(2-pyridyl)methyl, -(3-pyridyl)methyl, -(4-pyridyl)methyl, and —CH$_2$C$_6$H$_5$, the —CH$_2$C$_6$H$_5$ being unsubstituted or substituted on phenyl with one cyano or one or more halo, methoxyl, or trifluoromethyl groups;

$R_{10}$ is selected from the group consisting of $C_1$–$C_4$ straight or branched chain alkyl and —C$_6$H$_5$;

$R_{11}$ and $R_{12}$ are independently $C_1$–$C_3$ straight or branched chain alkyl; and $R_{16}$ and $R_{17}$ are —H; and m is an integer ranging from 1 to 5;

with the proviso that the compound of Formula (I) is not: metacycloprodigiosin.

28. The method of claim 3, wherein, in the compound of Formula (I):

each $R_1$ is independently selected from the group consisting of —H, and —CH$_3$;

$R_2$ is selected from the group consisting of —CH$_3$, —CH$_2$CH$_3$, and —CH$_2$C$_6$H$_5$;

$R_3$ is selected from the group consisting of —H, $C_1$–$C_{10}$ straight chain alkyl, (1-methyl)butyl, —CH$_2$C$_6$H$_5$, butyroyl, (1-hydroxy)butyl, and (1-chloro)butyl;

m is an integer ranging from 1 to 5;

with the proviso that the compound of Formula (I) is not: metacycloprodigiosin.

29. The method of claim 3, wherein, in the compound of Formula (I):

each $R_1$ is —H;

$R_2$ is selected from the group consisting of —CH$_3$, and —CH$_2$C$_6$H$_5$;

$R_3$ is selected from the group consisting of —H, $C_1$–$C_{10}$ straight chain alkyl, and —CH$_2$C$_6$H$_5$;

$R_{16}$ and $R_{17}$ are —H; and m is an integer ranging from 1 to 5;

with the proviso that the compound of Formula (I) is not: metacycloprodigiosin.

30. The method of claim 3, wherein, in the compound of Formula (I):

each $R_1$ is independently selected from the group consisting of —H, and —CH$_3$;

$R_2$ is selected from the group consisting of —CH$_3$, and —CH$_2$C$_6$H$_5$;

$R_3$ is selected from the group consisting of —H, $C_1$–$C_{10}$ straight chain alkyl, —CH$_2$C$_6$H$_5$, butyroyl, (1-hydroxy)butyl, and (1-chloro)butyl;

$R_{16}$ and $R_{17}$ are —H; and m is an integer ranging from 1 to 5;

with the proviso that when m is 3, $R_3$ not —CH$_2$CH$_3$ and when m is 1, $R_3$ not —(CH$_2$)$_3$CH$_3$.

31. The method of claim 3, wherein, in the compound of Formula (I):

each $R_1$ is independently selected from the group consisting of —H, and —CH$_3$;

$R_2$ is selected from the group consisting of —CH$_3$, and —CH$_2$C$_6$H$_5$;

$R_3$ is selected from the group consisting of —H, $C_1$–$C_{10}$ straight chain alkyl, (1-methyl)butyl, —CH$_2$C$_6$H$_5$, butyroyl, (1-hydroxy)butyl, and (1-chloro)butyl;

$R_{16}$ and $R_{17}$ are —H; and m is an integer ranging from 1 to 5.

32. The method of claim 3, wherein, in the compound of Formula (I):

each $R_1$ is independently selected from the group consisting of —H, and —CH$_3$;

$R_2$ is selected from the group consisting of —CH$_3$, and —CH$_2$C$_6$H$_5$;

$R_3$ is selected from the group consisting of —H, $C_1$–$C_{10}$ straight chain alkyl, —CH$_2$C$_6$H$_5$, butyroyl, (1-hydroxy)butyl, and (1-chloro)butyl;

$R_{16}$ and $R_{17}$ are —H; and m is 2,4 or 5.

33. The method of claim 3, wherein in the compound of Formula (I)

each $R_1$ is independently selected from the group consisting of —H, and —CH$_3$;

$R_2$ is selected from the group consisting of —CH$_3$, —CH$_2$CH$_3$, —(CH$_2$)$_2$CH$_3$, and —CH$_2$C$_6$H$_5$;

$R_3$ is selected from the group consisting of —H, $C_1$–$C_{10}$ straight chain alkyl, —CH$_2$C$_6$H$_5$, butyroyl, (1-hydxoxy)butyl, and (1-chloro)butyl;

m is an integer ranging from 1 to 5;

when m is 3 and $R_2$ is —CH$_3$, then $R_{16}$ is selected from the group consisting of —H, and —CH$_3$ and $R_{17}$ is selected from the group consisting of —H, and —COOEt; and when m is other than 3 and $R_2$ is other than —CH$_3$ or —CH$_2$CH$_3$, then $R_{16}$ and $R_{17}$ are —H only;

with the proviso that the compound of Formula (I) is not: metacycloprodigiosin.

34. The method of claim 3, wherein the compound of Formula I is selected from the group consisting of:

butyl-meta-cycloheptyiprodiginine;

2-Ethyl-11-((3-methoxy-5-(1H-pyrrol-2-yl)-2H-pyrrol-2-ylidene)methyl)-10-azabicyclo[7.2.1]dodeca-9(12),11-diene;

11-((3-methoxy-5-(1H-pyrrol-2-yl)-2H-pyrrol-2-ylidene)methyl)-10-azabicyclo[7.2.1]dodeca-9(12),11-diene;

2-Methyl-11-((3-methoxy-5-(1H-pyrrol-2-yl)-2H-pyrrol-2-ylidene)methyl)-10-azabicyclo[7.2.1]dodeca-9(12),11-diene;

2-n-Propyl-11-((3-methoxy-5-(1H-pyrrol-2-yl)-2H-pyrrol-2-ylidene)methyl)-10-azabicyclo[7.2.1]dodeca-9(12),11-diene;

2-n-Pentyl-11-((3-methoxy-5-(1H-pyrrol-2-yl)-2H-pyrrol-2-ylidene)methyl)-10-azabicyclo[7.2.1]dodeca-9(12),11-diene;

2-Benzyl-11-((3-methoxy-5-(1H-pyrrol-2-yl)-2H-pyrrol-2-ylidene)methyl)-10-azabicyclo[7.2.1]dodeca-9(12),11-diene;

(S)-2-n-Pentyl-11-((3-methoxy-5-(1H-pyrrol-2-yl)-2H-pyrrol-2-ylidene)methyl)-10-azabicyclo[7.2.1]dodeca-9(12),11-diene;

(R)-2-n-Pentyl-11-((3-methoxy-5-(1H-pyrrol-2-yl)-2H-pyrrol-2-ylidene)methyl)-10-azabicyclo[7.2.1]dodeca-9(12),11-diene;

(S)-2-n-Butyl-11-((3-methoxy-5-(1H-pyrrol-2-yl)-2H-pyrrol-2-ylidene)methyl)-10-azabicyclo[7.2.1]dodeca-9(12),11-diene;

(R)-2-n-Butyl-11-((3-methoxy-5-(1H-pyrrol-2-yl)-2H-pyrrol-2-ylidene)methyl)-10-azabicyclo[7.2.1]dodeca-9(12),11-diene;

(S)-2-Ethyl-11-((3-methoxy-5-(1H-pyrrol-2-yl)-2H-pyrrol-2-ylidene)methyl)-10-azabicyclo[7.2.1]dodeca-9(12),11-diene;

(R)-2-Ethyl-11-((3-methoxy-5-(1H-pyrrol-2-yl)-2H-pyrrol-2-ylidene)methyl)-10-azabicyclo[7.2.1]dodeca-9(12),11-diene;

(S)-2-Methyl-11-((3-methoxy-5-(1H-pyrrol-2-yl)-2H-pyrrol-2-ylidene)methyl)-10-azabicyclo[7.2.1]dodeca-9(12),11-diene;

(R)-2-Methyl-11-((3-methoxy-5-(1H-pyrrol-2-yl)-2H-pyrrol-2-ylidene)methyl)-10-azabicyclo[7.2.1]dodeca-9(12),11-diene;

(S)-2-n-Propyl-11-((3-methoxy-5-(1H-pyrrol-2-yl)-2H-pyrrol-2-ylidene)methyl)-10-azabicyclo[7.2.1]dodeca-9(12),11-diene;

(R)-2-n-Propyl-11-((3-methoxy-5-(1H-pyrrol-2-yl)-2H-pyrrol-2-ylidene)methyl)-10-azabicyclo[7.2.1]dodeca-9(12),11-diene;

2-Methyl-12-((3-methoxy-5-(1H-pyrrol-2-yl)-2H-pyrrol-2-ylidene)methyl)-11-azabicyclo[8.2.1]trideca-10(13),12-diene;

2-Ethyl-12-((3-methoxy-5-(1H-pyrrol-2-yl)-2H-pyrrol-2-ylidene)methyl)-11-azabicyclo[8.2.1]trideca-10(13),12-diene;

2-n-Propyl-12-((3-methoxy-5-(1H-pyrrol-2-yl)-2H-pyrrol-2-ylidene)methyl)-11-azabicyclo[8.2.1]trideca-10(13),12-diene;

2-n-Butyl-12-((3-methoxy-5-(1H-pyrrol-2-yl)-2H-pyrrol-2-ylidene)methyl)-11-azabicyclo[8.2.1]trideca-10(13),12-diene;

2-n-Pentyl-12-((3-methoxy-5-(1H-pyrrol-2-yl)-2H-pyrrol-2-ylidene)methyl)-11-azabicyclo[8.2.1]trideca-10(13),12-diene;

12-((3-methoxy-5-(1H-pyrrol-2-yl)-2H-pyrrol-2-ylidene)methyl)-11-azabicyclo[8.2.1]trideca-10(13),12-diene;

2-Methyl-13-((3-methoxy-5-(1H-pyrrol-2-yl)-2H-pyrrol-2-ylidene)methyl)-12-azabicyclo[9.2.1]tetradeca-11(14),13-diene;

13-((3-methoxy-5-(1H-pyrrol-2-yl)-2H-pyrrol-2-ylidene)methyl)-12-azabicyclo[9.2.1]tetradeca-11(14),13-diene;

2-Ethyl-12-methyl-13-((3-methoxy-5-(1-methyl-1H-pyrrol-2-yl)-2H-pyrrol-2-ylidene)methyl)-12-azabicyclo[9.2.1]tetradeca-11(14),13-diene;

2-Ethyl-12-methyl-13-((3-methoxy-5-(1H-pyrrol-2-yl)-2H-pyrrol-2-ylidene)methyl)-12-azabicyclo[9.2.1]tetradeca-11(14),13-diene;

2-n-Propyl-13-((3-methoxy-5-(1H-pyrrol-2-yl)-2H-pyrrol-2-ylidene)methyl)-12-azabicyclo[9.2.1]tetradeca-11(14),13-diene;

2-n-Butyl-13-((3-methoxy-5-(1H-pyrrol-2-yl)-2H-pyrrol-2-ylidene)methyl)-12-azabicyclo[9.2.1]tetradeca-11(14),13-diene;

14-((3-methoxy-5-(1H-pyrrol-2-yl)-2H-pyrrol-2-ylidene)methyl)-13-azabicyclo[10.2.1]pentadeca-12(15),14-diene;

2-Butyl-11-((3-methoxy-5-(1-methyl-1H-pyrrol-2-yl)-2H-pyrrol-2-ylidene)methyl)-10-azabicyclo[7.2.1]dodeca-9(12),11-diene;

2-Butyl-11-((3-methoxy-5-(1-methyl-1H-pyrrol-2-yl)-2H-pyrrol-2-ylidene)methyl)-10-methyl-10-azabicyclo[7.2.1]dodeca-9(12),11-diene;

2-Butyl-11-((3-methoxy-5-(1H-pyrrol-2-yl)-2H-pyrrol-2-ylidene)methyl)-10-methyl-10-azabicyclo[7.2.1]dodeca-9(12),11-diene;

2-Ethyl-11-((3-benzyloxy-5-(1H-pyrrol-2-yl)-2H-pyrrol-2-ylidene)methyl)-10-azabicyclo[7.2.1]dodeca-9(12),11-diene;

2-Butyl-11-((3-hydroxy-5-(1H-pyrrol-2-yl)-2H-pyrrol-2-ylidene)methyl)-10-azabicyclo[7.2.1]dodeca-9(12),11-diene;

2-Butyl-11-((3-benzyloxy-5-(1H-pyrrol-2-yl)-2H-pyrrol-2-ylidene)methyl)-10-azabicyclo[7.2.1]dodeca-9(12),11-diene;

11-((3-Benzyloxy-5-(1H-pyrrol-2-yl)-2H-pyrrol-2-ylidene)methyl)-10-azabicyclo[7.2.1]dodeca-9(12),11-diene;

2-Methyl-11-((3-benzyloxy-5-(1H-pyrrol-2-yl)-2H-pyrrol-2-ylidene)methyl)-10-azabicyclo[7.2.1]dodeca-9(12),11-diene;

2-n-Propyl-11-((3-benzyloxy-5-(1H-pyrrol-2-yl)-2H-pyrrol-2-ylidene)methyl)-10-azabicyclo[7.2.1]dodeca-9(12),11-diene;

2-n-Pentyl-11-((3-benzyloxy-5-(1H-pyrrol-2-yl)-2H-pyrrol-2-ylidene)methyl)-10-azabicyclo[7.2.1]dodeca-9(12),11-diene;

2-Benzyl-11-((3-benzyloxy-5-(1H-pyrrol-2-yl)-2H-pyrrol-2-ylidene)methyl)-10-azabicyclo[7.2.1]dodeca-9(12),11-diene;

2-Methyl-14-((3-methoxy-5-(1H-pyrrol-2-yl)-2H-pyrrol-2-ylidene)methyl)-13-azabicyclo[10.2.1]pentadeca-12(15),14-diene;

15-((3-methoxy-5-(1H-pyrrol-2-yl)-2H-pyrrol-2-ylidene)methyl)-14-azabicyclo[11.2.1]hexadeca-13(16),15-diene;

2-Methyl-15-((3-methoxy-5-(1H-pyrrol-2-yl)-2H-pyrrol-2-ylidene)methyl)-14-azabicyclo[11.2.1]hexadeca-13(16),15-diene;

2-(2-Hydroxy-n-butyl)-11-((3-methoxy-5-(1H-pyrrol-2-yl)-2H-pyrrol-2-ylidene)methyl)-10-azabicyclo[7.2.1]dodeca-9(12),11-diene;

2-(2-Chloro-n-butyl)-11-((3-methoxy-5-(1H-pyrrol-2-yl)-2H-pyrrol-2-ylidene)methyl)-10-azabicyclo[7.2.1]dodeca-9(12),11-diene;

2-Butyl-11-((3-ethoxy-5-(1H-pyrrol-2-yl)-2H-pyrrol-2-ylidene)methyl)-10-azabicyclo[7.2.1]dodeca-9(12),11-diene;

11-((3-Ethoxy-5-(1H-pyrrol-2-yl)-2H-pyrrol-2-ylidene)methyl)-10-azabicyclo[7.2.1]dodeca-9(12),11-diene;

2-Methyl-11-((3-ethoxy-5-(1H-pyrrol-2-yl)-2H-pyrrol-2-ylidene)methyl)-10-azabicyclo[7.2.1]dodeca-9(12),11-diene;

2-n-Propyl-11-((3-ethoxy-5-(1H-pyrrol-2-yl)-2H-pyrrol-2-ylidene)methyl)-10-azabicyclo[7.2.1]dodeca-9(12),11-diene;

2-n-Pentyl-11-((3-ethoxy-5-(1H-pyrrol-2-yl)-2H-pyrrol-2-ylidene)methyl)-10-azabicyclo[7.2.1]dodeca-9(12),11-diene;

2-Benzyl-11-((3-ethoxy-5-(1H-pyrrol-2-yl)-2H-pyrrol-2-ylidene)methyl)-10-azabicyclo[7.2.1]dodeca-9(12),11-diene;

2-Ethyl-11-((3-ethoxy-5-(1H-pyrrol-2-yl)-2H-pyrrol-2-ylidene)methyl)-10-azabicyclo[7.2.1]dodeca-9(12),11-diene;

2-Methyl-13-((3-benzyloxy-5-(1H-pyrrol-2-yl)-2H-pyrrol-2-ylidene)methyl)-12-azabicyclo[9.2.1]tetradeca-11(14),13-diene;

13-((3-Benzyloxy-5-(1H-pyrrol-2-yl)-2H-pyrrol-2-ylidene)methyl)-12-azabicyclo[9.2.1]tetradeca-11(14),13-diene;

2-Ethyl-12-methyl-13-((3-benzyloxy-5-(1-methyl-1H-pyrrol-2-yl)-2H-pyrrol-2-ylidene)methyl)-12-azabicyclo[9.2.1]tetradeca-11(14),13-diene;

2-Ethyl-12-methyl-13-((3-benzyloxy-5-(1H-pyrrol-2-yl)-2H-pyrrol-2-ylidene)methyl)-12-azabicyclo[9.2.1]tetradeca-11(14),13-diene;

2-n-Propyl-13-((3-benzyloxy-5-(1H-pyrrol-2-yl)-2H-pyrrol-2-ylidene)methyl)-2-n-Butyl-13-((3-benzyloxy-5-(1H-pyrrol-2-yl)-2H-pyrrol-2-ylidene)methyl)-12-azabicyclo[9.2.1]tetradeca-11(14),13-diene;

35. The method of claim 4, wherein the compound of Formula (I) is butyl-meta-cycloheptylprodiginine or a pharmaceutically acceptable salt thereof.

36. The method of claim 4, wherein, in the compound the compound of Formula (I):
- each $R_1$ is independently selected from the group consisting of —H, —$CH_3$, —$CH_2CH_3$, —$CH_2C_6H_5$, —C(O)OC($CH_3$)$_3$, —C(O)O$CH_2C_6H_5$, and —C(O)$CH_3$;
- $R_2$ is selected from the group consisting of —H, $C_1$–$C_{12}$ straight chain alkyl, —$CH_2C_6H_5$, —$SiR_{10}R_{11}R_{12}$, —C(O)$CH_3$, —C(O)$C_6H_5$, -2-tetrahydropyranyl, —$OCH_2OCH_3$, and —C(O)O$CH_2CCl_3$;
- $R_3$ is selected from the group consisting of —H, $C_1$–$C_{12}$ straight chain alkyl, —CH($R_{14}$)($R_{15}$) wherein $R_{14}$ and $R_{15}$ are independently $C_1$–$C_{12}$ straight chain alkyl, —C(O)$C_1$–$C_9$ straight chain alkyl, —CH(OH)$C_1$–$C_9$ straight chain alkyl, —CH(Cl)$C_1$–$C_9$ straight chain alkyl, -(2-pyridyl)methyl, -(3-pyridyl)methyl, -(4-pyridyl)methyl, and —$CH_2C_6H_5$, the —$CH_2C_6H_5$ being unsubstituted or substituted on phenyl with one cyano or one or more halo, methoxyl, or trifluoromethyl groups;
- $R_{10}$ is selected from the group consisting of $C_1$–$C_4$ straight or branched chain alkyl and
- $R_{11}$ and $R_{12}$ are independently $C_1$–$C_3$ straight or branched chain alkyl; and
- $R_{16}$ and $R_{17}$ are —H; and
- m is an integer ranging from 1 to 5;

with the proviso that the compound of Formula (I) is not: metacycloprodigiosin.

37. The method of claim 4, wherein, in the compound of Formula (I):
- each $R_1$ is independently selected from the group consisting of —H, and —$CH_3$;
- $R_2$ is selected from the group consisting of —$CH_3$, —$CH_2CH_3$, and —$CH_2C_6H_5$;
- $R_3$ is selected from the group consisting of —H, $C_1$–$C_{10}$ straight chain alkyl, (1-methyl)butyl, —$CH_2C_6H_5$, butyrol(1-hydroxy)butyl, and (1-chloro)butyl;
- m is an integer ranging from 1 to 5;

with the proviso that the compound of Formula (I) is not: metacycloprodigiosin.

38. The method of claim 4, wherein, in the compound of Formula (I):
- each $R_1$ is —H;
- $R_2$ is selected from the group consisting of —$CH_3$, and —$CH_2C_6H_5$;
- $R_3$ is selected from the group consisting of —H, $C_1$–$C_{10}$ straight chain alkyl, and —$CH_2C_6H_5$;
- $R_{16}$ and $R_{17}$ are —H; and
- m is an integer ranging from 1 to 5;

with the proviso that the compound of Formula (I) is not: metacycloprodigiosin.

39. The method of claim 4, wherein, in the compound of Formula (I):
- each $R_1$ is independently selected from the group consisting of —H, and —$CH_3$;
- $R_2$ is selected from the group consisting of —$CH_3$, and —$CH_2C_6H_5$;
- $R_3$ is selected from the group consisting of —H, $C_1$–$C_{10}$ straight chain alkyl, —$CH_2C_6H_5$, butyroyl, (1-hydroxy)butyl, and (1-chloro)butyl;
- $R_{16}$ and $R_{17}$ are —H; and
- m is an integer ranging from 1 to 5;

with the proviso that when m is 3, $R_3$ not —$CH_2CH_3$ and when m is1, $R_3$ not —($CH_2$)$_3CH_3$.

40. The method of claim 4, wherein, in the compound of Formula (I):
- each $R_1$ is independently selected from the group consisting of —H, and —$CH_3$;
- $R_2$ is selected from the group consisting of —$CH_3$, and —$CH_2C_6H_5$;
- $R_3$ is selected from the group consisting of —H, $C_1$–$C_{10}$ straight chain alkyl, (1-methyl)butyl, —$CH_2C_6H_5$, butyroyl, (1-hydroxy)butyl, and (1-chloro)butyl;
- $R_{16}$ and $R_{17}$ are —H; and
- m is an integer ranging from 1 to 5.

41. The method of claim 4, wherein, in the compound of Formula (I):
- each $R_1$ is independently selected from the group consisting of —H, and —$CH_3$;
- $R_2$ is selected from the group consisting of —$CH_3$, and —$CH_2C_6H_5$;
- $R_3$ is selected from the group consisting of —H, $C_1$–$C_{10}$ straight chain alkyl, —$CH_2C_6H_5$, butyroyl, (1-hydroxy)butyl, and (1-chloro)butyl;
- $R_{16}$ and $R_{17}$ are —H; and
- m is 2,4 or 5.

42. The method of claim 4, wherein, in the compound of Formula (I)
- each $R_1$ is independently selected from the group consisting of —H, and —$CH_3$;
- $R_2$ is selected from the group consisting of —$CH_3$, —$CH_2CH_3$, —($CH_2$)$_2CH_3$, and —$CH_2C_6H_5$;
- $R_3$ is selected from the group consisting of —H, $C_1$–$C_{10}$ straight chain alkyl, —$CH_2C_6H_5$, butyroyl, (1-hydxoxy)butyl, and (1-chloro)butyl;
- m is an integer ranging from 1 to 5;
- when m is 3 and $R_2$ is —$CH_3$, then $R_{16}$ is selected from the group consisting of —H, and —$CH_3$ and $R_{17}$ is selected from the group consisting of —H, and —COOEt; and
- when m is other than 3 and $R_2$ is other than —$CH_3$ or —$CH_2CH_3$, then $R_{16}$ and $R_{17}$ are —H only;

with the proviso that the compound of Formula (I) is not: metacycloprodigiosin.

43. The method of claim 4, wherein the compound of Formula I is selected from the group consisting of:
- butyl-meta-cycloheptyiprodiginine;
- 2-Ethyl-11-((3-methoxy-5-(1H-pyrrol-2-yl)-2H-pyrrol-2-ylidene)methyl)-10-azabicyclo[7.2.1]dodeca-9(12),11-diene;
- 11-((3-methoxy-5-(1H-pyrrol-2-yl)-2H-pyrrol-2-ylidene)methyl)-10-azabicyclo[7.2.1]dodeca-9(12),11-diene;
- 2-Methyl-11-((3-methoxy-5-(1H-pyrrol-2-yl)-2H-pyrrol-2-ylidene)methyl)-10-azabicyclo[7.2.1]dodeca-9(12),11-diene;
- 2-n-Propyl-11-((3-methoxy-5-(1H-pyrrol-2-yl)-2H-pyrrol-2-ylidene)methyl)-10-azabicyclo[7.2.1]dodeca-9(12),11-diene;
- 2-n-Pentyl-11-((3-methoxy-5-(1H-pyrrol-2-yl)-2H-pyrrol-2-ylidene)methyl)-10-azabicyclo[7.2.1]dodeca-9(12),11-diene;
- 2-Benzyl-11-((3-methoxy-5-(1H-pyrrol-2-yl)-2H-pyrrol-2-ylidene)methyl)-10-azabicyclo[7.2.1]dodeca-9(12),11-diene;

(S)-2-n-Pentyl-11-((3-methoxy-5-(1H-pyrrol-2-yl)-2H-pyrrol-2-ylidene)methyl)-10-azabicyclo[7.2.1]dodeca-9(12),11-diene;

(R)-2-n-Pentyl-11-((3-methoxy-5-(1H-pyrrol-2-yl)-2H-pyrrol-2-ylidene)methyl)-10-azabicyclo[7.2.1]dodeca-9(12),11-diene;

(S)-2-n-Butyl-11-((3-methoxy-5-(1H-pyrrol-2-yl)-2H-pyrrol-2-ylidene)methyl)-10-azabicyclo[7.2.1]dodeca-9(12),11-diene;

(R)-2-n-Butyl-11-((3-methoxy-5-(1H-pyrrol-2-yl)-2H-pyrrol-2-ylidene)methyl)-10-azabicyclo[7.2.1]dodeca-9(12),11-diene;

(S)-2-Ethyl-11-((3-methoxy-5-(1H-pyrrol-2-yl)-2H-pyrrol-2-ylidene)methyl)-10-azabicyclo[7.2.1]dodeca-9(12),11-diene;

(R)-2-Ethyl-11-((3-methoxy-5-(1H-pyrrol-2-yl)-2H-pyrrol-2-ylidene)methyl)-10-azabicyclo[7.2.1]dodeca-9(12),11-diene;

(S)-2-Methyl-11-((3-methoxy-5-(1H-pyrrol-2-yl)-2H-pyrrol-2-ylidene)methyl)-10-azabicyclo[7.2.1]dodeca-9(12),11-diene;

(R)-2-Methyl-11-((3-methoxy-5-(1H-pyrrol-2-yl)-2H-pyrrol-2-ylidene)methyl)-10-azabicyclo[7.2.1]dodeca-9(12),11-diene;

(S)-2-n-Propyl-11-((3-methoxy-5-(1H-pyrrol-2-yl)-2H-pyrrol-2-ylidene)methyl)-10-azabicyclo[7.2.1]dodeca-9(12),11-diene;

(R)-2-n-Propyl-11-((3-methoxy-5-(1H-pyrrol-2-yl)-2H-pyrrol-2-ylidene)methyl)-10-azabicyclo[7.2.1]dodeca-9(12),11-diene;

2-Methyl-12-((3-methoxy-5-(1H-pyrrol-2-yl)-2H-pyrrol-2-ylidene)methyl)-11-azabicyclo[8.2.1]trideca-10(13),12-diene;

2-Ethyl-12-((3-methoxy-5-(1H-pyrrol-2-yl)-2H-pyrrol-2-ylidene)methyl)-11-azabicyclo[8.2.1]trideca-10(13),12-diene;

2-n-Propyl-12-((3-methoxy-5-(1H-pyrrol-2-yl)-2H-pyrrol-2-ylidene)methyl)-11-azabicyclo[8.2.1]trideca-10(13),12-diene;

2-n-Butyl-12-((3-methoxy-5-(1H-pyrrol-2-yl)-2H-pyrrol-2-ylidene)methyl)-11-azabicyclo[8.2.1]trideca-10(13),12-diene;

2-n-Pentyl-12-((3-methoxy-5-(1H-pyrrol-2-yl)-2H-pyrrol-2-ylidene)methyl)-11-azabicyclo[8.2.1]trideca-10(13),12-diene;

12-((3-methoxy-5-(1H-pyrrol-2-yl)-2H-pyrrol-2-ylidene)methyl)-11-azabicyclo[8.2.1]trideca-10(13),12-diene;

2-Methyl-13-((3-methoxy-5-(1H-pyrrol-2-yl)-2H-pyrrol-2-ylidene)methyl)-12-azabicyclo[9.2.1]tetradeca-11(14),13-diene;

13-((3-methoxy-5-(1H-pyrrol-2-yl)-2H-pyrrol-2-ylidene)methyl)-12-azabicyclo[9.2.1]tetradeca-11(14),13-diene;

2-Ethyl-12-methyl-13-((3-methoxy-5-(1-methyl-1H-pyrrol-2-yl)-2H-pyrrol-2-ylidene)methyl)-12-azabicyclo[9.2.1]tetradeca-11(14),13-diene;

2-Ethyl-12-methyl-13-((3-methoxy-5-(1H-pyrrol-2-yl)-2H-pyrrol-2-ylidene)methyl)-12-azabicyclo[9.2.1]tetradeca-11(14),13-diene;

2-n-Propyl-13-((3-methoxy-5-(1H-pyrrol-2-yl)-2H-pyrrol-2-ylidene)methyl)-12-azabicyclo[9.2.1]tetradeca-11(14),13-diene;

2-n-Butyl-13-((3-methoxy-5-(1H-pyrrol-2-yl)-2H-pyrrol-2-ylidene)methyl)-12-azabicyclo[9.2.1]tetradeca-11(14),13-diene;

14-((3-methoxy-5-(1H-pyrrol-2-yl)-2H-pyrrol-2-ylidene)methyl)-13-azabicyclo[10.2.1]pentadeca-12(15),14-diene;

2-Butyl-11-((3-methoxy-5-(1-methyl-1H-pyrrol-2-yl)-2H-pyrrol-2-ylidene)methyl)-10-azabicyclo[7.2.1]dodeca-9(12),11-diene;

2-Butyl-11-((3-methoxy-5-(1-methyl-1H-pyrrol-2-yl)-2H-pyrrol-2-ylidene)methyl)-10-methyl-10-azabicyclo[7.2.1]dodeca-9(12),11-diene;

2-Butyl-11-((3-methoxy-5-(1H-pyrrol-2-yl)-2H-pyrrol-2-ylidene)methyl)-10-methyl-10-azabicyclo[7.2.1]dodeca-9(12),11-diene;

2-Ethyl-11-((3-benzyloxy-5-(1H-pyrrol-2-yl)-2H-pyrrol-2-ylidene)methyl)-10-azabicyclo[7.2.1]dodeca-9(12),11-diene;

2-Butyl-11-((3-hydroxy-5-(1H-pyrrol-2-yl)-2H-pyrrol-2-ylidene)methyl)-10-azabicyclo[7.2.1]dodeca-9(12),11-diene;

2-Butyl-11-((3-benzyloxy-5-(1H-pyrrol-2-yl)-2H-pyrrol-2-ylidene)methyl)-10-azabicyclo[7.2.1]dodeca-9(12),11-diene;

11-((3-Benzyloxy-5-(1H-pyrrol-2-yl)-2H-pyrrol-2-ylidene)methyl)-10-azabicyclo[7.2.1]dodeca-9(12),11-diene;

2-Methyl-11-((3-benzyloxy-5-(1H-pyrrol-2-yl)-2H-pyrrol-2-ylidene)methyl)-10-azabicyclo[7.2.1]dodeca-9(12),11-diene;

2-n-Propyl-11-((3-benzyloxy-5-(1H-pyrrol-2-yl)-2H-pyrrol-2-ylidene)methyl)-10-azabicyclo[7.2.1]dodeca-9(12),11-diene;

2-n-Pentyl-11-((3-benzyloxy-5-(1H-pyrrol-2-yl)-2H-pyrrol-2-ylidene)methyl)-10-azabicyclo[7.2.1]dodeca-9(12),11-diene;

2-Benzyl-11-((3-benzyloxy-5-(1H-pyrrol-2-yl)-2H-pyrrol-2-ylidene)methyl)-10-azabicyclo[7.2.1]dodeca-9(12),11-diene;

2-Methyl-14-((3-methoxy-5-(1H-pyrrol-2-yl)-2H-pyrrol-2-ylidene)methyl)-13-azabicyclo[10.2.1]pentadeca-12(15),14-diene;

15-((3-methoxy-5-(1H-pyrrol-2-yl)-2H-pyrrol-2-ylidene)methyl)-14-azabicyclo[11.2.1]hexadeca-13(16),15-diene;

2-Methyl-15-((3-methoxy-5-(1H-pyrrol-2-yl)-2H-pyrrol-2-ylidene)methyl)-14-azabicyclo[11.2.1]hexadeca-13(16),15-diene;

2-(2-Hydroxy-n-butyl)-11-((3-methoxy-5-(1H-pyrrol-2-yl)-2H-pyrrol-2-ylidene)methyl)-10-azabicyclo[7.2.1]dodeca-9(12),11-diene;

2-(2-Chloro-n-butyl)-11-((3-methoxy-5-(1H-pyrrol-2-yl)-2H-pyrrol-2-ylidene)methyl)-10-azabicyclo[7.2.1]dodeca-9(12),11-diene;

2-Butyl-11-((3-ethoxy-5-(1H-pyrrol-2-yl)-2H-pyrrol-2-ylidene)methyl)-10-azabicyclo[7.2.1]dodeca-9(12),11-diene;

11-((3-Ethoxy-5-(1H-pyrrol-2-yl)-2H-pyrrol-2-ylidene)methyl)-10-azabicyclo[7.2.1]dodeca-9(12),11-diene;

2-Methyl-11-((3-ethoxy-5-(1H-pyrrol-2-yl)-2H-pyrrol-2-ylidene)methyl)-10-azabicyclo[7.2.1]dodeca-9(12),11-diene;

2-n-Propyl-11-((3-ethoxy-5-(1H-pyrrol-2-yl)-2H-pyrrol-2-ylidene)methyl)-10-azabicyclo[7.2.1]dodeca-9(12),11-diene;

2-n-Pentyl-11-((3-ethoxy-5-(1H-pyrrol-2-yl)-2H-pyrrol-2-ylidene)methyl)-10-azabicyclo[7.2.1]dodeca-9(12),11-diene;

2-Benzyl-11-((3-ethoxy-5-(1H-pyrrol-2-yl)-2H-pyrrol-2-ylidene)methyl)-10-azabicyclo[7.2.1]dodeca-9(12),11-diene;

2-Ethyl-11-((3-ethoxy-5-(1H-pyrrol-2-yl)-2H-pyrrol-2-ylidene)methyl)-10-azabicyclo[7.2.1]dodeca-9(12),11-diene;

2-Methyl-13-((3-benzyloxy-5-(1H-pyrrol-2-yl)-2H-pyrrol-2-ylidene)methyl)-12-azabicyclo[9.2.1]tetradeca-11(14),13-diene;

13-((3-Benzyloxy-5-(1H-pyrrol-2-yl)-2H-pyrrol-2-ylidene)methyl)-12-azabicyclo[9.2.1]tetradeca-11(14),13-diene;

2-Ethyl-12-methyl-13-((3-benzyloxy-5-(1-methyl-1H-pyrrol-2-yl)-2H-pyrrol-2-ylidene)methyl)-12-azabicyclo[9.2.1]tetradeca-11(14),13-diene;

2-Ethyl-12-methyl-13-((3-benzyloxy-5-(1H-pyrrol-2-yl)-2H-pyrrol-2-ylidene)methyl)-12-azabicyclo[9.2.1]tetradeca-11(14),13-diene;

2-n-Propyl-13-((3-benzyloxy-5-(1H-pyrrol-2-yl)-2H-pyrrol-2-ylidene)methyl)-12-azabicyclo[9.2.1]tetradeca-11(14),13-diene; and 2-n-Butyl-13-((3-benzyloxy-5-(1H-pyrrol-2-yl)-2H-pyrrol-2-ylidene)methyl)-12-azabicyclo[9.2.1]tetradeca-11(14),13-diene;

and a pharmaceutically acceptable salt thereof.

44. A method for treating lung carcinoma comprising administering to a patient in need of such treatment a therapeutically effective amount of a compound of Formula (I):

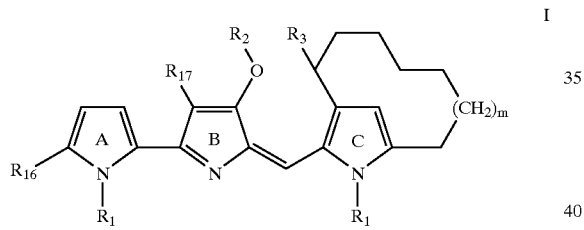

or a pharmaceutically acceptable salt thereof wherein, in the compound of Formula (I):

each $R_1$ is independently selected from the group consisting of —H, —$CH_3$, —$CH_2CH_3$, —$CH_2C_6H_5$, —$C(O)OC(CH_3)_3$, —$C(O)OCH_2C_6H_5$, and —$C(O)CH_3$;

$R_2$ is selected from the group consisting of —H, $C_1$–$C_{12}$ straight chain alkyl, —$CH_2C_6H_5$, —$SiR_{10}R_{11}R_{12}$, —$C(O)CH_3$, —$C(O)C_6H_5$, -2-tetrahydropyranyl, —$OCH_2OCH_3$, and —$C(O)OCH_2CCl_3$;

$R_3$ is selected from the group consisting of —H, $C_1$–$C_{12}$ straight chain alkyl, —$CH(R_{14})(R_{15})$ wherein $R_{14}$ and $R_{15}$ are independently $C_1$–$C_{12}$ straight chain alkyl, —$C(O)C_1$–$C_9$ straight chain alkyl, —$CH(OH)C_1$–$C_9$ straight chain alkyl, —$CH(Cl)C_1$–$C_9$ straight chain alkyl, -(2-pyridyl)methyl, -(3-pyridyl)methyl, -(4-pyridyl)methyl, and —$CH_2C_6H_5$, the —$CH_2C_6H_5$ being unsubstituted or substituted on phenyl with one cyano or one or more halo, methoxyl, or trifluoromethyl groups;

$R_{10}$ is selected from the group consisting of $C_1$–$C_4$ straight or branched chain alkyl and —$C_6H_5$;

$R_{11}$ and $R_{12}$ are independently $C_1$–$C_3$ straight or branched chain alkyl;

m is an integer ranging from 1 to 5; and when m is 3 and $R_2$ is —$CH_2CH_3$, then $R_{16}$ is —H or —$CH_3$ and $R_{17}$ is —H;

when m is 3 and $R_2$ is —$CH_3$, then $R_{16}$ is —H or —$CH_3$ and $R_{17}$ is —H or —COOEt; and when m is other than 3 and $R_2$ is other than —$CH_3$ or —$CH_2CH_3$, then $R_{16}$ and $R_{17}$ are —H only;

with the proviso that the compound of Formula (I) is not metacycloprodigiosin.

45. A method for treating bronchogenic carcinoma comprising administering to a patient in need of such treatment a therapeutically effective amount of a compound of Formula (I):

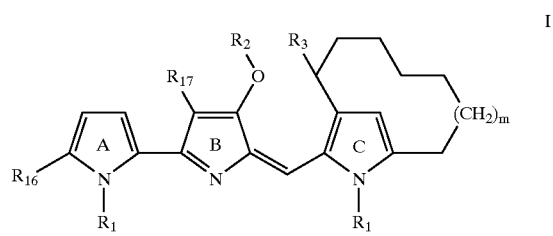

or a pharmaceutically acceptable salt thereof, wherein, in the compound of Formula (I):

each $R_1$ is independently selected from the group consisting of —H, —$CH_3$, —$CH_2CH_3$, —$CH_2C_6H_5$, —$C(O)OC(CH_3)_3$, —$C(O)OCH_2C_6H_5$, and —$C(O)CH_3$;

$R_2$ is selected from the group consisting of —H, $C_1$–$C_{12}$ straight chain alkyl, —$CH_2C_6H_5$, —$SiR_{10}R_{11}R_{12}$, —$C(O)CH_3$, —$C(O)C_6H_5$, -2-tetrahydropyranyl, —$OCH_2OCH_3$, and —$C(O)OCH_2CCl_3$;

$R_3$ is selected from the group consisting of —H, $C_1$–$C_{12}$ straight chain alkyl, —$CH(R_{14})(R_{15})$ wherein $R_{14}$ and $R_{15}$ are independently $C_1$–$C_{12}$ straight chain alkyl, —$C(O)C_1$–$C_9$ straight chain alkyl, —$CH(OH)C_1$–$C_9$ straight chain alkyl, —$CH(Cl)C_1$–$C_9$ straight chain alkyl, -(2-pyridyl)methyl, -(3-pyridyl)methyl, -(4-pyridyl)methyl, and —$CH_2C_6H_5$, the —$CH_2C_6H_5$ being unsubstituted or substituted on phenyl with one cyano or one or more halo, methoxyl, or trifluoromethyl groups;

$R_{10}$ is selected from the group consisting of $C_1$–$C_4$ straight or branched chain alkyl and —$C_6H_5$;

$R_{11}$ and $R_{12}$ are independently $C_1$–$C_3$ straight or branched chain alkyl;

m is an integer ranging from 1 to 5; and when m is 3 and $R_2$ is —$CH_2CH_3$, then $R_{16}$ is —H or —$CH_3$ and $R_{17}$ is —H;

when m is 3 and $R_2$ is —$CH_3$, then $R_{16}$ is —H or —$CH_3$ and $R_{17}$ is —H or —COOEt; and when m is other than 3 and $R_2$ is other than —$CH_3$ or —$CH_2CH_3$, then $R_{16}$ and $R_{17}$ are —H only;

with the proviso that the compound of Formula (I) is not metacycloprodigiosin.

46. A method for inhibiting the growth of a lung carcinoma cell comprising contacting a said cancer cell with an effective amount of a compound of Formula (I):

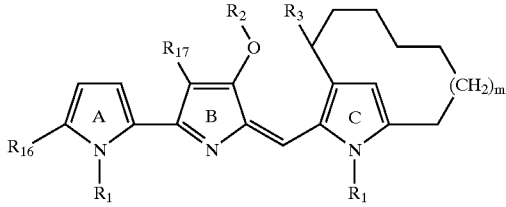

or a pharmaceutically acceptable salt thereof, wherein, in the compound of Formula (I):
- each $R_1$ is independently selected from the group consisting of —H, —$CH_3$, —$CH_2CH_3$, —$CH_2C_6H_5$, —C(O)OC($CH_3$)$_3$, —C(O)O$CH_2C_6H_5$, and —C(O)$CH_3$;
- $R_2$ is selected from the group consisting of —H, $C_1$–$C_{12}$ straight chain alkyl, —$CH_2C_6H_5$, —$SiR_{10}R_{11}R_{12}$, —C(O)$CH_3$, —C(O)$C_6H_5$, -2-tetrahydropyranyl, —$OCH_2OCH_3$, and —C(O)$OCH_2CCl_3$;
- $R_3$ is selected from the group consisting of —H, $C_1$–$C_{12}$ straight chain alkyl, —CH($R_{14}$)($R_{15}$) wherein $R_{14}$ and $R_{15}$ are independently $C_1$–$C_{12}$ straight chain alkyl, —C(O)$C_1$–$C_9$ straight chain alkyl, —CH(OH)$C_1$–$C_9$ straight chain alkyl, —CH(Cl)$C_1$–$C_9$ straight chain alkyl, -(2-pyridyl)methyl, -(3-pyridyl)methyl, -(4-pyridyl)methyl, and —$CH_2C_6H_5$, the —$CH_2C_6H_5$ being unsubstituted or substituted on phenyl with one cyano or one or more halo, methoxyl, or trifluoromethyl groups;
- $R_{10}$ is selected from the group consisting of $C_1$–$C_4$ straight or branched chain alkyl and $R_{11}$ and $R_{12}$ are independently $C_1$–$C_3$ straight or branched chain alkyl;
- m is an integer ranging from 1 to 5;
- when m is 3 and $R_2$ is —$CH_2CH_3$, then $R_{16}$ is —H or —$CH_3$ and $R_{17}$ is —H;
- when m is 3 and $R_2$ is —$CH_3$, then $R_{16}$ is —H or —$CH_3$ and $R_{17}$ is —H or —COOEt; and
- when m is other than 3 and $R_2$ is other than —$CH_3$ or —$CH_2CH_3$, then $R_{16}$ and $R_{17}$ are —H only;
- with the proviso that the compound of Formula (I) is not metacycloprodigiosin.

47. A method for inhibiting the growth of a bronchogenic carcinoma cell comprising
contacting a said cancer cell with an effective amount of a compound of Formula (I):

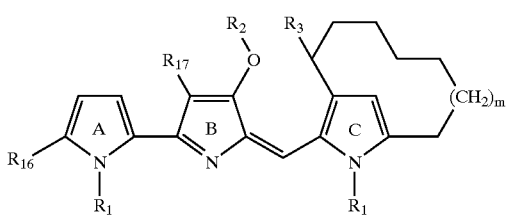

or a pharmaceutically acceptable salt thereof, wherein, in the compound of Formula (I):
- each $R_1$ is independently selected from the group consisting of —H, —$CH_3$, —$CH_2CH_3$, —$CH_2C_6H_5$, —C(O)OC($CH_3$)$_3$, —C(O)O$CH_2C_6H_5$, and —C(O)$CH_3$;
- $R_2$ is selected from the group consisting of —H, $C_1$–$C_{12}$ straight chain alkyl —$CH_2C_6H_5$, —$SiR_{10}R_{11}R_{12}$, —C(O)$CH_3$, —C(O)$C_6H_5$, -2-tetrahydropyranyl, —$OCH_2OCH_3$, and —C(O)$OCH_2CCl_3$;
- $R_3$ is selected from the group consisting of —H, $C_1$–$C_{12}$ straight chain alkyl, —CH($R_{14}$)($R_{15}$) wherein $R_{14}$ and $R_{15}$ are independently $C_1$–$C_{12}$ straight chain alkyl, —C(O)$C_1$–$C_9$ straight chain alkyl, —CH(OH)$C_1$–$C_9$ straight chain alkyl, —CH(Cl)$C_1$–$C_9$ straight chain alkyl, -(2-pyridyl)methyl, -(3-pyridyl)methyl, -(4-pyridyl)methyl, and —$CH_2C_6H_5$, the —$CH_2C_6H_5$ being unsubstituted or substituted on phenyl with one cyano or one or more halo, methoxyl, or trifluoromethyl groups;
- $R_{10}$ is selected from the group consisting of $C_1$–$C_4$ straight or branched chain alkyl and —$C_6H_5$;
- $R_{11}$ and $R_{12}$ are independently $C_1$–$C_3$ straight or branched chain alkyl;
- m is an integer ranging from 1 to 5;
- when m is 3 and $R_2$ is —$CH_2CH_3$, then $R_{16}$ is —H or —$CH_3$ and $R_{17}$ is —H;
- when m is 3 and $R_2$ is —$CH_3$, then $R_{16}$ is —H or —$CH_3$ and $R_{17}$ is —H or —COOEt; and
- when m is other than 3 and $R_2$ is other than —$CH_3$ or —$CH_2CH_3$, then $R_{16}$ and $R_{17}$ are —H only;
- with the proviso that the compound of Formula (I) is not metacycloprodigiosin.

48. The method of claim 44, wherein, in the compound of Formula (I):
- each $R_1$ is independently selected from the group consisting of —H, —$CH_3$, —$CH_2CH_3$, —$CH_2C_6H_5$, —C(O)OC($CH_3$)$_3$, —C(O)O$CH_2C_6H_5$, and —C(O)$CH_3$;
- $R_2$ is selected from the group consisting of —H, $C_1$–$C_{12}$ straight chain alkyl, —$CH_2C_6H_5$, —$SiR_{10}R_{11}R_{12}$, —C(O)$CH_3$, —C(O)$C_6H_5$, -2-tetrahydropyranyl, —$OCH_2OCH_3$, and —C(O)$OCH_2CCl_3$;
- $R_3$ is selected from the group consisting of —H, $C_1$–$C_{12}$ straight chain alkyl, —CH($R_{14}$)($R_{15}$) wherein $R_{14}$ and $R_{15}$ are independently $C_1$–$C_{12}$ straight chain alkyl, —C(O)$C_1$–$C_9$ straight chain alkyl, —CH(OH)$C_1$–$C_9$ straight chain alkyl, —CH(Cl)$C_1$–$C_9$ straight chain alkyl, -(2-pyridyl)methyl, -(3-pyridyl)methyl, -(4-pyridyl)methyl, and —$CH_2C_6H_5$, the —$CH_2C_6H_5$ being unsubstituted or substituted on phenyl with one cyano or one or more halo, methoxyl, or trifluoromethyl groups;
- $R_{10}$ is selected from the group consisting of $C_1$–$C_4$ straight or branched chain alkyl and
- $R_{11}$ and $R_{12}$ are independently $C_1$–$C_3$ straight or branched chain alkyl; and
- $R_{16}$ and $R_{17}$ are —H; and
- m is an integer ranging from 1 to 5;

with the proviso that the compound of Formula (I) is not: metacycloprodigiosin.

49. The method of claim 44, wherein the compound of Formula (I) is butyl-meta-cycloheptylprodiginine or a pharmaceutically acceptable salt thereof.

50. The method of claim 44, wherein, in the compound of Formula (I):
- each $R_1$ is independently selected from the group consisting of —H, and —$CH_3$;
- $R_2$ is selected from the group consisting of —$CH_3$, —$CH_2CH_3$, and —$CH_2C_6H_5$;
- $R_3$ is selected from the group consisting of —H, $C_1$–$C_{10}$ straight chain alkyl, (1-methyl)butyl, —$CH_2C_6H_5$, butyroyl, (1-hydroxy)butyl, and (1—CHloro)butyl;

$R_{16}$ and $R_{17}$ are —H; and m is an integer ranging from 1 to 5;

with the proviso that the compound of Formula (I) is not: metacycloprodigiosin.

51. The method of claim 44, wherein, in the compound of Formula (I):

each $R_1$ is —H;

$R_2$ is selected from the group consisting of —$CH_3$, and —$CH_2C_6H_5$;

$R_3$ is selected from the group consisting of —H, $C_1$–$C_{10}$ straight chain alkyl, and —$CH_2C_6H_5$;

$R_{16}$ and $R_{17}$ are —H; and m is an integer ranging from 1 to 5;

with the proviso that the compound of Formula (I) is not: metacycloprodigiosin.

52. The method of claim 44, wherein, in the compound of Formula (I):

each $R_1$ is independently selected from the group consisting of —H, and —$CH_3$;

$R_2$ is selected from the group consisting of —$CH_3$, and —$CH_2C_6H_5$;

$R_3$ is selected from the group consisting of —H, $C_1$–$C_{10}$ straight chain alkyl, —$CH_2C_6H_5$, butyroyl, (1-hydroxy)butyl, and (1-chloro)butyl;

$R_{16}$ and $R_{17}$ are —H; and m is an integer ranging from 1 to 5.

with the proviso that when m is 3, $R_3$ not —$CH_2CH_3$ and when m is 1, $R_3$ is not —$(CH_2)_3CH_3$.

53. The method of claim 44, wherein, in the compound of Formula (I):

each $R_1$ is independently selected from the group consisting of —H, and —$CH_3$;

$R_2$ is selected from the group consisting of —$CH_3$, and —$CH_2C_6H_5$;

$R_3$ is selected from the group consisting of —H, $C_1$–$C_{10}$ straight chain alkyl, (1-methyl)butyl, —$CH_2C_6H_5$, butyroyl, (1-hydroxy)butyl, and (1-chloro)butyl;

$R_{16}$ and $R_{17}$ are —H; and m is an integer ranging from 1 to 5.

54. The method of claim 44, wherein, in the compound of Formula (I):

each $R_1$ is independently selected from the group consisting of —H, and —$CH_3$;

$R_2$ is selected from the group consisting of —$CH_3$, and —$CH_2C_6H_5$;

$R_3$ is selected from the group consisting of —H, $C_1$–$C_{10}$ straight chain alkyl, —$CH_2C_6H_5$, butyroyl, (1-hydroxy)butyl), and (1-chloro)butyl;

$R_{16}$ and $R_{17}$ are —H; and m is 2, 4 or 5.

55. The method of claim 44, wherein, in the compound of Formula (I):

each $R_1$ is independently selected from the group consisting of —H, and —$CH_3$;

$R_2$ is selected from the group consisting of —$CH_3$, —$CH_2CH_3$, —$(CH_2)_2CH_3$, and —$CH_2C_6H_5$;

$R_3$ is selected from the group consisting of —H, $C_1$–$C_{10}$ straight chain alkyl, —$CH_2C_6H_5$, butyroyl, (1-hydxoxy)butyl, and (1-chloro)butyl;

m is an integer ranging from 1 to 5;

when m is 3 and $R_2$ is —$CH_3$, then $R_{16}$ is selected from the group consisting of —H, and —$CH_3$ and $R_{17}$ is selected from the group consisting of —H, and —COOEt; and when m is other than 3 and $R_2$ is other than —$CH_3$ or —$CH_2CH_3$, then $R_{16}$ and $R_{17}$ are —H only;

with the proviso that the compound of Formula (I) is not: metacycloprodigiosin.

56. The method of claim 44, wherein the compound of Formula I is selected from the group consisting of:

butyl-meta-cycloheptylprodiginine;

2-Ethyl-11-((3-methoxy-5-(1H-pyrrol-2-yl)-2H-pyrrol-2-ylidene)methyl)-10-azabicyclo[7.2.1]dodeca-9(12),11-diene;

11-((3-methoxy-5-(1H-pyrrol-2-yl)-2H-pyrrol-2-ylidene)methyl)-10-azabicyclo[7.2.1]dodeca-9(12),11-diene;

2-Methyl-11-((3-methoxy-5-(1H-pyrrol-2-yl)-2H-pyrrol-2-ylidene)methyl)-10-azabicyclo[7.2.1]dodeca-9(12),11-diene;

2-n-Propyl-11-((3-methoxy-5-(1H-pyrrol-2-yl)-2H-pyrrol-2-ylidene)methyl)-10-azabicyclo[7.2.1]dodeca-9(12),11-diene;

2-n-Pentyl-11-((3-methoxy-5-(1H-pyrrol-2-yl)-2H-pyrrol-2-ylidene)methyl)-10-azabicyclo[7.2.1]dodeca-9(12),11-diene;

2-Benzyl-11-((3-methoxy-5-(1H-pyrrol-2-yl)-2H-pyrrol-2-ylidene)methyl)-10-azabicyclo[7.2.1]dodeca-9(12),11-diene;

(S)-2-n-Pentyl-11-((3-methoxy-5-(1H-pyrrol-2-yl)-2H-pyrrol-2-ylidene)methyl)-10-azabicyclo[7.2.1]dodeca-9(12),11-diene;

(R)-2-n-Pentyl-11-((3-methoxy-5-(1H-pyrrol-2-yl)-2H-pyrrol-2-ylidene)methyl)-10-azabicyclo[7.2.1]dodeca-9(12),11-diene;

(S)-2-n-Butyl-11-((3-methoxy-5-(1H-pyrrol-2-yl)-2H-pyrrol-2-ylidene)methyl)-10-azabicyclo[7.2.1]dodeca-9(12),11-diene;

(R)-2-n-Butyl-11-((3-methoxy-5-(1H-pyrrol-2-yl)-2H-pyrrol-2-ylidene)methyl)-10-azabicyclo[7.2.1]dodeca-9(12),11-diene;

(S)-2-Ethyl-11-((3-methoxy-5-(1H-pyrrol-2-yl)-2H-pyrrol-2-ylidene)methyl)-10-azabicyclo[7.2.1]dodeca-9(12),11-diene;

(R)-2-Ethyl-11-((3-methoxy-5-(1H-pyrrol-2-yl)-2H-pyrrol-2-ylidene)methyl)-10-azabicyclo[7.2.1]dodeca-9(12),11-diene;

(S)-2-Methyl-11-((3-methoxy-5-(1H-pyrrol-2-yl)-2H-pyrrol-2-ylidene)methyl)-10-azabicyclo[7.2.1]dodeca-9(12),11-diene;

(R)-2-Methyl-11-((3-methoxy-5-(1H-pyrrol-2-yl)-2H-pyrrol-2-ylidene)methyl)-10-azabicyclo[7.2.1]dodeca-9(12),11-diene;

(S)-2-n-Propyl-11-((3-methoxy-5-(1H-pyrrol-2-yl)-2H-pyrrol-2-ylidene)methyl)-10-azabicyclo[7.2.1]dodeca-9(12),11-diene;

(R)-2-n-Propyl-11-((3-methoxy-5-(1H-pyrrol-2-yl)-2H-pyrrol-2-ylidene)methyl)-10-azabicyclo[7.2.1]dodeca-9(12),11-diene;

2-Methyl-12-((3-methoxy-5-(1H-pyrrol-2-yl)-2H-pyrrol-2-ylidene)methyl)-11-azabicyclo[8.2.1]trideca-10(13),12-diene;

2-Ethyl-12-((3-methoxy-5-(1H-pyrrol-2-yl)-2H-pyrrol-2-ylidene)methyl)-11-azabicyclo[8.2.1]trideca-10(13),12-diene;

2-n-Propyl-12-((3-methoxy-5-(1H-pyrrol-2-yl)-2H-pyrrol-2-ylidene)methyl)-11-azabicyclo[8.2.1]trideca-10(13),12-diene;

2-n-Butyl-12-((3-methoxy-5-(1H-pyrrol-2-yl)-2H-pyrrol-2-ylidene)methyl)-11-azabicyclo[8.2.1]trideca-10(13),12-diene;

2-n-Pentyl-12-((3-methoxy-5-(1H-pyrrol-2-yl)-2H-pyrrol-2-ylidene)methyl)-11-azabicyclo[8.2.1]trideca-10(13),12-diene;

12-((3-methoxy-5-(1H-pyrrol-2-yl)-2H-pyrrol-2-ylidene)methyl)-11-azabicyclo[8.2.1]trideca-10(13),12-diene;

2-Methyl-13-((3-methoxy-5-(1H-pyrrol-2-yl)-2H-pyrrol-2-ylidene)methyl)-12-azabicyclo[9.2.1]tetradeca-11(14),13-diene;

13-((3-methoxy-5-(1H-pyrrol-2-yl)-2H-pyrrol-2-ylidene)methyl)-12-azabicyclo[9.2.1]tetradeca-11(14),13-diene;

2-Ethyl-12-methyl-13-((3-methoxy-5-(1-methyl-1H-pyrrol-2-yl)-2H-pyrrol-2-ylidene)methyl)-12-azabicyclo[9.2.1]tetradeca-11(14),13-diene;

2-Ethyl-12-methyl-13-((3-methoxy-5-(1H-pyrrol-2-yl)-2H-pyrrol-2-ylidene)methyl)-12-azabicyclo[9.2.1]tetradeca-11(14),13-diene;

2-n-Propyl-13-((3-methoxy-5-(1H-pyrrol-2-yl)-2H-pyrrol-2-ylidene)methyl)-12-azabicyclo[9.2.1]tetradeca-11(14),13-diene;

2-n-Butyl-13-((3-methoxy-5-(1H-pyrrol-2-yl)-2H-pyrrol-2-ylidene)methyl)-12-azabicyclo[9.2.1]tetradeca-11(14),13-diene;

14-((3-methoxy-5-(1H-pyrrol-2-yl)-2H-pyrrol-2-ylidene)methyl)-13-azabicyclo[10.2.1]pentadeca-12(15),14-diene;

2-Butyl-11-((3-methoxy-5-(1-methyl-1H-pyrrol-2-yl)-2H-pyrrol-2-ylidene)methyl)-10-azabicyclo[7.2.1]dodeca-9(12),11-diene;

2-Butyl-11-((3-methoxy-5-(1-methyl-1H-pyrrol-2-yl)-2H-pyrrol-2-ylidene)methyl)-10-methyl-10-azabicyclo[7.2.1]dodeca-9(12),11-diene;

2-Butyl-11-((3-methoxy-5-(1H-pyrrol-2-yl)-2H-pyrrol-2-ylidene)methyl)-10-methyl-10-azabicyclo[7.2.1]dodeca-9(12),11-diene;

2-Ethyl-11-((3-benzyloxy-5-(1H-pyrrol-2-yl)-2H-pyrrol-2-ylidene)methyl)-10-azabicyclo[7.2.1]dodeca-9(12),11-diene;

2-Butyl-11-((3-hydroxy-5-(1H-pyrrol-2-yl)-2H-pyrrol-2-ylidene)methyl)-10-azabicyclo[7.2.1]dodeca-9(12),11-diene;

2-Butyl-11-((3-benzyloxy-5-(1H-pyrrol-2-yl)-2H-pyrrol-2-ylidene)methyl)-10-azabicyclo[7.2.1]dodeca-9(12),11-diene;

11-((3-Benzyloxy-5-(1H-pyrrol-2-yl)-2H-pyrrol-2-ylidene)methyl)-10-azabicyclo[7.2.1]dodeca-9(12),11-diene;

2-Methyl-11-((3-benzyloxy-5-(1H-pyrrol-2-yl)-2H-pyrrol-2-ylidene)methyl)-10-azabicyclo[7.2.1]dodeca-9(12),11-diene;

2-n-Propyl-11-((3-benzyloxy-5-(1H-pyrrol-2-yl)-2H-pyrrol-2-ylidene)methyl)-10-azabicyclo[7.2.1]dodeca-9(12),11-diene;

2-n-Pentyl-11-((3-benzyloxy-5-(1H-pyrrol-2-yl)-2H-pyrrol-2-ylidene)methyl)-10-azabicyclo[7.2.1]dodeca-9(12),11-diene;

2-Benzyl-11-((3-benzyloxy-5-(1H-pyrrol-2-yl)-2H-pyrrol-2-ylidene)methyl)-10-azabicyclo[7.2.1]dodeca-9(12),11-diene;

2-Methyl-14-((3-methoxy-5-(1H-pyrrol-2-yl)-2H-pyrrol-2-ylidene)methyl)-13-azabicyclo[10.2.1]pentadeca-12(15),14-diene;

15-((3-methoxy-5-(1H-pyrrol-2-yl)-2H-pyrrol-2-ylidene)methyl)-14-azabicyclo[11.2.1]hexadeca-13(16),15-diene;

2-Methyl-15-((3-methoxy-5-(1H-pyrrol-2-yl)-2H-pyrrol-2-ylidene)methyl)-14-azabicyclo[11.2.1]hexadeca-13(16),15-diene;

2-(2-Hydroxy-n-butyl)-11-((3-methoxy-5-(1H-pyrrol-2-yl)-2H-pyrrol-2-ylidene)methyl)-10-azabicyclo[7.2.1]dodeca-9(12),11-diene;

2-(2-chloro-n-butyl)-11-((3-methoxy-5-(1H-pyrrol-2-yl)-2H-pyrrol-2-ylidene)methyl)-10-azabicyclo[7.2.1]dodeca-9(12),11-diene;

2-Butyl-11-((3-ethoxy-5-(1H-pyrrol-2-yl)-2H-pyrrol-2-ylidene)methyl)-10-azabicyclo[7.2.1]dodeca-9(12),11-diene;

11-((3-Ethoxy-5-(1H-pyrrol-2-yl)-2H-pyrrol-2-ylidene)methyl)-10-azabicyclo[7.2.1]dodeca-9(12),11-diene;

2-Methyl-11-((3-ethoxy-5-(1H-pyrrol-2-yl)-2H-pyrrol-2-ylidene)methyl)-10-azabicyclo[7.2.1]dodeca-9(12),11-diene;

2-n-Propyl-11-((3-ethoxy-5-(1H-pyrrol-2-yl)-2H-pyrrol-2-ylidene)methyl)-10-azabicyclo[7.2.1]dodeca-9(12),11-diene;

2-n-Pentyl-11-((3-ethoxy-5-(1H-pyrrol-2-yl)-2H-pyrrol-2-ylidene)methyl)-10-azabicyclo[7.2.1]dodeca-9(12),11-diene;

2-Benzyl-11-((3-ethoxy-5-(1H-pyrrol-2-yl)-2H-pyrrol-2-ylidene)methyl)-10-azabicyclo[7.2.1]dodeca-9(12),11-diene;

2-Ethyl-11-((3-ethoxy-5-(1H-pyrrol-2-yl)-2H-pyrrol-2-ylidene)methyl)-10-azabicyclo[7.2.1]dodeca-9(12),11-diene;

2-Methyl-13-((3-benzyloxy-5-(1H-pyrrol-2-yl)-2H-pyrrol-2-ylidene)methyl)-12-azabicyclo[9.2.1]tetradeca-11(14),13-diene;

13-((3-Benzyloxy-5-(1H-pyrrol-2-yl)-2H-pyrrol-2-ylidene)methyl)-12-azabicyclo[9.2.1]tetradeca-11(14),13-diene;

2-Ethyl-12-methyl-13-((3-benzyloxy-5-(1-methyl-1H-pyrrol-2-yl)-2H-pyrrol-2-ylidene)methyl)-12-azabicyclo[9.2.1]tetradeca-11(14),13-diene;

2-Ethyl-12-methyl-13-((3-benzyloxy-5-(1H-pyrrol-2-yl)-2H-pyrrol-2-ylidene)methyl)-12-azabicyclo[9.2.1]tetradeca-11(14),13-diene;

2-n-Propyl-13-((3-benzyloxy-5-(1H-pyrrol-2-yl)-2H-pyrrol-2-ylidene)methyl)-12-azabicyclo[9.2.1]tetradeca-11(14),13-diene;

2-n-Butyl-13-((3-benzyloxy-5-(1H-pyrrol-2-yl)-2H-pyrrol-2-ylidene)methyl)-12-azabicyclo[9.2.1]tetradeca-11-(14),13-diene;

and a pharmaceutically acceptable salt thereof.

57. The method of claim 45, wherein, in the compound of Formula (I):

each $R_1$ is independently selected from the group consisting of —H —$CH_3$—$CH_2CH_3$, —$CH_2C_6H_5$, —$C(O)OC(CH_3)_3$, —$C(O)OCH_2C_6H_5$, and —$C(O)CH_3$;

$R_2$ is selected from the group consisting of —H, $C_1$–$C_{12}$ straight chain alkyl, —$CH_2C_6H_5$, —$SiR_{10}R_{11}R_{12}$, —$C(O)CH_3$, —$C(O)C_6H_5$, -2-tetrahydropyranyl, —$OCH_2OCH_3$, and —$C(O)OCH_2CCl_3$;

$R_3$ is selected from the group consisting of —H, $C_1$–$C_{12}$ straight chain alkyl, —$CH(R_{14})(R_{15})$ wherein $R_{14}$ and $R_{15}$ are independently $C_1$–$C_{12}$ straight chain alkyl, —C(O)C$_1$–C$_9$ straight chain alkyl, —CH(OH)C$_1$–C$_9$ straight chain alkyl, —CH(Cl)C$_1$–C$_9$ straight chain alkyl, -(2-pyridyl)methyl, -(3-pyridyl)methyl, -(4-pyridyl)methyl, and —CH$_2$C$_6$H$_5$, the —CH$_2$C$_6$H$_5$ being unsubstituted or substituted on phenyl with one cyano or one or more halo, methoxyl, or trifluoromethyl groups;

R$_{10}$ is selected from the group consisting of C$_1$–C$_4$ straight or branched chain alkyl and —C$_6$H$_5$;

R$_{11}$ and R$_{12}$ are independently C$_1$–C$_3$ straight or branched chain alkyl; and R$_{16}$ and R$_{17}$ are —H; and m is an integer ranging from 1 to 5;

with the proviso that the compound of Formula (I) is not: metacycloprodigiosin.

58. The method of claim 45, wherein the compound of Formula (I) is butyl-meta-cycloheptylprodiginine or a pharmaceutically acceptable salt thereof.

59. The method of claim 45, wherein, in the compound of Formula (I):

each R$_1$ is independently selected from the group consisting of —H, and —CH$_3$;

R$_2$ is selected from the group consisting of —CH$_3$, —CH$_2$CH$_3$, and —CH$_2$C$_6$H$_5$;

R$_3$ is selected from the group consisting of —H, C$_1$–C$_{10}$ straight chain alkyl, (1-methyl)butyl, —CH$_2$C$_6$H$_5$, butyroyl, (1-hydroxy)butyl, and (1-chloro)butyl;

R$_{16}$ and R$_{17}$ are —H; and m is an integer ranging from 1 to 5;

with the proviso that the compound of Formula (I) is not: metacycloprodigiosin.

60. The method of claim 45, wherein, in the compound of Formula (I):

each R$_1$ is —H;

R$_2$ is selected from the group consisting of —CH$_3$, and —CH$_2$C$_6$H$_5$;

R$_3$ is selected from the group consisting of —H, C$_1$–C$_{10}$ straight chain alkyl, and —CH$_2$C$_6$H$_5$;

R$_{16}$ and R$_{17}$ are —H; and m is an integer ranging from 1 to 5;

with the proviso that the compound of Formula (I) is not: metacycloprodigiosin.

61. The method of claim 45, wherein, in the compound of Formula (I):

each R$_1$ is independently selected from the group consisting of —H, and —CH$_3$;

R$_2$ is selected from the group consisting of —CH$_3$, and —CH$_2$C$_6$H$_5$;

R$_3$ is selected from the group consisting of —H, C$_1$–C$_{10}$ straight chain alkyl, —CH$_2$C$_6$H$_5$, butyroyl, (1-hydroxy)butyl, and (1-chloro)butyl;

R$_{16}$ and R$_{17}$ are —H; and m is an integer ranging from 1 to 5.

with the proviso that when m is 3, R$_3$ is not —CH$_2$CH$_3$ and when m is 1, R$_3$ is not —(CH$_2$)$_3$CH$_3$.

62. The method of claim 45, wherein in the compound of Formula (I):

each R$_1$ is independently selected from the group consisting of —H, and —CH$_3$;

R$_2$ is selected from the group consisting of —CH$_3$, and —CH$_2$C$_6$H$_5$;

R$_3$ is selected from the group consisting of —H, C$_1$–C$_{10}$ straight chain alkyl, (1-methyl)butyl, —CH$_2$C$_6$H$_5$, butyroyl, (1-hydroxy)butyl, and (1-chloro)butyl;

R$_{16}$ and R$_{17}$ are —H; and m is an integer ranging from 1 to 5.

63. The method of claim 45, wherein, in the compound of Formula (I):

each R$_1$ is independently selected from the group consisting of —H, and —CH$_3$;

R$_2$ is selected from the group consisting of —CH$_3$, and —CH$_2$C$_6$H$_5$;

R$_3$ is selected from the group consisting of —H, C$_1$–C$_{10}$ straight chain alkyl, —CH$_2$C$_6$H$_5$, butyroyl, (1-hydroxy)butyl, and (1-chloro)butyl;

R$_{16}$ and R$_{17}$ are —H; and m is 2, 4 or 5.

64. The method of claim 45, wherein, in the compound of Formula (I):

each R$_1$ is independently selected from the group consisting of —H, and —CH$_3$;

R$_2$ is selected from the group consisting of —CH$_3$, —CH$_2$CH$_3$, —(CH$_2$)$_2$CH$_3$, and —CH$_2$C$_6$H$_5$;

R$_3$ is selected from the group consisting of —H, C$_1$–C$_{10}$ straight chain alkyl, —CH$_2$C$_6$H$_5$, butyroyl, (1-hydxoxy)butyl, and (1-chloro)butyl;

m is an integer ranging from 1 to 5;

when m is 3 and R$_2$ is —CH$_3$, then R$_{16}$ is selected from the group consisting of —H, and —CH$_3$ and R$_{17}$ is selected from the group consisting of —H, and —COGEt; and when m is other than 3 and R$_2$ is other than —CH$_3$ or —CH$_2$CH$_3$, then R$_{16}$ and R$_{17}$ are —H only;

with the proviso that the compound of Formula (I) is not: metacycloprodigiosin.

65. The method of claim 45, wherein the compound of Formula I is selected from the group consisting of:

butyl-meta-cycloheptylprodiginine;

2-Ethyl-11-((3-methoxy-5-(1H-pyrrol-2-yl)-2H-pyrrol-2-ylidene)methyl)-10-azabicyclo[7.2.1]dodeca-9(12),11-diene;

11-((3-Methoxy-5-(1H-pyrrol-2-yl)-2H-pyrrol-2-ylidene)methyl)-10-azabicyclo[7.2.1]dodeca-9(12),11-diene;

2-Methyl-11-((3-methoxy-5-(1H-pyrrol-2-yl)-2H-pyrrol-2-ylidene)methyl)-10-azabicyclo[7.2.1]dodeca-9(12),11-diene;

2-n-Propyl-11-((3-methoxy-5-(1H-pyrrol-2-yl)-2H-pyrrol-2-ylidene)methyl)-10-azabicyclo[7.2.1]dodeca-9(12),11-diene;

2-n-Pentyl-11-((3-methoxy-5-(1H-pyrrol-2-yl)-2H-pyrrol-2-ylidene)methyl)-10-azabicyclo[7.2.1]dodeca-9(12),11-diene;

2-Benzyl-11-((3-methoxy-5-(1H-pyrrol-2-yl)-2H-pyrrol-2-ylidene)methyl)-10-azabicyclo[7.2.1]dodeca-9(12),11-diene;

(S)-2-n-Pentyl-11-((3-methoxy-5-(1H-pyrrol-2-yl)-2H-pyrrol-2-ylidene)methyl)-10-azabicyclo[7.2.1]dodeca-9(12),11-diene;

(R)-2-n-Pentyl-11-((3-methoxy-5-(1H-pyrrol-2-yl)-2H-pyrrol-2-ylidene)methyl)-10-azabicyclo[7.2.1]dodeca-9(12),11-diene;

(S)-2-n-Butyl-11-((3-methoxy-5-(1H-pyrrol-2-yl)-2H-pyrrol-2-ylidene)methyl)-10-azabicyclo[7.2.1]dodeca-9(12),11-diene;

(R)-2-n-Butyl-11-((3-methoxy-5-(1H-pyrrol-2-yl)-2H-pyrrol-2-ylidene)methyl)-10-azabicyclo[7.2.1]dodeca-9(12),11-diene;

(S)-2-Ethyl-11-((3-methoxy-5-(1H-pyrrol-2-yl)-2H-pyrrol-2-ylidene)methyl)-10-azabicyclo[7.2.1]dodeca-9(12),11-diene;

(R)-2-Ethyl-11-((3-methoxy-5-(1H-pyrrol-2-yl)-2H-pyrrol-2-ylidene)methyl)-10-azabicyclo[7.2.1]dodeca-9(12),11-diene;

(S)-2-Methyl-11-((3-methoxy-5-(1H-pyrrol-2-yl)-2H-pyrrol-2-ylidene)methyl)-10-azabicyclo[7.2.1]dodeca-9(12),11-diene;

(R)-2-Methyl-11-((3-methoxy-5-(1H-pyrrol-2-yl)-2H-pyrrol-2-ylidene)methyl)-10-azabicyclo[7.2.1]dodeca-9(12),11-diene;

(S)-2-n-Propyl-11-((3-methoxy-5-(1H-pyrrol-2-yl)-2H-pyrrol-2-ylidene)methyl)-10-azabicyclo[7.2.1]dodeca-9(12),11-diene;

(R)-2-n-Propyl-11-((3-methoxy-5-(1 H-pyrrol-2-yl)-2H-pyrrol-2-ylidene)methyl)-10-azabicyclo[7.2.1]dodeca-9(12),11-diene;

2-Methyl-12-((3-methoxy-5-(1H-pyrrol-2-yl)-2H-pyrrol-2-ylidene)methyl)-11-azabicyclo[8.2.1]trideca-10(13),12-diene;

2-Ethyl-12-((3-methoxy-5-(1H-pyrrol-2-yl)-2H-pyrrol-2-ylidene)methyl)-11-azabicyclo[8.2.1]trideca-10(13),12-diene;

2-n-Propyl-12-((3-methoxy-5-(1H-pyrrol-2-yl)-2H-pyrrol-2-ylidene)methyl)-11-azabicyclo[8.2.1]trideca-10(13),12-diene;

2-n-Butyl-12-((3-methoxy-5-(1H-pyrrol-2-yl)-2H-pyrrol-2-ylidene)methyl)-11-azabicyclo[8.2.1]trideca-10(13),12-diene;

2-n-Pentyl-12-((3-methoxy-5-(1H-pyrrol-2-yl)-2H-pyrrol-2-ylidene)methyl)-11-azabicyclo[8.2.1]trideca-10(13),12-diene;

12-((3-Methoxy-5-(1H-pyrrol-2-yl)-2H-pyrrol-2-ylidene)methyl)-11-azabicyclo[8.2.1]trideca-10(13),12-diene;

2-Methyl-13-((3-methoxy-5-(1H-pyrrol-2-yl)-2H-pyrrol-2-ylidene)methyl)-12-azabicyclo[9.2.1]tetradeca-11(14),13-diene;

13-((3-Methoxy-5-(1H-pyrrol-2-yl)-2H-pyrrol-2-ylidene)methyl)-12-azabicyclo[9.2.1]tetradeca-11(14),13-diene;

2-Ethyl-12-methyl-13-((3-methoxy-5-(1-methyl-1H-pyrrol-2-yl)-2H-pyrrol-2-ylidene)methyl)-12-azabicyclo[9.2.1]tetradeca-11(14),13-diene;

2-Ethyl-12-methyl-13-((3-methoxy-5-(1H-pyrrol-2-yl)-2H-pyrrol-2-ylidene)methyl)-12-azabicyclo[9.2.1]tetradeca-11(14),13-diene;

2-n-Propyl-13-((3-methoxy-5-(1H-pyrrol-2-yl)-2H-pyrrol-2-ylidene)methyl)-12-azabicyclo[9.2.1]tetradeca-11(14),13-diene;

2-n-Butyl-13-((3-methoxy-5-(1H-pyrrol-2-yl)-2H-pyrrol-2-ylidene)methyl)-12-azabicyclo[9.2.1]tetradeca-11(14),13-diene;

14-((3-Methoxy-5-(1H-pyrrol-2-yl)-2H-pyrrol-2-ylidene)methyl)-13-azabicyclo[10.2.1]pentadeca-12(15),14-diene;

2-Butyl-11-((3-methoxy-5-(1-methyl-1H-pyrrol-2-yl)-2H-pyrrol-2-ylidene)methyl)-10-azabicyclo[7.2.1]dodeca-9(12),11-diene;

2-Butyl-11-((3-methoxy-5-(1-methyl-1H-pyrrol-2-yl)-2H-pyrrol-2-ylidene)methyl)-10-methyl-10-azabicyclo[7.2.1]dodeca-9(12),11-diene;

2-Butyl-11-((3-methoxy-5-(1H-pyrrol-2-yl)-2H-pyrrol-2-ylidene)methyl)-10-methyl-10-azabicyclo[7.2.1]dodeca-9(12),11-diene;

2-Ethyl-11-((3-benzyloxy-5-(1H-pyrrol-2-yl)-2H-pyrrol-2-ylidene)methyl)-10-azabicyclo[7.2.1]dodeca-9(12),11-diene;

2-Butyl-11-((3-hydroxy-5-(1H-pyrrol-2-yl)-2H-pyrrol-2-ylidene)methyl)-10-azabicyclo[7.2.1]dodeca-9(12),11-diene;

2-Butyl-11-((3-benzyloxy-5-(1H-pyrrol-2-yl)-2H-pyrrol-2-ylidene)methyl)-10-azabicyclo[7.2.1]dodeca-9(12),11-diene;

11-((3-Benzyloxy-5-(1H-pyrrol-2-yl)-2H-pyrrol-2-ylidene)methyl)-10-azabicyclo[7.2.1]dodeca-9(12),11-diene;

2-Methyl-11-((3-benzyloxy-5-(1H-pyrrol-2-yl)-2H-pyrrol-2-ylidene)methyl)-10-azabicyclo[7.2.1]dodeca-9(12),11-diene;

2-n-Propyl-11-((3-benzyloxy-5-(1H-pyrrol-2-yl)-2H-pyrrol-2-ylidene)methyl)-10-azabicyclo[7.2.1]dodeca-9(12),11-diene;

2-n-Pentyl-11-((3-benzyloxy-5-(1H-pyrrol-2-yl)-2H-pyrrol-2-ylidene)methyl)-10-azabicyclo[7.2.1]dodeca-9(12),11-diene;

2-Benzyl-11-((3-benzyloxy-5-(1H-pyrrol-2-yl)-2H-pyrrol-2-ylidene)methyl)-10-azabicyclo[7.2.1]dodeca-9(12),11-diene;

2-Methyl-14-((3-methoxy-5-(1H-pyrrol-2-yl)-2H-pyrrol-2-ylidene)methyl)-13-azabicyclo[10.2.1]pentadeca-12(15),14-diene;

15-((3-Methoxy-5-(1H-pyrrol-2-yl)-2H-pyrrol-2-ylidene)methyl)-14-azabicyclo[11.2.1]hexadeca-13(16),15-diene;

2-Methyl-15-((3-methoxy-5-(1H-pyrrol-2-yl)-2H-pyrrol-2-ylidene)methyl)-14-azabicyclo[11.2.1]hexadeca-13(16),15-diene;

2-(2-Hydroxy-n-butyl)-11-((3-methoxy-5-(1H-pyrrol-2-yl)-2H-pyrrol-2-ylidene)methyl)-10-azabicyclo[7.2.1]dodeca-9(12),11-diene;

2-(2-chloro-n-butyl)-11-((3-methoxy-5-(1H-pyrrol-2-yl)-2H-pyrrol-2-ylidene)methyl)-10-azabicyclo[7.2.1]dodeca-9(12),11-diene;

2-Butyl-11-((3-ethoxy-5-(1H-pyrrol-2-yl)-2H-pyrrol-2-ylidene)methyl)-10-azabicyclo[7.2.1]dodeca-9(12),11-diene;

11-((3-Ethoxy-5-(1H-pyrrol-2-yl)-2H-pyrrol-2-ylidene)methyl)-10-azabicyclo[7.2.1]dodeca-9(12),11-diene;

2-Methyl-11-((3-ethoxy-5-(1H-pyrrol-2-yl)-2H-pyrrol-2-ylidene)methyl)-10-azabicyclo[7.2.1]dodeca-9(12),11-diene;

2-n-Propyl-11-((3-ethoxy-5-(1H-pyrrol-2-yl)-2H-pyrrol-2-ylidene)methyl)-10-azabicyclo[7.2.1]dodeca-9(12),11-diene;

2-n-Pentyl-11-((3-ethoxy-5-(1H-pyrrol-2-yl)-2H-pyrrol-2-ylidene)methyl)-10-azabicyclo[7.2.1]dodeca-9(12),11-diene;

2-Benzyl-11-((3-ethoxy-5-(1H-pyrrol-2-yl)-2H-pyrrol-2-ylidene)methyl)-10-azabicyclo[7.2.1]dodeca-9(12),11-diene;

2-Ethyl-11-((3-ethoxy-5-(1H-pyrrol-2-yl)-2H-pyrrol-2-ylidene)methyl)-10-azabicyclo[7.2.1]dodeca-9(12),11-diene;

2-Methyl-13-((3-benzyloxy-5-(1H-pyrrol-2-yl)-2H-pyrrol-2-ylidene)methyl)-12-azabicyclo[9.2.1]tetradeca-11(14),13-diene;

13-((3-Benzyloxy-5-(1H-pyrrol-2-yl)-2H-pyrrol-2-ylidene)methyl)-12-azabicyclo[9.2.1]tetradeca-11(14),13-diene;

2-Ethyl-12-methyl-13-((3-benzyloxy-5-(1-methyl-1H-pyrrol-2-yl)-2H-pyrrol-2-ylidene)methyl)-12-azabicyclo[9.2.1]tetradeca-11(14),13-diene;

2-Ethyl-12-methyl-13-((3-benzyloxy-5-(1H-pyrrol-2-yl)-2H-pyrrol-2-ylidene)methyl)-12-azabicyclo[9.2.1]tetradeca-11(14),13-diene;

2-n-Propyl-13-((3-benzyloxy-5-(1H-pyrrol-2-yl)-2H-pyrrol-2-ylidene)methyl)-12-azabicyclo[9.2.1]tetradeca-11(14),13-diene; and 2-n-Butyl-13-((3-benzyloxy-5-(1H-pyrrol-2-yl)-2H-pyrrol-2-ylidene)methyl)-12-azabicyclo[9.2.1]tetradeca-11(14),13-diene;

and a pharmaceutically acceptable salt thereof.

66. The method of claim 47, wherein the compound of Formula (I) is butyl-meta-cycloheptylprodiginine or a pharmaceutically acceptable salt thereof.

67. The method of claim 46, wherein the compound of Formula (I) is butyl-meta-cycloheptylprodiginine or a pharmaceutically acceptable salt thereof.

68. The method of claim 47, wherein the compound of Formula (I) is butyl-meta-cycloheptylprodiginine or a pharmaceutically acceptable salt thereof.

69. The method of claim 46, wherein the compound of Formula (I) is butyl-meta-cycloheptylprodiginine or a pharmaceutically acceptable salt thereof.

70. The method of claim 46, wherein, in the compound of Formula (I):

each $R_1$ is independently selected from the group consisting of —H, —$CH_3$, —$CH_2CH_3$, —$CH_2C_6H_5$, —C(O)OC($CH_3$)$_3$, —C(O)O$CH_2C_6H_5$, and —C(O)$CH_3$;

$R_2$ is selected from the group consisting of —H, $C_1$–$C_{12}$ straight chain alkyl, —$CH_2C_6H_5$, —$SiR_{10}R_{11}R_{12}$, —C(O)$CH_3$, —C(O)$C_6H_5$, -2-tetrahydropyranyl, —$OCH_2OCH_3$, and —C(O)O$CH_2CCl_3$;

$R_3$ is selected from the group consisting of —H, $C_1$–$C_{12}$ straight chain alkyl, —CH($R_{14}$)($R_{15}$) wherein $R_{14}$ and $R_{15}$ are independently $C_1$–$C_{12}$ straight chain alkyl, —C(O)$C_1$–$C_9$ straight chain alkyl, —CH(OH)$C_1$–$C_9$ straight chain alkyl, —CH(Cl)$C_1$–$C_9$ straight chain alkyl, -(2-pyridyl)methyl, -(3-pyridyl)methyl, -(4-pyridyl)methyl, and —$CH_2C_6H_5$, the —$CH_2C_6H_5$ being unsubstituted or substituted on phenyl with one cyano or one or more halo, methoxyl, or trifluoromethyl groups;

$R_{10}$ is selected from the group consisting of $C_1$–$C_4$ straight or branched chain alkyl and —$C_6H_5$;

$R_{11}$ and $R_{12}$ are independently $C_1$–$C_3$ straight or branched chain alkyl; and $R_{16}$ and $R_{17}$ are —H; and m is an integer ranging from 1 to 5;

with the proviso that the compound of Formula (I) is not: metacycloprodigiosin.

71. The method of claim 46, wherein, in the compound of Formula (I):

each $R_1$ is independently selected from the group consisting of —H, and —$CH_3$;

$R_2$ is selected from the group consisting of —$CH_3$, —$CH_2CH_3$, and —$CH_2C_6H_5$;

$R_3$ is selected from the group consisting of —H, $C_1$–$C_{10}$ straight chain alkyl, (1-methyl)butyl, —$CH_2C_6H_5$, butyroyl, (1-hydroxy)butyl, and (1-chloro)butyl;

m is an integer ranging from 1 to 5;

with the proviso that the compound of Formula (I) is not: metacycloprodigiosin.

72. The method of claim 46, wherein, in the compound of Formula (I):

each $R_1$ is —H;

$R_2$ is selected from the group consisting of —$CH_3$, and —$CH_2C_6H_5$;

$R_3$ is selected from the group consisting of —H, $C_1$–$C_{10}$ straight chain alkyl, and —$CH_2C_6H_5$;

$R_{16}$ and $R_{17}$ are —H; and m is an integer ranging from 1 to 5;

with the proviso that the compound of Formula (I) is not: metacycloprodigiosin.

73. The method of claim 46, wherein, in the compound of Formula (I):

each $R_1$ is independently selected from the group consisting of —H, and —$CH_3$;

$R_2$ is selected from the group consisting of —$CH_3$, and —$CH_2C_6H_5$;

$R_3$ is selected from the group consisting of —H, $C_1$–$C_{10}$ straight chain alkyl, —$CH_2C_6H_5$, butyroyl, (1-hydroxy)butyl, and (1-chloro)butyl;

$R_{16}$ and $R_{17}$ are —H; and m is an integer ranging from 1 to 5;

with the proviso that when m is 3, $R_3$ is not —$CH_2CH_3$ and when m is 1 $R_3$ is not —($CH_2$)$_3CH_3$.

74. The method of claim 46, wherein, in the compound of Formula (I):

each $R_1$ is independently selected from the group consisting of —H, and —$CH_3$;

$R_2$ is selected from the group consisting of —$CH_3$, and —$CH_2C_6H_5$;

$R_3$ is selected from the group consisting of —H, $C_1$–$C_{10}$ straight chain alkyl, (1-methyl)butyl, —$CH_2C_6H_5$, butyrol, (hydroxy)butyl, and (1-chloro)butyl;

$R_{16}$ and $R_{17}$ are —H; and m is an integer ranging from 1 to 5.

75. The method of claim 46, wherein, in the compound of Formula (I):

each $R_1$ is independently selected from the group consisting of —H, and —$CH_3$;

$R_2$ is selected from the group consisting of —$CH_3$, and —$CH_2C_6H_5$;

$R_3$ is selected from the group consisting of —H, $C_1$–$C_{10}$ straight chain alkyl, —$CH_2C_6H_5$, butyroyl, (1-hydroxy)butyl, and (1-chloro)butyl;

$R_{16}$ and $R_{17}$ are —H; and m is 2, 4 or 5.

76. The method of claim 46, wherein, in the compound of Formula (I)

each $R_1$ is independently selected from the group consisting of —H, and —$CH_3$;

$R_2$ is selected from the group consisting of —$CH_3$, —$CH_2CH_3$, —($CH_2$)$_2CH_3$, and —$CH_2C_6H_5$;

$R_3$ is selected from the group consisting of —H, $C_1$–$C_{10}$ straight chain alkyl, —$CH_2C_6H_5$, butyroyl, (1-hydxoxy)butyl, and (1-chloro)butyl;

m is an integer ranging from 1 to 5;

when m is 3 and $R_2$ is —$CH_3$, then $R_{16}$ is selected from the group consisting of —H, and —$CH_3$ and $R_{17}$ is selected from the group consisting of —H, and —COOEt; and when m is other than 3 and $R_2$ is other than —$CH_3$ or —$CH_2CH_3$, then $R_{16}$ and $R_{17}$ are —H only;

with the proviso that the compound of Formula (I) is not: metacycloprodigiosin.

77. The method of claim 46, wherein the compound of Formula I is selected from the group consisting of:

butyl-meta-cycloheptylprodiginine;

2-Ethyl-11-((3-methoxy-5-(1H-pyrrol-2-yl)-2H-pyrrol-2-ylidene)methyl)-10-azabicyclo[7.2.1]dodeca-9(12),11-diene;

11-((3-methoxy-5-(1H-pyrrol-2-yl)-2H-pyrrol-2-ylidene)methyl)-10-azabicyclo[7.2.1]dodeca-9(12),11-diene;

2-Methyl-11-((3-methoxy-5-(1H-pyrrol-2-yl)-2H-pyrrol-2-ylidene)methyl)-10-azabicyclo[7.2.1]dodeca-9(12),11-diene;

2-n-Propyl-11-((3-methoxy-5-(1H-pyrrol-2-yl)-2H-pyrrol-2-ylidene)methyl)-10-azabicyclo[7.2.1]dodeca-9(12),11-diene;

2-n-Pentyl-11-((3-methoxy-5-(1H-pyrrol-2-yl)-2H-pyrrol-2-ylidene)methyl)-10-azabicyclo[7.2.1]dodeca-9(12),11-diene;

2-Benzyl-11-((3-methoxy-5-(1H-pyrrol-2-yl)-2H-pyrrol-2-ylidene)methyl)-10-azabicyclo[7.2.1]dodeca-9(12),11-diene;

(S)-2-n-Pentyl-11-((3-methoxy-5-(1H-pyrrol-2-yl)-2H-pyrrol-2-ylidene)methyl)-10-azabicyclo[7.2.1]dodeca-9(12),11-diene;

(R)-2-n-Pentyl-11-((3-methoxy-5-(1H-pyrrol-2-yl)-2H-pyrrol-2-ylidene)methyl)-10-azabicyclo[7.2.1]dodeca-9(12),11-diene;

(S)-2-n-Butyl-11-((3-methoxy-5-(1H-pyrrol-2-yl)-2H-pyrrol-2-ylidene)methyl)-10-azabicyclo[7.2.1]dodeca-9(12),11-diene;

(R)-2-n-Butyl-11-((3-methoxy-5-(1H-pyrrol-2-yl)-2H-pyrrol-2-ylidene)methyl)-10-azabicyclo[7.2.1]dodeca-9(12),11-diene;

(S)-2-Ethyl-11-((3-methoxy-5-(1H-pyrrol-2-yl)-2H-pyrrol-2-ylidene)methyl)-10-azabicyclo[7.2.1]dodeca-9(12),11-diene;

(R)-2-Ethyl-11-((3-methoxy-5-(1H-pyrrol-2-yl)-2H-pyrrol-2-ylidene)methyl)-10-azabicyclo[7.2.1]dodeca-9(12),11-diene;

(S)-2-Methyl-11-((3-methoxy-5-(1H-pyrrol-2-yl)-2H-pyrrol-2-ylidene)methyl)-10-azabicyclo[7.2.1]dodeca-9(12),11-diene;

(R)-2-Methyl-11-((3-methoxy-5-(1H-pyrrol-2-yl)-2H-pyrrol-2-ylidene)methyl)-10-azabicyclo[7.2.1]dodeca-9(12),11-diene;

(S)-2-n-Propyl-11-((3-methoxy-5-(1H-pyrrol-2-yl)-2H-pyrrol-2-ylidene)methyl)-10-azabicyclo[7.2.1]dodeca-9(12),11-diene;

(R)-2-n-Propyl-11-((3-methoxy-5-(1H-pyrrol-2-yl)-2H-pyrrol-2-ylidene)methyl)-10-azabicyclo[7.2.1]dodeca-9(12),11-diene;

2-Methyl-12-((3-methoxy-5-(1H-pyrrol-2-yl)-2H-pyrrol-2-ylidene)methyl)-11-azabicyclo[8.2.1]trideca-10(13),12-diene;

2-Ethyl-12-((3-methoxy-5-(1H-pyrrol-2-yl)-2H-pyrrol-2-ylidene)methyl)-11-azabicyclo[8.2.1]trideca-10(13),12-diene;

2-n-Propyl-12-((3-methoxy-5-(1H-pyrrol-2-yl)-2H-pyrrol-2-ylidene)methyl)-11-azabicyclo[8.2.1]trideca-10(13),12-diene;

2-n-Butyl-12-((3-methoxy-5-(1H-pyrrol-2-yl)-2H-pyrrol-2-ylidene)methyl)-11-azabicyclo[8.2.1]trideca-10(13),12-diene;

2-n-Pentyl-12-((3-methoxy-5-(1H-pyrrol-2-yl)-2H-pyrrol-2-ylidene)methyl)-11-azabicyclo[8.2.1]trideca-10(13),12-diene;

12-((3-Methoxy-5-(1H-pyrrol-2-yl)-2H-pyrrol-2-ylidene)methyl)-11-azabicyclo[8.2.1]trideca-10(13),12-diene;

2-Methyl-13-((3-methoxy-5-(1H-pyrrol-2-yl)-2H-pyrrol-2-ylidene)methyl)-12-azabicyclo[9.2.1]tetradeca-11(14),13-diene;

13-((3-Methoxy-5-(1H-pyrrol-2-yl)-2H-pyrrol-2-ylidene)methyl)-12-azabicyclo[9.2.1]tetradeca-11(14),13-diene;

2-Ethyl-12-methyl-13-((3-methoxy-5-(1-methyl-1H-pyrrol-2-yl)-2H-pyrrol-2-ylidene)methyl)-12-azabicyclo[9.2.1]tetradeca-11(14),13-diene;

2-Ethyl-12-methyl-13-((3-methoxy-5-(1H-pyrrol-2-yl)-2H-pyrrol-2-ylidene)methyl)-12-azabicyclo[9.2.1]tetradeca-11(14),13-diene;

2-n-Propyl-13-((3-methoxy-5-(1H-pyrrol-2-yl)-2H-pyrrol-2-ylidene)methyl)-12-azabicyclo[9.2.1]tetradeca-11(14),13-diene;

2-n-Butyl-13-((3-methoxy-5-(1H-pyrrol-2-yl)-2H-pyrrol-2-ylidene)methyl)-12-azabicyclo[9.2.1]tetradeca-11(14),13-diene;

14-((3-Methoxy-5-(1H-pyrrol-2-yl)-2H-pyrrol-2-ylidene)methyl)-13-azabicyclo[10.2.1]pentadeca-12(15),14-diene;

2-Butyl-11-((3-methoxy-5-(1-methyl-1H-pyrrol-2-yl)-2H-pyrrol-2-ylidene)methyl)-10-azabicyclo[7.2.1]dodeca-9(12),11-diene;

2-Butyl-11-((3-methoxy-5-(1-methyl-1H-pyrrol-2-yl)-2H-pyrrol-2-ylidene)methyl)-10-methyl-10-azabicyclo[7.2.1]dodeca-9(12),11-diene;

2-Butyl-11-((3-methoxy-5-(1H-pyrrol-2-yl)-2H-pyrrol-2-ylidene)methyl)-10-methyl-10-azabicyclo[7.2.1]dodeca-9(12),11-diene;

2-Ethyl-11-((3-benzyloxy-5-(1H-pyrrol-2-yl)-2H-pyrrol-2-ylidene)methyl)-10-azabicyclo[7.2.1]dodeca-9(12),11-diene;

2-Butyl-11-((3-hydroxy-5-(1H-pyrrol-2-yl)-2H-pyrrol-2-ylidene)methyl)-10-azabicyclo[7.2.1]dodeca-9(12),11-diene;

2-Butyl-11-((3-benzyloxy-5-(1H-pyrrol-2-yl)-2H-pyrrol-2-ylidene)methyl)-10-azabicyclo[7.2.1]dodeca-9(12),11-diene;

11-((3-Benzyloxy-5-(1H-pyrrol-2-yl)-2H-pyrrol-2-ylidene)methyl)-10-azabicyclo[7.2.1]dodeca-9(12),11-diene;

2-Methyl-11-((3-benzyloxy-5-(1H-pyrrol-2-yl)-2H-pyrrol-2-ylidene)methyl)-10-azabicio[7.2.1]dodeca-9(12),11-diene;

2-n-Propyl-11-((3-benzyloxy-5-(1H-pyrrol-2-yl)-2H-pyrrol-2-ylidene)methyl)-10-azabicyclo[7.2.1]dodeca-9(12),11-diene;

2-n-Pentyl-11-((3-benzyloxy-5-(1H-pyrrol-2-yl)-2H-pyrrol-2-ylidene)methyl)-10-azabicyclo[7.2.1]dodeca-9(12),11-diene;

2-Benzyl-11-((3-benzyloxy-5-(1H-pyrrol-2-yl)-2H-pyrrol-2-ylidene)methyl)-10-azabicyclo[7.2.1]dodeca-9(12),11-diene;

2-Methyl-14-((3-methoxy-5-(1H-pyrrol-2-yl)-2H-pyrrol-2-ylidene)methyl)-13-azabicyclo[10.2.1]pentadeca-12(15),14-diene;

15-((3-Methoxy-5-(1H-pyrrol-2-yl)-2H-pyrrol-2-ylidene)methyl)-14-azabicyclo[11.2.1]hexadeca-13(16),15-diene;

2-Methyl-15-((3-methoxy-5-(1H-pyrrol-2-yl)-2H-pyrrol-2-ylidene)methyl)-14-azabicyclo[11.2.1]hexadeca-13(16),15-diene;

2-(2-Hydroxy-n-butyl)-11-((3-methoxy-5-(1H-pyrrol-2-yl)-2H-pyrrol-2-ylidene)methyl)-10-azabicyclo[7.2.1]dodeca-9(12),11-diene;

2-(2-chloro-n-butyl)-11-((3-methoxy-5-(1H-pyrrol-2-yl)-2H-pyrrol-2-ylidene)methyl)-10-azabicyclo[7.2.1]dodeca-9(12),11-diene;

2-Butyl-11-((3-ethoxy-5-(1H-pyrrol-2-yl)-2H-pyrrol-2-ylidene)methyl)-10-azabicyclo[7.2.1]dodeca-9(12),11-diene;

11-((3-Ethoxy-5-(1H-pyrrol-2-yl)-2H-pyrrol-2-ylidene)methyl)-10-azabicyclo[7.2.1]dodeca-9(12),11-diene;

2-Methyl-11-((3-ethoxy-5-(1H-pyrrol-2-yl)-2H-pyrrol-2-ylidene)methyl)-10-azabicyclo[7.2.1]dodeca-9(12),11-diene;

2-n-Propyl-11-((3-ethoxy-5-(1H-pyrrol-2-yl)-2H-pyrrol-2-ylidene)methyl)-10-azabicyclo[7.2.1]dodeca-9(12),11-diene;

2-n-Pentyl-11-((3-ethoxy-5-(1H-pyrrol-2-yl)-2H-pyrrol-2-ylidene)methyl)-10-azabicyclo[7.2.1]dodeca-9(12),11-diene;

2-Benzyl-11-((3-ethoxy-5-(1H-pyrrol-2-yl)-2H-pyrrol-2-ylidene)methyl)-10-azabicyclo[7.2.1]dodeca-9(12),11-diene;

2-Ethyl-11-((3-ethoxy-5-(1H-pyrrol-2-yl)-2H-pyrrol-2-ylidene)methyl)-10-azabicyclo[7.2.1]dodeca-9(12),11-diene;

2-Methyl-13-((3-benzyloxy-5-(1H-pyrrol-2-yl)-2H-pyrrol-2-ylidene)methyl)-12-azabicyclo[9.2.1]tetradeca-11(14),13-diene;

13-((3-Benzyloxy-5-(1H-pyrrol-2-yl)-2H-pyrrol-2-ylidene)methyl)-12-azabicyclo[9.2.1]tetradeca-11(14),13-diene;

2-Ethyl-12-methyl-13-((3-benzyloxy-5-(1-methyl-1H-pyrrol-2-yl)-2H-pyrrol-2-ylidene)methyl)-12-azabicyclo[9.2.1]tetradeca-11(14),13-diene;

2-Ethyl-12-methyl-13-((3-benzyloxy-5-(1H-pyrrol-2-yl)-2H-pyrrol-2-ylidene)methyl)-12-azabicyclo[9.2.1]tetradeca-11(14),13-diene;

2-n-Propyl-13-((3-benzyloxy-5-(1H-pyrrol-2-yl)-2H-pyrrol-2-ylidene)methyl)-12-azabicyclo[9.2.1]tetradeca-11(14),13-diene; and 2-n-Butyl-13-((3-benzyloxy-5-(1H-pyrrol-2-yl)-2H-pyrrol-2-ylidene)methyl)-12-azabicyclo[9.2.1]tetradeca-11(14),13-diene;

and a pharmaceutically acceptable salt thereof.

78. The method of claim 47, wherein the compound of Formula (I) is butyl-meta-cycloheptylprodiginine or a pharmaceutically acceptable salt thereof.

79. The method of claim 47, wherein, in the compound the compound of Formula (I):

each $R_1$ is independently selected from the group consisting of —H, —$CH_3$, —$CH_2CH_3$, —$CH_2C_6H_5$, —C(O)OC($CH_3$)$_3$, —C(O)O$CH_2C_6H_5$, and —C(O)$CH_3$;

$R_2$ is selected from the group consisting of —H, $C_1$–$C_{12}$ straight chain alkyl, —$CH_2C_6H_5$, —Si$R_{10}R_{11}R_{12}$, —C(O)$CH_3$, —C(O)$C_6H_5$, -2-tetrahydropyranyl, —O$CH_2$O$CH_3$, and —C(O)O$CH_2CCl_3$;

$R_3$ is selected from the group consisting of —H, $C_1$–$C_{12}$ straight chain alkyl, —CH($R_{14}$)($R_{15}$) wherein $R_{14}$ and $R_{15}$ are independently $C_1$–$C_{12}$ straight chain alkyl, —C(O)$C_1$–$C_9$ straight chain alkyl, —CH(OH)$C_1$–$C_9$ straight chain alkyl, —CH(Cl)$C_1$–$C_9$ straight chain alkyl, -(2-pyridyl)methyl, -(3-pyridyl)methyl, -(4-pyridyl)methyl, and —$CH_2C_6H_5$, the —$CH_2C_6H_5$ being unsubstituted or substituted on phenyl with one cyano or one or more halo, methoxyl, or trifluoromethyl groups;

$R_{10}$ is selected from the group consisting of $C_1$–$C_4$ straight or branched chain alkyl and $R_{11}$ and $R_{12}$ are independently $C_1$–$C_3$ straight or branched chain alkyl; and $R_{16}$ and $R_{17}$ are —H; and m is an integer ranging from 1 to 5;

with the proviso that the compound of Formula (I) is not: metacycloprodigiosin.

80. The method of claim 47, wherein, in the compound of Formula (I):

each $R_1$ is independently selected from the group consisting of —H, and —$CH_3$;

$R_2$ is selected from the group consisting of —$CH_3$, —$CH_2CH_3$, and —$CH_2C_6H_5$;

$R_3$ is selected from the group consisting of —H, $C_1$–$C_{10}$ straight chain alkyl, (1-methyl)butyl, —$CH_2C_6H_5$, butyrol, (1-hydroxy)butyl, and (1-chloro)butyl;

m is an integer ranging from 1 to 5;

with the proviso that the compound of Formula (I) is not: metacycloprodigiosin.

81. The method of claim 47, wherein, in the compound of Formula (I):

each $R_1$ is —H;

$R_2$ is selected from the group consisting of —$CH_3$, and —$CH_2C_6H_5$;

$R_3$ is selected from the group consisting of —H, $C_1$–$C_{10}$ straight chain alkyl, and —$CH_2C_6H_5$;

$R_{16}$ and $R_{17}$ are —H; and m is an integer ranging from 1 to 5;

with the proviso that the compound of Formula (I) is not: metacycloprodigiosin.

82. The method of claim 47, wherein, in the compound of Formula (I):

each $R_1$ is independently selected from the group consisting of —H, and —$CH_3$;

$R_2$ is selected from the group consisting of —$CH_3$, and —$CH_2C_6H_5$;

$R_3$ is selected from the group consisting of —H, $C_1$–$C_{10}$ straight chain alkyl, —$CH_2C_6H_5$, butyroyl, (1-hydroxy)butyl, and (1-chloro)butyl;

$R_{16}$ and $R_{17}$ are —H; and m is an integer ranging from 1 to 5;

with the proviso that when m is 3, $R_3$ is not —$CH_2CH_3$ and when m is 1, $R_3$ is not —($CH_2$)$_3CH_3$.

83. The method of claim 47, wherein, in the compound of Formula (I):

each $R_1$ is independently selected from the group consisting of —H, and —$CH_3$;

$R_2$ is selected from the group consisting of —$CH_3$, and —$CH_2C_6H_5$;

$R_3$ is selected from the group consisting of —H, $C_1$–$C_{10}$ straight chain alkyl, (1-methyl)butyl, —$CH_2C_6H_5$, butyroyl, (1-hydroxy)butyl, and (1-chloro)butyl;

$R_{16}$ and $R_{17}$ are —H; and m is an integer ranging from 1 to 5.

84. The method of claim 47, wherein, in the compound of Formula (I):

each $R_1$ is independently selected from the group consisting of —H, and —$CH_3$;

$R_2$ is selected from the group consisting of —$CH_3$, and —$CH_2C_6H_5$;

$R_3$ is selected from the group consisting of —H, $C_1$–$C_{10}$ straight chain alkyl, —$CH_2C_6H_5$, butyroyl, (1-hydroxy)butyl, and (1-chloro)butyl;

$R_{16}$ and $R_{17}$ are —H; and m is 2, 4 or 5.

85. The method of claim 47, wherein, in the compound of Formula (I)

each $R_1$ is independently selected from the group consisting of —H, and —$CH_3$;

$R_2$ is selected from the group consisting of —$CH_3$, —$CH_2CH_3$, —$(CH_2)_2CH_3$, and —$CH_2C_6H_5$;

$R_3$ is selected from the group consisting of —H, $C_1$–$C_{10}$ straight chain alkyl, —$CH_2C_6H_5$, butyroyl, (1-hydxoxy)butyl, and (1-chloro)butyl;

m is an integer ranging from 1 to 5;

when m is 3 and $R_2$ is —$CH_3$, then $R_{16}$ is selected from the group consisting of —H, and —$CH_3$ and $R_{17}$ is selected from the group consisting of —H, and —COOEt; and when m is other than 3 and $R_2$ is other than —$CH_3$ or —$CH_2CH_3$, then $R_{16}$ and $R_{17}$ are —H only;

with the proviso that the compound of Formula (I) is not:

metacycloprodigiosin.

86. The method of claim 47, wherein the compound of Formula I is selected from the group consisting of:

butyl-meta-cycloheptylprodiginine

2-Ethyl-11-((3-methoxy-5-(1H-pyrrol-2-yl)-2H-pyrrol-2-ylidene)methyl)-10-azabicyclo[7.2.1]dodeca-9(12),11-diene;

11-((3-Methoxy-5-(1H-pyrrol-2-yl)-2H-pyrrol-2-ylidene) methyl)-10-azabicyclo[7.2.1]dodeca-9(12),11-diene;

2-Methyl-11-((3-methoxy-5-(1H-pyrrol-2-yl)-2H-pyrrol-2-ylidene)methyl)-10-azabicyclo[7.2.1]dodeca-9(12),11-diene;

2-n-Propyl-11-((3-methoxy-5-(1H-pyrrol-2-yl)-2H-pyrrol-2-ylidene)methyl)-10-azabicyclo[7.2.1]dodeca-9(12),11-diene;

2-n-Pentyl-11-((3-methoxy-5-(1H-pyrrol-2-yl)-2H-pyrrol-2-ylidene)methyl)-10-azabicyclo[7.2.1]dodeca-9(12),11-diene;

2-Benzyl-11-((3-methoxy-5-(1H-pyrrol-2-yl)-2H-pyrrol-2-ylidene)methyl)-10-azabicyclo[7.2.1]dodeca-9(12),11-diene;

(S)-2-n-Pentyl-11-((3-methoxy-5-(1H-pyrrol-2-yl)-2H-pyrrol-2-ylidene)methyl)-10-azabicyclo[7.2.1]dodeca-9(12),11-diene;

(R)-2-n-Pentyl-11-((3-methoxy-5-(1H-pyrrol-2-yl)-2H-pyrrol-2-ylidene)methyl)-10-azabicyclo[7.2.1]dodeca-9(12),11-diene;

(S)-2-n-Butyl-11-((3-methoxy-5-(1H-pyrrol-2-yl)-2H-pyrrol-2-ylidene)methyl)-10-azabicyclo[7.2.1]dodeca-9(12),11-diene;

(R)-2-n-Butyl-11-((3-methoxy-5-(1H-pyrrol-2-yl)-2H-pyrrol-2-ylidene)methyl)-10-azabicyclo[7.2.1]dodeca-9(12),11-diene;

(S)-2-Ethyl-11-((3-methoxy-5-(1H-pyrrol-2-yl)-2H-pyrrol-2-ylidene)methyl)-10-azabicyclo[7.2.1]dodeca-9(12),11-diene;

(R)-2-Ethyl-11-((3-methoxy-5-(1H-pyrrol-2-yl)-2H-pyrrol-2-ylidene)methyl)-10-azabicyclo[7.2.1]dodeca-9(12),11-diene;

(S)-2-Methyl-11-((3-methoxy-5-(1H-pyrrol-2-yl)-2H-pyrrol-2-ylidene)methyl)-10-azabicyclo[7.2.1]dodeca-9(12),11-diene;

(R)-2-Methyl-11-((3-methoxy-5-(1H-pyrrol-2-yl)-2H-pyrrol-2-ylidene)methyl)-10-azabicyclo[7.2.1]dodeca-9(12),11-diene;

(S)-2-n-Propyl-11-((3-methoxy-5-(1H-pyrrol-2-yl)-2H-pyrrol-2-ylidene)methyl)-10-azabicyclo[7.2.1]dodeca-9(12),11-diene;

(R)-2-n-Propyl-11-((3-methoxy-5-(1H-pyrrol-2-yl)-2H-pyrrol-2-ylidene)methyl)-10-azabicyclo[7.2.1]dodeca-9(12),11-diene;

2-Methyl-12-((3-methoxy-5-(1H-pyrrol-2-yl)-2H-pyrrol-2-ylidene)methyl)-11-azabicyclo[8.2.1]trideca-10(13),12-diene;

2-Ethyl-12-((3-methoxy-5-(1H-pyrrol-2-yl)-2H-pyrrol-2-ylidene)methyl)-11-azabicyclo[8.2.1]trideca-10(13),12-diene;

2-n-Propyl-12-((3-methoxy-5-(1H-pyrrol-2-yl)-2H-pyrrol-2-ylidene)methyl)-11-azabicyclo[8.2.1]trideca-10(13),12-diene;

2-n-Butyl-12-((3-methoxy-5-(1H-pyrrol-2-yl)-2H-pyrrol-2-ylidene)methyl)-11-azabicyio[8.2.1]trideca-10(13),12-diene;

2-n-Pentyl-12-((3-methoxy-5-(1H-pyrrol-2-yl)-2H-pyrrol-2-ylidene)methyl)-11-azabicyclo[8.2.1]trideca-10(13),12-diene;

12-((3-methoxy-5-(1H-pyrrol-2-yl)-2H-pyrrol-2-ylidene) methyl)-11-azabicyclo[8.2.1]trideca-10(13),12-diene;

2-Methyl-13-((3-methoxy-5-(1H-pyrrol-2-yl)-2H-pyrrol-2-ylidene)methyl)-12-azabicyclo[9.2.1]tetradeca-11(14),13-diene;

13-((3-Methoxy-5-(1H-pyrrol-2-yl)-2H-pyrrol-2-ylidene) methyl)-12-azabicyclo[9.2.1]tetradeca-11(14),13-diene;

2-Ethyl-12-methyl-13-((3-methoxy-5-(1-methyl-1H-pyrrol-2-yl)-2H-pyrrol-2-ylidene)methyl)-12-azabicyclo[9.2.1]tetradeca-11(14),13-diene;

2-Ethyl-12-methyl-13-((3-methoxy-5-(1H-pyrrol-2-yl)-2H-pyrrol-2-ylidene)methyl)-12-azabicyclo[9.2.1]tetradeca-11(14),13-diene;

2-n-Propyl-13-((3-methoxy-5-(1H-pyrrol-2-yl)-2H-pyrrol-2-ylidene)methyl)-12-azabicyclo[9.2.1]tetradeca-11(14),13-diene;

2-n-Butyl-13-((3-methoxy-5-(1H-pyrrol-2-yl)-2H-pyrrol-2-ylidene)methyl)-12-azabicyclo[9.2.1]tetradeca-11(14),13-diene;

14-((3-Methoxy-5-(1H-pyrrol-2-yl)-2H-pyrrol-2-ylidene) methyl)-13-azabicyclo[10.2.1]pentadeca-12(15),14-diene;

2-Butyl-11-((3-methoxy-5-(1-methyl-1H-pyrrol-2-yl)-2H-pyrrol-2-ylidene)methyl)-10-azabicyclo[7.2.1]dodeca-9(12),11-diene;

2-Butyl-11-((3-methoxy-5-(1-methyl-1H-pyrrol-2-yl)-2H-pyrrol-2-ylidene)methyl)-10-methyl-10-azabicyclo[7.2.1]dodeca-9(12),11-diene;

2-Butyl-11-((3-methoxy-5-(1H-pyrrol-2-yl)-2H-pyrrol-2-ylidene)methyl)-10-methyl-10-azabicyclo[7.2.1]dodeca-9(12),11-diene;

2-Ethyl-11-((3-benzyloxy-5-(1H-pyrrol-2-yl)-2H-pyrrol-2-ylidene)methyl)-10-azabicyclo[7.2.1]dodeca-9(12),11-diene;

2-Butyl-11-((3-hydroxy-5-(1H-pyrrol-2-yl)-2H-pyrrol-2-ylidene)methyl)-10-azabicyclo[7.2.1]dodeca-9(12),11-diene;

2-Butyl-11-((3-benzyloxy-5-(1H-pyrrol-2-yl)-2H-pyrrol-2-ylidene)methyl)-10-azabicyclo[7.2.1]dodeca-9(12),11-diene;

11-((3-Benzyloxy-5-(1H-pyrrol-2-yl)-2H-pyrrol-2-ylidene)methyl)-10-azabicyclo[7.2.1]dodeca-9(12),11-diene;

2-Methyl-11-((3-benzyloxy-5-(1H-pyrrol-2-yl)-2H-pyrrol-2-ylidene)methyl)-10-azabicyclo[7.2.1]dodeca-9(12),11-diene;

2-n-Propyl-11-((3-benzyloxy-5-(1H-pyrrol-2-yl)-2H-pyrrol-2-ylidene)methyl)-10-azabicyclo[7.2.1]dodeca-9(12),11-diene;

2-n-Pentyl-11-((3-benzyloxy-5-(1H-pyrrol-2-yl)-2H-pyrrol-2-ylidene)methyl)-10-azabicyclo[7.2.1]dodeca-9(12),11-diene;

2-Benzyl-11-((3-benzyloxy-5-(1H-pyrrol-2-yl)-2H-pyrrol-2-ylidene)methyl)-10-azabicyclo[7.2.1]dodeca-9(12),11-diene;

2-Methyl-14-((3-methoxy-5-(1H-pyrrol-2-yl)-2H-pyrrol-2-ylidene)methyl)-13-azabicyclo[10.2.1]pentadeca-12(15),14-diene;

15-((3-Methoxy-5-(1H-pyrrol-2-yl)-2H-pyrrol-2-ylidene)methyl)-14-azabicyclo[11.2.1]hexadeca-13(16),15-diene;

2-Methyl-15-((3-methoxy-5-(1H-pyrrol-2-yl)-2H-pyrrol-2-ylidene)methyl)-14-azabicyclo[11.2.1]hexadeca-13(16),15-diene;

2-(2-Hydroxy-n-butyl)-11-((3-methoxy-5-(1H-pyrrol-2-yl)-2H-pyrrol-2-ylidene)methyl)-10-azabicyclo[7.2.1]dodeca-9(12),11-diene;

2-(2-chloro-n-butyl)-11-((3-methoxy-5-(1H-pyrrol-2-yl)-2H-pyrrol-2-ylidene)methyl)-10-azabicyclo[7.2.1]dodeca-9(12),11-diene;

2-Butyl-11-((3-ethoxy-5-(1H-pyrrol-2-yl)-2H-pyrrol-2-ylidene)methyl)-10-azabicyclo[7.2.1]dodeca-9(12),11-diene;

11-((3-Ethoxy-5-(1H-pyrrol-2-yl)-2H-pyrrol-2-ylidene)methyl)-10-azabicyclo[7.2.1]dodeca-9(12),11-diene;

2-Methyl-11-((3-ethoxy-5-(1H-pyrrol-2-yl)-2H-pyrrol-2-ylidene)methyl)-10-azabicyclo[7.2.1]dodeca-9(12),11-diene;

2-n-Propyl-11-((3-ethoxy-5-(1H-pyrrol-2-yl)-2H-pyrrol-2-ylidene)methyl)-10-azabicyclo[7.2.1]dodeca-9(12),11-diene;

2-n-Pentyl-11-((3-ethoxy-5-(1H-pyrrol-2-yl)-2H-pyrrol-2-ylidene)methyl)-10-azabicyclo[7.2.1]dodeca-9(12),11-diene;

2-Benzyl-11-((3-ethoxy-5-(1H-pyrrol-2-yl)-2H-pyrrol-2-ylidene)methyl)-10-azabicyclo[7.2.1]dodeca-9(12),11-diene;

2-Ethyl-11-((3-ethoxy-5-(1H-pyrrol-2-yl)-2H-pyrrol-2-ylidene)methyl)-10-azabicyclo[7.2.1]dodeca-9(12),11-diene;

2-Methyl-13-((3-benzyloxy-5-(1H-pyrrol-2-yl)-2H-pyrrol-2-ylidene)methyl)-12-azabicyclo[9.2.1]tetradeca-11(14),13-diene;

13-((3-Benzyloxy-5-(1H-pyrrol-2-yl)-2H-pyrrol-2-ylidene)methyl)-12-azabicyclo[9.2.1]tetradeca-11(14),13-diene;

2-Ethyl-12-methyl-13-((3-benzyloxy-5-(1-methyl-1H-pyrrol-2-yl)-2H-pyrrol-2-ylidene)methyl)-12-azabicyclo[9.2.1]tetradeca-11(14),13-diene;

2-Ethyl-12-methyl-13-((3-benzyloxy-5-(1H-pyrrol-2-yl)-2H-pyrrol-2-ylidene)methyl)-12-azabicyclo[9.2.1]tetradeca-11(14),13-diene;

2-n-Propyl-13-((3-benzyloxy-5-1H-pyrrol-2-yl)-2H-pyrrol-2-ylidene)methyl)-12-azabicyclo[9.2.1]tetradeca-11(14),13-diene; and 2-n-Butyl-13-((3-benzyloxy-5-(1H-pyrrol-2-yl)-2H-pyrrol-2-ylidene)methyl-12-azabicyclo[9.2.1]tetradeca-11(14),13-diene;

and a pharmaceutically acceptable salt thereof.

87. The method of claim 44, wherein the lung carcinoma is small cell lung carcinoma.

88. The method of claim 46, wherein the lung carcinoma cell is a small cell lung carcinoma cell.

\* \* \* \* \*

UNITED STATES PATENT AND TRADEMARK OFFICE
CERTIFICATE OF CORRECTION

PATENT NO. : 6,602,879 B2
DATED : August 5, 2003
INVENTOR(S) : Murthy et al.

It is certified that error appears in the above-identified patent and that said Letters Patent is hereby corrected as shown below:

Column 139,
Line 12, replace "thereof wherein," with -- thereof, wherein, -- thereof.
Line 67, replace "branched chain alkyl and" with -- branched chain alkyl and —$C_6H_5$; -- thereof.

Column 141,
Line 3, replace "(1-hydroxy)butyl)" with -- (1-hydroxy)butyl --

Column 142,
Line 47, replace "methyl)13-azabicyclo" with -- methyl)-13-azabicyclo --

Column 145,
Line 31, replace "(1-hydroxy)butyl)" with -- (1-hydroxy)butyl --
Lines 54-55, replace "butyl-meta-cycloheptyiprodiginine" with -- butyl-meta-cycloheptylprodiginine --

Column 148,
Line 28, replace "-diene; and" with -- -diene; --

Signed and Sealed this

Twenty-first Day of October, 2003

JAMES E. ROGAN
*Director of the United States Patent and Trademark Office*

UNITED STATES PATENT AND TRADEMARK OFFICE
CERTIFICATE OF CORRECTION

PATENT NO. : 6,602,879 B2
DATED : August 5, 2003
INVENTOR(S) : Murthy et al.

It is certified that error appears in the above-identified patent and that said Letters Patent is hereby corrected as shown below:

Column 139,
Line 12, replace "thereof wherein," with -- thereof, wherein, -- thereof.
Line 67, replace "branched chain alkyl and" with -- branched chain alkyl and —$C_6H_5$; -- thereof.

Column 141,
Line 3, replace "(1-hydroxy)butyl)" with -- (1-hydroxy)butyl --

Column 142,
Line 47, replace "methyl)13-azabicyclo" with -- methyl)-13-azabicyclo --

Column 145,
Line 31, replace "(1-hydroxy)butyl)" with -- (1-hydroxy)butyl --
Lines 54-55, replace "butyl-meta-cycloheptyiprodiginine" with -- butyl-meta-cycloheptylprodiginine --

Column 148,
Line 28, replace "-diene; and" with -- -diene; --

Column 150,
Line 2, "2,4 or 5." should read -- 2, 4 or 5. -- thereof,
Line 23, "butyl-meta-cycloheptyiprodiginine" with -- butyl-meta-cycloheptylprodiginine -- thereof, Column 152,
Line 61, "methyl)-2-n Butyl" should read -- methyl)-12-azabicyclo[9.2.1] tetradeca - 11 (14), 13-diene;
2-n Butyl ; --

Column 153,
Line 26, "branched chain alkyl and" should read -- branched chain alkyl and —$C_6H_5$; -- thereof
Line 41, "butyrol(1-hydroxy)" should read -- butyroyl, (1-hydroxy) -- thereof, Column 154,
Line 4, "m is1" should read -- m is 1 -- thereof,
Line 26, "2,4 or 5" should read -- 2, 4 or 5 -- thereof, Column 159,
Line 33, "alkyl and $R_{11}$" should read -- alkyl and —$C_6H_5$; $R_{11}$ -- thereof,

UNITED STATES PATENT AND TRADEMARK OFFICE
CERTIFICATE OF CORRECTION

PATENT NO. : 6,602,879 B2
DATED : August 5, 2003
INVENTOR(S) : Murthy et al.

It is certified that error appears in the above-identified patent and that said Letters Patent is hereby corrected as shown below:

Column 160,
Line 48, "branched chain alkyl and" should read -- branched chain alkyl and —$C_6H_5$; --
Line 66, "(1—CHloro)" should read -- (1—chloro) -- thereof, Column 162,
Line 3, "other than 3 and" should read -- other than 3 and -- thereof, Column 164,
Line 11, "10-azabicycio[7.2.1]" should read -- 10-azabicyclo[7.2.1] -- thereof, Column 166,
Line 11, "(1-hydroxy)butyl)" should read -- (1-hydroxy)butyl -- thereof,
Line 27, "—COGEt;" should read -- —COOEt; -- thereof, Column 170,
Line 30, "when m is 1 $R_3$ is not" should read -- when m is 1, $R_3$ is not -- thereof, Column 172,
Line 55, "10-azabicycio[7.2.1]" should read -- 10-azabicyclo[7.2.1] -- thereof, Column 174,
Line 14, "branched chain alkyl and" should read -- branched chain alkyl and —$C_6H_5$; -- thereof,
Line 29, "butyrol" should read -- butyroyl -- thereof, This certificate supersedes Certificate of Correction issued October 21, 2003.

Signed and Sealed this

Third Day of February, 2004

JON W. DUDAS
*Acting Director of the United States Patent and Trademark Office*